US007794977B2

(12) United States Patent
Otte et al.

(10) Patent No.: US 7,794,977 B2
(45) Date of Patent: Sep. 14, 2010

(54) MEANS AND METHODS FOR REGULATING GENE EXPRESSION

(75) Inventors: Arie P. Otte, Amersfoort (NL); Arthur L. Kruckeberg, Shoreline, WA (US); David P. E. Satijn, Nieuwegein (NL)

(73) Assignee: Chromagenics B.V., Leiden (NL)

( * ) Notice: Subject to any disclaimer, the term of this patent is extended or adjusted under 35 U.S.C. 154(b) by 55 days.

(21) Appl. No.: 11/888,568

(22) Filed: Jul. 31, 2007

(65) Prior Publication Data
US 2008/0131930 A1 Jun. 5, 2008

Related U.S. Application Data

(60) Division of application No. 11/012,546, filed on Dec. 14, 2004, now Pat. No. 7,267,965, which is a continuation of application No. PCT/NL03/00410, filed on May 30, 2003.

(30) Foreign Application Priority Data
Jun. 14, 2002 (EP) ................... 02077344

(51) Int. Cl.
C12P 21/06 (2006.01)
C12P 21/04 (2006.01)
C12N 15/00 (2006.01)
C12N 5/00 (2006.01)
C12N 5/10 (2006.01)
C12N 15/64 (2006.01)

(52) U.S. Cl. .................. 435/69.1; 435/70.1; 435/320.1; 435/325; 435/326; 435/358; 435/372.1; 435/369; 435/363; 435/364; 435/371

(58) Field of Classification Search ........................ None
See application file for complete search history.

(56) References Cited

U.S. PATENT DOCUMENTS

| 5,610,053 | A | 3/1997 | Chung et al. | |
|---|---|---|---|---|
| 5,773,695 | A | 6/1998 | Thompson et al. | |
| 5,888,809 | A | 3/1999 | Allison | |
| 6,395,549 | B1 | 5/2002 | Tuan et al. | |
| 6,521,419 | B1 | 2/2003 | Koduri et al. | |
| 6,586,205 | B1 | 7/2003 | Glucksmann et al. | |
| 6,800,457 | B2 | 10/2004 | Koduri et al. | |
| 6,872,524 | B1 | 3/2005 | Otte | |
| 7,192,741 | B2 * | 3/2007 | Otte et al. ................... | 435/70.3 |
| 7,267,965 | B2 | 9/2007 | Otte et al. | |
| 2005/0106609 | A1 | 5/2005 | Otte | |
| 2007/0026498 | A1 * | 2/2007 | Otte et al. ................... | 435/69.1 |
| 2007/0026499 | A1 * | 2/2007 | Otte et al. ................... | 435/69.1 |
| 2007/0031933 | A1 * | 2/2007 | Otte et al. ................... | 435/69.1 |
| 2007/0031934 | A1 * | 2/2007 | Otte et al. ................... | 435/69.1 |
| 2007/0031935 | A1 * | 2/2007 | Otte et al. ................... | 435/69.1 |
| 2007/0037256 | A1 * | 2/2007 | Otte et al. ................... | 435/69.1 |
| 2007/0128717 | A1 * | 6/2007 | Otte et al. ................. | 435/320.1 |

FOREIGN PATENT DOCUMENTS

| EP | 1 273 666 | 1/2003 |
|---|---|---|
| WO | WO 96/04390 | 2/1996 |
| WO | WO 97/27207 | 7/1997 |
| WO | WO 98/11207 | 3/1998 |
| WO | WO 98/49289 | 11/1998 |
| WO | WO 00/05393 | 2/2000 |
| WO | WO 00/09749 | 2/2000 |
| WO | WO 00/17337 | 3/2000 |
| WO | WO 00/23606 | 4/2000 |
| WO | WO 01/59117 | 8/2001 |
| WO | WO 01/59118 | 8/2001 |
| WO | WO 02/24930 A2 | 3/2002 |
| WO | WO 03/004704 | 1/2003 |
| WO | WO 2004/055215 A1 | 7/2004 |
| WO | WO 2004/056986 A2 | 7/2004 |

OTHER PUBLICATIONS

Aranda et al., Definition of Transcriptional Pause Elements in Fission Yeast, Molecular and Cellular Biology, Feb. 1999, pp. 1251-61, vol. 19, No. 2.

Auten et al., "Effect of Scaffold Attachment Region on Transgene Expression in Retrovirus Vector-Transduced Primary T cells and Macrophages," Human Gene Therapy, May 20, 1999, pp. 1389-1399, vol. 10, No. 8.

Burgess-Beusse et al., The insulation of genes from external enhancers and silencing chromatin, PNAS, Dec. 10, 2002, pp. 16433-37, vol. 99, Suppl. 4.

Chan et al., p300-CBP proteins: HATs for transcriptional bridges and scaffolds, Journal of Cell Science, 2001, pp. 2363-2373, vol. 114.

Eggermont et al., Poly(A) signals and transcriptional pause sites combine to prevent interference between RNA polymerase II promoters, The EMBO Journal, 1993, pp. 2539-2548, vol. 12, No. 6.

(Continued)

*Primary Examiner*—Nancy Vogel
*Assistant Examiner*—Catherine Hibbert
(74) *Attorney, Agent, or Firm*—TraskBritt

(57) ABSTRACT

The invention relates to means and methods for regulating gene expression and production of proteinaceous molecules. The invention provides a method for producing a proteinaceous molecule in a cell comprising selecting a cell for its suitability for producing the proteinaceous molecule, providing a nucleic acid encoding the proteinaceous molecule with a nucleic acid comprising a STAR (STabilizing Anti-Repression) sequence, expressing the resulting nucleic acid in the cell and collecting the proteinaceous molecule. Providing at least one STAR sequence to a nucleic acid encoding a proteinaceous molecule will enhance production (yield) of the proteinaceous molecule by a host cell, increase the proportion of host cells with acceptable expression levels, and/or increase stability of a gene expression level.

18 Claims, 22 Drawing Sheets

OTHER PUBLICATIONS

Farrell et al., Conserved CTCF Insulator Elements Flank the Mouse and Human Beta-Globin Loci, Molecular and Cellular Biology, Jun. 2002, pp. 3820-3831, vol. 22. No. 11.

Glucksmann et al., Database accession No. AAH76193, Oct. 29, 2001.

Han et al., "Matrix attachment regions (MARs) enhance transformation frequency and transgene expression in poplar," Transgenic Research, 1997, pp. 415-420, vol. 6.

Johnson et al., Requirements for utilization of CREB binding protein by hypersensitive site two of the Beta-globin locus control region, Nucleic Acids Research 2002, pp. 1522-1530, vol. 30, No. 7.

Maniatis et al., Recognition Sequences of Repressor and Polymerase in the Operators of Bacteriophage Lambda, Cell, Jun. 1975, pp. 109-113, vol. 5.

Martinez-Balbas et al., The acetyltransferase activity of CBP stimulates transcription, The EMBO Journal, 1998, pp. 2886-2893, vol. 17, No. 10.

Mielke et al., "Stabilized, long-term expression of heterodimeric proteins from tricistronic mRNA," Gene, Aug. 22, 2000, pp. 1-8, vol. 254, No. 1-2.

Migliaccio et al., "Stable and unstable transgene integration sites in the human genome: extinction of the Green Fluorescent Protein transgene in K562 cells," Gene, Oct. 3, 2000, pp. 197-214, vol. 256, No. 1-2.

Reik et al., Biotechnologies and therapeutics: Chromatin as a target, Current Opinion in Genetics & Development, 2002, pp. 233-242, vol. 12.

Seum et al., A GAL4-HP1 fusion protein targeted near heterochromatin promotes gene silencing, Chromosoma, 2000, pp. 453-459, vol. 109.

Bell et al., Insulators and Boundaries: Versatile Regulatory Elements in the Eukaryotic Genome, Science, pp. 447-450, vol. 291, No. 5503.

Chung et al., A 5' Element of the Chicken Beta-Globin Domain Serves as an Insulator in Human Erythroid Cells and Protects against Position Effect in Drosophila, Aug. 13, 1993, Cell, pp. 505-514, vol. 74.

Database EMBL 'Online!, Jul. 8, 1992, H. sapiens HOX4B gene upstream sequence XP002348163 retrieved from EBI, Database accession No. X67079, Abstract.

Kellum et al., A Group of scs Elements Function as Domain Boundaries in an Enhancer-Blocking Assay, Molecular and Cellular Biology, May 1992, pp. 2424-2431, vol. 12, No. 5.

Partial European Search Report, EP 05 07 6209, dated Oct. 7, 2005.

European Search Report dated Dec. 22, 2005.

Database EMBL 'Online! Aug. 4, 1999, "Homo sapiens chromosome 19 clone CTD-2540B15, complete sequence," XP002359985 retrieved from EBI accession No. EM_PRO:AC008738, database accession No. AC008738 for SEQ ID No. 7.

Database EMBL 'Online! Feb. 3, 2004, "Sequence 33099 from Patent W002068579," XP002359986 retrieved from EBI accession No. EM_PRO:CQ747165, database accession No. CQ747165 for SEQ ID No. 9.

Database EMBL 'Online! Sep. 24, 2000, "Homo sapiens chromosome 4 clone RP11-680II8, working draft sequence, 25 unordered pieces," XP002359987 retrieved from EBI accession No. EM_PRO:AC080087, database accession No. AC080087 for SEQ ID No. 9.

Database EMBL 'Online! Dec. 15, 1999, "Homo sapiens BAC clone RP11-572N21 from 2, complete sequence," XP002359988 retrieved from EBI accession No. EM_PRO:AC018470, database accession No. AC018470, for SEQ ID No. 17.

Database EMBL 'Online! Dec. 23, 1999, "Human DNA sequence from clone RP11-54H19 on chromosome 1 Contains the 3' end of the LMNA gene for lamin A/C, the gene for a novel protein similar to semaphorins (FLJ12287), a novel gene (KIAA0446), the PMFI gene for polyamine-modulated factor 1, the BGLAP gene for bone gamma-carboxyglutamate (gla) p," XP002359989, retrieved from EBI accession No. EM_PRO:AL135927, database accession No. AL135927 for SEQ ID No. 27.

Database EMBL 'Online! Apr. 26, 2001, "RST28606 Athersys RAGE Library Homo sapiens cDNA, mRNA sequence," XP002359990 retrieved from EBI accession No. EM_PRO:BG209092, database accession No. BG209092 for SEQ ID No. 40.

Database EMBL 'Online! Sep. 29, 1999, "Homo sapiens genomic DNA, chromosome 22q11.2, Cat Eye Syndrome region, clone:N64E9," XP002359991, retrieved from EBI accession No. EM_PRO:AP000526, database accession No. AP000526 for SEQ ID No. 40.

Database EMBL 'Online! Oct. 28, 1998, "Homo sapiens neurexin III-alpha gene, partial cds," XP002359992, retrieved from EBI accession No. EM_PRO:AF099810, database accession No. AF099810 for SEQ ID No. 43.

Database EMBL 'Online! Jan. 25, 2001, "QV2-NN0045-081200-535-c10 NN0045 Homo sapiens cDNA, mRNA sequence." XP002359993 retrieved from EBI accession No. EM_PRO:BF960930, database accession No. BF960930 for SEQ ID No. 43.

Database EMBL 'Online! Sep. 29, 1999, Homo sapiens genomic DNA, chromosome 22q11.2, Cat Eye Syndrome region, clone:N14H11, XP002359994 retrieved from EBI accession No. EM_PRO:AP000525, database accession No. AP000525 for SEQ ID No. 44.

Database EMBL 'Online! Mar. 19, 1998, CIT-HSP-2172C8.TF CIT-HSP Homo sapiens genomic clone 2172C8, genomic survey sequence, XP002359995 retrieved from EBI accession No. EM_PRO:B92131, database accession No. B92131 for SEQ ID No. 44.

Database EMBL 'Online! Sep. 29, 1999, "Homo sapiens genomic DNA, chromosome 22q11.2, Cat Eye Syndrome region, clone:c91G6," XP002359996 retrieved from EBI accession No. EM_PRO:AP000528, database accession No. AP000528 for SEQ ID No. 45.

Database EMBL 'Online! Mar. 15, 1999, "Homo sapiens chromosome UNK clone CTA-435J10, working draft sequence, 1 unordered pieces," XP002359997 retrieved from EBI accession No. EM_PRO:AC007044, database accession No. AC007044 for SEQ ID No. 61.

Van Der Vlag et al., "Transcriptional Repression Mediated by Polycomb Group Proteins and Other Chromatin-associated Repressors Is Selectively Blacked by Insulators," J. of Biological Chemistry, Jan. 7, 2000, pp. 697-704, vol. 275, No. 1.

Emery et al., "A chromatin insulator protects retrovirus vectors from chromosomal position effects," Proceedings of the National Academy of Sciences of USA, Aug. 1, 2000, pp. 9150-9155, vol. 97, No. 16.

West et al., "Insulators: many functions, many mechanisms," Genes and Development, 1 Feb. 2002, pp. 271-288, vol. 16, No. 3.

Kwaks et al., "Identification of anti-repressor elements that confer high stable protein in production in mammalian cells," Nature Biotechnology, May 20, 2003, pp. 553-558, vol. 21, No. 5.

Pile et al., "GAGA Factor-dependent Transcription and Establishment of DNase Hypersensitivity Are Independent and Unrelated Events In Vivo," J. of Biological Chemistry, Jan. 14, 2000, pp. 1398-1404, vol. 275, No. 2.

Sigrist et al., "Chromatin Insulator Elements Black the Silencing of a Target Gene by the Drosophila Polycomb Response Element (PRE) but Allow trans Interactions Between PREs on Different Chromosomes," Genetics, Sep. 1997, pp. 209-211, vol. 147, No. 1.

PCT International Search Report, PCT/NL2003/00410, dated Dec. 15, 2003.

U.S. Appl. No. 11/899,505, filed Sep. 6, 2007, Otte et al., Selection of Host Cells Expressing Protein at High Levels.

U.S. Appl. No. 11/978,109, filed Oct. 26, 2007, Otte et al., A Method for Simultaneous Production of Multiple Proteins; Vectors and Cells for use Therein.

U.S. Appl. No. 11/978,134, filed Oct. 26, 2007, Otte et al., A Method for Simultaneous Production of Multiple Proteins; Vectors and Cells for use Therein.

U.S. Appl. No. 11/978,483, filed Oct. 26, 2007, Otte et al., Means and Methods for Regulating Gene Expression.

U.S. Appl. No. 12/218,128, filed Jul. 11, 2008, Otte et al., A Method for Improving Protein Production.

U.S. Appl. No. 12/223,801, filed Aug. 6, 2008, Otte et al., Selection of Host Cells Expressing Protein at High Levels.

U.S. Appl. No. 12/225,355, filed Sep. 19, 2008, Otte et al., Expression Augmenting DNA Fragments, use Thereof, and Methods for Finding Thereof.

U.S. Appl. No. 12/226,706, filed Oct. 24, 2008, Otte et al., Selection of Host Cells Expressing Protein at High Levels.

* cited by examiner

CHO cells, CMV promoter, SEAP, linear

FIG. 9
STAR element orientation
A. pSelect vector with cloned STAR element:
B. pSDH vector, STARs in native orientation:
C. pSDH vector, STARs in opposite orientation

STAR copy number dependency

Schematic diagram of Enhancer and Enhancer-blocking Assays

Enhancer assay

Schematic Diagram of STAR Element Bioinformatic Analysis

Classification of STARs by Discriminant Analysis with Oligo and Dyad Models
Training Set of 65 STARs

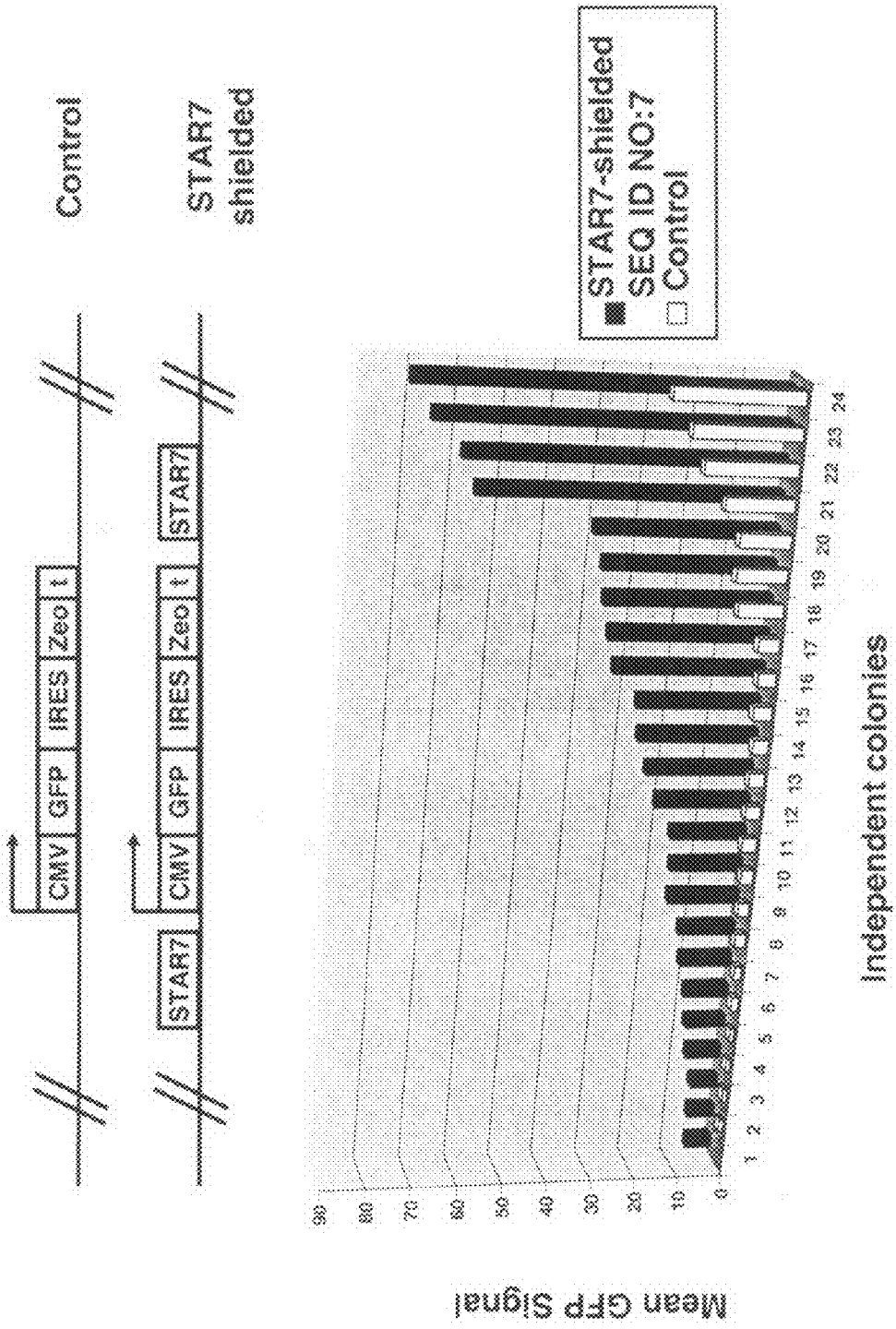

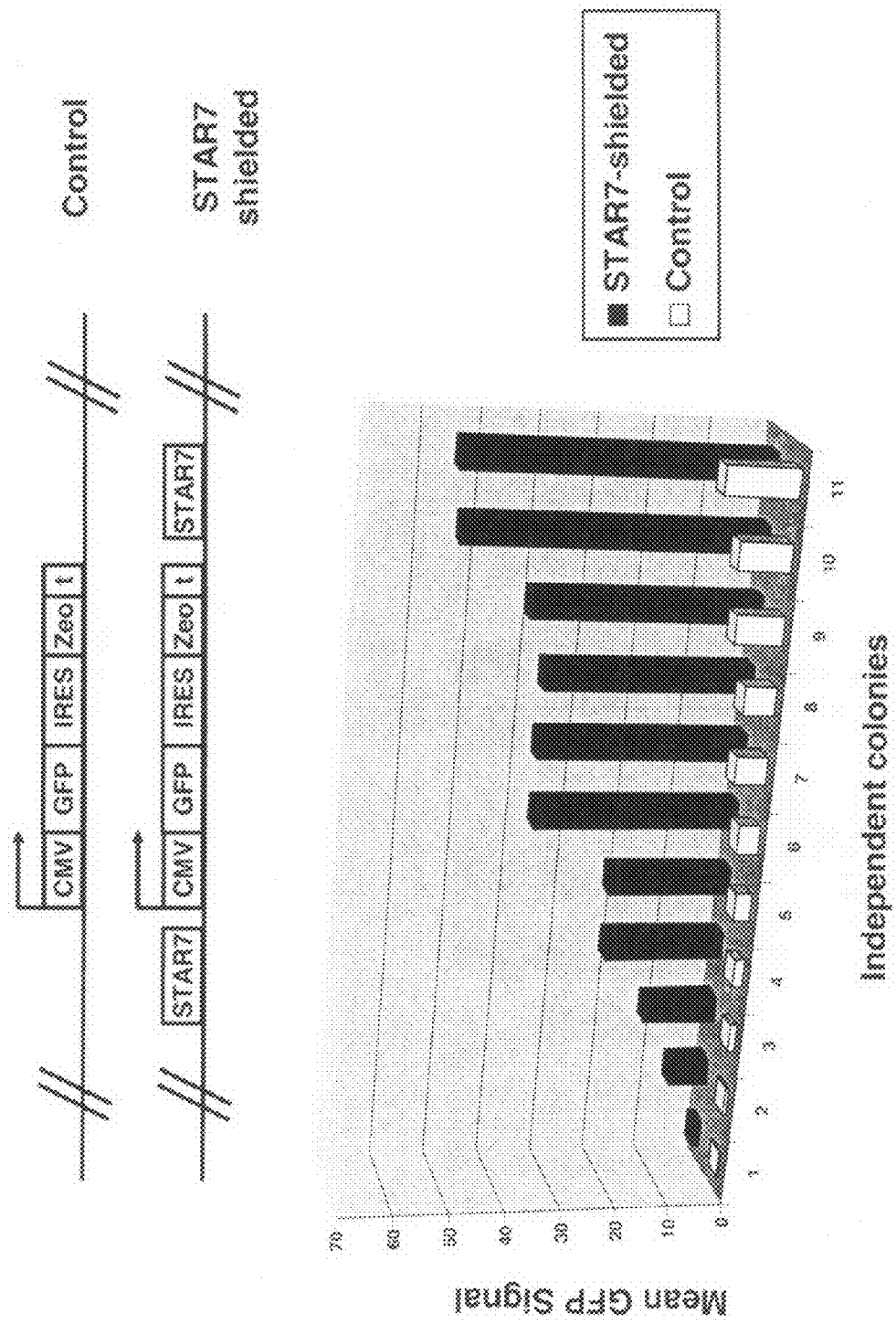

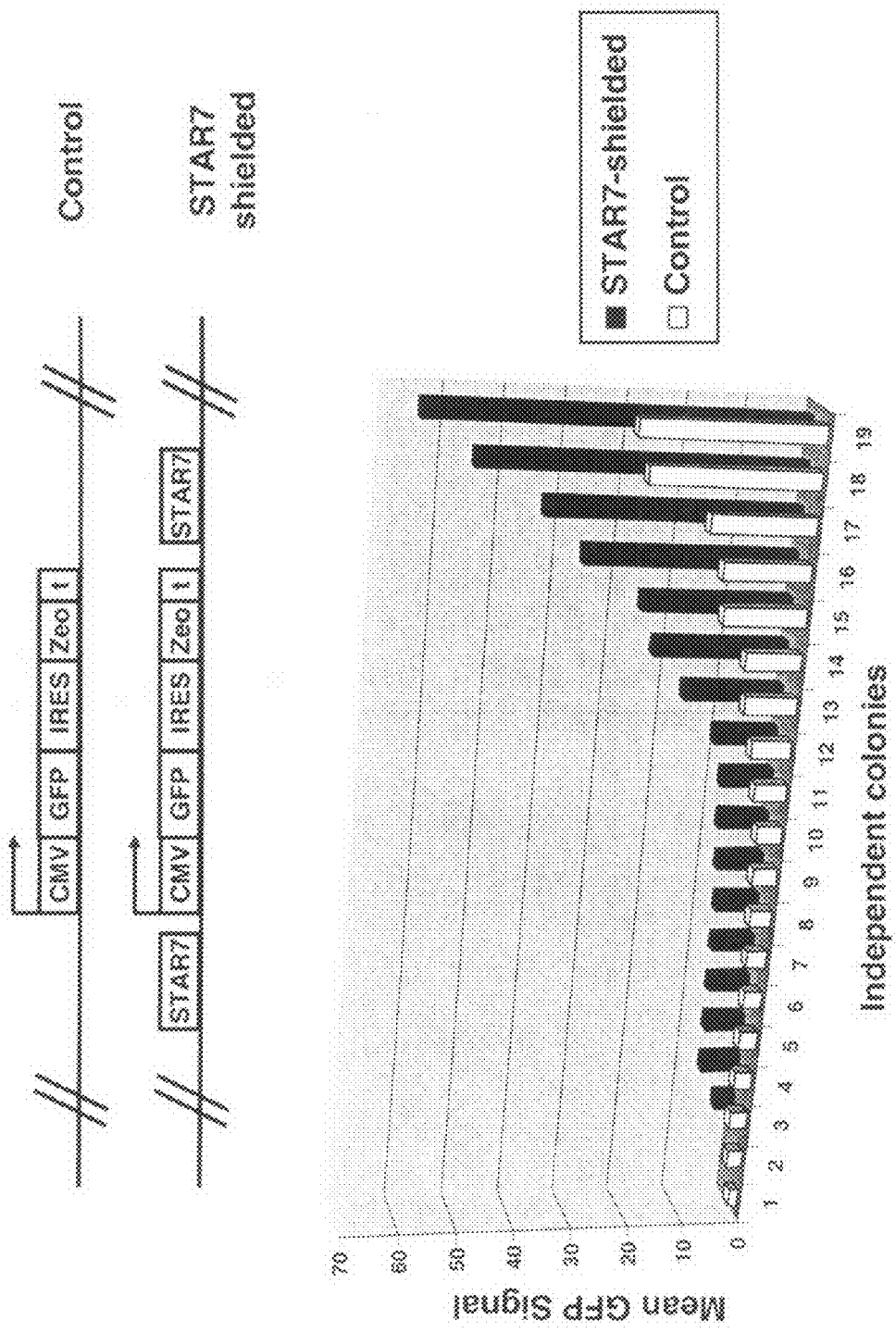

MEANS AND METHODS FOR REGULATING GENE EXPRESSION

CROSS-REFERENCE TO RELATED APPLICATIONS

This application is a divisional of U.S. patent application Ser. No. 11/012,546, filed Dec. 14, 2004, now U.S. Pat. No. 7,267,965, which application is a continuation of International Patent Application No. PCT/NL03/00410, filed May 30, 2003, published in English as International Patent Publication No. WO 03/106674 on Dec. 24, 2003, which claims the benefit under 35 U.S.C. §119 of European Patent Application No. EP 02077344.6, filed Jun. 14, 2002, the entirety of each of which are hereby incorporated by reference.

STATEMENT ACCORDING TO 37 C.F.R §1.52(e)(5)—SEQUENCE LISTING SUBMITTED ON COMPACT DISC

Pursuant to 37 C.F.R. §1.52(e)(1)(iii), a compact disc containing an electronic version of the Sequence Listing has been submitted concomitant with this application, the contents of which are hereby incorporated by reference. The compact disc contains the file "P60555PC00 final.txt" which is 496 KB, and created on Dec. 14, 2004. A second compact disk is submitted and is an identical copy of the first compact disc (labeled, "copy 1" and "copy 2," respectively).

TECHNICAL FIELD

The invention relates to the fields of medicine and cellular biology. More specifically, the invention relates to means and methods for regulating gene expression, and production of proteinaceous molecules.

BACKGROUND OF THE INVENTION

Polypeptide production at industrial scale currently provides many biologically active polypeptides for a variety of uses, including diagnostic and therapeutic pharmaceuticals, industrial catalysts and nourishment. Polypeptides are produced in a variety of host systems, including transgenic animals and plants, microbes, and cultured mammalian cells. In most cases, the host system is modified by recombinant DNA techniques, for instance resulting in introduction into the host cell of a transgene which encodes a polypeptide of interest. Such a transgene typically includes elements that influence the transcription, translation, and/or processing of the transgene's polypeptide coding sequence. A recombinant host is then identified and isolated which has a suitable yield of a polypeptide of interest, and the cell population of this recombinant host is increased to an extent that it can produce the required amount of polypeptide.

The choice of the host system depends on a number of factors including: (1) the nature and intended use of a polypeptide, and (2) the cost of production. For production of biopharmaceuticals, e.g., therapeutic proteins such as hormones, cytokines, and antibodies, the host system of choice is usually cultured mammalian cells. Considerations with respect to product use and production cost with host cells will be discussed below.

(1) For in vivo therapeutic use, a therapeutic protein must not only have the correct biological activity to alter the course of a disease. It must also do no harm. Most therapeutic proteins are exported from the cell by the secretory pathway. Secreted proteins are modified by a series of post-translational events, including glycosylation, disulfide bond formation, and proteolytic processing. The post-translational modification systems vary among different species and cell types in their detailed mechanisms of action. As a result, the same polypeptide chain can be detectably different when it is produced in different host cells. These differences can be analytical, such as differences in physical properties such as molecular mass, net electrical charge, carbohydrate composition, or structure. The differences can also be functional, affecting for instance the biological activity of the protein itself (catalytic activity, ligand binding characteristics, etc.), and/or its in vivo properties (immunogenicity, biological half life, biodistribution, etc.). Functional differences can, therefore, affect both function and possible side effect(s) of a therapeutic protein. Host cell lines that produce proteins with low efficacy are not suitable for commercial exploitation. Furthermore, host cells which produce modified protein that involves significant side effects in a patient should not be used. These factors are becoming increasingly important considerations during selection of a host cell line for production of a therapeutic protein.

(2) Therapeutic protein production in host cells is an intrinsically costly process. Current methods for industrial production of such proteins often perform poorly, resulting in products that are prohibitively expensive. Poor performance can be due to limitations of protein expression systems and host cell lines currently in use. These limitations mostly have a few specific causes, including (a) failure to identify and isolate recombinant host cell lines that have suitable productivity of proteins (poor predictability), (b) silencing, during the industrial production cycle, of the transgenes that encode proteins (poor stability), and (c) low or incorrect post-translational processing and secretory capacity of the host cell line. These limitations will be considered separately below.

(a) Conventional methods furnish only low frequencies of recombinant host cells that have suitable yields of proteins. Identifying and isolating these rare recombinant cell lines is a laborious and expensive process. The poor predictability of conventional methods means that often a recombinant host cell line is selected for production that has sub-optimal productivity characteristics, simply because a superior recombinant cell line was not identified and isolated during the selection process.

(b) Transgenes are often subject to silencing during cultivation of recombinant host cells. Silencing acts by suppressing transcription of a transgene. Detailed mechanisms of silencing are still not known, and different conventional methods are prone to different kinds of silencing phenomena. With one phenomenon, an individual transgene is silenced by formation of transcriptionally refractory heterochromatin at the transgenic locus. Heterochromatin formation is influenced by the position of genomic integration of a transgene ("position effects" (Boivin and Dura, 1998)). Transgene integration occurs more or less at random. Since most of the genome is heterochromatin, most transgene loci are prone to silencing due to position effects.

A second transgene-silencing phenomenon can occur when two or more copies of a transgene are integrated into a genome during construction of a recombinant cell line. Formation of tandem transgene repeats often occurs during the initial integration step. Furthermore, in order to increase product yield, many recombinant host cell lines are engineered after the integration step to amplify the copy number of a transgene, which also results in tandem transgene repeats (Kaufman, 1990). Tandem repeats and other configurations of multiple transgene copies are particularly prone to silencing ("repeat-induced gene silencing" (Garrick et al., 1998)).

In case that a genome contains multiple copies of a transgene, the yield can also decline via another phenomenon than transcriptional silencing. The number of copies of the transgene can decline during cultivation of a recombinant host cell line. The productivity of such cell lines at the time of selection for use is correlated with a transgene copy number, and consequently as copies of a transgene are lost, the yield declines (Kaufman, 1990).

(c) Different cell types in a mammalian organism have different capacities for post-translational modification and secretion of proteins. The functions of some cell types include production of large quantities of secreted proteins; examples include lymphocytes (producing immunoglobulins), hepatocytes (producing serum proteins), and fibroblasts (producing extracellular matrix proteins). These cell types are favorable sources for deriving host cell lines for production of secreted heterologous proteins. More favorable is the use of a cell line whose progenitor organismal cell type secretes a protein or class of proteins of interest. For example, it is particularly favorable to express recombinant monoclonal antibodies in lymphocytes (or host cells derived from lymphocytes), erythropoietin in hepatocytes (or host cells derived from hepatocytes), and blood clotting factors (e.g., Factor VIII and van Willebrand's factor) in endothelial cells (or host cells derived from endothelial cells).

The use of specific cell types (or cell lines derived therefrom) for production of their affiliated proteins is favorable because such specific cell types will carry out proper post-translational modifications of produced proteins. However, specific cell types often do not have high secretory capacities. For example, cells of the central nervous system, such as neurons, have low intrinsic protein secretion capacities. These cells do secrete proteins, however, including neurotrophins. Neurotrophins regulate the fate and shape of neuronal cells during fetal and juvenile development. Moreover, they influence patterns of neuronal degeneration and regeneration in adults (Bibel and Barde, 2000). Production of neurotrophins for therapeutic applications has considerable biopharmaceutical value (e.g., Axokine™, recombinant ciliary neurotrophic factor from Regeneron). In order to produce heterologous neurotrophins with post-translational modifications (and hence functional properties) that match the naturally-occurring proteins, expression in host cells derived from the central nervous system is favorable. However, production of polypeptides such as neurotrophins in host cell lines such as those derived from neural tissue is inefficient using conventional methods. The predictability of identifying high-expressor isolates from these types of cell lines is often poor; the yield of proteins from such cell lines is generally low, and production levels are characteristically unstable.

Another drawback to a use of specific host cells for production of affiliated proteins is that it is usually difficult to isolate cell lines with favorable biotechnological characteristics. These characteristics for instance include the mode and rate of growth, and the ease of introduction of a transgene. Consequently, various general host cell lines have been established. Examples of these include CHO cells from Chinese hamster ovary (ATCC (American Type Culture Collection) CCL-61), BHK cells from baby hamster kidney (ATCC CCL-10), and Vero cells from African green monkey kidney (ATCC CCL-81). These "general purpose" host cell lines are widely used for production of a number of heterologous proteins. A disadvantage of general purpose cell lines is that the post-translational modifications of heterologous proteins produced by them often differ from the post-translational modifications of the naturally occurring proteins. These differences can have functional consequences resulting in side effects, as discussed above.

Table 1 lists a number of proteins that are currently in use or under development for biopharmaceutical applications. It also lists the tissue or cell type in which each protein is normally produced in the human body. These 24 proteins (or protein classes) come from a wide range of cells and tissue, ranging from highly secretory cells (hepatocytes, endothelial cells) to cells with low secretory capacity (e.g., neural tissue). Currently, neither general-purpose host cells nor specific host cells have qualities that enable optimal expression of the broad spectrum of biopharmaceutically important secreted proteins.

Hence, protein production by conventional host cell lines involves a lot of disadvantages and complications, for instance with respect to yield and post-translational modifications. There is a need in the art for improved protein production in recombinant host cell lines.

SUMMARY OF THE INVENTION

The present invention provides a method for producing a proteinaceous molecule in a cell comprising selecting a cell for its suitability for producing the proteinaceous molecule, providing a nucleic acid encoding the proteinaceous molecule with a nucleic acid comprising a STAR (STabilizing Anti-Repression) sequence, expressing the resulting nucleic acid in the cell and collecting the proteinaceous molecule.

The STAR sequence has to be operably linked to the nucleic acid encoding the proteinaceous molecule in order to be effective. In one embodiment of the invention, one STAR element is used. Preferably however, more than one STAR element is used. In a particularly preferred embodiment, the nucleic acid encoding the proteinaceous molecule is provided with two STAR sequences; one STAR sequence at the 5' side of the coding sequence of the nucleic acid and one STAR sequence at the 3' side of the coding sequence of the nucleic acid.

Description of STAR Elements

New transcription regulatory elements were disclosed by the present inventors, which are named STAR sequences (See EP 01202581.3). STAR sequences are nucleic acid sequences that comprise a capacity to influence transcription of genes in cis. Typically, although not necessarily, the STAR sequences do not code by themselves for a functional protein.

A STAR sequence has a gene transcription modulating quality in at least one type of cell. A STAR sequence is capable of enhancing gene transcription resulting in a higher yield, increasing the proportion of transgene-comprising host cells with acceptable expression levels, and/or increasing stability of transgenes in recombinant cell lines.

In EP 01202581.3 a method of detecting, and optionally selecting, a STAR sequence is provided, comprising providing a transcription system with a variety of a fragment-comprising vectors, the vectors comprising i) an element with a gene-transcription repressing quality, and ii) a promoter directing transcription of a reporter gene, the method further comprising performing a selection step in the transcription system in order to identify the STAR sequence. In a preferred embodiment, the fragments are located between i) the element with a gene-transcription repressing quality, and ii) the promoter directing transcription of the reporter gene. RNA polymerase initiates the transcription process after binding to a specific sequence, called the promoter, that signals where RNA synthesis should begin. A STAR sequence can enhance transcription from the promoter in cis, in a given cell type and/or a given promoter.

Methods disclosed in EP 01202581.3 have been used to isolate STAR elements from the human genome. Isolated human STAR elements have been placed in DNA vectors so as to flank transgene expression units, and the vectors have subsequently been integrated into host cell genomes. Transgene expression in these recombinant host cells has been compared to expression in similar host cells in which the expression units are not flanked by STAR elements. The results show that STAR elements have at least one of three consequences for production of (heterologous) proteinaceous molecule (also referred to as (heterologous) protein): (1) they increase the predictability of identifying host cell lines that express a proteinaceous molecule at industrially acceptable levels; (2) they result in host cell lines with increased protein yields; and/or (3) they result in host cell lines that exhibit more stable protein production during prolonged cultivation. Each of these attributes is discussed in more detail below:

(1) Increased predictability: Integration of transgene expression units can occur at random positions throughout the host cell genome. However, much of the genome is transcriptionally silent heterochromatin. When the expression units include STAR elements flanking the transgene, the position of integration has a reduced effect on expression. The STAR elements impair the ability of adjacent heterochromatin to silence the transgene. Consequently, the proportion of transgene-containing host cells with acceptable expression levels is increased.

(2) Yield: The levels of protein expression in primary populations of recombinant host cells, directly after transgene integration, have been surveyed. The expression level of individuals in the populations varies. However, when the transgenes are protected by STAR elements, the variability is reduced. This reduced variability is most conspicuous in that fewer clones are recovered that have low levels of expression. Furthermore, the populations with STAR elements commonly have individuals with strikingly high expression. These high-yielding individuals are favorable for production of proteinaceous molecules.

(3) Increased stability: STAR elements increase the stability of transgenes in recombinant host cell lines by ensuring that the transgenes are not transcriptionally silenced during prolonged cultivation. Comparative trials show that, under conditions in which transgenes that are not protected by STAR elements are progressively silenced (5 to 25 passages in cultivation), STAR element-protected transgenes continue to be expressed at high levels. This is an advantage during industrial production of proteinaceous molecules, during which cell cultivation continues for prolonged periods, from a few weeks to many months.

Hence, a STAR sequence can enhance expression of a heterologous proteinaceous molecule. In addition, a STAR sequence can enhance expression of a naturally produced proteinaceous molecule.

Transcription can be influenced through a direct effect of the STAR sequence (or the protein(s) binding to it) on the transcription of a particular promoter. Transcription can however, also be influenced by an indirect effect, for instance because the STAR sequence affects the function of one or more other regulatory elements. A STAR sequence can also comprise a stable gene transcription quality. Frequently, expression levels drop dramatically with increasing numbers of cell divisions. With the methods disclosed in EP 01202581.3 it is possible to detect and optionally select a DNA sequence that is capable of at least in part preventing the dramatic drop in transcription levels with increasing numbers of cell divisions. Strikingly, fragments comprising a STAR sequence can be detected and optionally selected with a method EP 01202581.3, in spite of the fact that the method does not necessarily measure long term stability of transcription.

A STAR sequence is suitable for enhancing the level of transcription of a gene of interest in a host cell. If, together with a gene of interest, a STAR sequence is also introduced into host cells, more clones can be detected that express more than a certain amount of the gene of interest. As used herein, such host cells are termed "host cells with acceptable expression levels."

Furthermore, if, together with a gene of interest, a STAR sequence is also introduced into host cells, a higher yield of produced proteinaceous molecules can be obtained, while gene expression level is also more stable than in the absence of such STAR sequences. Preferably, a STAR sequence derived from a plant and/or vertebrate is used. More preferably a human STAR sequence is used.

Sequences comprising a STAR sequence can be found by using a functional assay, as described above. However, once a collection of such sequences has been identified, bioinformatics can be used to find other STAR sequences. Several methods are available in the art to extract sequence identifiers from a family of DNA sequences sharing a certain common feature. Such sequence identifiers can subsequently be used to identify sequences that share one or more identifiers. Sequences sharing such one or more identifiers are likely to be a member of the same family of sequences, i.e., are likely to share the common feature of the family. By the present inventors a large number of sequences comprising STAR activity (so-called STAR sequences) were used to obtain sequence identifiers (patterns) which are characteristic for sequences comprising STAR activity. These patterns can be used to determine whether a test sequence is likely to contain STAR activity. A method for detecting the presence of a STAR sequence within a nucleic acid sequence of about 50-5000 base pairs is thus provided, comprising determining the frequency of occurrence in the sequence of at least one sequence pattern and determining that the frequency of occurrence is representative of the frequency of occurrence of at least one sequence pattern in at least one sequence comprising a STAR sequence. In principle any method is suited for determining whether a sequence pattern is representative of a STAR sequence. Many different methods are available in the art. Preferably, the step of determining that the occurrence is representative of the frequency of occurrence of at least one sequence pattern in at least one sequence comprising a STAR sequence comprises, determining that the frequency of occurrence of at least one sequence pattern significantly differs between at least one STAR sequence and at least one control sequence. In principle any significant difference is discriminative for the presence of a STAR sequence. However, in a particularly preferred embodiment, the frequency of occurrence of at least one sequence pattern is significantly higher in at least one sequence comprising a STAR sequence compared to at least one control sequence.

A considerable number of sequences comprising a STAR sequence have been identified by the present inventors. It is possible to use these sequences to test how efficient a pattern is in discriminating between a control sequence and a sequence comprising a STAR sequence. Using so-called discriminant analysis it is possible to determine on the basis of any set of STAR sequences in a species, the most optimal discriminative sequence patterns or combination thereof.

Thus, preferably, at least one of the patterns is selected on the basis of optimal discrimination between at least one sequence comprising a STAR sequence and a control sequence.

In a preferred embodiment, the frequency of occurrence of a sequence pattern in a test nucleic acid is compared with the frequency of occurrence in a sequence known to contain a STAR sequence. In this case, a pattern is considered representative for a sequence comprising a STAR sequence if the frequencies of occurrence are similar. In a preferred embodiment, another criterion is used. The frequency of occurrence of a pattern in a sequence comprising a STAR sequence is compared to the frequency of occurrence of the pattern in a control sequence. By comparing the two frequencies it is possible to determine for each pattern thus analyzed, whether the frequency in the sequence comprising the STAR sequence is significantly different from the frequency in the control sequence. In this embodiment, a sequence pattern is considered to be representative of a sequence comprising a STAR sequence, if the frequency of occurrence of the pattern in at least one sequence comprising a STAR sequence is significantly different from the frequency of occurrence of the same pattern in a control sequence. By using larger numbers of sequences comprising a STAR sequence the number of patterns for which a statistical difference can be established increases, thus enlarging the number of patterns for which the frequency of occurrence is representative for a sequence comprising a STAR sequence. Preferably, the frequency of occurrence is representative of the frequency of occurrence of at least one sequence pattern in at least two sequences comprising a STAR sequence; more preferably, in at least five sequences comprising a STAR sequence; and, even more preferably, in at least ten sequences comprising a STAR sequence. More preferably, the frequency of occurrence is representative of the frequency of occurrence of at least one sequence pattern in at least 20 sequences comprising a STAR sequence. In a particularly preferred embodiment, the frequency of occurrence is representative of the frequency of occurrence of at least one sequence pattern in at least 50 sequences comprising a STAR.

The patterns that are indicative for a sequence comprising a STAR sequence are also dependent on the type of control nucleic acid used. The type of control sequence used is preferably selected on the basis of the sequence in which the presence of a STAR sequence is to be detected. In a preferred embodiment, the control sequence comprises a random sequence comprising a similar AT/CG content as at least one sequence comprising a STAR sequence. In another preferred embodiment, the control sequence is derived from the same species as the sequence comprising the STAR sequence. For instance, if a test sequence is scrutinized for the presence of a STAR sequence, active in a plant cell, then preferably the control sequence is also derived from a plant cell. Similarly, for testing for STAR activity in a human cell, the control nucleic acid is preferably also derived from a human genome. In a preferred embodiment, the control sequence comprises between 50% and 150% of the bases of at least one sequence comprising a STAR sequence. In a particularly preferred embodiment, the control sequence comprises between 90% and 110% of the bases of at least one sequence comprising a STAR sequence. More preferably, between 95% and 105%.

A pattern can comprise any number of bases larger than two. Preferably, at least one sequence pattern comprises at least five, more preferably at least six, bases. In another embodiment, at least one sequence pattern comprises at least eight bases. In a preferred embodiment, the at least one sequence pattern comprises a pattern listed in Table 6 and/or Table 7. A pattern may consist of a consecutive list of bases.

However, the pattern may also comprise bases that are interrupted one or more times by a number of bases that are not or only partly discriminative. A partly discriminative base is, for instance, indicated as a purine.

Preferably, the presence of STAR activity is verified using a functional assay. Several methods are presented herein to determine whether a sequence comprises STAR activity. STAR activity is confirmed if the sequence is capable of performing at least one of the following functions: (i) at least in part inhibiting the effect of sequence comprising a gene transcription repressing element of the invention, (ii) at least in part blocking chromatin-associated repression, (iii) at least in part blocking activity of an enhancer, (iv) conferring upon an operably linked nucleic acid encoding a transcription unit compared to the same nucleic acid alone, (iv-a) a higher predictability of transcription, (iv-b) a higher transcription, and/or (iv-c) a higher stability of transcription over time.

The large number of sequences comprising STAR activity identified by the present inventors open up a wide variety of possibilities to generate and identify sequences comprising the same activity in kind not necessarily in amount. For instance, it is well within the reach of a skilled person to alter the sequences identified in the present invention and test the altered sequence for STAR activity. Such altered sequences are, therefore, also part of the present invention. Alteration can include deletion, insertion and mutation of one or more bases in the sequences.

Sequences comprising STAR activity were identified in stretches of 400 bases. However, it is expected that not all of these 400 bases are required to retain STAR activity. Methods to delimit the sequences that confer a certain property to a fragment of between 400 and 5000 bases are well known. The minimal sequence length of a fragment comprising STAR activity is estimated to be about 50 bases.

Table 6 (SEQ ID NOS:177-342) and Table 7 (SEQ ID NOS:343-1072) list patterns of six bases that have been found to be over represented in nucleic acid molecules comprising STAR activity. This over representation is considered to be representative for a STAR sequence. The tables were generated for a family of 65 STAR sequences (SEQ ID NOS:1-65). Similar tables can be generated starting from a different set of STAR sequences, or from a smaller or larger set of STAR sequences. A pattern is representative for a STAR sequence if it is over represented in the STAR sequence compared to a sequence not comprising a STAR element. This can be a random sequence. However, to exclude a non relevant bias, the sequence comprising a STAR sequence is preferably compared to a genome or a significant part thereof. Preferably, a genome of a vertebrate or plant, more preferably, a human genome. A significant part of a genome is, for instance, a chromosome. Preferably the sequence comprising a STAR sequence and the control sequence are derived from nucleic acid of the same species.

The more STAR sequences are used for the determination of the frequency of occurrence of sequence patterns, the more representative for STARs the patterns are that are over- or under-represented. Considering that many of the functional features that can be expressed by nucleic acids are mediated by proteinaceous molecules binding to them, it is preferred that the representative pattern is over-represented in the STAR sequences. Such over-represented pattern can be part of a binding site for such a proteinaceous molecule. Preferably, the frequency of occurrence is representative of the frequency of occurrence of at least one sequence pattern in at least two sequences comprising a STAR sequence; more preferably, in at least five sequences comprising a STAR sequence; and, even more preferably, in at least ten sequences comprising a STAR sequence. More preferably, the frequency of occurrence is representative of the frequency of occurrence of at least one sequence pattern in at least 20 sequences comprising a STAR sequence. In a particularly preferred embodiment, the frequency of occurrence is representative of the frequency of occurrence of at least one sequence pattern in at least 50 sequences comprising a STAR. Preferably, the sequences comprising a STAR sequence comprises at least one of the sequences depicted in the sequences comprising STAR1-STAR65 (SEQ ID NOS:1-65), sequences comprising STAR66 and testing set (SEQ ID NOS: 66-84), and sequences comprising *Arabidopsis* STAR A1-A35 (SEQ ID NOS:85-119) (hereinafter SEQ ID NOS: 1-119).

STAR activity is a feature shared by the sequences listed in SEQ ID NOS:1-119. However, this does not mean that they must all share the same identifier sequence. It is very well possible that different identifiers exist. Identifiers may confer this common feature onto a fragment containing it, though this is not necessarily so.

By using more sequences comprising STAR activity for determining the frequency of occurrence of a sequence pattern or patterns, it is possible to select patterns that are more often than others present or absent in such a STAR sequence. In this way it is possible to find patterns that are very frequently over- or under-represented in STAR sequences. Frequently, over- or under-represented patterns are more likely to identify candidate STAR sequences in test sets. Another way of using a set of over- or under-represented patterns is to determine which pattern or combination of patterns is best suited to identify a STAR in a sequence. Using so-called discriminative statistics, we have identified a set of patterns that performs best in identifying a sequence comprising a STAR element. In a preferred embodiment, at least one of the sequence patterns for detecting a STAR sequence comprises a sequence pattern GGACCC (SEQ ID NO:464), CCCTGC (SEQ ID NO:816), AAGCCC (SEQ ID NO:270), CCCCCA (SEQ ID NO:298) and/or AGCACC (SEQ ID NO:336). In another embodiment, at least one of the sequence patterns for detecting a STAR sequence comprises a sequence pattern CCCN{16}AGC (SEQ ID NO:415), GGCN{9}GAC (SEQ ID NO:536), CACN{13}AGG (SEQ ID NO:761), and/or CTGN{4}GCC (SEQ ID NO:839).

A list of STAR sequences can also be used to determine one or more consensus sequences therein. The invention, therefore, also provides a consensus sequence for a STAR element. This consensus sequence can of course be used to identify candidate STAR elements in a test sequence.

Moreover, once a sequence comprising a STAR element has been identified in a vertebrate it can be used by means of sequence homology to identify sequences comprising a STAR element in other species belonging to vertebrate. Preferably a mammalian STAR sequence is used to screen for STAR sequences in other mammalian species. Similarly, once a STAR sequence has been identified in a plant species, it can be used to screen for homologous sequences with similar function in other plant species. The invention in one aspect provides a STAR sequence obtainable by a method according to the invention. Further provided is a collection of STAR sequences. Preferably, the STAR sequence is a vertebrate or plant STAR sequence. More preferably, the STAR sequence is a mammalian STAR sequence or an angiosperm (monocot, such as rice or dicot, such as *Arabidopsis*). More preferably, the STAR sequence is a primate and/or human STAR sequence.

A list of sequences comprising STAR activity can be used to determine whether a test sequence comprises a STAR element. There are, as mentioned above, many different methods for using such a list for this purpose. In a preferred embodiment, the invention provides a method for determining whether a nucleic acid sequence of about 50-5000 base pairs comprises a STAR sequence, the method comprising: generating a first table of sequence patterns comprising the frequency of occurrence of the patterns in a collection of STAR sequences of the invention; generating a second table of the patterns comprising the frequency of occurrence of the patterns in at least one reference sequence; selecting at least one pattern of which the frequency of occurrence differs between the two tables; determining, within the nucleic acid sequence of about 50-5000 base pairs, the frequency of occurrence of at least one of the selected patterns; and determining whether the occurrence in the test nucleic acid is representative of the occurrence of the selected pattern in the collection of STAR sequences. Alternatively, determining comprises determining whether the frequency of occurrence in the test nucleic acid is representative of the frequency occurrence of the selected pattern in the collection of STAR sequences. Preferably, the method further comprises determining whether the candidate STAR comprises a gene transcription modulating quality using a method of the invention. Preferably, the collection of STARS comprises sequence as depicted in SEQ ID NOS:1-119. In another aspect, the invention provides an isolated and/or recombinant nucleic acid sequence comprising a STAR sequence obtainable by a method of the invention.

As mentioned above, a STAR sequence can exert its activity in a directional way, i.e., more to one side of the fragment containing it than to the other. Moreover, STAR activity can be amplified in amount by multiplying the number of STAR elements. The latter suggests that a STAR element may comprise one or more elements comprising STAR activity. Another way of identifying a sequence capable of conferring STAR activity on a fragment containing it comprises selecting from a vertebrate or plant sequence, a sequence comprising STAR activity and identifying whether the selected sequence and sequences flanking the selected sequence are conserved in another species. Such conserved flanking sequences are likely to be functional sequences. In one aspect, the invention, therefore, provides a method for identifying a sequence comprising a STAR element comprising selecting a sequence of about 50 to 5000 base pairs from a vertebrate or plant species comprising a STAR element and identifying whether sequences flanking the selected sequence in the species are conserved in at least one other species. The invention, therefore, further provides a method for detecting the presence of a STAR sequence within a nucleic acid sequence of about 50-5000 base pairs, comprising identifying a sequence comprising a STAR sequence in a part of a chromosome of a cell of a species and detecting significant homology between the sequence and a sequence of a chromosome of a different species. Preferably, the species comprises a plant or vertebrate species, ideally a mammalian species. The invention also provides a method for detecting the presence of a STAR element within a nucleic acid sequence of about 50-5000 base pairs of a vertebrate or plant species, comprising identifying whether a flanking sequence of the nucleic acid sequence is conserved in at least one other species.

It is important to note that methods of the invention for detecting the presence of a sequence comprising a STAR sequence using bioinformatical information are iterative in nature. The more sequences comprising a STAR sequence are identified with a method of the invention, the more patterns are found to be discriminative between a sequence comprising a STAR sequence and a control sequence. Using these newly found discriminative patterns, more sequences comprising a STAR sequence can be identified, which, in turn, enlarges the set of patterns that can discriminate and so on. This iterative aspect is an important aspect of methods provided in the present invention.

BRIEF DESCRIPTION OF THE DRAWINGS

FIG. 9 is a schematic diagram of the orientation of STAR elements as they are cloned in the pSelect vector (panel A), as they are cloned into pSDH vectors to preserve their native orientation (panel B), and as they are cloned into pSDH vector in the opposite orientation (panel C).

FIG. 20 is a schematic diagram and graph illustrating that STAR elements improve GFP expression in CHO cells. The ppGIZ and ppGIZ-STAR7 plasmids used for testing STAR activity are shown. The expression unit comprises (from 5' to 3') a transgene (encoding for the GFP protein), an IRES, and a selectable marker (zeo, conferring zeocin resistance) under control of the CMV promoter. The expression unit has the SV40 transcriptional terminator at its 3' end (t). The entire cassette with the expression unit is either flanked by STAR7 (SEQ ID NO:7) elements (STAR7-shielded) or not (Control). The constructs are transfected to CHO-K1 cells. Stable colonies are expanded and the GFP signal is determined on a XL-MCL Beckman Coulter flow cytometer. For each independent colony the mean of the GFP signal is plotted. This is taken as measure for the level of GFP expression. The results in FIG. 20 show that in CHO cells the STAR7-shielded construct confers greater predictability and elevated GFP expression relative to the ppGIZ control construct alone.

FIG. 21 is a schematic diagram and graph showing that STAR elements improve GFP expression in NSO cells. The ppGIZ and ppGIZ-STAR7 plasmids used for testing STAR activity are shown as in FIG. 20. The constructs are transfected to NSO cells. Stable colonies are expanded and the GFP signal is determined on a XL-MCL Beckman Coulter flow cytometer. For each independent colony the mean of the GFP signal is plotted. This is taken as measure for the level of GFP expression. The results in FIG. 21 show that in NSO cells the STAR7-shielded (SEQ ID NO:7) construct confers greater predictability and elevated GFP expression relative to the ppGIZ control construct alone.

FIG. 22 is a schematic diagram and graph depicting that STAR elements improve GFP expression in 293 cells. The ppGIZ and ppGIZ-STAR7 plasmids used for testing STAR activity are shown as in FIG. 20. The constructs are transfected to 293 cells. Stable colonies are expanded and the GFP signal is determined on a XL-MCL Beckman Coulter flow cytometer. For each independent colony, the mean of the GFP signal is plotted. This is taken as measure for the level of GFP expression. The results in FIG. 22 show that in 293 cells the STAR7-shielded (SEQ ID NO:7) construct confers greater predictability and elevated GFP expression relative to the ppGIZ control construct alone.

DETAILED DESCRIPTION OF THE INVENTION

Definitions

Quality

Figure 1:
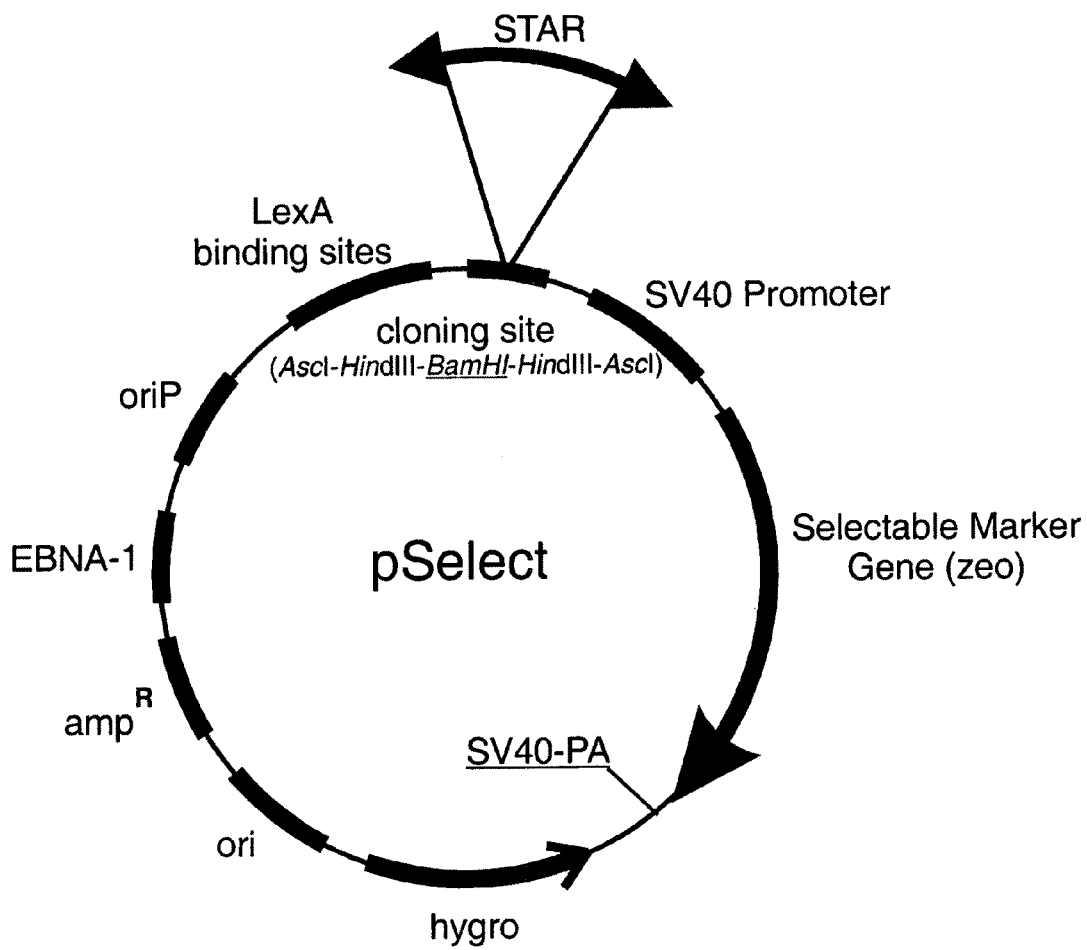
FIG. 1 is a diagram illustrating the pSelect plasmid used for isolating STAR elements. The zeocin resistance gene is under control of the SV40 promoter, and is upstream of the SV40 polyadenylation site. Upstream of the SV40 promoter is a tandem array of lexA operator sites. Between the lexA operators and the SV40 promoter is a cloning site; test DNAs (e.g., size-fractionated genomic DNA) are cloned into the BamHI site. The plasmid also has the hygromycin resistance gene (hygro) for selection of transformed cells, the EBNA-1 and oriP sequences for plasmid replication in mammalian cells, and the ampicillin resistance gene (ampR) and ori sequence for propagation in *Escherichia coli*.

The term "quality" in relation to a sequence refers to an activity of the sequence.

STAR and STAR Sequence

The terms "STAR," "STAR sequence" or "STAR element," as used herein, refer to a DNA sequence comprising one or more of the mentioned gene transcription modulating qualities.

DNA Sequence

The term "DNA sequence" as used herein, unless otherwise specified, does not refer to a listing of specific ordering of bases, but rather to a physical piece of DNA. A transcription quality with reference to a DNA sequence refers to an effect that the DNA sequence has on transcription of a gene of interest. "Quality" as used herein refers to detectable properties or attributes of a nucleic acid or protein in a transcription system.

Proteinaceous Molecule

By a "proteinaceous molecule" is meant herein a molecule comprising amino acids. At least a part of the amino acids are bound to each other to form a peptide. Preferably, the proteinaceous molecule comprises a polypeptide. In this application, the term "proteinaceous molecule" also includes "polypeptide."

Essentially the Same Properties

By "essentially the same properties" is meant that the properties are essentially the same in kind, not necessarily in amount. For instance, if a proteinaceous molecule has essentially the same properties as a pharmaceutically active compound, the proteinaceous molecule also displays such pharmaceutical activity in kind, not necessarily in amount.

Naturally Occurring Proteinaceous Molecule of the Same Kind

By a "naturally occurring proteinaceous molecule of the same kind" is meant a proteinaceous molecule with the same primary structure, which is naturally produced in vivo, not influenced by human interference. Examples comprise an antibody produced in vivo by a lymphocyte and erythropoietin produced in vivo by a hepatocyte.

Host Cell, Host Cell Line

As used herein, the terms "host cell" and "host cell line" refer to a cell and to homogeneous populations thereof that are capable of expressing a nucleic acid encoding a proteinaceous molecule.

Recombinant Host Cell, Recombinant Host Cell Line

The terms "recombinant host cell" and "recombinant host cell line" refer to a host cell and to homogeneous populations thereof into which a nucleic acid has been introduced.

Expression

As used herein, the term "expression" refers to production of a proteinaceous molecule, encoded by a nucleic acid. The production, for instance, involves transcription of a DNA sequence, translation of the corresponding mRNA sequence, and/or posttranslational modification. In case of secreted proteins, it can also refer to the processes of transcription, translation, and/or post-translational modification (e.g., glycosylation, disulfide bond formation, etc.), followed by exocytosis. In the case of multimeric proteins, it can include assembly of the multimeric structure from the polypeptide monomers.

Silencing

The term "silencing" refers to diminution of a level of expression of a gene or genes, including transgenes, typically over time. The expression level can be diminished but still detectable, or diminished below the threshold of detection.

Enhanced Expression

As used herein, "enhanced expression" of a gene encoding a proteinaceous molecule, or enhanced production of a proteinaceous molecule, can either involve a higher yield of the proteinaceous molecule, a higher proportion of host cells with acceptable expression levels, and/or a higher stability of a gene expression level.

Affiliated Proteinaceous Molecule of a Cell

By an "affiliated proteinaceous molecule of a cell" is meant a proteinaceous molecule which is naturally produced by the kind of cell in the organism from which the cell is derived.

For instance, erythropoietin is an affiliated proteinaceous molecule of a hepatocyte, or of a hepatocyte-derived cell line. Likewise, an antibody is an affiliated proteinaceous molecule of a lymphocyte, or of a lymphocyte-derived cell line, typically of a B-cell or a B-cell derived cell line.

Specific Host Cell Line

A "specific host cell line" is a host cell line derived from a cell which normally expresses a particular proteinaceous molecule (or class of proteinaceous molecules) in the organism from which the cell is derived.

Heterologous STAR Sequence

The term "heterologous STAR sequence" is herein used to define a STAR sequence that is, for example, obtained from a different cell type (from the same species or organism) or is obtained from a different species or organism (either from the same cell type or a different cell type) compared to the cell in which it is used.

Stable

"Stable" means that the observed transcription level is not significantly changed over at least 30 cell divisions. A stable quality is useful in situations wherein expression characteristics should be predictable over many cell divisions. Typical examples are cell lines transfected with foreign genes. Other examples are transgenic animals and plants and gene therapies. Very often, introduced expression cassettes function differently after increasing numbers of cell divisions or plant or animal generations. A stable quality preferably comprises a capacity to maintain gene transcription in subsequent generations of a transgenic plant or animal. Of course, in the case where expression is inducible, the quality comprises the quality to maintain inducibility of expression in subsequent generations of a transgenic plant or animal.

Acceptable Expression Level

An "acceptable expression level" means an acceptable expression level for commercial exploitation. Whether or not a certain expression level is acceptable for commercial exploitation often depends on the kind of proteinaceous molecule that is produced. Acceptable expression levels of different kinds of proteinaceous molecules often involve different amounts of produced proteinaceous molecule.

A STAR sequence, a collection of STAR sequences, and/or a nucleic acid comprising a STAR sequence obtainable by a method of the invention, is of course suitable for use in a method of the invention for producing a proteinaceous molecule in a cell. In one aspect, the invention, therefore, provides a method for producing a proteinaceous molecule in a cell comprising selecting a cell for its suitability for producing the proteinaceous molecule, providing a nucleic acid encoding the proteinaceous molecule with a nucleic acid comprising a STAR sequence, expressing the resulting nucleic acid in the cell and collecting the proteinaceous molecule, wherein the nucleic acid comprising a STAR sequence is obtainable by a method of the invention for identifying and obtaining a nucleic acid comprising a STAR sequence. The nucleic acid comprising a STAR sequence can be identified and obtained using at least one pattern that is representative for sequences comprising STAR activity. Preferably, the nucleic acid comprising a STAR sequence is identified and obtained using at least one pattern as depicted in Table 6 (SEQ ID NOS:177-342) or Table 7 (SEQ ID NOS:343-1072).

A cell can be selected for its suitability for producing a proteinaceous molecule in many different ways. For instance, it can be determined whether the cell is competent of nucleic acid uptake. A nucleic acid encoding a proteinaceous molecule is preferably easily introduced into the cell. Furthermore it can be determined whether the cell secretes produced proteinaceous molecule. Secreted proteinaceous molecule can usually be easily collected. Collecting proteinaceous molecules that are not secreted usually involves sacrificing at least part of a culture. This implicates separating a proteinaceous molecule of interest from other cell components, optionally starting up a new culture, etc. This is more cumbersome. Hence, in a preferred embodiment, a method of the invention is provided wherein the proteinaceous molecule is secreted by the cell.

In another preferred embodiment, a method of the invention is provided wherein the cell is selected for its capability of post-translationally modifying the proteinaceous molecule, such that the proteinaceous molecule has essentially the same properties as a naturally occurring proteinaceous molecule of the same kind. As has been explained above, different kinds of cells display different post-translational modifications. As a result, the same proteinaceous molecule can be modified differently when produced in different host cells. These differences can affect the properties of such proteinaceous molecules, such as for instance pharmaceutical properties. It is, therefore, highly preferred to select a cell which produces a proteinaceous molecule with essentially the same properties as its naturally occurring counterpart. This does not necessarily mean that the host cell has to display exactly the same kind of post-translational modifications, as long as the produced proteinaceous molecule has essentially the same properties. A proteinaceous molecule can be produced that is physically different from its natural counterpart, but which is functionally essentially the same.

In one embodiment, of the invention, however, a cell is selected for its capability of post-translationally modifying the proteinaceous molecule in essentially the same way as the proteinaceous molecule is post-translationally modified in nature.

In one aspect, the invention provides a method of the invention wherein the proteinaceous molecule comprises an affiliated proteinaceous molecule of the cell.

It is especially preferred to choose a host cell, or a cell line derived from a cell, which normally produces a proteinaceous molecule of interest in the organism from which the cell is derived. These cells are capable of carrying out post-translational modifications of their affiliated proteinaceous molecules such that the resulting proteinaceous molecule has the same kind of properties in kind, not necessarily in amount, as a proteinaceous molecule of the same kind which is normally present in the organism. Such specific cells are naturally adapted for production of the affiliated proteinaceous molecule. Apart from other activities of STAR sequences it is also possible to at least partly solve a problem of low production of proteinaceous molecules, which often occurs with such specific cells. Providing at least one STAR sequence to a nucleic acid encoding such proteinaceous molecule will enhance production (yield) of the proteinaceous molecule by the specific cell, increase the proportion of host cells with acceptable expression levels, and/or increase stability of a gene expression level.

In another preferred embodiment, a method of the invention is disclosed wherein the cell is selected for suitable growth in a suspension culture. This facilitates culturing of the cell, and collection of produced proteinaceous molecule, especially when the proteinaceous molecule is secreted into the suspension. More preferably, the cell is selected for suitable growth in a serum-free culture, since serum can contain contaminants and pathogens. Such contaminants/pathogens often have to be separated from produced proteinaceous molecule. This requires an extra step, which consumes time and chemicals, with a potential loss of produced proteinaceous molecule. Moreover, a possibility of a presence of pathogens involves a potential risk for employees. If a pathogen has been present in a culture, a produced proteinaceous molecule is not allowed to be used anymore for commercial and/or medical applications.

In yet another preferred embodiment, the cell is selected for the presence of an adenovirus Early Region 1 (E1) sequence. The presence of an adenoviral E1 sequence enhances protein production in a cell. Hence, an adenoviral E1 sequence is suitable for host cells engineered for protein production.

The invention also provides a method for producing a proteinaceous molecule comprising:
providing a host cell with a nucleic acid comprising a STAR sequence;
selecting a cell with enhanced expression of a proteinaceous molecule; and
collecting the proteinaceous molecule.

In one embodiment, the method is performed with a host cell whose genome has not been modified by human interference. The method then results in enhanced expression of a proteinaceous molecule which is encoded by the genome of the host cell. The proteinaceous molecule may be normally expressed by the host cell in the organism from which the cell is derived, but it may also normally be subject to silencing, resulting in little or no expression in the host cell under normal conditions. Introduction of at least one STAR sequence can at least in part inhibit silencing of a gene of interest induced by gene-transcription repressing chromatin. Expression of a proteinaceous molecule is enhanced by introduction of a STAR sequence.

In another embodiment, the host cell is transfected with a nucleic acid of interest. Such nucleic acid for instance, encodes a heterologous proteinaceous molecule which is not naturally encoded by the genome of the host cell. Introduction of a STAR sequence also enhances expression of such heterologous proteinaceous molecule.

The STAR sequence can be introduced randomly into the genome of the host cell, using methods known in the art (for instance calcium precipitation, transfection with a vector comprising a nucleic acid of interest, use of a gene delivery vehicle, etc). If a STAR sequence is introduced near a nucleic acid sequence encoding a proteinaceous molecule, it is capable of enhancing expression of the proteinaceous molecule. Cells expressing a desired proteinaceous molecule can be isolated from cultures with randomly inserted STAR sequences.

Preferably, the STAR sequence is introduced into the host cell by homologous recombination. A nucleic acid comprising a STAR sequence can be provided with an additional sequence. The additional sequence can be chosen such that it is at least in part homologous to a nucleic acid sequence in the host cell which is known to be present in vicinity of a gene encoding a proteinaceous molecule of interest. If a nucleic acid comprising a STAR sequence and such additional sequence is provided to the host cell, it can be incorporated into the host cell's genome by homologous recombination at the site with the (partly) homologous nucleic acid sequence. As a result, the STAR sequence is introduced in vicinity of the gene encoding the proteinaceous molecule of interest. Expression of the proteinaceous molecule is then enhanced by the introduced STAR sequence.

A preferred embodiment of the present invention provides a method of the invention wherein the STAR sequence comprises a species-specific STAR sequence. More preferably, the STAR sequence comprises a cell type-specific STAR sequence.

Two types of STAR elements have been identified. Promiscuous STAR elements are able to function in more than one host cell line. For example, STAR6 (SEQ ID NO:6) increases the predictability, yield, and stability of a transgene in both the U-2 OS human osteosarcoma cell line and in CHO (Chinese hamster ovary) cells. Other STAR elements are species-specific and/or cell type-specific; for example, STAR8 (SEQ ID NO:8) increases the predictability, yield, and stability of transgenes in U-2 OS cells, but not in CHO cells (see Examples 2 and 3 and FIGS. 3 and 4).

If a certain type of host cell (line) is chosen for expression of a proteinaceous molecule (for instance, because it is known to possess a preferred post-translational modification system) a STAR sequence which is naturally present in the cell can be used in a method of the invention. Such STAR sequence is referred to as a cell type-specific STAR sequence. A STAR sequence which is naturally present in a species from which the cell is derived can also be used. Such STAR sequence is referred to as a species-specific STAR sequence. A species-specific STAR sequence may be naturally present in the cell type, although this is not necessary.

A known species-specific STAR sequence or cell-type specific STAR sequence can be used in a method of the invention. Alternatively, a (previously unknown) species-specific STAR sequence or cell-type specific STAR sequence can be detected and isolated by a method as described by the present inventors (EP 01202581.3). The use of a species-specific STAR sequence or cell type-specific STAR sequence is preferred because such sequence is especially active in the host cell and is adapted to the specific circumstances within the cell. For instance, such cell type-specific STAR sequence may interact with a protein which is not present in some other cell-types. In that case, the cell type-specific STAR sequence will be less capable—if at all—of enhancing expression in cells lacking the protein. A species-specific or cell type-specific STAR element often has functional characteristics that are superior to promiscuous STAR elements. Furthermore, a cell line-specific STAR element can satisfy product safety or ethical considerations for use of the host cell line.

A promiscuous STAR sequence is particularly useful if no tissue specific or cell-type specific STAR sequence is known. In that case a known promiscuous STAR sequence can be used. This saves efforts to detect and isolate a cell-type specific STAR sequence.

Several STAR sequences are listed in SEQ ID NOS:1-119. Hence, in one aspect, a method of the invention is provided wherein the STAR sequence comprises a sequence as depicted in SEQ ID NOS:1-119.

In a preferred embodiment, the invention provides a cell line that comprises at least one heterologous STAR sequence or a functional equivalent and/or a functional fragment thereof. In an even more preferred embodiment, the cell line is a human cell line. The invention provides multiple examples of STAR sequences and also methods of testing STAR sequences and hence, a person skilled in the art is very well capable of obtaining a functional equivalent and/or a functional fragment of a STAR sequence, for example by deletion or mutation. In yet another preferred embodiment, the invention provides a non-human cell line that comprises at least one recombinant STAR sequence derived or obtained from a human cell, i.e., a human STAR sequence. It is clear that the amount of STAR sequences may vary, for example, a cell line according to the invention may comprise two, three, or four, or even more STAR sequences which may either be identical or different from each other.

In one aspect, the invention provides a cell line provided with a nucleic acid comprising a STAR sequence, wherein the cell line is selected for its suitability for producing a proteinaceous molecule. Preferably, a cell line of the invention comprises a vertebrate or plant cell line. A vertebrate cell line is very suitable for producing a human proteinaceous molecule of interest, because vertebrates are phylogenetically close related.

Plant cells are for instance very suitable for vaccine production. Vaccine production in plants can be inexpensive, while the vaccine can be easily delivered to an individual by eating the edible portion of the plant (Mercenier et al., 2001).

A cell line of the invention is particularly suitable for production of a proteinaceous molecule of interest, because the STAR sequence can enhance expression of a gene of interest (higher yield of a proteinaceous molecule, higher proportion of host cells with acceptable expression levels, and/or higher stability of a gene expression level). Methods for generating a cell line are known in the art and many techniques are known to provide a cell with a nucleic acid of interest. Furthermore, many general purpose cell lines are available. Such cell lines can be dedicated to production of a certain proteinaceous molecule using recombinant techniques. Examples of available cell lines include CHO cells from Chinese hamster ovary and BHK cells from baby hamster kidney (as described above).

Another embodiment of the invention provides a cell line provided with a nucleic acid comprising a STAR sequence, wherein the cell line comprises an adenovirus Early Region 1 sequence. As has been described above, an adenoviral E1 sequence enhances cellular protein production. More preferably a cell line of the invention is provided wherein the cell line comprises a U-2 OS osteosarcoma, CHO, 293, HuNS-1 myeloma, WERI-Rb-1 retinoblastoma, BHK, Vero, non-secreting mouse myeloma Sp2/0-Ag 14, non-secreting mouse myeloma NSO, or NCI-H295R adrenal gland carcinoma (ATCC CRL-2128) cell line.

A cell line of the invention is particularly suitable for production of a proteinaceous molecule, because production can be enhanced by one or more STAR sequences (higher yield of a proteinaceous molecule, higher proportion of host cells with acceptable expression levels, and/or higher stability of a gene expression level). A cell line of the invention can comprise promiscuous, species-specific and/or cell type-specific STAR sequences. Furthermore, a cell line of the invention can be used to produce a heterologous proteinaceous molecule, and/or an affiliated proteinaceous molecule.

Hence, a use of a cell line of the invention for the production of a proteinaceous molecule is also herewith provided. Preferably, the proteinaceous molecule comprises an affiliated protein of the cell line.

Of course, a proteinaceous molecule obtainable by a method of the invention is also provided by the present invention.

In one aspect, the invention provides a method for selecting a cell suitable for producing a proteinaceous molecule comprising:
  providing a nucleic acid encoding the proteinaceous molecule with a nucleic acid comprising a STAR sequence;
  expressing the resulting nucleic acid in the cell; and
  determining whether produced proteinaceous molecule has a desired property.

The desired property, for instance, comprises a pharmaceutical property. The property can be influenced by post translational modification(s), a configuration of a produced proteinaceous molecule, etc.

In yet another aspect, the invention provides a method for selecting a cell suitable for producing a proteinaceous molecule comprising:
  providing a host cell with a nucleic acid comprising a STAR sequence;
  selecting a cell with enhanced expression of a proteinaceous molecule; and
  determining whether the proteinaceous molecule has a desired property.

As has been discussed above, the nucleic acid comprising a STAR sequence can be randomly introduced into the genome of the host cell. Preferably, however, the nucleic acid sequence is introduced into the genome of the host cell by homologous recombination.

The invention is further explained in the following examples. The examples do not limit the invention in any way. They merely serve to clarify the invention.

EXAMPLES

Example 1

Method for Isolation of Star Elements from the Human Genome

STAR elements are identified and cloned from human genomic DNA based on their ability to block the spread of transcriptional repression from DNA binding sites for repressor proteins in a test vector, as described in this example. The method described in this example is applicable in principle to any mammalian cell line, for isolation of both promiscuous and cell line-specific STAR elements.

A Method to Isolate Human Star Elements Functional in U-2 Os Cell

Materials and Methods

Plasmids and strains. The selection vector for STAR elements, pSelect-SV40-zeo ("pSelect," FIG. 1) was constructed as follows: the pREP4 vector (Invitrogen V004-50) was used as the plasmid backbone. It provides the Epstein Barr oriP origin of replication and EBNA-1 nuclear antigen for high-copy episomal replication in primate cell lines; the hygromycin resistance gene with the thymidine kinase promoter and polyadenylation site, for selection in mammalian cells; and the ampicillin resistance gene and colE1 origin of replication for maintenance in *Escherichia coli*. The vector contains four consecutive LexA operator sites between XbaI and NheI restriction sites (Bunker and Kingston, 1994). Embedded between the LexA operators and the NheI site is a polylinker consisting of the following restriction sites: HindIII-AscI-BamHI-AscI-HindIII. Between the NheI site and a SalI site is the zeocin resistance gene with the SV40 promoter and polyadenylation site, derived from pSV40/Zeo (Invitrogen V502-20); this is the selectable marker for the STAR screen.

Gene libraries were constructed by Sau3AI digestion of human genomic DNA, either purified from placenta (Clontech 6550-1) or carried in bacterial/P1 (BAC/PAC) artificial chromosomes. The BAC/PAC clones contain genomic DNA from the 1q12 cytogenetic region (clones RP1154H19 and RP3328E19), from the HOX cluster of homeotic genes (clones RP1167F23, RP1170019, and RP11387A1), or from human chromosome 22 (Research Genetics 96010-22). The DNAs were size-fractionated, and the 0.5-2 kb size fraction ligated into BamHI-digested pSelect vector, by standard techniques (Sambrook et al., 1989).

The construction of the host strains has been described (van der Vlag et al., 2000). Briefly, they are based on the U-2 OS human osteosarcoma cell line (American Type Culture Collection HTB-96). U-2 OS was stably transfected with the pTet-Off plasmid (Clontech K1620-A), encoding a protein chimera consisting of the Tet-repressor DNA binding domain and the VP16 transactivation domain. The cell line was subsequently stably transfected with fusion protein genes containing the LexA DNA binding domain, and the coding regions of HP1, MeCP2, or HPC2 (three *Drosophila* proteins that repress gene expression when tethered to DNA). The LexA-repressor genes are under control of the Tet-Off transcriptional regulatory system (Gossen and Bujard, 1992).

Library screening and STAR element characterization. The gene libraries in pSelect were transfected into U-2 OS/Tet-Off/LexA-repressor cell lines by calcium phosphate precipitation (Graham and van der Eb, 1973, Wigler et al., 1978) as recommended by the supplier of the transfection reagent (Life Technologies). Transfected cells were cultured under hygromycin selection (25 µg/ml) and tetracycline repression (doxycycline, 10 ng/ml) for one week (50% confluence). Then the doxycycline concentration was reduced to 0.1 ng/ml to induce the LexA-repressor genes, and after two days zeocin was added to 250 µg/ml. The cells are cultured for a further four to five weeks, until the control cultures (transfected with empty pSelect) were killed by the zeocin.

Zeocin-resistant colonies from the library transfection were propagated, and plasmid DNA isolated and rescued into *E. coli* by standard techniques (Sambrook et al., 1989). The candidate STAR elements in the rescued DNA were analyzed by restriction endonuclease mapping (Sambrook et al., 1989), and tested for STAR activity (zeocin resistance) after re-transfection to U-2 OS/Tet-Off/LexA-repressor cells and lowering the doxycycline concentration.

The human genomic DNA inserts in these plasmids were sequenced by the dideoxy method (Sanger et al., 1977) using a Beckman CEQ™2000 automated DNA sequencer, using the manufacturer's instructions. Briefly, DNA was purified from *E. coli* using QIAprep® Spin Miniprep and Plasmid Midi Kits (QIAGEN® 27106 and 12145, respectively). Cycle sequencing was carried out using custom oligonucleotides corresponding to the pSelect vector (primers D89 (SEQ ID NO:149) and D95 (SEQ ID NO:154); all oligonucleotides are described in Table 2), in the presence of dye terminators (CEQ™ Dye Terminator Cycle Sequencing Kit, Beckman 608000). Assembled STAR DNA sequences were located in the human genome using BLAST (Basic Local Alignment Search Tool (Altschul et al., 1990); worldwideweb.ncbi.nlm.nih.gov/BLAST/).

Results

The screens of human genomic DNA have yielded 66 STAR elements; the lengths and chromosomal locations of these elements are tabulated in SEQ ID NO:1-SEQ ID NO:66. They confer zeocin resistance on U-2 OS host cells when placed between LexA-repressor binding sites and the zeocin resistance gene. Their anti-repression activity was demonstrated both in the initial screen and upon re-transfection (demonstrating that the anti-repression activity is due to the STAR element and not to somatic acquisition of zeocin resistance). The STAR elements correspond to known and unique sequences in the human genome, as demonstrated by BLAST searches (Table 3). In some cases, the cloned element is a chimera of two unlinked genomic loci (e.g., STAR3 (SEQ ID NO:3), Table 3). They range in length from 500 to 2361 base pairs in length.

Example 2

Predictability and Yield is Improved by Promiscuous Star Elements in More than One Host Cell Line STAR elements function to block the effect of transcriptional repression influences on transgene expression units. These repression influences can be due to heterochromatin ("position effects") or to adjacent copies of the transgene ("repeat-induced gene silencing"). Two of the benefits of STAR elements for heterologous protein production are increased predictability of finding high-expressing primary recombinant host cells and increased yield during production cycles. These benefits are illustrated in this example.

Materials and Methods

Figure 2:
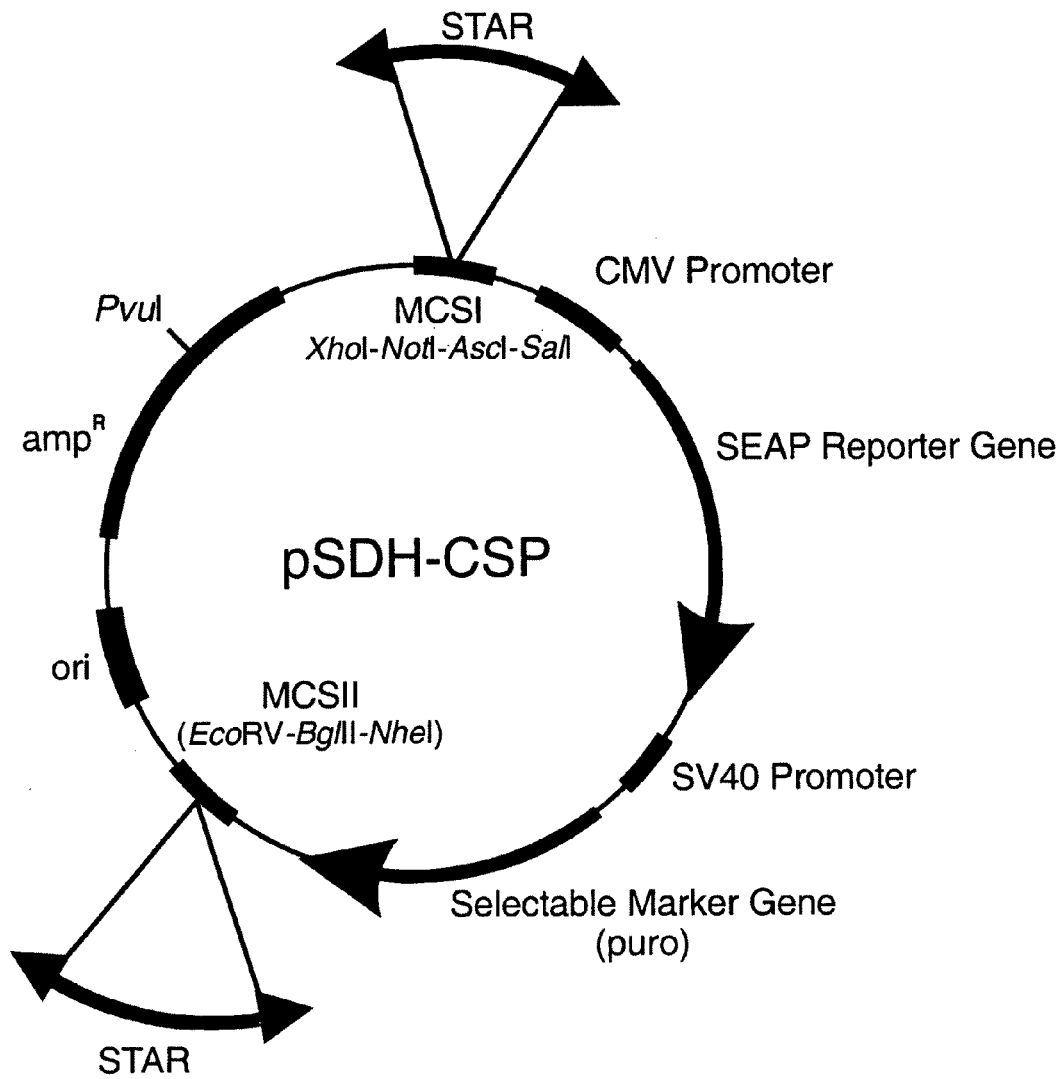
FIG. 2 is a diagram depicting the pSDH-CSP plasmid used for testing STAR activity. The Secreted Alkaline Phosphatase (SEAP) reporter gene is under control of the CMV promoter, and the puromycin resistance selectable marker (puro) is under control of the SV40 promoter. Flanking these two genes are multiple cloning sites (MCSI and MCSII) into which STAR elements can be cloned. The plasmid also has an origin of replication (ori) and ampicillin resistance gene ($amp^R$) for propagation in *Escherichia coli*.

Construction of the pSDH vectors and STAR-containing derivatives: The pSDH-Tet vector was constructed by polymerase chain reaction amplification (PCR) of the luciferase open reading frame from plasmid pREP4-HSF-Luc (van der Vlag et al., 2000) using primers C67 (SEQ ID NO:136) and C68 (SEQ ID NO:137), and insertion of the SacII/BamHI fragment into SacII/BamHI-digested pUHD10-3 (Gossen and Bujard, 1992). The luciferase expression unit was re-amplified with primers C65 (SEQ ID NO:134) and C66 (SEQ ID NO:135), and re-inserted into pUHD10-3 in order to flank it with multiple cloning sites (MCSI and MCSII). An AscI site was then introduced into MCSI by digestion with EcoRI and insertion of a linker (comprised of annealed oligonucleotides D93 (SEQ ID NO:152) and D94 (SEQ ID NO:153)). The CMV promoter was amplified from plasmid pCMV-Bsd (Invitrogen K510-01) with primers D90 (SEQ ID NO:150) and D91 (SEQ ID NO:151), and used to replace the Tet-Off promoter in pSDH-Tet by SalI/SacII digestion and ligation to create vector pSDH-CMV. The luciferase open reading frame in this vector was replaced by SEAP (Secreted Alkaline Phosphatase) as follows: vector pSDH-CMV was digested with SacII and BamHI and made blunt; the SEAP open reading frame was isolated from pSEAP-basic (Clontech 6037-1) by EcoRI/SalI digestion, made blunt and ligated into pSDH-CMV to create vector pSDH-CS. The puromycin resistance gene under control of the SV40 promoter was isolated from plasmid pBabe-Puro (Morgenstern and Land, 1990) by PCR, using primers C81 (SEQ ID NO:138) and C82 (SEQ ID NO:139). This was ligated into vector pGL3-control (BamHI site removed) (Promega E1741) digested with NcoI/XbaI to create pGL3-puro. pGL3-puro was digested with BglII/SalI to isolate the SV40-puro resistance unit, which was made blunt and ligated into NheI digested, blunt-ended pSDH-CS. The resulting vector, pSDH-CSP, is shown in FIG. 2. All cloning steps were carried out following the instructions provided by the manufacturers of the reagents used, according to methods known in the art (Sambrook et al., 1989).

STAR elements were inserted into MCSI and MCSII in two steps, by digestion of the STAR element and the pSDH-CSP vector with an appropriate restriction enzyme, followed by ligation. The orientation of STAR elements in recombinant pSDH vectors was determined by restriction mapping, and in all cases verified by DNA sequence analysis using primers C85 (SEQ ID NO:140), E42 (SEQ ID NO:168), and E25 (SEQ ID NO:167) (Table 2; see Example 1).

Transfection and culture of U-2 OS cells with pSDH-CMV plasmids: The human osteosarcoma U-2 OS cell line (ATCC #HTB-96) was cultured in Dulbecco's Modified Eagle Medium+10% Fetal Calf Serum containing glutamine, penicillin, and streptomycin (supra) at 37° C./5% $CO_2$. Cells were co-transfected with the pSDH-CMV vector and its derivatives containing STAR6 (SEQ ID NO:6) or STAR8 (SEQ ID NO:8) in MCSI and MCSII (along with plasmid pBabe-Puro) using SuperFect® (supra). Puromycin selection was complete in two weeks, after which time individual puromycin resistant U-2 OS/pSDH-CMV clones were isolated at random and cultured further.

Luciferase assay: Luciferase activity (Himes and Shannon, 2000) was assayed in resuspended cells according to the instructions of the assay kit manufacturer (Roche 1669893), using a luminometer (Turner 20/20TD). Total cellular protein concentration was determined by the bicinchoninic acid method according to the manufacturer's instructions (Sigma B-9643), and used to normalize the luciferase data.

Transfection and culture of CHO cells with pSDH-CSP plasmids: The Chinese Hamster Ovary cell line CHO-K1 (ATCC CCL-61) was cultured in HAMS-F12 medium+10% Fetal Calf Serum containing 2 mM glutamine, 100 U/ml penicillin, and 100 micrograms/ml streptomycin at 37° C./5% $CO_2$. Cells were transfected with recombinant pSDH-CSP vectors using SuperFect® (QIAGEN®) as described by the manufacturer. Briefly, cells were seeded to culture vessels and grown overnight to 70-90% confluence. SuperFect® reagent was combined with plasmid DNA (linearized in this example by digestion with PvuI) at a ratio of 6 microliters per microgram (e.g., for a 10 cm Petri dish, 20 micrograms DNA and 120 microliters SuperFect®) and added to the cells. After overnight incubation, the transfection mixture was replaced with fresh medium, and the transfected cells were incubated further. After overnight cultivation, 5 micrograms/ml puromycin was added. Puromycin selection was complete in two weeks, after which time individual puromycin resistant CHO/pSDH-CSP clones were isolated at random and cultured further.

Secreted Alkaline Phosphatase (SEAP) assay: SEAP activity (Berger et al., 1988, Henthorn et al., 1988, Kain, 1997, Yang et al., 1997) in the culture medium of CHO/pSDH-CSP clones was determined as described by the manufacturer (Clontech Great EscAPe kit #K2041). Briefly, an aliquot of medium was heat inactivated at 65° C., then combined with assay buffer and CSPD chemiluminescent substrate and incubated at room temperature for ten minutes. The rate of substrate conversion was then determined in a luminometer (Turner 20/20TD). Cell density was determined by counting trypsinized cells in a Coulter ACT10 cell counter. Luminescence units were converted into picograms SEAP based on a SEAP positive control calibration curve, and normalized to cell number.

Results

Recombinant U-2 OS cell clones containing the pSDH-CMV vector, or a pSDH-CMV plasmid containing STAR6 (SEQ ID NO:6) (Table 3), were cultured for three weeks. The luciferase activity in the host cells was then determined, and is expressed as relative luciferase units (FIG. 3), normalized to total cell protein. The recombinant U-2 OS clones with STAR6 (SEQ ID NO:6) flanking the expression units had higher yields than the STAR-less clones: the STAR6 clones had maximal luciferase expression levels five-fold higher than the STAR-less clones. The STAR6 (SEQ ID NO:6) element conferred greater predictability as well: 15-20% of the clones expressed luciferase at levels comparable to or greater than the STAR-less clone with the highest expression level.

Figure 4:
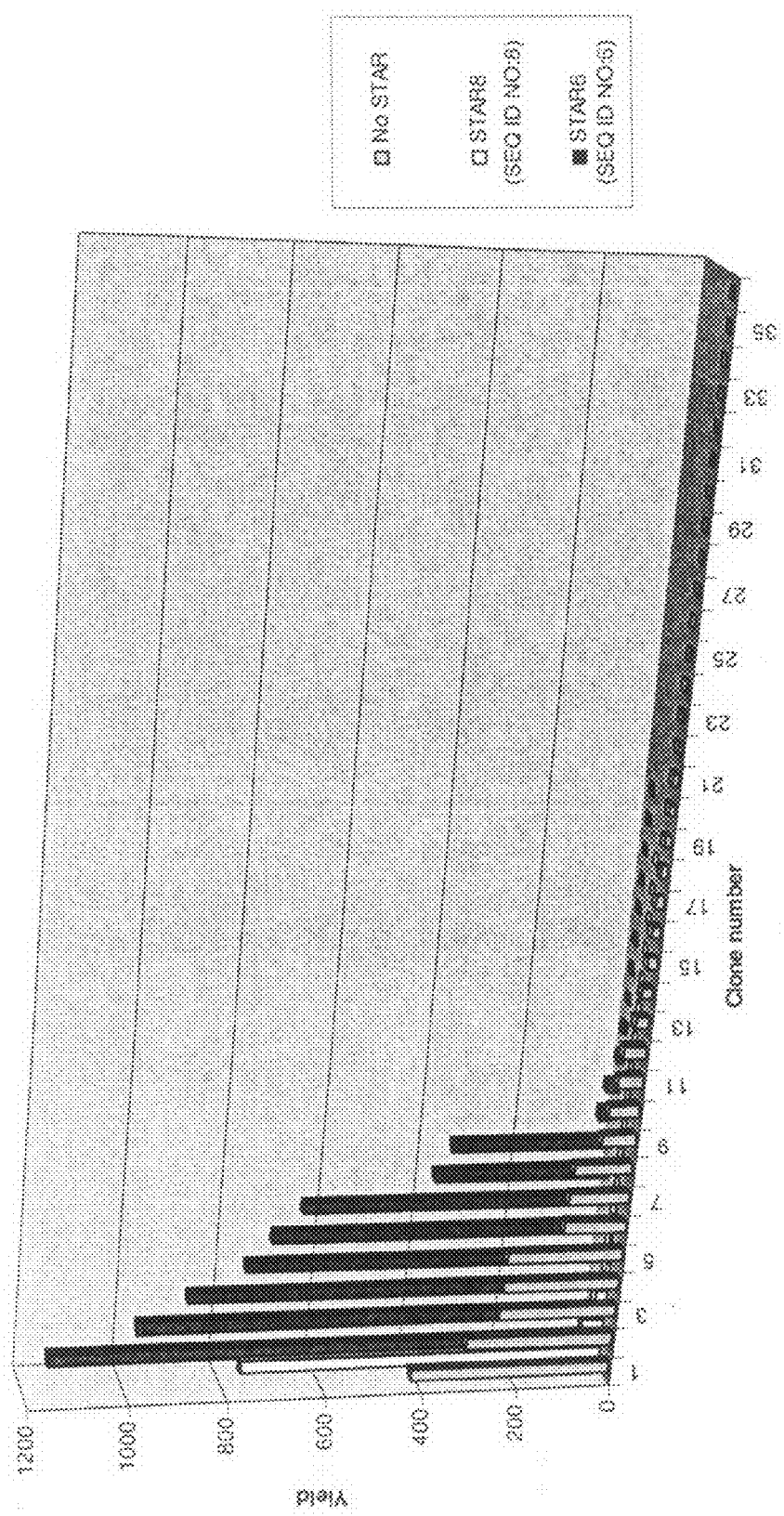
FIG. 4 is a graph illustrating that STAR6 (SEQ ID NO:6), but not STAR8 (SEQ ID NO:8), improves predictability and yield of transgene expression in CHO cells. Expression of SEAP from the CMV promoter by CHO cells transfected with pSDH-CSP, pSDH-CSP-STAR6, or pSDH-CSP-STAR8 was determined. The STAR6-containing constructs confer greater predictability and elevated yield relative to the pSDH-CSP construct alone, identifying STAR6 (SEQ ID NO:6) as a promiscuous STAR element. In contrast, the STAR8-containing constructs do not consistently increase yield or predictability relative to the pSDH-CSP construct, suggesting that STAR8 (SEQ ID NO:8) is a cell line-specific STAR element.
Figure 5:
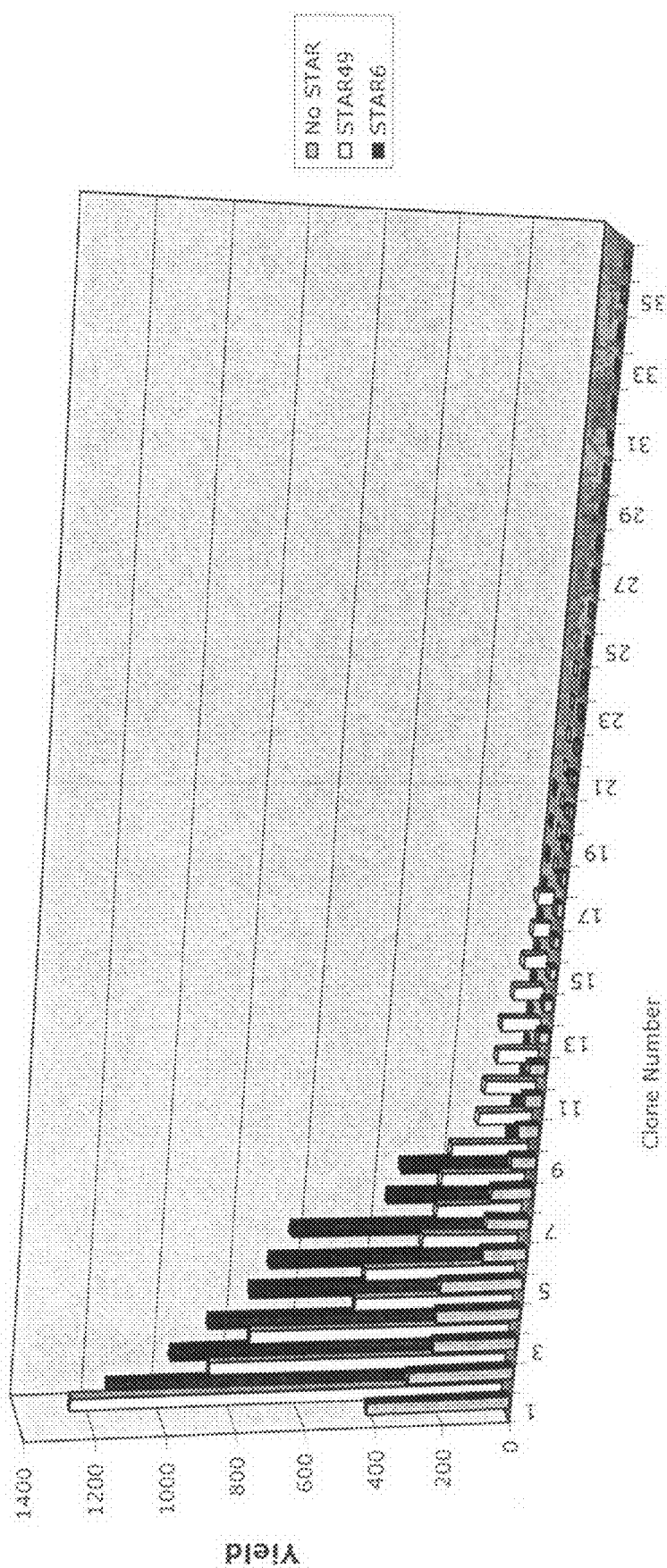
FIG. 5 is a graph depicting that STAR6 (SEQ ID NO:6) and STAR49 (SEQ ID NO:49) improve predictability and yield of transgene expression. Expression of SEAP from the CMV promoter by CHO cells transfected with pSDH-CSP, pSDH-CSP-STAR6, or pSDH-CSP-STAR49 was determined. The STAR-containing constructs confer greater predictability and elevated yield relative to the pSDH-CSP construct alone.

Recombinant CHO cell clones containing the pSDH-CSP vector, or a pSDH-CSP plasmid containing STAR6 (SEQ ID NO:6), were cultured for three weeks. The SEAP activity in the culture supernatants was then determined, and is expressed on the basis of cell number (FIG. 4). As can be seen, clones with the STAR6 (SEQ ID NO:6) element in the expression units were isolated that express two- to three-fold higher SEAP activity than clones whose expression units do not include this STAR element. Furthermore, the number of STAR6-containing (SEQ ID NO:6-containing) clones that express SEAP activity at or above the maximal activity of the STAR-less clones is quite high: 40% of the STAR6 clone populations exceed the highest SEAP expression of the pSDH-CSP clones.

These results demonstrate that, when used with the strong CMV promoter, the STAR6 (SEQ ID NO:6) element increases the yield of this heterologous protein in both of the host cell lines tested. STAR6 (SEQ ID NO:6) also confers increased predictability, as manifested by the large proportion of the clones with yields equal to or greater than the highest yield displayed by the STAR-less clones. Thus, STAR6 (SEQ ID NO:6) is an example of a promiscuous STAR element, able to suppress transgene repression in more than one host cell line. The cell lines used are derived from different species (human and hamster) and different tissue types (bone and ovary), reflecting the broad range of host cells in which this STAR element can be utilized in improving heterologous protein expression.

Example 3

STAR8 (SEQ ID NO:8) is a Cell Line-Specific STAR Element

The patterns of gene expression and epigenetic gene regulation in a host cell line reflect the developmental state of the somatic cells from which they are derived. Furthermore, the biotechnology industry takes advantage of general purpose cell lines from different species according to specific requirements of a heterologous protein production process. Therefore, it is expected that some STAR elements will not function in cell lines other than those in which they are isolated. This expectation has been fulfilled by some of the STAR elements shown in Table 3. One example will be given here.

Materials and Methods pSDH vector construction, transfection and cultivation of CHO and U-2 OS cell lines, and assay methods for the SEAP and luciferase reporter genes has been described in Example 2.

Results

Recombinant U-2 OS cell clones containing the pSDH-CMV vector, or a pSDH-CMV plasmid containing STAR8 (SEQ ID NO:8) (Table 3), were cultured for three weeks. The luciferase activity in the host cells was then determined, and is expressed as relative luciferase units (FIG. 3), normalized to total cell protein. The recombinant U-2 OS clones with the STAR8 (SEQ ID NO:8) element flanking the expression units had higher yields than the STAR-less clones: the highest expression observed from STAR8 clones was two- to three-fold higher than the expression from STAR-less clones. The STAR8 (SEQ ID NO:8) element conferred greater predictability as well: for this STAR element, ~15% of the clones displayed luciferase expression at levels comparable to or greater than the STAR-less clone with the highest expression level.

Recombinant CHO cell clones transfected with the pSDH-CSP vector, or a pSDH-CSP plasmid containing STAR8 (SEQ ID NO:8), were cultured for three weeks. The SEAP activity in the culture supernatants was then determined, and is expressed on the basis of cell number (FIG. 4). As can be seen, one clone with the STAR8 (SEQ ID NO:8) element in the expression unit had a yield approximately two-fold higher than the highest-expressing STAR-less clone. However, the rest of the STAR8 clones expressed very poorly relative to the STAR-less clone population. Since only one individual in the STAR8 population had a good yield, it is probable that the expression unit in this clone was integrated in open, transcriptionally active chromatin, and the high yield does not reflect anti-repression activity of STAR8 (SEQ ID NO:8) in CHO cells. Certainly in the CHO clones transfected with STAR8-containing (SEQ ID NO:8-containing) expression units the predictability is quite poor; of the 17 puromycin-resistant clones, only one clone had a yield of SEAP activity above the background level of expression.

This example demonstrates that good performance of a STAR element in one cell line (in this case, the U-2 OS cell line in which STAR8 (SEQ ID NO:8) was originally isolated) is not an accurate predictor of its performance in other cell lines. STAR8 (SEQ ID NO:8) is thus an example of a cell line-specific STAR element.

Example 4

STAR Elements Functionality in Diverse Cell Line

Materials and Methods

Cell lines including the U-2 OS osteosarcoma and CHO (Chinese hamster ovary) cell lines (supra), the 293 cell line (ATCC CRL-1573) derived from human embryonal kidney (immortalized by adenovirus 5 transfection), the HuNS-1 myeloma (ATCC CRL-8644) and the WERI-Rb-1 retinoblastoma cell line (ATCC HTB-169), the NCI-H295R adrenal gland carcinoma (ATCC CRL-2128), and the non-secreting mouse myelomas Sp2/0-Ag 14 and NSO are examined according to the previous examples.

Example 5

STAR Elements Improve the Stability of Transgene Expression

During cultivation of recombinant host cells, it is common practice to maintain antibiotic selection. This is intended to prevent transcriptional silencing of the transgene, or loss of the transgene from the genome by processes such as recombination. However it is undesirable for production of heterologous proteins, for a number of reasons. First, the antibiotics that are used are quite expensive, and contribute significantly to the unit cost of the product. Second, for biopharmaceutical use, the protein must be demonstrably pure, with no traces of the antibiotic in the product. One advantage of STAR elements for heterologous protein production is that they confer stable expression on transgenes during prolonged cultivation, even in the absence of antibiotic selection; this property is demonstrated in this example.

Materials and Methods

The U-2 OS cell line was transfected with the plasmid pSDH-Tet-STAR6 and cultivated as described in Example 2. Individual puromycin-resistant clones were isolated and cultivated further in the absence of doxycycline. At weekly intervals the cells were transferred to fresh culture vessels at a dilution of 1:20. Luciferase activity was measured at periodic intervals as described in Example 2. After 15 weeks, the cultures were divided into two replicates; one replicate continued to receive puromycin, while the other replicate received no antibiotic for the remainder of the experiment (25 weeks total).

Results

Table 4 presents the data on luciferase expression by an expression unit flanked with STAR6 (SEQ ID NO:6) during prolonged growth with or without antibiotic. As can be seen, the expression of the reporter transgene, luciferase, remains stable in the U-2 OS host cells for the duration of the experiment. After the cultures were divided into two treatments (plus antibiotic and without antibiotic) the expression of luciferase was essentially stable in the absence of antibiotic selection. This demonstrates the ability of STAR elements to protect transgenes from silencing or loss during prolonged cultivation. It also demonstrates that this property is independent of antibiotic selection. Therefore, production of heterologous proteins is possible without incurring the costs of the antibiotic or of difficult downstream processing.

Example 6

Minimal Essential Sequences of STAR Elements

STAR elements are isolated from the genetic screen described in Example 1. The screen uses libraries constructed with human genomic DNA that was size-fractionated to approximately 0.5-2 kilobases (supra). The STAR elements range from 500 to 2361 base pairs (Table 3). It is likely that, for many of the STAR elements that have been isolated, STAR activity is conferred by a smaller DNA fragment than the initially isolated clone. It is useful to determine these minimum fragment sizes that are essential for STAR activity, for two reasons. First, smaller functional STAR elements would be advantageous in the design of compact expression vectors, since smaller vectors transfect host cells with higher efficiency. Second, determining minimum essential STAR sequences permits the modification of those sequences for enhanced functionality. Two STAR elements have been fine-mapped to determine their minimal essential sequences.

Materials and Methods

Figure 6:
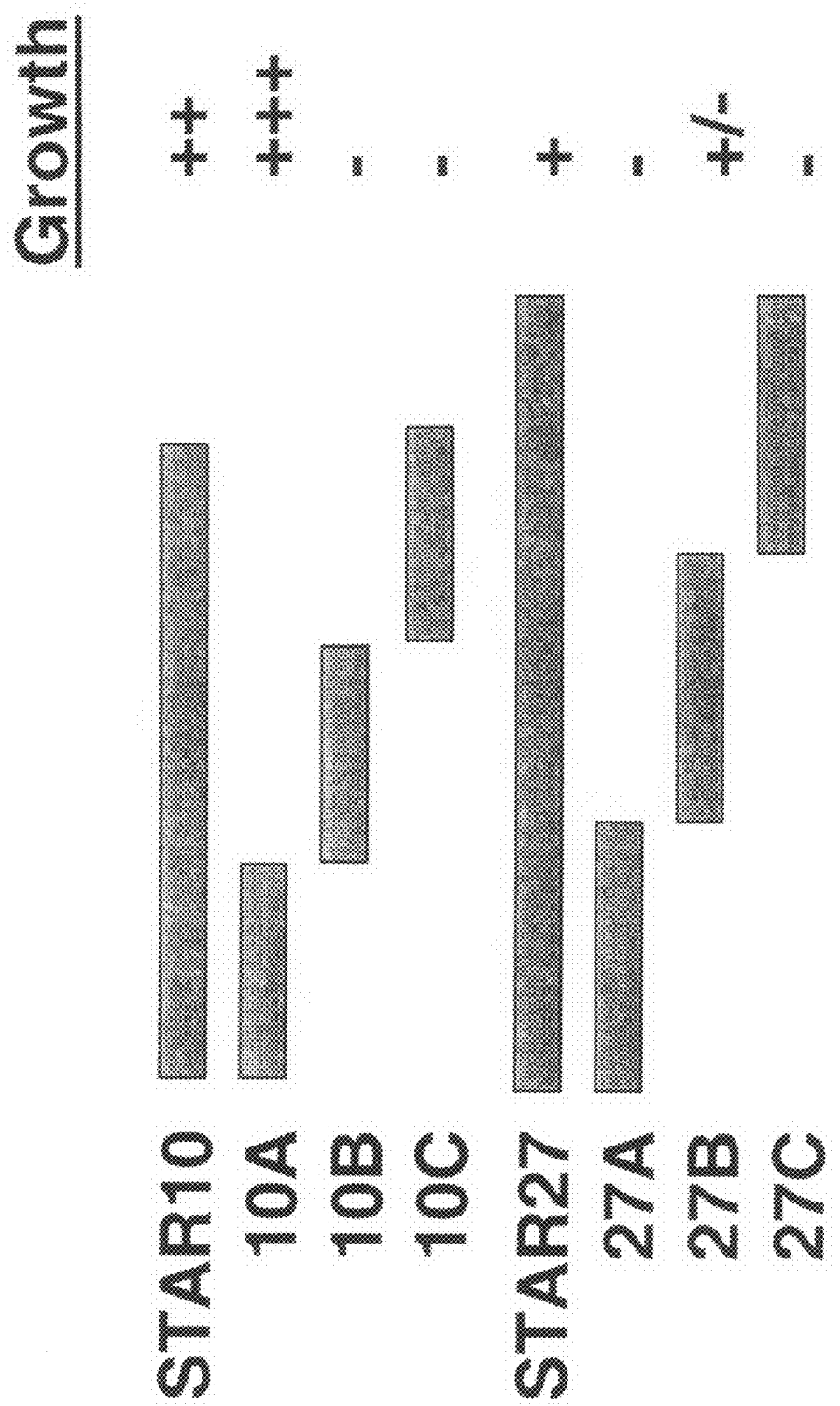
FIG. 6 is a graph showing the minimal essential sequences of STAR10 (SEQ ID NO:10) and STAR27 (SEQ ID NO:27). Portions of the STAR elements were amplified by PCR: STAR10 (SEQ ID NO:10) was amplified with primers E23 (SEQ ID NO:166) and E12 (SEQ ID NO:155) to yield fragment 10A (corresponding approximately to the first 400 nucleotides of SEQ ID NO:10), E13 (SEQ ID NO:156) and E14 (SEQ ID NO:157) to yield fragment 10B (corresponding approximately to the second 400 nucleotides of SEQ ID NO:10), and E15 (SEQ ID NO:158) and E16 (SEQ ID NO:159) to yield fragment 10C (corresponding approximately to the third 400 nucleotides of SEQ ID NO:10). STAR27 (SEQ ID NO:27) was amplified with primers E17 (SEQ ID NO:160) and E18 (SEQ ID NO:161) to yield fragment 27A (corresponding approximately to the first 500 nucleotides of SEQ ID NO:27), E19 (SEQ ID NO:162) and E20 (SEQ ID NO:163) to yield fragment 27B (corresponding to the second 500 nucleotides of SEQ ID NO:27), and E21 (SEQ ID NO:164) and E22 (SEQ ID NO:165) to yield fragment 27C (corresponding approximately to the third 500 nucleotides of SEQ ID NO:27). These sub-fragments were cloned into the pSelect vector. After transfection into U-2 OS/Tet-Off/LexA-HP1 cells, the growth of the cultures in the presence of zeocin was monitored. Growth rates varied from vigorous (+++) to poor (+/−), while some cultures failed to survive zeocin treatment (−) due to absence of STAR activity in the DNA fragment tested.

STAR10 (SEQ ID NO:10) (1167 base pairs) and STAR27 (SEQ ID NO:27) (1520 base pairs) have been fine-mapped. They have been amplified by PCR to yield sub-fragments of approximately equal length (FIG. 6 legend). For initial testing, these have been cloned into the pSelect vector at the BamHI site, and transfected into U-2 OS/Tet-Off/LexA-HP1 cells as described in Example 1. After selection for hygromycin resistance, LexA-HP1 was induced by lowering the doxycycline concentration. Transfected cells were then incubated with zeocin to test the ability of the STAR fragments to protect the SV40-Zeo expression unit from repression due to LexA-HP1 binding.

Results

In this experiment STAR10 (SEQ ID NO:10) and STAR 27 (SEQ ID NO:27) confer good protection against gene silencing, as expected (FIG. 6). This is manifested by robust growth in the presence of zeocin.

Of the three STAR10 (SEQ ID NO:10) sub-fragments, 10A (~400 base pairs, corresponding to approximately the first 400 nucleotides of SEQ ID NO:10) confers on transfected cells vigorous growth in the presence of zeocin, exceeding that of the full-length STAR element. Cells transfected with pSelect constructs containing the other two sub-fragments do not grow in the presence of zeocin. These results identify the ~400 base pair 10A fragment as encompassing the DNA sequence responsible for the anti-repression activity of STAR10 (SEQ ID NO:10).

STAR27 (SEQ ID NO:27) confers moderate growth in zeocin to transfected cells in this experiment (FIG. 6). One of the sub-fragments of this STAR, 27B (~500 base pairs, corresponding to approximately the second 500 nucleotides of SEQ ID NO:27), permits weak growth of the host cells in zeocin-containing medium. This suggests that the anti-repression activity of this STAR is partially localized on sub-fragment 27B, but full activity requires sequences from 27A (corresponding to approximately the first 500 nucleotides of SEQ ID NO:27) and/or 27C (corresponding to approximately the third 500 nucleotides of SEQ ID NO:27) (each ~500 base pairs) as well.

Example 7

STAR Elements Function in the Context of Various Transcriptional Promoters

Transgene transcription is achieved by placing the transgene open reading frame under control of an exogenous promoter. The choice of promoter is influenced by the nature of the heterologous protein and the production system. In most cases, strong constitutive promoters are preferred because of the high yields they can provide. Some viral promoters have these properties; the promoter/enhancer of the cytomegalovirus immediate early gene ("CMV promoter") is generally regarded as the strongest promoter in common biotechnological use (Boshart et al., 1985, Doll et al., 1996, Foecking and Hofstetter, 1986). The simian virus SV40 promoter is also moderately strong (Boshart et al., 1985, Foecking and Hofstetter, 1986) and is frequently used for ectopic expression in mammalian cell vectors. The Tet-Off promoter is inducible: the promoter is repressed in the presence of tetracycline or related antibiotics (doxycycline is commonly used) in cell-lines which express the tTA plasmid (Clontech K1620-A), and removal of the antibiotic results in transcriptional induction (Deuschle et al., 1995, Gossen and Bujard, 1992, Izumi and Gilbert, 1999, Umana et al., 1999).

Materials and Methods

The construction of the pSDH-Tet and pSDH-CMV vectors is described in Example 2. pSDH-SV40 was constructed by PCR amplification of the SV40 promoter (primers D41 (SEQ ID NO:142) and D42 (SEQ ID NO:143)) from plasmid pSelect-SV40-Zeo (Example 1), followed by digestion of the PCR product with SacII and SalI. The pSDH-CMV vector was digested with SacII and SalI to remove the CMV promoter, and the vector and SV40 fragment were ligated together to create pSDH-SV40. STAR6 (SEQ ID NO:6) was cloned into MCSI and MCSII as described in Example 2. The plasmids pSDH-Tet, pSDH-Tet-STAR6, pSDH-Tet-STAR7, pSDH-SV40 and pSDH-SV40-STAR6 were co-transfected with pBabe-Puro into U-2 OS using SuperFect® as described by the manufacturer. Cell cultivation, puromycin selection, and luciferase assays were carried out as described in Example 2.

Results

Figure 3:
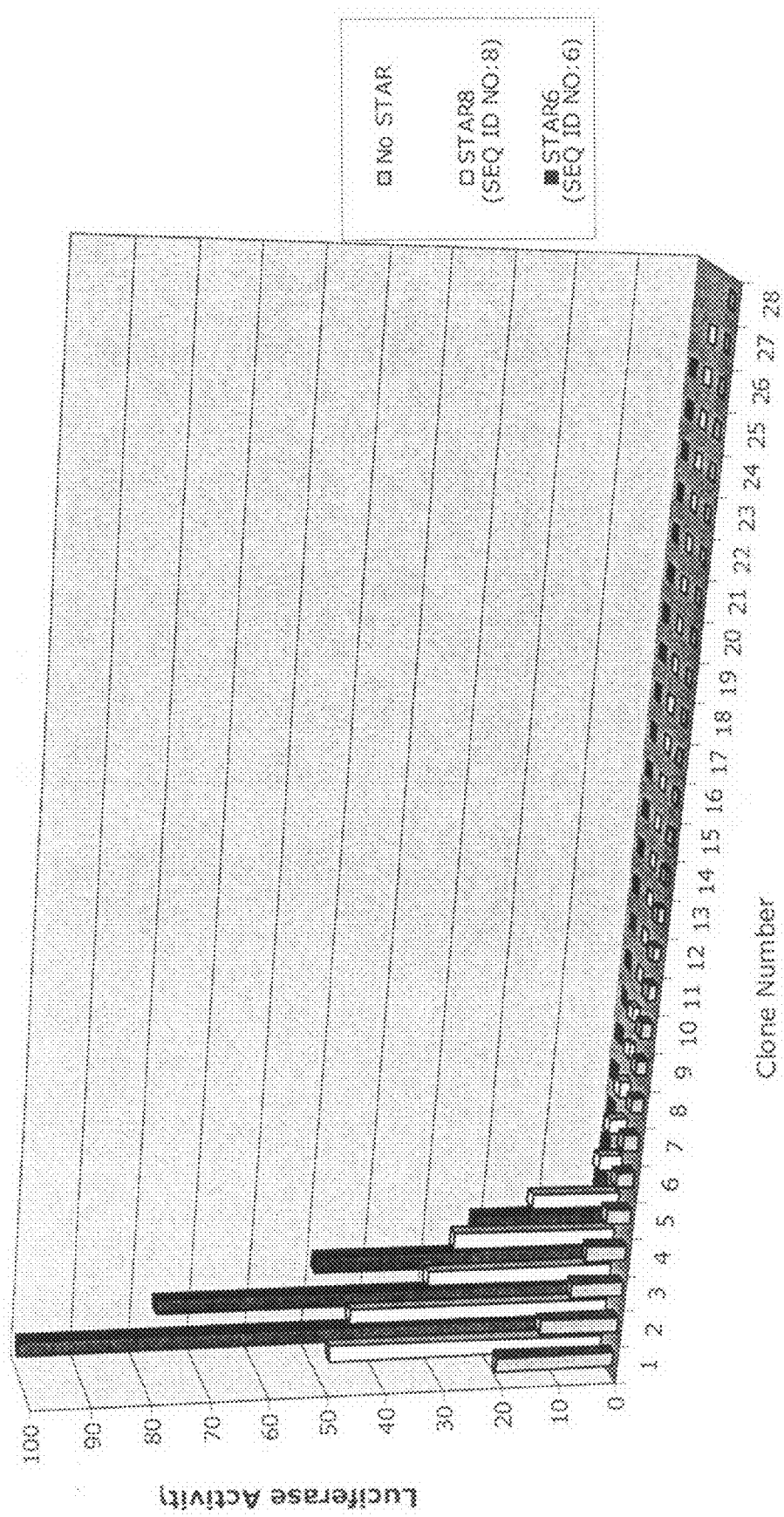
FIG. 3 is a graph showing that STAR6 (SEQ ID NO:6) and STAR8 (SEQ ID NO:8) improve predictability and yield of transgene expression in U-2 OS cells. Expression of luciferase from the CMV promoter by U-2 OS cells transfected with pSDH-CMV, pSDH-CMV-STAR6, or pSDH-CMV-STAR8 was determined. The STAR-containing constructs confer greater predictability and elevated yield relative to the pSDH-CMV construct alone.
Figure 7:
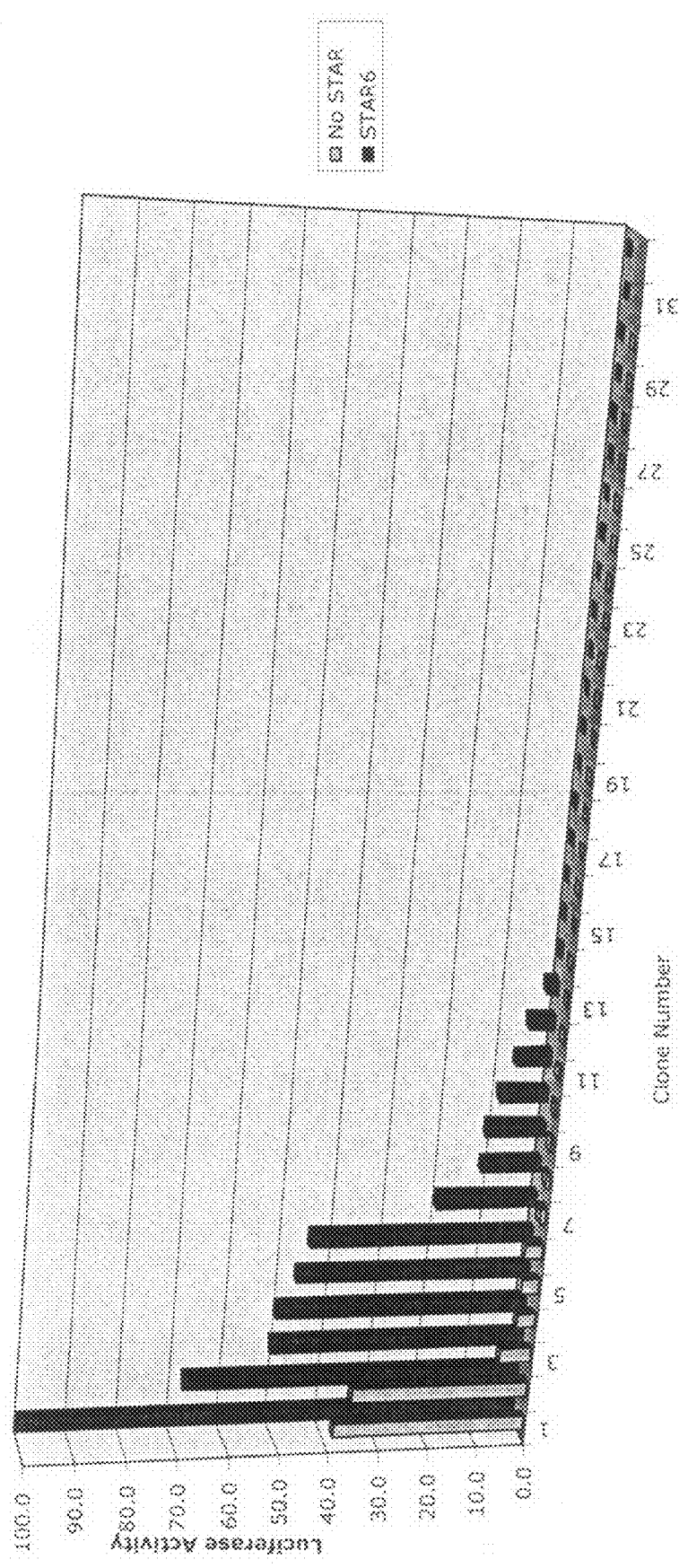
FIG. 7 is a graph illustrating the STAR element function in the context of the SV40 promoter. pSDH-SV40 and pSDH-SV40-STAR6 were transfected into the human osteosarcoma U-2 OS cell line, and expression of luciferase was assayed with or without protection from gene silencing by STAR6 (SEQ ID NO:6) in puromycin-resistant clones.
Figure 8:
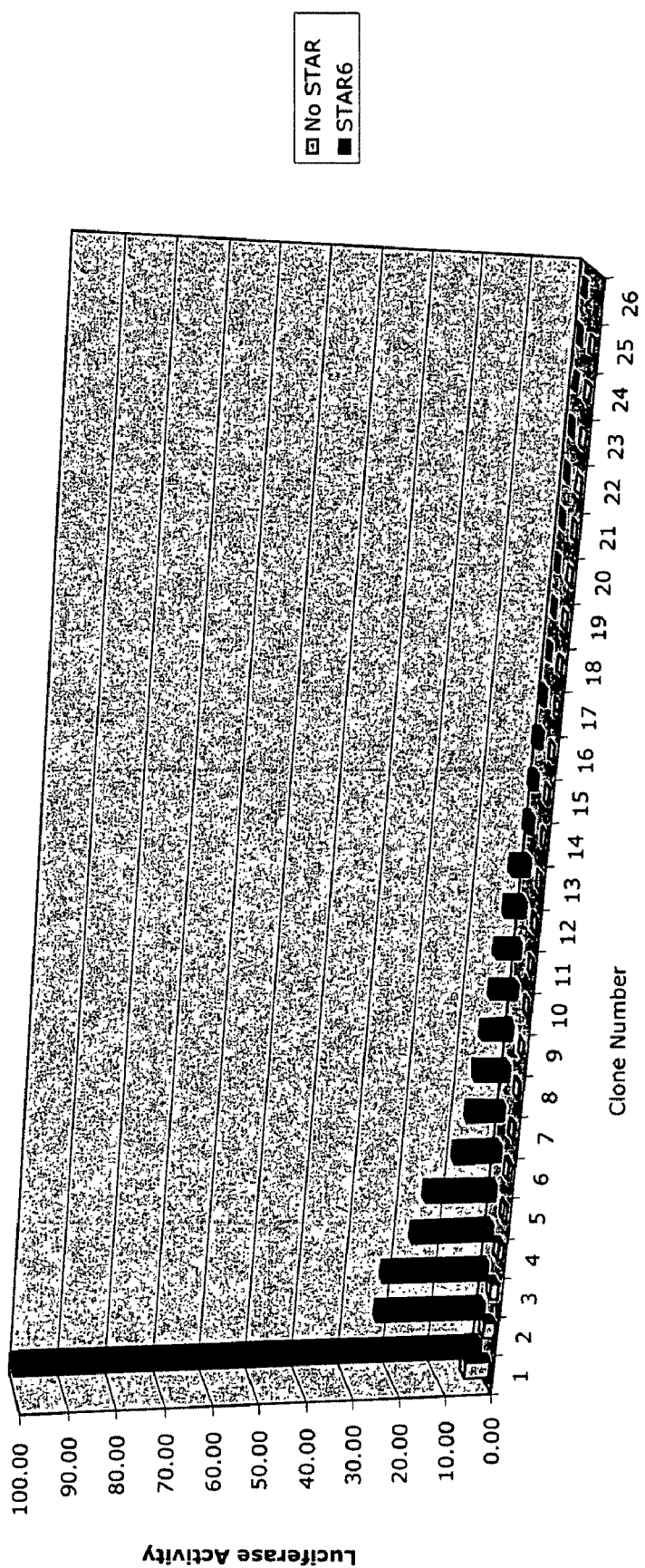
FIG. 8 is a graph showing the STAR element function in the context of the Tet-Off promoter. pSDH-Tet and pSDH-Tet-STAR6 were transfected into the human osteosarcoma U-2 OS cell line, and expression of luciferase was assayed with or without protection from gene silencing by STAR6 (SEQ ID NO:6) in puromycin-resistant clones.

FIGS. 3, 7, and 8 compare the expression of the luciferase reporter gene from three different promoters: two strong and constitutive viral promoters (CMV and SV40), and the inducible Tet-Off promoter. All three promoters were tested in the context of the STAR6 (SEQ ID NO:6) element in U-2 OS cells. The results demonstrate that the yield and predictability from all three promoters are increased by STAR6 (SEQ ID NO:6). As described in Examples 2 and 5, STAR6 (SEQ ID NO:6) is beneficial in the context of the CMV promoter (FIG. 3). Similar improvements are seen in the context of the SV40 promoter (FIG. 7): the yield from the highest-expressing STAR6 clone is two- to three-fold greater than the best pSDH-SV40 clones, and six STAR clones (20% of the population) have yields higher than the best STAR-less clones. In the context of the Tet-Off promoter under inducing (low doxycycline) concentrations, STAR6 (SEQ ID NO:6) also improves the yield and predictability of transgene expression (FIG. 8): the highest-expressing STAR6 clone has a 20-fold higher yield than the best pSDH-Tet clone, and nine STAR6 clones (35% of the population) have yields higher than the best STAR-less clone. It is concluded that this STAR element is versatile in its transgene-protecting properties, since it functions in the context of various biotechnologically useful promoters of transcription.

Example 8

STAR Element Function can be Directional

While short nucleic acid sequences can be symmetrical (e.g., palindromic), longer, naturally-occurring sequences are typically asymmetrical. As a result, the information content of nucleic acid sequences is directional and the sequences themselves can be described with respect to their 5' and 3' ends. The directionality of nucleic acid sequence information affects the arrangement in which recombinant DNA molecules are assembled using standard cloning techniques known in the art (Sambrook et al., 1989). STAR elements are long, asymmetrical DNA sequences, and have a directionality based on the orientation in which they were originally cloned in the pSelect vector. In the examples given above, using two STAR elements in pSDH vectors, this directionality was preserved. This orientation is described as the native or 5'-3' orientation, relative to the zeocin resistance gene (see FIG. 9). In this example the importance of directionality for STAR function is tested in the pSDH-Tet vector. Since the reporter genes in the pSDH vectors are flanked on both sides by copies of the STAR element of interest, the orientation of each STAR copy must be considered. This example compares the native orientation with the opposite orientation (FIG. 9).

Materials and Methods

The STAR66 (SEQ ID NO:66) element was cloned into pSDH-Tet as described in Example 2. U-2 OS cells were co-transfected with plasmids pSDH-Tet-STAR66-native and pSDH-Tet-STAR66-opposite, and cultivated as described in Example 2. Individual clones were isolated and cultivated; the level of luciferase expression was determined as described (supra).

Results

Figure 10:
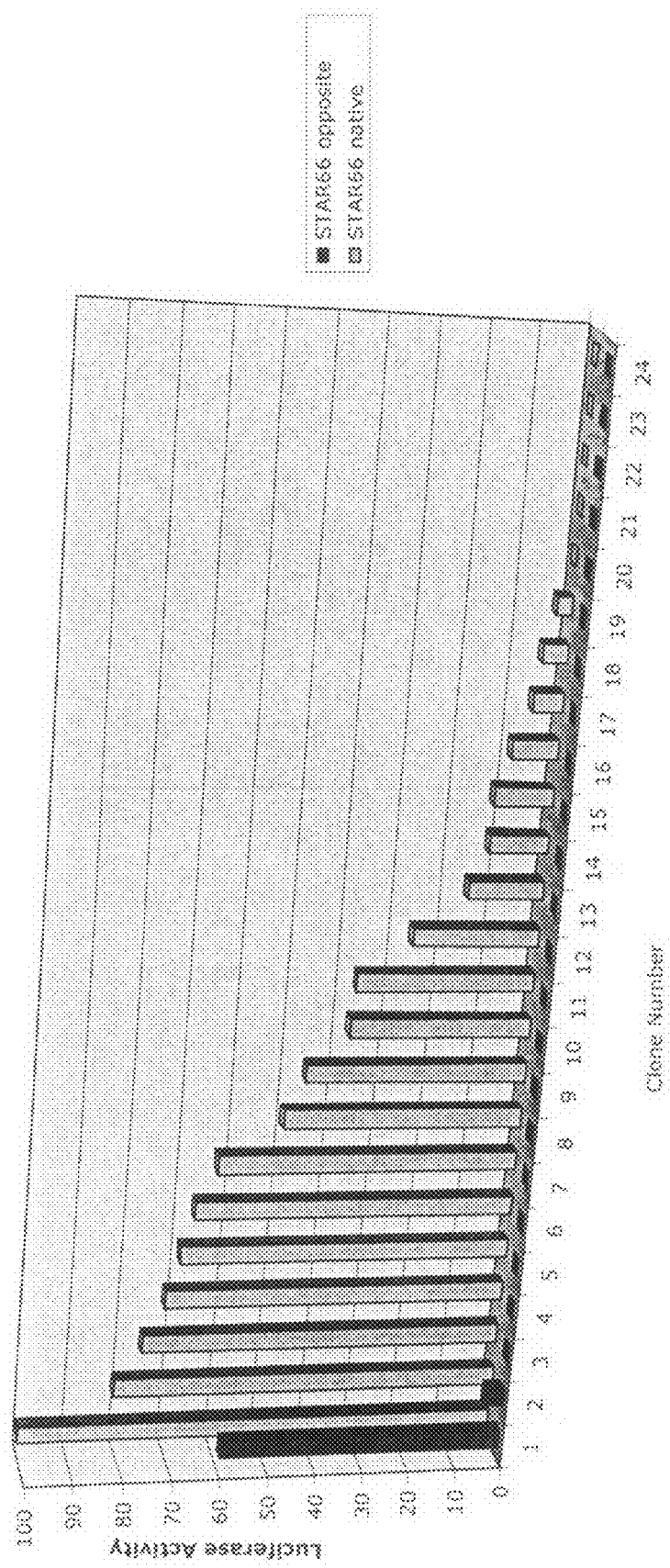
FIG. 10 is a graph showing directionality of STAR66 (SEQ ID NO:66) function. The STAR66 (SEQ ID NO:66) element was cloned into pSDH-Tet in either the native (STAR66 native) or the opposite orientation (STAR66 opposite) and transfected into U-2 OS cells. Luciferase activity was assayed in puromycin resistant clones.

The results of the comparison of STAR66 (SEQ ID NO:66) activity in the native orientation and the opposite orientation are shown in FIG. 10. When STAR66 (SEQ ID NO:66) is in the opposite orientation, the yield of only one clone is reasonably high (60 luciferase units). In contrast, the yield of the highest-expressing clone when STAR66 (SEQ ID NO:66) is in the native orientation is considerably higher (100 luciferase units) and the predictability is much higher, as well: seven clones of the native-orientation population (30%) express luciferase above the level of the highest-expressing clone from the opposite-orientation population, and 15 of the clones in the native-orientation population (60%) express luciferase above ten relative luciferase units. Therefore, it is demonstrated that STAR66 (SEQ ID NO:66) function is directional.

Example 9

Transgene Expression in the Context of STAR Elements is Copy Number-Dependent

Transgene expression units for heterologous protein expression are generally integrated into the genome of the host cell to ensure stable retention during cell division. Integration can result in one or multiple copies of the expression unit being inserted into the genome; multiple copies may or may not be present as tandem arrays. The increased yield demonstrated for transgenes protected by STAR elements (supra) suggests that STAR elements are able to permit the transgene expression units to function independently of influences on transcription associated with the site of integration in the genome (independence from position effects (Boivin and Dura, 1998)). It suggests further that the STAR elements permit each expression unit to function independently of neighboring copies of the expression unit when they are integrated as a tandem array (independence from repeat-induced gene silencing (Garrick et al., 1998)). Copy number-dependence is determined from the relationship between transgene expression levels and copy number, as described in the example below.

Materials and Methods

Figure 11:
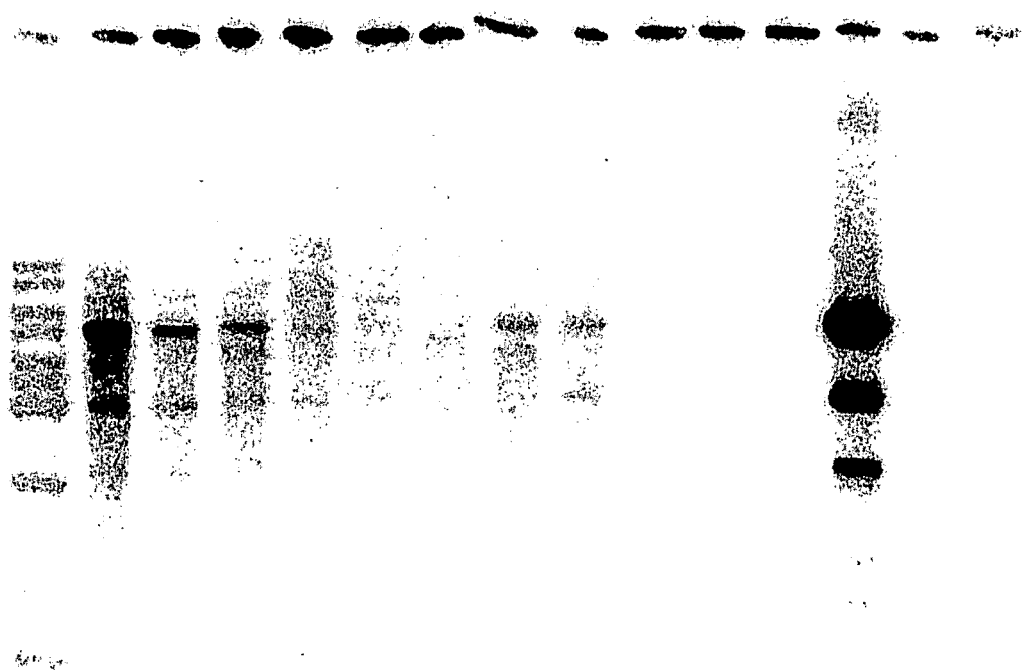
FIG. 11 is a southern blot showing copy number-dependence of STAR function. Southern blot of luciferase expression units in pSDH-Tet-STAR10, integrated into U-2 OS genomic DNA. Radioactive luciferase DNA probe was used to detect the amount of transgene DNA in the genome of each clone, which was then quantified with a phosphorimager.

U-2 OS cells were co-transfected with pSDH-Tet-STAR10 and cultivated under puromycin selection as described (supra). Eight individual clones were isolated and cultivated further. Then cells were harvested, and one portion was assayed for luciferase activity as described (supra). The remaining cells were lysed and the genomic DNA purified using the DNeasy® Tissue Kit (QIAGEN® 69504) as described by the manufacturer. DNA samples were quantitated by UV spectrophotometry. Three micrograms of each genomic DNA sample were digested with PvuII and XhoI overnight as described by the manufacturer (New England Biolabs), and resolved by agarose gel electrophoresis. DNA fragments were transferred to a nylon membrane as described (Sambrook et al., 1989), and hybridized with a radioactively labeled probe to the luciferase gene (isolated from BamHI/SacII-digested pSDH-Tet). The blot was washed as described (Sambrook et al., 1989) and exposed to a phosphorimager screen (Personal F/X, BioRad). The resulting autoradiogram (FIG. 11) was analyzed by densitometry to determine the relative strength of the luciferase DNA bands, which represents the transgene copy number.

Results

Figure 12:
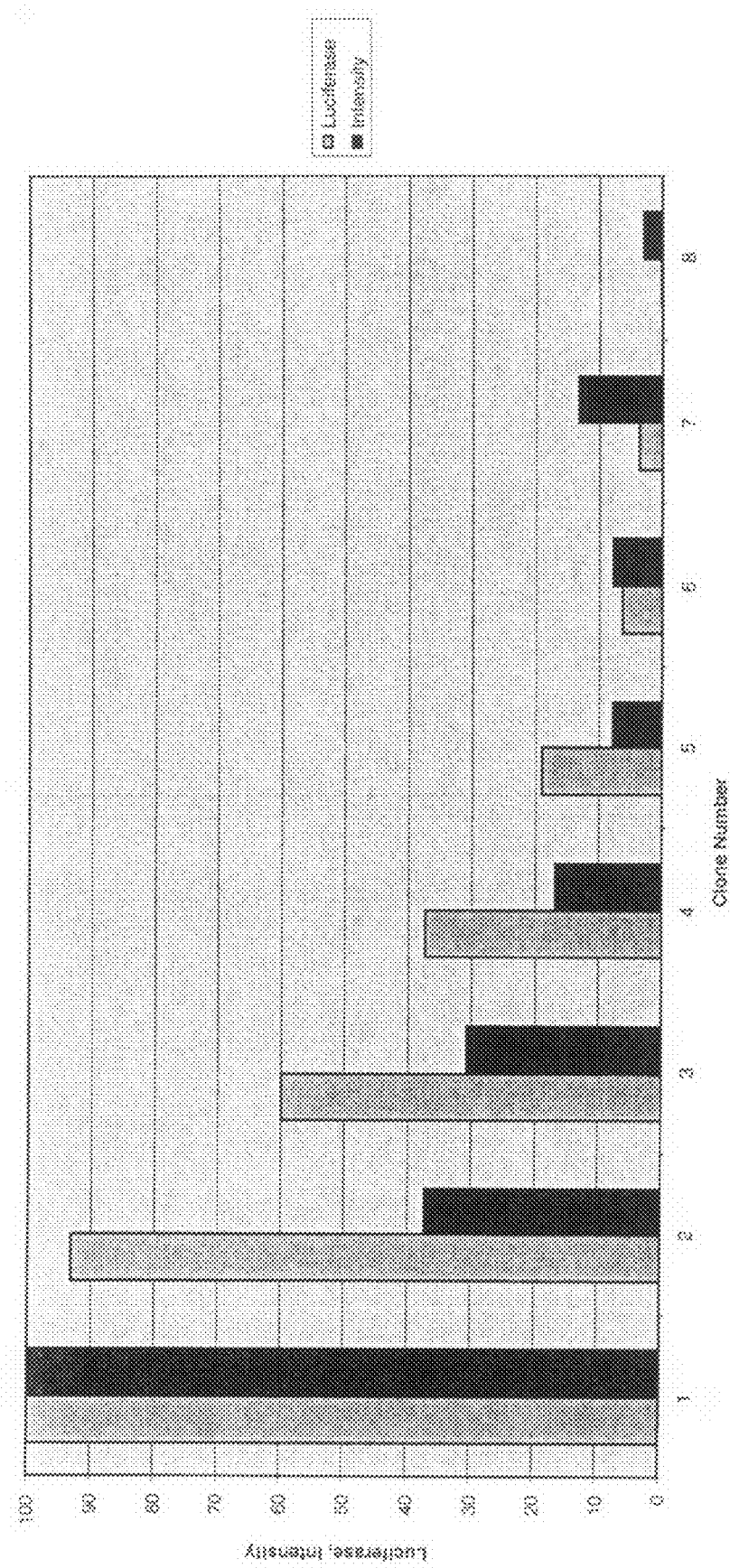
FIG. 12 is a graph illustrating copy number-dependence of STAR function. The copy number of pSDH-Tet-STAR10 expression units in each clone was determined by phosphorimagery and compared with the activity of the luciferase reporter enzyme expressed by each clone.

The enzyme activities and copy numbers (DNA band intensities) of luciferase in the clones from the pSDH-Tet-STAR10 clone population is shown in FIG. 12. The transgene copy number is highly correlated with the level of luciferase expression in these pSDH-Tet-STAR10 clones (r=0.86). This suggests that STAR10 (SEQ ID NO:10) confers copy number-dependence on the transgene expression units, making transgene expression independent of other transgene copies in tandem arrays and independent of gene-silencing influences at the site of integration.

Example 10

STAR Elements Function as Enhancer Blockers but not Enhancers

Gene promoters are subject to both positive and negative influences on their ability to initiate transcription. An important class of elements that exert positive influences are enhancers. Enhancers are characteristically able to affect promoters even when they are located far away (many kilobase pairs) from the promoter. Negative influences that act by heterochromatin formation (e.g., Polycomb group proteins) have been described above, and these are the target of STAR activity. The biochemical basis for enhancer function and for heterochromatin formation is fundamentally similar, since they both involve binding of proteins to DNA. Therefore, it is important to determine whether STAR elements are able to block positive influences as well as negative influences, in other words, to shield transgenes from genomic enhancers in the vicinity of the site of integration. The ability to shield transgenes from enhancer activity ensures stable and predictable performance of transgenes in biotechnological applications. This example examines the performance of STAR elements in an enhancer-blocking assay.

Another feature of STAR activity that is important to their function is the increased yield they confer on transgenes (Example 2). STARs are isolated on the basis of their ability to maintain high levels of zeocin expression when heterochromatin-forming proteins are bound adjacent to the candidate STAR elements. High expression is predicted to occur because STARs are anticipated to block the spread of heterochromatin into the zeocin expression unit. However, a second scenario is that the DNA fragments in zeocin-resistant clones contain enhancers. Enhancers have been demonstrated to have the ability to overcome the repressive effects of Polycomb-group proteins such as those used in the method of the STAR screen (Zink and Paro, 1995). Enhancers isolated by this phenomenon would be considered false positives, since enhancers do not have the properties claimed here for STARs. In order to demonstrate that STAR elements are not enhancers, they have been tested in an enhancer assay.

Figure 13:
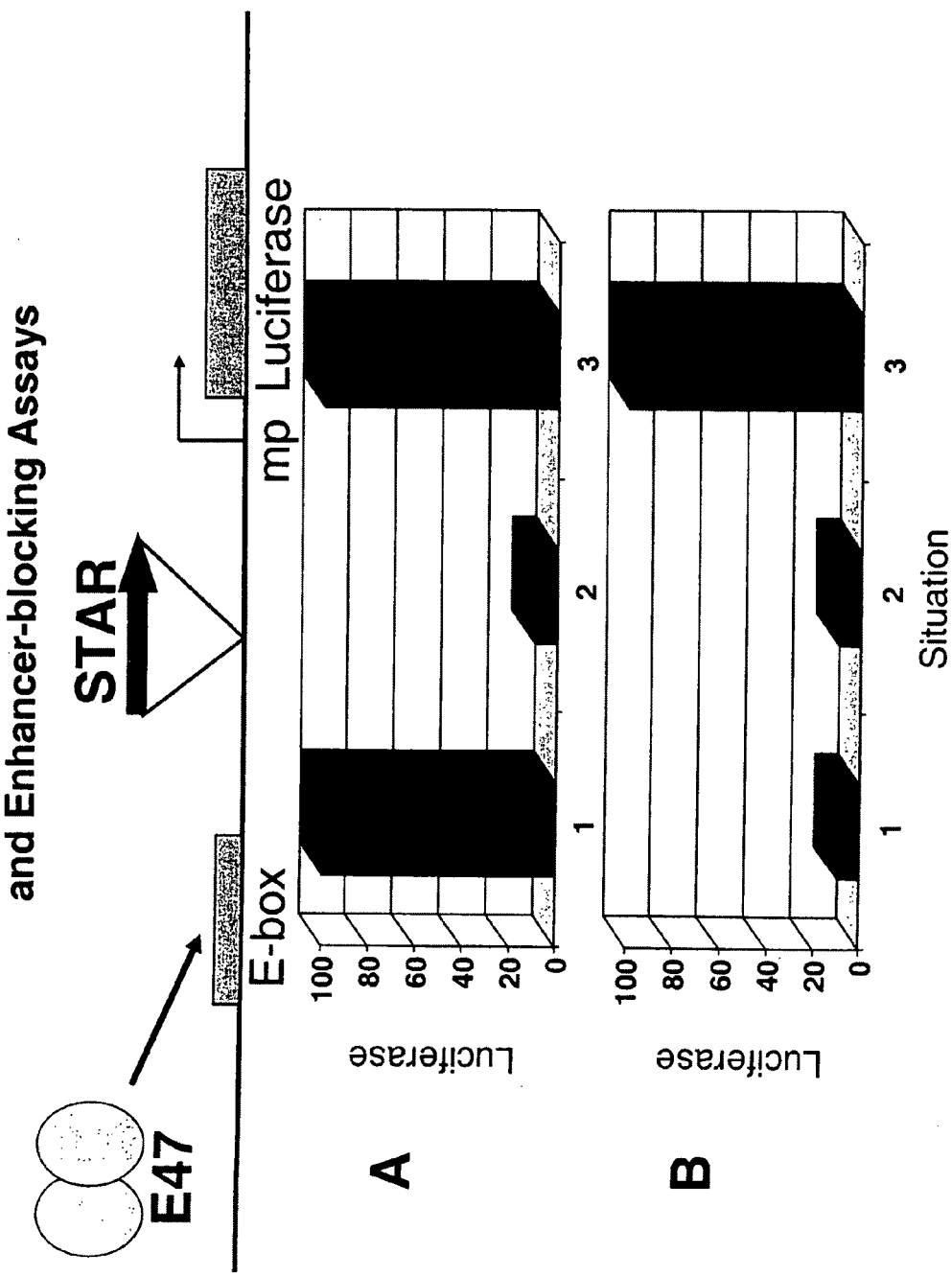
FIG. 13 is a schematic diagram and graphs depicting enhancer-blocking and enhancer assays. The luciferase expression vectors used for testing STARs for enhancer-blocking and enhancer activity are shown schematically. The E-box binding site for the E47 enhancer protein is upstream of a cloning site for STAR elements. Downstream of the STAR cloning site is the luciferase gene under control of a human alkaline phosphatase minimal promoter (mp). The histograms indicate the expected outcomes for the three possible experimental situations (see text). Panel A: Enhancer-blocking assay. Panel B: Enhancer assay.

The enhancer-blocking assay and the enhancer assay are methodologically and conceptually similar. The assays are shown schematically in FIG. 13. The ability of STAR elements to block enhancers is performed using the E47/E-box enhancer system. The E47 protein is able to activate transcription by promoters when it is bound to an E-box DNA sequence located in the vicinity of those promoters (Quong et al., 2002). E47 is normally involved in regulation of B and T lymphocyte differentiation (Quong et al., 2002), but it is able to function in diverse cell types when expressed ectopically (Petersson et al., 2002). The E-box is a palindromic DNA sequence, CANNTG (Knofler et al., 2002). In the enhancer-blocking assay, an E-box is placed upstream of a luciferase reporter gene (including a minimal promoter) in an expression vector. A cloning site for STAR elements is placed between the E-box and the promoter. The E47 protein is encoded on a second plasmid. The assay is performed by transfecting both the E47 plasmid and the luciferase expression vector into cells; the E47 protein is expressed and binds to the E-box, and the E47/E-box complex is able to act as an enhancer. When the luciferase expression vector does not contain a STAR element, the E47/E-box complex enhances luciferase expression (FIG. 13A, situation 1). When STAR elements are inserted between the E-box and the promoter, their ability to block the enhancer is demonstrated by reduced expression of luciferase activity (FIG. 13A, situation 2); if STARs cannot block enhancers, luciferase expression is activated (FIG. 13A, situation 3).

The ability of STAR elements to act as enhancers utilizes the same luciferase expression vector. In the absence of E47, the E-box itself does not affect transcription. Instead, enhancer behavior by STAR elements will result in activation of luciferase transcription. The assay is performed by transfecting the luciferase expression vector without the E47 plasmid. When the expression vector does not contain STAR elements, luciferase expression is low (FIG. 13B, situation 1). If STAR elements do not have enhancer properties, luciferase expression is low when a STAR element is present in the vector (FIG. 13B, situation 2). If STAR elements do have enhancer properties, luciferase expression will be activated in the STAR-containing vectors (FIG. 13B, situation 3).

Materials and Methods

The luciferase expression vector was constructed by inserting the E-box and a human alkaline phosphatase minimal promoter from plasmid mu-E5+E2x6-cat(x) (Ruezinsky et al., 1991) upstream of the luciferase gene in plasmid pGL3-basic (Promega E1751), to create pGL3-E-box-luciferase (gift of W. Romanow). The E47 expression plasmid contains the E47 open reading frame under control of a beta-actin promoter in the pHBAPr-1-neo plasmid; E47 in constitutively expressed from this plasmid (gift of W. Romanow).

STAR elements 1, 2, 3, 6, 10, 11, 18, and 27 (SEQ ID NOS:1, 2, 3, 6, 10, 11, 18, and 27, respectively) have been cloned into the luciferase expression vector. Clones containing the Drosophila scs element and the chicken beta-globin HS4-6x core ("HS4") element have been included as positive controls (they are known to block enhancers, and to have no intrinsic enhancer properties (Chung et al., 1993, Kellum and Schedl, 1992)), and the empty luciferase expression vector has been included as a negative control. All assays were performed using the U-2 OS cell line. In the enhancer-blocking assay, the E47 plasmid was co-transfected with the luciferase expression vectors (empty vector, or containing STAR or positive-control elements). In the enhancer assay, the E47 plasmid was co-transfected with STARless luciferase expression vector as a positive control for enhancer activity; all other samples received a mock plasmid during co-transfection. The transiently transfected cells were assayed for luciferase activity 48 hours after plasmid transfection (supra). The luciferase activity expressed from a plasmid containing no E-box or STAR/control elements was subtracted, and the luciferase activities were normalized to protein content as described (supra).

Results

Figure 14:
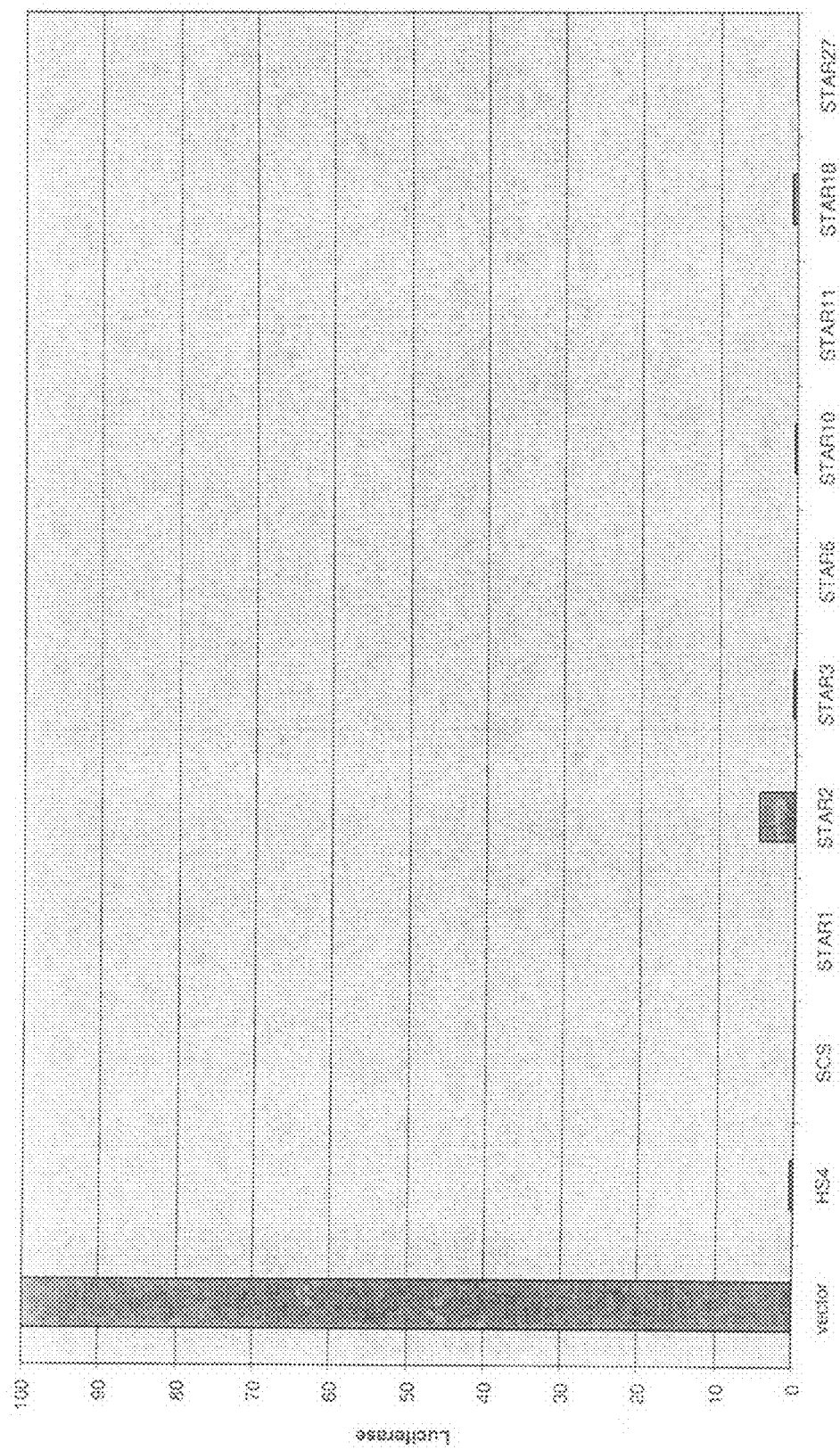
FIG. 14 is a graph showing enhancer-blocking assay. Luciferase expression from a minimal promoter is activated by the E47/E-box enhancer in the empty vector (vector). Insertion of enhancer-blockers (scs, HS4) or STAR elements (STAR elements 1, 2, 3, 6, 10, 11, 18, and 27; SEQ ID NOS:1, 2, 3, 6, 10, 11, 18 and 27, respectively) block luciferase activation by the E47/E-box enhancer.

FIG. 14 shows the results of the enhancer-blocking assay. In the absence of STAR elements (or the known enhancer-blocking elements scs and HS4), the E47/E-box enhancer complex activates expression of luciferase ("vector"); this enhanced level of expression has been normalized to 100. Enhancer activity is blocked by all STAR elements tested. Enhancer activity is also blocked by the HS4 and scs elements, as expected (Bell et al., 2001, Gerasimova and Corces, 2001). These results demonstrate that in addition to their ability to block the spreading of transcriptional silencing (negative influences), STAR elements are able to block the action of enhancers (positive influences).

Figure 15:
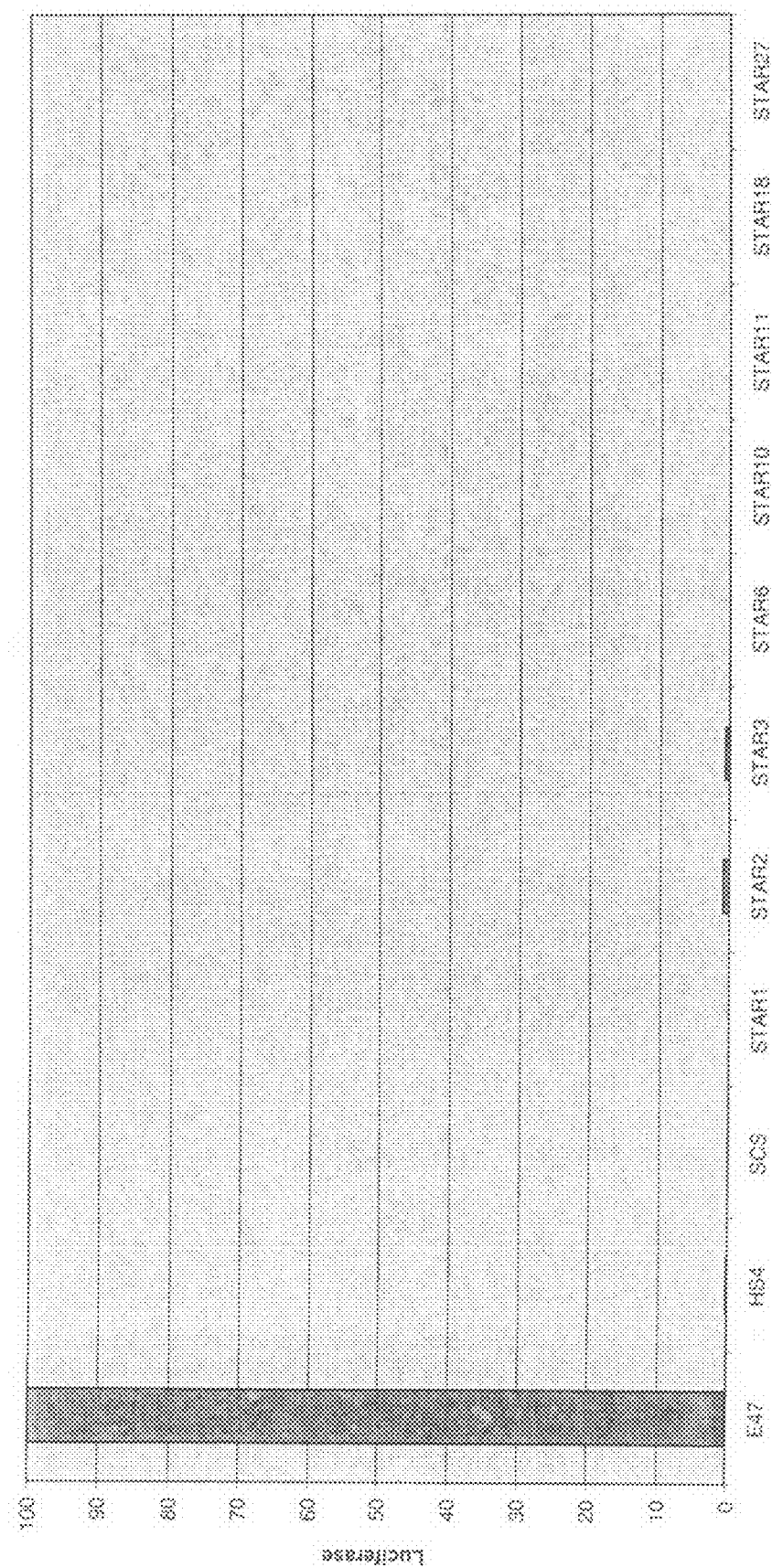
FIG. 15 is a graph illustrating enhancer assay. Luciferase expression from a minimal promoter is activated by the E47/E-box enhancer in the empty vector (E47). Insertion of the scs and HS4 elements or various STAR elements (STARs 1, 2, 3, 6, 10, 11, 18, and 27; SEQ ID NOS:1, 2, 3, 6, 10, 11, 18 and 27, respectively) do not activate transcription of the reporter gene.

FIG. 15 shows the results of the enhancer assay. The level of luciferase expression due to enhancement by the E47/E-box complex is set at 100 ("E47"). By comparison, none of the STAR elements bring about significant activation of luciferase expression. As expected, the scs and HS4 elements also do not bring about activation of the reporter gene. Therefore, it is concluded that at least the tested STAR elements do not possess enhancer properties.

Example 11

Star Elements are Conserved Between Mouse and Human

BLAT analysis of the STAR DNA sequence against the human genome database (http://genome.ucsc.edu/cgi-bin/hgGateway) reveals that some of these sequences have high sequence conservation with other regions of the human genome. These duplicated regions are candidate STAR elements; if they do show STAR activity, they would be considered paralogs of the cloned STARs (two genes or genetic elements are said to be paralogous if they are derived from a duplication event (Li, 1997)).

BLAST analysis of the human STARs against the mouse genome (http://www.ensembl.org/Mus_musculus/blastview) also reveals regions of high sequence conservation between mouse and human. This sequence conservation has been shown for fragments of 15 out of the 65 human STAR elements. The conservation ranges from 64% to 89%, over lengths of 141 base pairs to 909 base pairs (Table 5). These degrees of sequence conservation are remarkable and suggest that these DNA sequences may confer STAR activity within the mouse genome as well. Some of the sequences from the mouse and human genomes in Table 5 could be strictly defined as orthologs (two genes or genetic elements are said to be orthologous if they are derived from a speciation event (Li, 1997)). For example, STAR6 (SEQ ID NO:6) is between the SLC8A1 and HAAO genes in both the human and mouse genomes. In other cases, a cloned human STAR has a paralog within the human genome, and its ortholog has been identified in the mouse genome. For example, STAR3a is a fragment of the 15q11.2 region of human chromosome 15. This region is 96.9% identical (paralogous) with a DNA fragment at 5q33.3 on human chromosome 5, which is near the IL12B interleukin gene. These human DNAs share approximately 80% identity with a fragment of the 11B2 region on mouse chromosome 11. The 11B2 fragment is also near the (mouse) IL12B interleukin gene. Therefore, STAR3a and the mouse 11B2 fragment can be strictly defined as paralogs.

In order to test the hypothesis that STAR activity is shared between regions of high sequence conservation in the mouse and human genome, one of the human STARs with a conserved sequence in mouse, STAR18 (SEQ ID NO:18), has been analyzed in greater detail. The sequence conservation in the mouse genome detected with the original STAR18 clone extends leftward on human chromosome 2 for about 500 base pairs (FIG. 16; left and right relate to the standard description of the arms of chromosome 2). In this example, we examine whether the region of sequence conservation defines a "naturally occurring" STAR element in human that is more extensive in length than the original clone. We also examine whether the STAR function of this STAR element is conserved between mouse and human.

Materials and Methods

The region of mouse/human sequence conservation around STAR18 (SEQ ID NO:18) was recovered from human BAC clone RP11-387A1 by PCR amplification, in three fragments: the entire region (primers E93 (SEQ ID NO:171) and E94 (SEQ ID NO:172)), the leftward half (primers E93 (SEQ ID NO:171) and E92 (SEQ ID NO:170)), and the rightward half (primers E57 (SEQ ID NO:169) and E94 (SEQ ID NO:172)). The corresponding fragments from the homologous mouse region were recovered from BAC clone RP23-400H17 in the same fashion (primers E95 (SEQ ID NO:173) and E98 (SEQ ID NO:176), E95 (SEQ ID NO:173) and E96 (SEQ ID NO:174), and E97 (SEQ ID NO:175) and E98 (SEQ ID NO:176), respectively). All fragments were cloned into the pSelect vector and transfected into a U-2 OS/Tet-Off/LexA-HP1 cell line (supra). Following transfection, hygromycin selection was carried out to select for transfected cells. The LexA-HP1 protein was induced by lowering the doxycycline concentration, and the ability of the transfected cells to withstand the antibiotic zeocin (a measure of STAR activity) was assessed by monitoring cell growth.

Results

Figure 16:
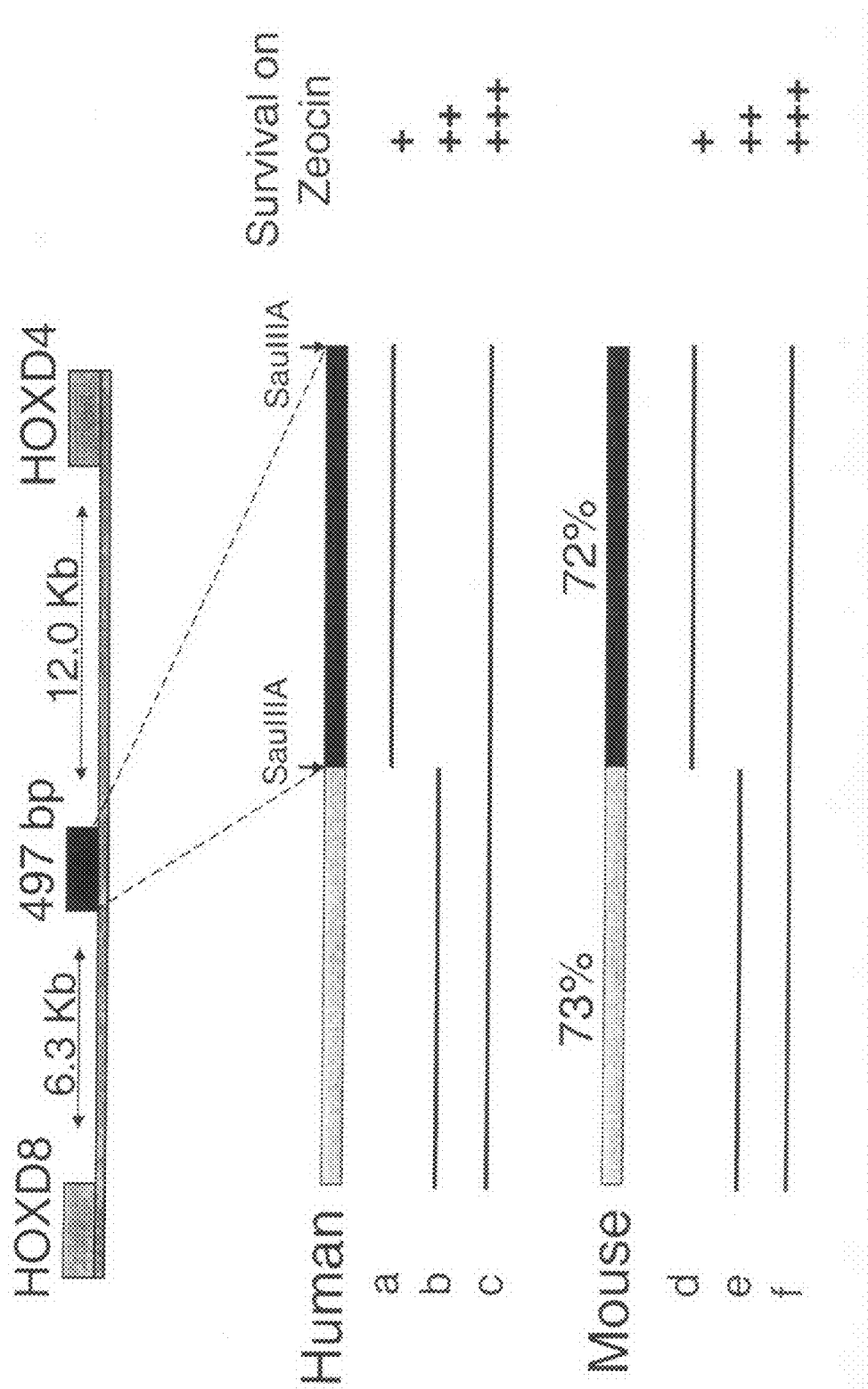
FIG. 16 illustrates STAR18 (SEQ ID NO:18) sequence conservation between mouse and human. The region of the human genome containing 497 base pair STAR18 (SEQ ID NO:18) is shown (black boxes); the element occurs between the HOXD8 and HOXD4 homeobox genes on human chromosome 2. It is aligned with a region in mouse chromosome 2 that shares 72% sequence identity. The region of human chromosome 2 immediately to the left of STAR18 (SEQ ID NO:18) is also highly conserved with mouse chromosome 2 (73% identity; gray boxes); beyond these region, the identity drops below 60%. The ability of these regions from human and mouse, either separately or in combination, to confer growth on zeocin is indicated: −, no growth; +, moderate growth; ++, vigorous growth; +++, rapid growth.

The original STAR18 clone was isolated from Sau3AI digested human DNA ligated into the pSelect vector on the basis of its ability to prevent silencing of a zeocin resistance gene. Alignment of the human STAR18 clone (497 base pairs) with the mouse genome revealed high sequence similarity (72%) between the orthologous human and mouse STAR18 (SEQ ID NO:18) regions. It also uncovered high similarity (73%) in the region extending for 488 base pairs immediately to the left of the Sau3AI site that defines the left end of the cloned region (FIG. 16). Outside these regions the sequence similarity between human and mouse DNA drops below 60%.

As indicated in FIG. 16, both the human and the mouse STAR18 (SEQ ID NO:18) elements confer survival on zeocin to host cells expressing the lexA-HP1 repressor protein. The original 497 base pair STAR18 clone and its mouse ortholog both confer the ability to grow (FIG. 16, a and d). The adjacent 488 base pair regions of high similarity from both genomes also confer the ability to grow, and in fact their growth phenotype is more vigorous than that of the original STAR18 clone (FIG. 16, b and e). When the entire region of sequence similarity was tested, these DNAs from both mouse and human confer growth, and the growth phenotype is more vigorous than the two sub-fragments (FIG. 16, c and f). These results demonstrate that the STAR activity of human STAR18 (SEQ ID NO:18) is conserved in its ortholog from mouse. The high sequence conservation between these orthologous regions is particularly noteworthy because they are not protein-coding sequences, leading to the conclusion that they have some regulatory function that has prevented their evolutionary divergence through mutation.

This analysis demonstrates that cloned STAR elements identified by the original screening program may in some cases represent partial STAR elements, and that analysis of the genomic DNA in which they are embedded can identify sequences with stronger STAR activity.

Example 12

STAR Elements Contain Characteristic DNA Sequence Motifs

STAR elements are isolated on the basis of their anti-repression phenotype with respect to transgene expression. This anti-repression phenotype reflects underlying biochemical processes that regulate chromatin formation which are associated with the STAR elements. These processes are typically sequence-specific and result from protein binding or DNA structure. This suggests that STAR elements will share DNA sequence similarity. Identification of sequence similarity among STAR elements will provide sequence motifs that are characteristic of the elements that have already been identified by functional screens and tests. The sequence motifs will also be useful to recognize and claim new STAR elements whose functions conform to the claims of this patent. The functions include improved yield and stability of transgenes expressed in eukaryotic host cells.

Other benefits of identifying sequence motifs that characterize STAR elements include: (1) provision of search motifs for prediction and identification of new STAR elements in genome databases, (2) provision of a rationale for modification of the elements, and (3) provision of information for functional analysis of STAR activity. Using bio-informatics, sequence similarities among STAR elements have been identified; the results are presented in this example.

Bio-Informatic and Statistical Background

Regulatory DNA elements typically function via interaction with sequence-specific DNA-binding proteins. Bio-informatic analysis of DNA elements, such as STAR elements whose regulatory properties have been identified, but whose interacting proteins are unknown, requires a statistical approach for identification of sequence motifs. This can be achieved by a method that detects short DNA sequence patterns that are over-represented in a set of regulatory DNA elements (e.g., the STAR elements) compared to a reference sequence (e.g., the complete human genome). The method determines the number of observed and expected occurrences of the patterns in each regulatory element. The number of expected occurrences is calculated from the number of observed occurrences of each pattern in the reference sequence.

The DNA sequence patterns can be oligonucleotides of a given length, e.g., six base pairs. In the simplest analysis, for a six-base-pair oligonucleotide (hexamer) composed of the four nucleotides (A, C, G, and T) there are $4^6=4096$ distinct oligonucleotides (all combinations from AAAAAA (SEQ ID NO:121) to TTTTTT (SEQ ID NO:122)). If the regulatory and reference sequences were completely random and had equal proportions of the A, C, G, and T nucleotides, then the expected frequency of each hexamer would be 1/4096 (~0.00024). However, the actual frequency of each hexamer in the reference sequence is typically different than this due to biases in the content of G:C base pairs, etc. Therefore, the frequency of each oligonucleotide in the reference sequence is determined empirically by counting, to create a "frequency table" for the patterns.

The pattern frequency table of the reference sequence is then used to calculate the expected frequency of occurrence of each pattern in the regulatory element set. The expected frequencies are compared with the observed frequencies of occurrence of the patterns. Patterns that are "over-represented" in the set are identified; for example, if the hexamer ACGTGA (SEQ ID NO:123) is expected to occur five times in 20 kilobase pairs of sequence, but is observed to occur 15 times, then it is three-fold over-represented. Ten of the 15 occurrences of that hexameric sequence pattern would not be expected in the regulatory elements if the elements had the same hexamer composition as the entire genome. Once the over-represented patterns are identified, a statistical test is applied to determine whether their over-representation is significant, or may be due to chance. For this test, a significance index, "sig," is calculated for each pattern. The significance index is derived from the probability of occurrence of each pattern, which is estimated by a binomial distribution. The probability takes into account the number of possible patterns (4096 for hexamers). The highest sig values correspond to the most overrepresented oligonucleotides (van Helden et al., 1998). In practical terms, oligonucleotides with sig $\geq 0$ are considered as over-represented. A pattern with sig $\geq 0$ is likely to be over-represented due to chance once ($=10^0$) in the set of regulatory element sequences. However, at sig $\geq 1$ a pattern is expected to be over-represented once in ten ($=10^1$) sequence sets, sig $\geq 2$ once in 100 ($=10^2$) sequence sets, etc.

The patterns that are significantly over-represented in the regulatory element set are used to develop a model for classification and prediction of regulatory element sequences. This employs Discriminant Analysis, a so-called "supervised" method of statistical classification known to one of ordinary skill in the art (Huberty, 1994). In Discriminant Analysis, sets of known or classified items (e.g., STAR elements) are used to "train" a model to recognize those items on the basis of specific variables (e.g., sequence patterns such as hexamers). The trained model is then used to predict whether other items should be classified as belonging to the set of known items (e.g., is a DNA sequence a STAR element). In this example, the known items in the training set are STAR elements (positive training set). They are contrasted with sequences that are randomly selected from the genome (negative training set) which have the same length as the STAR elements. Discriminant Analysis establishes criteria for discriminating positives from negatives based on a set of variables that distinguish the positives; in this example, the variables are the significantly over-represented patterns (e.g., hexamers).

When the number of over-represented patterns is high compared to the size of the training set, the model could become biased due to over-training. Over-training is circumvented by applying a forward stepwise selection of variables (Huberty, 1994). The goal of Stepwise Discriminant Analysis is to select the minimum number of variables that provides maximum discrimination between the positives and negatives. The model is trained by evaluating variables one-by-one for their ability to properly classify the items in the positive and negative training sets. This is done until addition of new variables to the model does not significantly increase the model's predictive power (i.e., until the classification error rate is minimized). This optimized model is then used for testing, in order to predict whether "new" items are positives or negatives (Huberty, 1994).

It is inherent in classification statistics that for complex items such as DNA sequences, some elements of the positive training set will be classified as negatives (false negatives), and some members of the negative training set will be classified as positives (false positives). When a trained model is applied to testing new items, the same types of misclassifications are expected to occur.

In the bio-informatic method described here, the first step, Pattern Frequency Analysis, reduces a large set of sequence patterns (e.g., all 4096 hexamers) to a smaller set of significantly over-represented patterns (e.g., 100 hexamers); in the second step, Stepwise Discriminant Analysis reduces the set of over-represented patterns to the subset of those patterns that have maximal discriminative power (e.g., five to ten hexamers). Therefore, this approach provides simple and robust criteria for identifying regulatory DNA elements such as STAR elements.

DNA-binding proteins can be distinguished on the basis of the type of binding site they occupy. Some recognize contiguous sequences; for this type of protein, patterns that are oligonucleotides of length six base pairs (hexamers) are fruitful for bio-informatic analysis (van Helden et al., 1998). Other proteins bind to sequence dyads: contact is made between pairs of highly conserved trinucleotides separated by a non-conserved region of fixed width (van Helden et al., 2000). In order to identify sequences in STAR elements that may be bound by dyad-binding proteins, frequency analysis was also conducted for this type of pattern, where the spacing between the two trinucleotides was varied from 0 to 20 (i.e., XXXN{0-20}XXX where X's are specific nucleotides composing the trinucleotides, and N's are random nucleotides from 0 to 20 base pairs in length). The results of dyad frequency analysis are also used for Linear Discriminant Analysis as described above.

Materials and Methods

Using the genetic screen described in the original patent application, sixty-six (66) STAR elements were initially isolated from human genomic DNA and characterized in detail (Table 3). The screen was performed on gene libraries constructed by Sau3AI digestion of human genomic DNA, either purified from placenta (Clontech 6550-1) or carried in bacterial/P1 (BAC/PAC) artificial chromosomes. The BAC/PAC clones contain genomic DNA from regions of chromosome 1 (clones RP1154H19 and RP3328E19), from the HOX cluster of homeotic genes (clones RP1167F23, RP1170019, and RP11387A1), or from human chromosome 22 (Research Genetics 96010-22). The DNAs were size-fractionated, and the 0.5-2 kb size fraction was ligated into BamHI-digested pSelect vector, by standard techniques (Sambrook et al., 1989). pSelect plasmids containing human genomic DNA that conferred resistance to zeocin at low doxycycline concentrations were isolated and propagated in *Escherichia coli*. The screens that yielded the STAR elements of Table 3 have assayed approximately 1-2% of the human genome.

The human genomic DNA inserts in these 66 plasmids were sequenced by the dideoxy method (Sanger et al., 1977) using a Beckman CEQ™2000 automated DNA sequencer, using the manufacturer's instructions. Briefly, DNA was purified from *E. coli* using QIAprep® Spin Miniprep and Plasmid Midi Kits (QIAGEN® 27106 and 12145, respectively). Cycle sequencing was carried out using custom oligonucleotides corresponding to the pSelect vector (primers D89 (SEQ ID NO:149) and D95 (SEQ ID NO:154), Table 2), in the presence of dye terminators (CEQ™ Dye Terminator Cycle Sequencing Kit, Beckman 608000). Assembled STAR DNA sequences were located in the human genome (database builds August and December 2001) using BLAT (Basic Local Alignment Tool (Kent, 2002); http://genome.ucsc.edu/cgi-bin/hgGateway; Table 3). In aggregate, the combined STAR sequences comprise 85.6 kilobase pairs, with an average length of 1.3 kilobase pairs.

Figure 17:
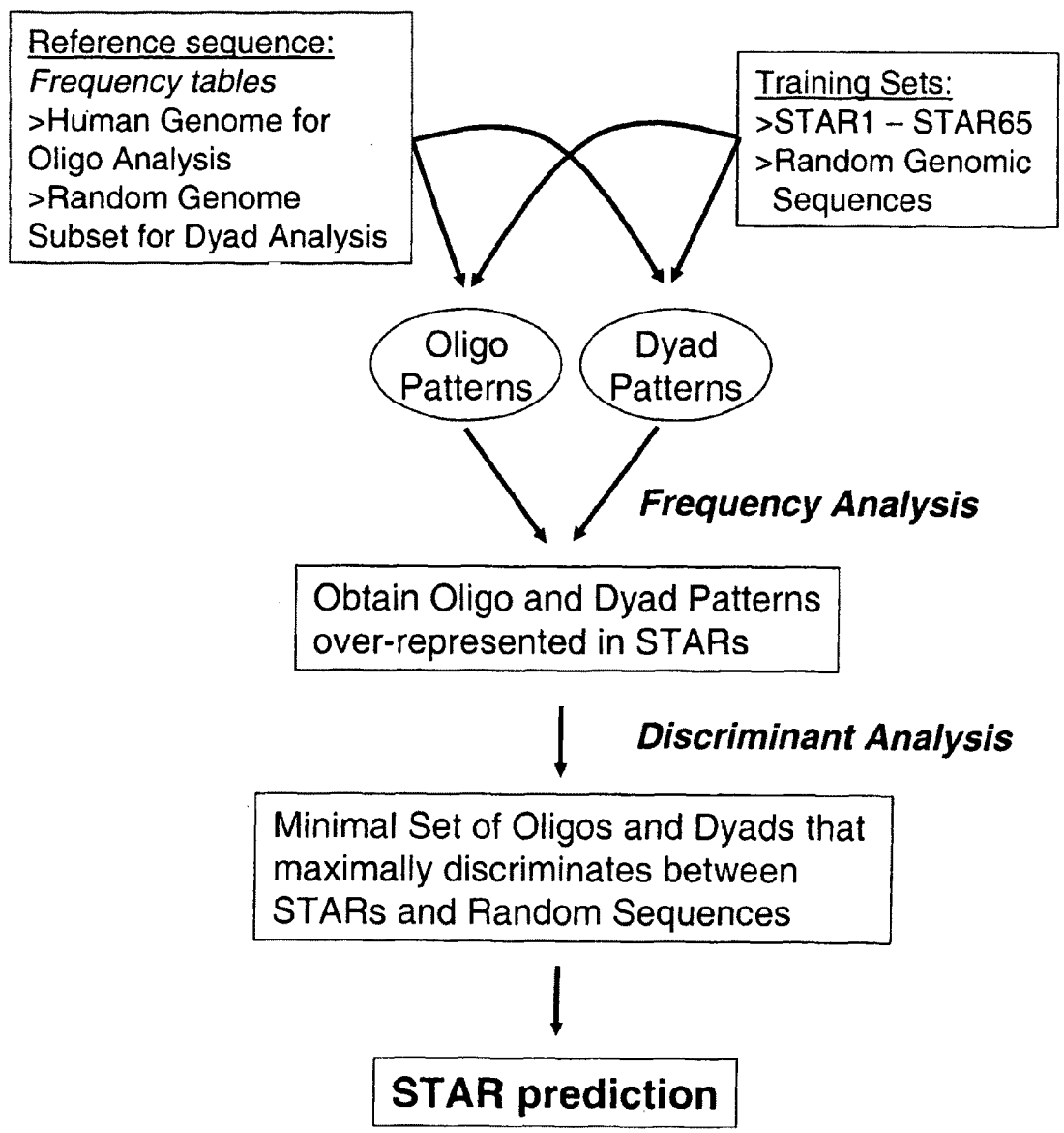
FIG. 17 is a schematic diagram of bio-informatic analysis workflow. For details, see text.

Sequence motifs that distinguish STAR elements within human genomic DNA were identified by bio-informatic analysis using a two-step procedure, as follows (see FIG. 17 for a schematic diagram). The analysis has two input datasets: (1) the DNA sequences of the STAR elements (STAR1-STAR65 (SEQ ID NOS:1-65) were used; Table 3); and (2) the DNA sequence of the human genome (except for chromosome 1, which was not feasible to include due to its large size; for dyad analysis a random subset of human genomic DNA sequence (~27 Mb) was used).

Pattern Frequency Analysis

The first step in the analysis uses RSA-Tools software (Regulatory Sequence Analysis Tools; http://www.ucmb.ulb.ac.be/bioinformatics/rsa-tools/; references (van Helden et al., 1998, van Helden et al., 2000, van Helden et al., 2000)) to determine the following information: (1) the frequencies of all dyads and hexameric oligonucleotides in the human genome; (2) the frequencies of the oligonucleotides and dyads in the 65 STAR elements; and (3) the significance indices of those oligonucleotides and dyads that are over-represented in the STAR elements compared to the genome. A control analysis was done with 65 sequences that were selected at random from the human genome (i.e., from 2689×$10^3$ kilobase pairs) that match the length of the STAR elements of Table 3.

Discriminant Analysis

The over-represented oligonucleotides and dyads were used to train models for prediction of STAR elements by Linear Discriminant Analysis (Huberty, 1994). A pre-selection of variables was performed by selecting the 50 patterns with the highest individual discriminatory power from the over-represented oligos or dyads of the frequency analyses. These pre-selected variables were then used for model training in a Stepwise Linear Discriminant Analysis to select the most discriminant combination of variables (Huberty, 1994). Variable selection was based on minimizing the classification error rate (percentage of false negative classifications). In addition, the expected error rate was estimated by applying the same discriminant approach to the control set of random sequences (minimizing the percentage of false positive classifications).

The predictive models from the training phase of Discriminant Analysis were tested in two ways. First, the STAR elements and random sequences that were used to generate the model (the training sets) were classified. Second, sequences in a collection of 19 candidate STAR elements (recently cloned by zeocin selection as described above) were classified. These candidate STAR elements are listed in Table 8 (SEQ ID NOS:66-84).

Results

Pattern frequency analysis was performed with RSA-Tools on 65 STAR elements, using the human genome as the reference sequence. One hundred sixty-six (166) hexameric oligonucleotides were found to be over-represented in the set of STAR elements (sig ≧0) compared to the entire genome (Table 6). The most significantly over-represented oligonucleotide, CCCCAC (SEQ ID NO:177), occurs 107 times among the 65 STAR elements, but is expected to occur only 49 times. It has a significance coefficient of 8.76; in other words, the probability that its over-representation is due to random chance is $\frac{1}{10^{8.76}}$, i.e., less than one in 500 million.

Ninety-five of the oligonucleotides have a significance coefficient greater than one, and are, therefore, highly over-represented in the STAR elements. Among the over-represented oligonucleotides, their observed and expected occurrences, respectively, range from 6 and 1 (for oligo 163, CGCGAA (SEQ ID NO:339), sig=0.02) to 133 and 95 (for oligo 120, CCCAGG (SEQ ID NO:296), sig=0.49). The differences in expected occurrences reflect factors such as the G:C content of the human genome. Therefore, the differences among the oligonucleotides in their number of occurrences is less important than their over-representation; for example, oligo 2 (CAGCGG (SEQ ID NO:178)) is 36/9=four-fold over-represented, which has a probability of being due to random chance of one in fifty million (sig=7.75).

Table 6 also presents the number of STAR elements in which each over-represented oligonucleotide is found. For example, the most significant oligonucleotide, oligo 1 (CCCCAC (SEQ ID NO:177)), occurs 107 times, but is found in only 51 STARs, i.e., on average it occurs as two copies per STAR. The least abundant oligonucleotide, number 166 (AATCGG (SEQ ID NO:342)), occurs on average as a single copy per STAR (thirteen occurrences on eleven STARs); single-copy oligonucleotides occur frequently, especially for the lower-abundance oligos. At the other extreme, oligo 4 (CAGCCC (SEQ ID NO:527)) occurs on average three times in those STARs in which it is found (37 STARs). The most widespread oligonucleotide is number 120 (CCCAGG (SEQ ID NO:296)), which occurs on 58 STARs (on average twice per STAR), and the least widespread oligonucleotide is number 114 (CGTCGC (SEQ ID NO:290)), which occurs on only six STARs (and on average only once per STAR).

Results of dyad frequency analysis are given in Table 7. Seven hundred thirty (730) dyads were found to be over-represented in the set of STAR elements (sig ≧0) compared to the reference sequence. The most significantly over-represented dyad, CCCN{2}CGG (SEQ ID NO:343), occurs 36 times among the 65 STAR elements, but is expected to occur only seven times. It has a significance coefficient of 9.31; in other words, the probability that its over-representation is due to chance is $\frac{1}{10^{9.31}}$, i.e., less than one in two billion.

Three hundred ninety-seven (397) of the dyads have a significance coefficient greater than 1, and are, therefore, highly over-represented in the STAR elements. Among the over-represented dyads, their observed and expected occurrences, respectively, range from 9 and 1 (for five dyads (numbers 380, 435, 493, 640, and 665)) to 118 and 63 (for number 30 (AGGN{2}GGG (SEQ ID NO:372)), sig=4.44).

The oligonucleotides and dyads found to be over-represented in STAR elements by pattern frequency analysis were tested for their discriminative power by Linear Discriminant Analysis. Discriminant models were trained by step-wise selection of the best combination among the 50 most discriminant oligonucleotide (Table 6) or dyad (Table 7) patterns. The models achieved optimal error rates after incorporation of four (dyad) or five variables. The discriminative variables from oligo analysis are numbers 11, 30, 94, 122, and 160 (Table 6); those from dyad analysis are numbers 73, 194, 419, and 497 (Table 7).

Figure 18:
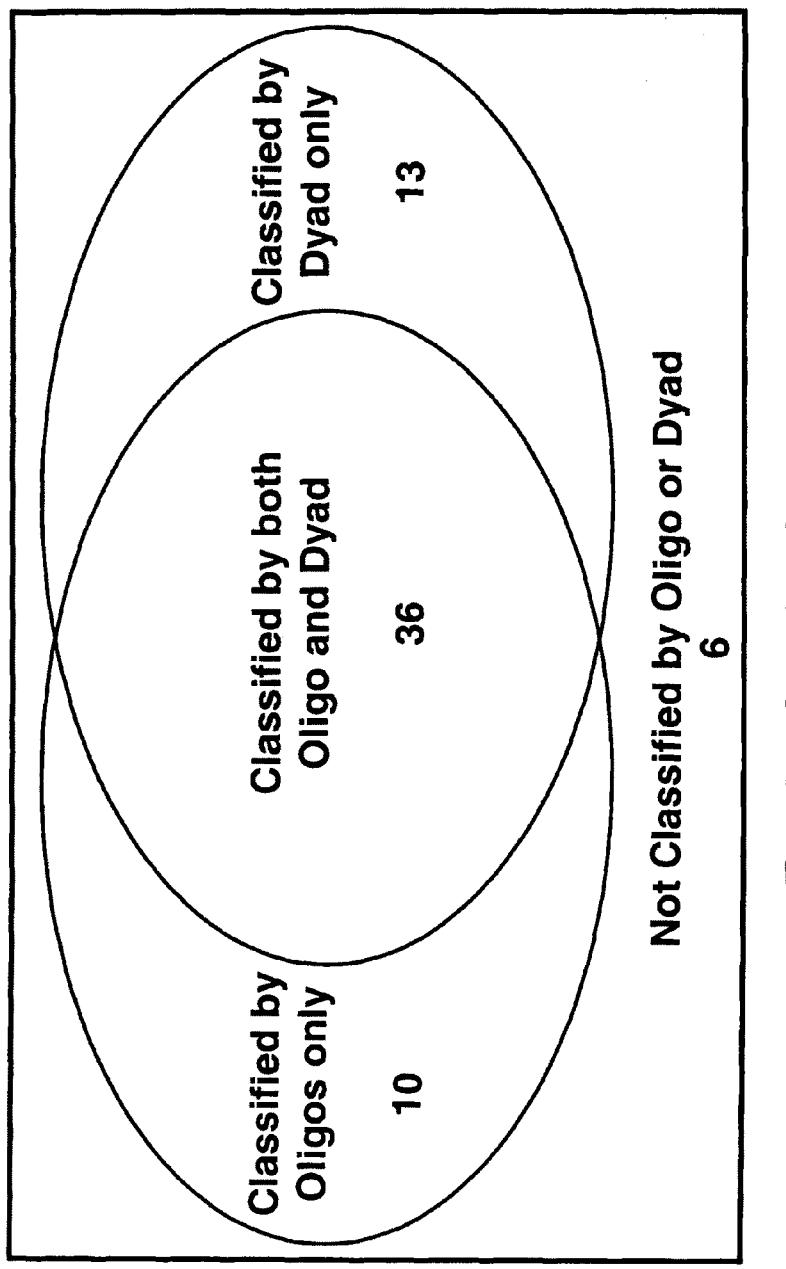
FIG. 18 is a schematic diagram showing the results of discriminant analysis on classification of the training set of 65 STAR elements. STAR elements that are correctly classified as STARs by Stepwise Linear Discriminant Analysis (LDA) are shown in a Venn diagram. The variables for LDA were selected from frequency analysis results for hexameric oligonucleotides ("oligos") and for dyads. The diagram indicates the concordance of the two sets of variables in correctly classifying STARs.

The discriminant models were then used to classify the 65 STAR elements in the training set and their associated random sequences. The model using oligonucleotide variables classifies 46 of the 65 STAR elements as STAR elements (true positives); the dyad model classifies 49 of the STAR elements as true positives. In combination, the models classify 59 of the 65 STAR elements as STAR elements (91%; FIG. 18). The false positive rates (random sequences classified as STARs) were seven for the dyad model, eight for the oligonucleotide model, and 13 for the combined predictions of the two models (20%). The STAR elements of Table 3 that were not classified as STARs by LDA are STAR7, STAR22, STAR35, STAR44, STAR46, and STAR65 (SEQ ID NOS:7, 22, 35, 44, 46 and 65, respectively). These elements display stabilizing anti-repressor activity in functional assays, so the fact that they are not classified as STARs by LDA suggests that they represent another class (or classes) of STAR elements.

The models were then used to classify the 19 candidate STAR elements in the testing set listed in Table 8. The dyad model classifies 12 of these candidate STARs as STAR elements, and the oligonucleotide model classifies 14 as STARs. The combined number of the candidates that are classified as STAR elements is 15 (79%). This is a lower rate of classification than obtained with the training set of 65 STARs; this is expected for two reasons. First, the discriminant models were trained with the 65 STARs of Table 3, and discriminative variables based on this training set may be less well represented in the testing set. Second, the candidate STAR sequences in the testing set have not yet been fully characterized in terms of in vivo function, and may include elements with only weak anti-repression properties.

This analysis demonstrates the power of a statistical approach to bio-informatic classification of STAR elements. The STAR sequences contain a number of dyad and hexameric oligonucleotide patterns that are significantly over-represented in comparison with the human genome as a whole. These patterns may represent binding sites for proteins that confer STAR activity; in any case they form a set of sequence motifs that can be used to recognize STAR element sequences.

Using these patterns to recognize STAR elements by Discriminant Analysis, a high proportion of the elements obtained by the genetic screen of the invention are in fact classified as STARs. This reflects underlying sequence and functional similarities among these elements. An important aspect of the method described here (pattern frequency analysis followed by Discriminant Analysis) is that it can be reiterated; for example, by including the 19 candidate STAR elements of Table 8 with the 66 STAR elements of Table 3 into one training set, an improved discriminant model can be trained. This improved model can then be used to classify other candidate regulatory elements as STARs. Large-scale in vivo screening of genomic sequences using the method of the invention, combined with reiteration of the bio-informatic analysis, will provide a means of discriminating STAR elements that asymptotically approaches 100% recognition and prediction of elements as the genome is screened in its entirety. These stringent and comprehensive predictions of STAR function will ensure that all human STAR elements are recognized, and are available for use in improving transgene expression.

Example 13

Cloning and Characterization of STAR Elements from *Arabidopsis thaliana*

Transgene silencing occurs in transgenic plants at both the transcriptional and post-transcriptional levels (Meyer, 2000, Vance and Vaucheret, 2001). In either case, the desired result of transgene expression can be compromised by silencing; the low expression and instability of the transgene results in poor expression of desirable traits (e.g., pest resistance) or low yields of recombinant proteins. It also results in poor predictability: the proportion of transgenic plants that express the transgene at biotechnologically useful levels is low, which necessitates laborious and expensive screening of transformed individuals for those with beneficial expression characteristics. This example describes the isolation of STAR elements from the genome of the dicot plant *Arabidopsis thaliana* for use in preventing transcriptional transgene silencing in transgenic plants. *Arabidopsis* was chosen for this example because it is a well-studied model organism: it has a compact genome, it is amenable to genetic and recombinant DNA manipulations, and its genome has been sequenced (Bevan et al., 2001, Initiative, 2000, Meinke et al., 1998).

Materials and Methods

Genomic DNA was isolated from *Arabidopsis thaliana* ecotype Columbia as described (Stam et al., 1998) and partially digested with MboI. The digested DNA was size-fractionated to 0.5-2 kilobase pairs by agarose gel electrophoresis and purification from the gel (QIAquick® Gel Extraction Kit, QIAGEN® 28706), followed by ligation into the pSelect vector (supra). Transfection into the U-2 OS/Tet-Off/LexA-HP1 cell line and selection for zeocin resistance at low doxycycline concentration was performed as described (supra). Plasmids were isolated from zeocin resistant colonies and re-transfected into the U-2 OS/Tet-Off/LexA-HP1 cell line.

Sequencing of *Arabidopsis* genomic DNA fragments that conferred zeocin resistance upon re-transfection was performed as described (supra). The DNA sequences were compared to the sequence of the *Arabidopsis* genome by BLAST analysis ((Altschul et al., 1990); URL http://www.ncbi.nlm.nih.gov/blast/Blast).

STAR activity was tested further by measuring mRNA levels for the hygromycin- and zeocin-resistance genes in recombinant host cells by reverse transcription PCR (RT-PCR). Cells of the U-2 OS/Tet-Off/lexA-HP1 cell line were transfected with pSelect plasmids containing *Arabidopsis* STAR elements, the *Drosophila* scs element, or containing no insert (supra). These were cultivated on hygromycin for two weeks at high doxycycline concentration, then the doxycycline concentration was lowered to 0.1 ng/ml to induce the lexA-HP1 repressor protein. After ten days, total RNA was isolated by the RNeasy® mini kit (QIAGEN® 74104) as described by the manufacturer. First-strand cDNA synthesis was carried out using the RevertAid™ First Strand cDNA Synthesis kit (MBI Fermentas 1622) using oligo(dT)18 primer as described by the manufacturer. An aliquot of the cDNA was used as the template in a PCR reaction using primers D58 (SEQ ID NO:145) and D80 (SEQ ID NO:148) (for the zeocin marker), and D70 (SEQ ID NO:146) and D71 (SEQ ID NO:147) (for the hygromycin marker), and Taq DNA polymerase (Promega M2661). The reaction conditions were 15-20 cycles of 94° C. for one minute, 54° C. for one minute, and 72° C. for 90 seconds. These conditions result in a linear relationship between input RNA and PCR product DNA. The PCR products were resolved by agarose gel electrophoresis, and the zeocin and hygromycin bands were detected by Southern blotting as described (Sambrook et al., 1989), using PCR products produced as above with purified pSelect plasmid as template. The ratio of the zeocin and hygromycin signals corresponds to the normalized expression level of the zeocin gene.

Results

The library of *Arabidopsis* genomic DNA in the pSelect vector comprised 69,000 primary clones in *E. coli*, 80% of which carried inserts. The average insert size was approximately 1000 base pairs; the library, therefore, represents approximately 40% of the *Arabidopsis* genome.

A portion of this library (representing approximately 16% of the *Arabidopsis* genome) was transfected into the U-2 OS/Tet-Off/LexA-HP1 cell line. Hygromycin selection was imposed to isolate transfectants, which resulted in 27,000 surviving colonies. These were then subjected to zeocin selection at low doxycycline concentration. Putative STAR-containing plasmids from 56 zeocin-resistant colonies were rescued into *E. coli* and re-transfected into U-2 OS/Tet-Off/ LexA-HP1 cells. Forty-four of these plasmids (79% of the plasmids tested) conferred zeocin resistance on the host cells at low doxycycline concentrations, demonstrating that the plasmids carried STAR elements. This indicates that the pSelect screen in human U-2 OS cells is highly efficient at detection of STAR elements from plant genomic DNA.

The DNA sequences of these 44 candidate STAR elements were determined. Thirty-five of them were identified as single loci in the database of *Arabidopsis* nuclear genomic sequence (Table 9; SEQ ID NO:85-SEQ ID NO:119). Four others were identified as coming from the chloroplast genome, four were chimeras of DNA fragments from two loci, and one was not found in the *Arabidopsis* genome database.

Figure 19:
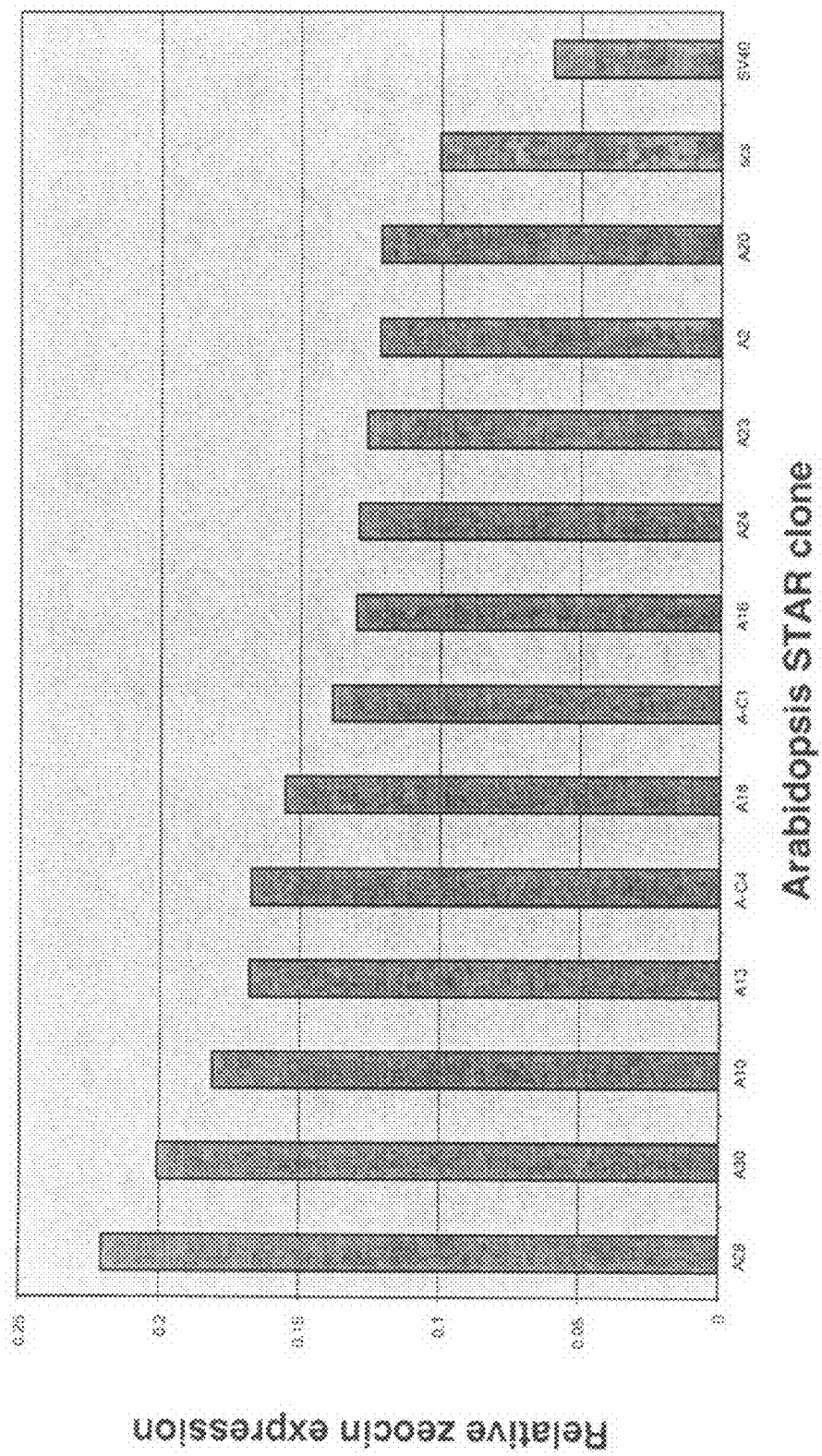
FIG. 19 is a graph illustrating that U-2 OS/Tet-Off/lexA-HP1 cells were transfected with candidate *Arabidopsis* STAR elements and cultivated at low doxycycline concentrations. Total RNA was isolated and subjected to RT-PCR; the bands corresponding to the zeocin and hygromycin resistance mRNAs were detected by Southern blotting and quantified with a phosphorimager. The ratio of the zeocin to hygromycin signals is shown for transfectants containing zeocin expression units flanked by 12 different *Arabidopsis* STAR elements, the *Drosophila* scs element, or no flanking element.

The strength of the cloned *Arabidopsis* STAR elements was tested by assessing their ability to prevent transcriptional repression of the zeocin-resistance gene, using an RT-PCR assay. As a control for RNA input among the samples, the transcript levels of the hygromycin-resistance gene for each STAR transfection were assessed too. This analysis has been performed for 12 of the *Arabidopsis* STAR elements. The results (FIG. 19) demonstrate that the *Arabidopsis* STAR elements are superior to the *Drosophila* scs element (positive control) and the empty vector ("SV40"; negative control) in their ability to protect the zeocin-resistance gene from transcriptional repression. In particular, STAR-A28 (SEQ ID NO:112) and STAR-A30 (SEQ ID NO:114) enable two-fold higher levels of zeocin-resistance gene expression than the scs element (normalized to the internal control of hygromycin-resistance gene mRNA) when the lexA-HP1 repressor is expressed.

These results demonstrate that the method of the invention can be successfully applied to recovery of STAR elements from genomes of other species than human. Its successful application to STAR elements from a plant genome is particularly significant because it demonstrates the wide taxonomic range over which the method of the invention is applicable and because plants are an important target of biotechnological development.

Example 14

STAR Elements Function in CHO Cells

STAR elements function to block the effect of transcriptional repression influences on transgene expression units. Two of the benefits of STAR elements for heterologous protein production are an increased predictability to find high-expressing primary recombinant host cells as well as increased protein production or yield in these cells. Importantly, the disclosed STAR elements are human DNA sequences, isolated in the human U-2 OS osteosarcoma cell line. It is, therefore, an important question whether the human STAR elements are functional in a) cell lines derived from species other than man, and/or in b) human cell lines other than the U-2 OS osteosarcoma cell line. In this example the functionality of STAR 7 (SEQ ID NO:7) in (CHO) Chinese hamster ovary are illustrated.

Material and Methods

The STAR7 (SEQ ID NO:7) element is tested in the ppGIZ-STAR7 vector (FIG. 20). The construction of the pPlug&Play-GFP-ires-Zeo (ppGIZ) vector is described below. Plasmid pGFP (Clontech 6010-1) is modified by insertion of a linker at the BsiWI site to yield pGFP-link. The linker (made by annealing oligonucleotides 5' GTACG-GATATCAGATCTTTAATTAAG 3' (SEQ ID NO:124) and 5' GTACCTTAATTAAAGATCTGATATCC 3' (SEQ ID NO:125)) introduces sites for the PacI, BglII, and EcoRV restriction endonucleases. This creates the multiple cloning site MCSII for insertion of STAR elements. Then primers 5' ATCAGATCTGGCGCGCCATTTAAATCGTC TCGCGCGTTTCGGTGATGACGG 3' (SEQ ID NO:126) and 5' AGGCGGATCCGAATG TATTTAGAAAAATAAA-CAAATAGGGG 3' (SEQ ID NO:127) are used to amplify a region of 0.37 kb from pGFP, which is inserted into the BglII site of pIRES (Clontech 6028-1) to yield pIRES-stuf. This introduces sites for the AscI and SwaI restriction endonucleases at MCSI, and acts as a "stuffer fragment" to avoid potential interference between STAR elements and adjacent promoters. pIRES-stuf is digested with BglII and FspI to liberate a DNA fragment composed of the stuffer fragment, the CMV promoter, the IRES element (flanked by multiple cloning sites MCS A and MCS B), and the SV40 polyadenylation signal. This fragment is ligated with the vector backbone of pGFP-link produced by digestion with BamHI and StuI, to yield pIRES-link.

The open reading frames of the zeocin-resistance gene is inserted into the BamHI/NotI sites of MCS B in pIRES-link as follows: the zeocin-resistance ORF is amplified by PCR with primers 5' GATCGGATCCTTCGAAATGGCCAAGT-TGACCAGTGC 3' (SEQ ID NO:128) and 5' AGGCGCG-GCCGCAATTCTCAGTCCTGCTCCTC 3' (SEQ ID NO:129) from plasmid pEM7/zeo, digested with BamHI and NotI, and ligated with BamHI/NotI-digested pIRES-link to yield pIRES-link-zeo. The GFP reporter ORF was introduced into pIRES-link-zeo by amplification of phr-GFP-1 with primers 5' GATCGAATTCTCGCGAATGGTGAGCAAG-CAGATCCTGAAG 3' (SEQ ID NO:130) and 5' AGGC-GAATTCACCGGTGTTTAAACTTACAC-CCACTCGTGCAGGCTGCCCAGG 3' (SEQ ID NO:131), and insertion of the EcoRI-digested GFP cassette into the EcoRI site in MCS A of the pIRES-link-zeo plasmid. This created the ppGIZ (for ppGFP-IRES-zeo). STAR7 (SEQ ID NO:7) is cloned into the SalI site (5') and into the PacI site (3').

Transfection and Culture of CHO Cells

The Chinese Hamster Ovary cell line CHO-K1 (ATCC CCL-61) is cultured in HAMS-F12 medium+10% Fetal Calf Serum containing 2 mM glutamine, 100 U/ml penicillin, and 100 micrograms/ml streptomycin at 37° C./5% $CO_2$. Cells are transfected with the plasmids using Lipofectamine 2000 (Invitrogen) as described by the manufacturer. Briefly, cells are seeded to culture vessels and grown overnight to 70-90% confluence. Lipofectamine reagent is combined with plasmid DNA at a ratio of 7.5 microliters per 3 microgram (e.g., for a 10 cm Petri dish, 20 micrograms DNA and 120 microliters Lipofectamine) and added after a 30-minute incubation at 25° C. to the cells. After a six-hour incubation, the transfection mixture is replaced with fresh medium, and the transfected cells are incubated further. After overnight cultivation, cells are trypsinized and seeded into fresh petri dishes with fresh medium with zeocin added to a concentration of 100 μg/ml and the cells are cultured further. When individual colonies become visible (approximately ten days after transfection) medium is removed and replaced with fresh medium without zeocin. Individual clones are isolated and transferred to 24-well plates in medium with zeocin. Expression of the GFP reporter gene is assessed approximately three weeks after transfection.

The tested constructs consist of a bicistronic gene with the GFP gene, an IRES and the Zeocin resistance gene under control of the CMV promoter, but either with or without STAR7 (SEQ ID NO:7) element to flank the entire construct (FIG. 20). The constructs are transfected to CHO-K1 cells. Stable colonies are expanded before the GFP signal is determined on a XL-MCL Beckman Coulter flow cytometer. The mean of the GFP signal is taken as measure for the level of GFP expression and this is plotted in FIG. 20.

Results

FIG. 20 shows that flanking a GFP reporter gene that is under the control of the CMV promoter results in a higher number of CHO colonies that express significantly higher levels of GFP protein, as compared to the control without STAR7 (SEQ ID NO:7) element. The STAR7 (SEQ ID NO:7) element, therefore, conveys a higher degree of predictability of transgene expression in CHO cells. The highest GFP expression level in STAR-shielded CHO colonies is also higher than in STAR-less control colonies. In addition, when the tested colonies were further grown for another 30 days without Zeocin in the culture medium, the GFP expression levels in the STAR-shielded colonies remained equally high, whereas the GFP expression levels in the STAR-less colonies dropped to at least below 50% of the original values. It is, therefore, concluded that STAR7 (SEQ ID NO:7) is able to convey higher as well as more stable expression levels to a transgene in CHO cells, this being a cell line derived from another species than man.

Example 15

STAR Elements Function in NSO Cells

STAR elements function to block the effect of transcriptional repression influences on transgene expression units. Two of the benefits of STAR elements for heterologous protein production are an increased predictability to find high-expressing primary recombinant host cells, as well as increased protein production or yield in these cells. Importantly, the disclosed STAR elements are human DNA sequences, isolated in the human U-2 OS osteosarcoma cell line. It is, therefore, an important question whether the human STAR elements are functional in a) cell lines derived from species other than man, and/or in b) human cell lines other than the U-2 OS osteosarcoma cell line. In this example the functionality of STAR 7 (SEQ ID NO:7) in non-secreting mouse myeloma (NSO) cells are illustrated.

Materials and Methods

The tested constructs are the same as described in Example 14. NSO (Non-Secreting mouse myeloma) cells (ECACC 85110503) are suspension cells that are cultured in RPMI 1640 medium+10% Fetal Calf Serum containing 2 mM glutamine, 100 U/ml penicillin, and 100 micrograms/ml streptomycin at 37° C./5% $CO_2$. Cells are transfected with the plasmids using Lipofectamine 2000 (Invitrogen) as described by the manufacturer. Briefly, cells are seeded to culture vessels and grown overnight to $4 \times 10^5$/ml. Lipofectamine reagent is combined with plasmid DNA at a ratio of 3 microliters per microgram DNA (e.g., for a 10 cm Petri dish, 20 micrograms DNA and 60 microliters Lipofectamine) and added after 30 minutes incubation at 25° C. temperature to the cells. After overnight incubation, the transfection mixture is replaced with fresh medium and the transfected cells are incubated further. After another overnight incubation, zeocin is added to a concentration of 100 μg/ml and the cells are cultured and further incubated for three days. Then the cells are seeded in 96-well plates in such dilutions that one well will contain ~1 cell. After ten days growing colonies are transferred to 24-well plates.

Results

FIG. 21 shows that flanking a GFP reporter gene that is under the control of the CMV promoter results in a higher number of NSO colonies that express significantly higher levels of GFP protein, as compared to the control without STAR7 (SEQ ID NO:7) element. The STAR7 (SEQ ID NO:7) element, therefore, conveys a higher degree of predictability of transgene expression in NSO cells. The highest GFP expression level in STAR-shielded NSO colonies is also higher than in STAR-less control colonies. It is, therefore, concluded that STAR7 (SEQ ID NO:7) is able to convey higher expression levels to a transgene in NSO cells, this being a cell line derived from another species than man.

Example 16

STAR Elements Function in Human 293 Cells

STAR elements function to block the effect of transcriptional repression influences on transgene expression units. Two of the benefits of STAR elements for heterologous protein production are an increased predictability to find high-expressing primary recombinant host cells as well as increased protein production or yield in these cells. Importantly, the disclosed STAR elements are human DNA sequences, isolated in the human U-2 OS osteosarcoma cell line. It is, therefore, an important question whether the human STAR elements are functional in a) cell lines derived from species other than man, and/or in b) human cell lines other than the U-2 OS osteosarcoma cell line. In this example, the functionality of STAR7 (SEQ ID NO:7) in human 293 cells are illustrated.

Materials and Methods

The tested constructs are the same as described in Example 14. The 293 cell line (ATCC CRL-1573) is derived from human embryonal kidney (immortalized by adenovirus 5 transfection) and is cultured in Dulbecco's Modified Eagle Medium+10% Fetal Calf Serum containing 2 mM glutamine, 100 U/ml penicillin, and 100 micrograms/ml streptomycin at 37° C./5% $CO_2$. Cells are transfected with the plasmids using Lipofectamine 2000 (Invitrogen) as described by the manufacturer. Selection and propagation of the 293 colonies are as described in Example 14 for U-2 OS cells.

Results

FIG. 22 shows that flanking a GFP reporter gene that is under the control of the CMV promoter results in a higher number of 293 colonies that express significantly higher levels of GFP protein, as compared to the control without STAR7 (SEQ ID NO:7) element. The STAR7 (SEQ ID NO:7) element, therefore, conveys a higher degree of predictability of transgene expression in 293 cells. The highest GFP expression level in STAR-shielded colonies is also higher than in STAR-less control colonies. It is, therefore, concluded that STAR7 (SEQ ID NO:7) is able to convey higher expression levels to a transgene in 293 cells, this being another human cell line, distinct from the human U-2 OS cell line.

TABLE 1

Biopharmaceutical Proteins, Their Tissue or Cell Type of Origin

| Protein | Tissue/Somatic Cells | Cell Lines (ATCC #)[1] | Indications |
|---|---|---|---|
| alpha-1 Antitrypsin | Liver, leukocytes | Hep G2 (HB-8065) | Cystic fibrosis, emphysema |
| alpha-Galactosidase A; -Glucosidase | Fibroblasts | WI 38 (CCL-75) | Fabry disease; Pompe's disease |
| Antibodies (monoclonal, single-chain, etc) | Lymphocytes | Transfectomas | Various therapeutic strategies |
| Antithrombin III | Liver | Hep G2 (HB-8065) | Thrombophilia |
| Calcitonin | Thyroid (parafollicular cells) | TT (CRL-1803) | Osteoporosis |
| Ciliary neurotrophic factor | Neural tissue (e.g., astrocytes) | HCN-1A (CRL-10442) | Motor neuron disease |
| Epidermal Growth Factor | Kidney | G-401 (CRL-1441) | Wound healing |
| Erythropoietin | Liver, kidney | Hep G2 (HB-8065), G-401 (CRL-1441) | Anemia |
| Factors VII, VIII, IX | Endothelial cells | HUV-EC-C (CRL-1730) | Hemophilia |
| Famoxin (recombinant gAcrp30) | Adipocytes | NA[2] | Obesity |
| Fibroblast growth factor (basic) | Cerebral cortex, hypothalamus | HCN-1A (CRL-10442) | Wound healing, angiogenesis |
| Gastric lipase | Pancreas | BxPC-3 (CRL-1687) | Pancreatic insufficiency, cystic fibrosis |
| Glucocerebrosidase | Macrophages | U-937 (CRL-1593.2) | Gaucher disease |
| Granulocyte macrophage-colony stimulatin factor | T-lymphocytes | J.CaM1.6 (CRL-2063) | Chemotherapy neutropenia |
| Human growth hormone (somatotropin) | Pituitary gland | HP75 (CRL-2506) | Growth retardation, Turner's syndrome |
| Human serum albumin | Liver (hepatocytes) | Hep G2 (HB-8065) | Blood replacement (surgery, burns) |
| Insulin | Pancreas (Islet beta cells) | BxPC-3 (CRL-1687) | Diabetes |
| Interferons alpha | Leukocytes | WBC264-9C (HB-8902) | Cancer, hepatitis C |
| Interferons beta | Fibroblasts | WI 38 (CCL-75) | Multiple sclerosis |
| Interleukin-2, -4, -10 | T-lymphocytes | J.CaM1.6 (CRL-2063) | Cancer, rheumatoid arthritis, hepatitis |
| Interleukin-18 | Monocytes and macrophages | U-937 (CRL-1593.2) | Cancer, bacterial infections |
| Interleukin-1 Receptor Antagonist | Epithelium | HBE4-E6/E7 (CRL-2078) | Rheumatoid arthritis |
| Soluble Tumor Necrosis Factor receptor | Placenta, spleen, fibroblasts | BeWo (CCL-98) | Rheumatoid arthritis, multiple sclerosis |
| van Willebrand's factor | Endothelial cells | HUV-EC-C (CRL-1730) | Hemophilia |

[1] These cell lines are offered only as examples of cultured cells corresponding to the tissues and somatic cells; ATCC #: American Type Culture Collection accession number
[2] NA: Not Available; adipocytes can be differentiated from various other cell types

TABLE 2

Oligonucleotides used for polymerase chain reactions (PCR primers) or DNA mutagenesis (SEQ ID NOS:134-176)

| SEQ ID NO: | Number | Sequence |
|---|---|---|
| 134 | C65 | AACAAGCTTGATATCAGATCTGCTAGCTTGGT CGAGCTGATACTTCCC |
| 135 | C66 | AAACTCGAGCGGCCGCGAATTCGTCGACTTTA CCACTCCCTATCAGTGATAGAG |
| 136 | C67 | AAACCGCGGCATGGAAGACGCCAAAAACATAA AGAAAGG |
| 137 | C68 | TATGGATCCTAGAATTACACGGCGATCTTTCC |
| 138 | C81 | AAACCATGGCCGAGTACAAGCCCACGGTGCG CC |
| 139 | C82 | AAATCTAGATCAGGCACCGGGCTTGCGGGTCA TGC |
| 140 | C85 | CATTTCCCCGAAAAGTGCCACC |
| 141 | D30 | TCACTGCTAGCGAGTGGTAAACTC |
| 142 | D41 | GAAGTCGACGAGGCAGGCAGAAGTATGC |
| 143 | D42 | GAGCCGCGGTTTAGTTCCTCACCTTGTCG |
| 144 | D51 | TCTGGAAGCTTTGCTGAAGAAAC |
| 145 | D58 | CCAAGTTGACCAGTGCC |
| 146 | D70 | TACAAGCCAACCACGGCCT |
| 147 | D71 | CGGAAGTGCTTGACATTGGG |
| 148 | D80 | GTTCGTGGACACGACCTCCG |
| 149 | D89 | GGGCAAGATGTCGTAGTCAGG |
| 150 | D90 | AGGCCCATGGTCACCTCCATCGCTACTGTG |
| 151 | D91 | CTAATCACTCACTGTGTAAT |
| 152 | D93 | AATTACAGGCGCGCC |
| 153 | D94 | AATTGGCGCGCCTGT |
| 154 | D95 | TGCTTTGCATACTTCTGCCTGCCTC |
| 155 | E12 | TAGGGGGGATCCAAATGTTC |
| 156 | E13 | CCTAAAAGAAGATCTTTAGC |
| 157 | E14 | AAGTGTTGGATCCACTTTGG |
| 158 | E15 | TTTGAAGATCTACCAAATGG |

TABLE 2-continued

Oligonucleotides used for polymerase chain reactions (PCR primers) or DNA mutagenesis (SEQ ID NOS:134-176)

| SEQ ID NO: | Number | Sequence |
|---|---|---|
| 159 | E16 | GTTCGGGATCCACCTGGCCG |
| 160 | E17 | TAGGCAAGATCTTGGCCCTC |
| 161 | E18 | CCTCTCTAGGGATCCGACCC |
| 162 | E19 | CTAGAGAGATCTTCCAGTAT |
| 163 | E20 | AGAGTTCCGGATCCGCCTGG |
| 164 | E21 | CCAGGCAGACTCGGAACTCT |
| 165 | E22 | TGGTGAAACCGGATCCCTAC |
| 166 | E23 | AGGTCAGGAGATCTAGACCA |
| 167 | E25 | CCATTTTCGCTTCCTTAGCTCC |
| 168 | E42 | CGATGTAACCCACTCGTGCACC |
| 169 | E57 | AGAGATCTAGGATAATTTCG |
| 170 | E92 | AGGCGCTAGCACGCGTTCTACTCTTTTCCTACTCTG |
| 171 | E93 | GATCAAGCTTACGCGTCTAAAGGCATTTTATATAG |
| 172 | E94 | AGGCGCTAGCACGCGTTCAGAGTTAGTGATCCAGG |
| 173 | E95 | GATCAAGCTTACGCGTCAGTAAAGGTTTCGTATGG |
| 174 | E96 | AGGCGCTAGCACGCGTTCTACTCTTTCATTACTCTG |
| 175 | E97 | CGAGGAAGCTGGAGAAGGAGAAGCTG |
| 176 | E98 | CAAGGGCCGCAGCTTACACATGTTC |

TABLE 3

STAR elements of the invention, including genomic location and length (SEQ ID NOS: 1-66)

| STAR | SEQ ID NO: | Location[1] | Length |
|---|---|---|---|
| 1 | 1 | 2q31.1 | 750 |
| 2 | 2 | 7p15.2 | 916 |
| 3 | 3 | 15q11.2 and 10q22.2 | 2132 |
| 4 | 4 | 1p31.1 and 14q24.1 | 1625 |
| 5 | 5 | 20q13.32 | 1571 |
| 6 | 6 | 2p21 | 1173 |
| 7 | 7 | 1q34 | 2101 |
| 8 | 8 | 9q32 | 1839 |
| 9 | 9 | 10p15.3 | 1936 |
| 10 | 10 | Xp11.3 | 1167 |
| 11 | 11 | 2p25.1 | 1377 |
| 12 | 12 | 5q35.3 | 1051 |
| 13 | 13 | 9q34.3 | 1291 |
| 14 | 14 | 22q11.22 | 732 |
| 15 | 15 | 1p36.31 | 1881 |
| 16 | 16 | 1p21.2 | 1282 |
| 17 | 17 | 2q31.1 | 793 |
| 18 | 18 | 2q31.3 | 497 |
| 19 | 19 | 6p22.1 | 1840 |
| 20 | 20 | 8p13.3 | 780 |
| 21 | 21 | 6q24.2 | 620 |
| 22 | 22 | 2q12.2 | 1380 |
| 23 | 23 | 6p22.1 | 1246 |
| 24 | 24 | 1q21.2 | 948 |
| 25 | 25 | 1q21.3 | 1067 |
| 26 | 26 | 1q21.1 | 540 |
| 27 | 27 | 1q23.1 | 1520 |
| 28 | 28 | 22q11.23 | 961 |
| 29 | 29 | 2q13.31 | 2253 |
| 30 | 30 | 22q12.3 | 1851 |
| 31 | 31 | 9q34.11 and 22q11.21 | 1165 |
| 32 | 32 | 21q22.2 | 771 |
| 33 | 33 | 21q22.2 | 1368 |
| 34 | 34 | 9q34.14 | 755 |
| 35 | 35 | 7q22.3 | 1211 |
| 36 | 36 | 21q22.2 | 1712 |
| 37 | 37 | 22q11.23 | 1331 |
| 38 | 38 | 22q11.1 and 22q11.1 | ~1000 |
| 39 | 39 | 22q12.3 | 2331 |
| 40 | 40 | 22q11.21 | 1071 |
| 41 | 41 | 22q11.21 | 1144 |
| 42 | 42 | 22q11.1 | 735 |
| 43 | 43 | 14q24.3 | 1231 |
| 44 | 44 | 22q11.1 | 1591 |
| 45 | 45 | 22q11.21 | 1991 |
| 46 | 46 | 22q11.23 | 1871 |
| 47 | 47 | 22q11.21 | 1082 |
| 48 | 48 | 22q11.22 | 1242 |
| 49 | 49 | Chr 12 random clone, and 3q26.32 | 1015 |
| 50 | 50 | 6p21.31 | 2361 |
| 51 | 51 | 5q21.3 | 2289 |
| 52 | 52 | 7p15.2 | 1200 |
| 53 | 53 | Xp11.3 | 1431 |
| 54 | 54 | 4q21.1 | 981 |
| 55 | 55 | 15q13.1 | 501 |
| 56 | 56 | includes 3p25.3 | 741 |
| 57 | 57 | 4q35.2 | 1371 |
| 58 | 58 | 21q11.2 | 1401 |
| 59 | 59 | 17 random clone | 872 |
| 60 | 60 | 4p16.1 and 6q27 | 2068 |
| 61 | 61 | 7p14.3 and 11q25 | 1482 |
| 62 | 62 | 14q24.3 | 1011 |
| 63 | 63 | 22q13.3 | 1421 |
| 64 | 64 | 17q11.2 | 1414 |
| 65 | 65 | 7q21.11 = 28.4 | 1310 |
| 66 | 66 | 20q13.33 and 6q14.1 | ~2800 |

[1]Chromosomal location is determined by BLAST search of DNA sequence data from the STAR elements against the human genome database. The location is given according to standard nomenclature referring to the cytogenetic ideogram of each chromosome; e.g., 1p2.3 is the third cytogenetic sub-band of the second cytogenetic band of the short arm of chromosome 1 (http://www.ncbi.nlm.nih.gov/Class/MLACourse/Genetics/chrombanding-.html). F, forward sequencing reaction result; R, reverse sequencing reaction result.

TABLE 4

STAR elements convey stability over time on transgene expression[1]

| | Cell Divisions[2] | Luciferase Expression[3] |
|---|---|---|
| STAR6 (SEQ ID NO: 6) plus puromycin | 42 | 18,000 |
| | 60 | 23,000 |
| | 84 | 20,000 |
| | 108 | 16,000 |

TABLE 4-continued

STAR elements convey stability over time on transgene expression[1]

|  | Cell Divisions[2] | Luciferase Expression[3] |
|---|---|---|
| STAR6 (SEQ ID NO: 6) | 84 | 12,000 |
| without puromycin[4] | 108 | 15,000 |
|  | 144 | 12,000 |

[1]Plasmid pSDH-Tet-STAR6 was transfected into U-2 OS cells, and clones were isolated and cultivated in doxycycline-free medium as described in Example 1. Cells were transferred to fresh culture vessels weekly at a dilution of 1:20.
[2]The number of cell divisions is based on the estimation that in one week the culture reaches cell confluence, which represents ~6 cell divisions.
[3]Luciferase was assayed as described in Example 1.
[4]After 60 cell divisions the cells were transferred to two culture vessels; one was supplied with culture medium that contained puromycin, as for the first 60 cell divisions, and the second was supplied with culture medium lacking antibiotic.

TABLE 5

Human STAR elements and their putative mouse orthologs and paralogs

| NUMBER | STAR | Human[1] | Mouse[2] | Similarity[3] | SEQ ID NO: |
|---|---|---|---|---|---|
| 1 | 1 | 2q31.1 | 2D | 600 bp 69% | 1 |
| 2 | 2 | 7p15.2 | 6B3 | 909 bp 89% | 2 |
| 3 | 3a | 5q33.3 | 11B2 | 248 bp 83% | 3 |
| 4 | 3b | 10q22.2 | 14B | 1. 363 bp 89%<br>2. 163 bp 86% | 3 |
| 5 | 6 | 2p21 | 17E4 | 437 bp 78% | 6 |
| 6 | 12 | 5q35.3 | 11b1.3 | 796 bp 66% | 12 |
| 7 | 13 | 9q34.3 | 2A3 | 753 bp 77% | 13 |
| 8 | 18 | 2q31.3 | 2E1 | 497 bp 72% | 18 |
| 9 | 36 | 21q22.2 | 16C4 | 166 bp 79% | 36 |
| 10 | 40 | 22q11.1 | 6F1 | 1. 270 bp 75%<br>2. 309 bp 70% | 40 |
| 11 | 50 | 6p21.31 | 17B1 | 1. 451 bp 72%<br>2. 188 bp 80%<br>3. 142 bp 64% | 50 |
| 12 | 52 | 7p15.2 | 6B3 | 1. 846 bp 74%<br>2. 195 bp 71% | 52 |
| 13 | 53 | Xp11.3 | XA2 | 364 bp 64% | 53 |
| 14 | 54 | 4q21.1 | 5E3 | 1. 174 bp 80%<br>2. 240 bp 73%<br>3. 141 bp 67%<br>4. 144 bp 68% | 54 |
| 15 | 61a | 7p14.3 | 6B3 | 188 bp 68% | 61 |

[1]Cytogenetic location of STAR element in the human genome.
[2]Cytogenetic location of STAR element ortholog in the mouse genome.
[3]Length of region(s) displaying high sequence similarity, and percentage similarity. In some cases more than one block of high similarity occurs; in those cases, each block is described separately. Similarity <60% is not considered significant.

The patterns are ranked according to significance coefficient. These were determined using RSA-Tools with the sequence of the human genome as reference. Patterns that comprise the most discriminant variables in Linear Discriminant Analysis are indicated with an asterisk. (SEQ ID NOS: 177-342)

TABLE 6

Oligonucleotide patterns (6 base pairs) over-represented in STAR elements.

| Number | Oligonucleotide sequence | Observed occurrences | Expected occurrences | Significance coefficient | Number of matching STARs | SEQ ID NO: |
|---|---|---|---|---|---|---|
| 1 | CCCCAC | 107 | 49 | 8.76 | 51 | 177 |
| 2 | CAGCGG | 36 | 9 | 7.75 | 23 | 178 |
| 3 | GGCCCC | 74 | 31 | 7.21 | 34 | 179 |
| 4 | CAGCCC | 103 | 50 | 7.18 | 37 | 180 |
| 5 | GCCCCC | 70 | 29 | 6.97 | 34 | 181 |
| 6 | CGGGGC | 40 | 12 | 6.95 | 18 | 182 |
| 7 | CCCCGC | 43 | 13 | 6.79 | 22 | 183 |
| 8 | CGGCAG | 35 | 9 | 6.64 | 18 | 184 |
| 9 | AGCCCC | 83 | 38 | 6.54 | 40 | 185 |
| 10 | CCAGGG | 107 | 54 | 6.52 | 43 | 186 |
| 11 | GGACCC * | 58 | 23 | 6.04 | 35 | 187 |
| 12 | GCGGAC | 20 | 3 | 5.94 | 14 | 188 |
| 13 | CCAGCG | 34 | 10 | 5.9 | 24 | 189 |
| 14 | GCAGCC | 92 | 45 | 5.84 | 43 | 190 |
| 15 | CCGGCA | 28 | 7 | 5.61 | 16 | 191 |
| 16 | AGCGGC | 27 | 7 | 5.45 | 17 | 192 |
| 17 | CAGGGG | 86 | 43 | 5.09 | 43 | 193 |

TABLE 6-continued

Oligonucleotide patterns (6 base pairs) over-represented in STAR elements.

| Number | Oligonucleotide sequence | Observed occurrences | Expected occurrences | Significance coefficient | Number of matching STARs | SEQ ID NO: |
|---|---|---|---|---|---|---|
| 18 | CCGCCC | 43 | 15 | 5.02 | 18 | 194 |
| 19 | CCCCCG | 35 | 11 | 4.91 | 20 | 195 |
| 20 | GCCGCC | 34 | 10 | 4.88 | 18 | 196 |
| 21 | GCCGGC | 22 | 5 | 4.7 | 16 | 197 |
| 22 | CGGACC | 19 | 4 | 4.68 | 14 | 198 |
| 23 | CGCCCC | 35 | 11 | 4.64 | 19 | 199 |
| 24 | CGCCAG | 28 | 8 | 4.31 | 19 | 200 |
| 25 | CGCAGC | 29 | 8 | 4.29 | 20 | 201 |
| 26 | CAGCCG | 32 | 10 | 4 | 24 | 202 |
| 27 | CCCACG | 33 | 11 | 3.97 | 26 | 203 |
| 28 | GCTGCC | 78 | 40 | 3.9 | 43 | 204 |
| 29 | CCCTCC | 106 | 60 | 3.87 | 48 | 205 |
| 30 | CCCTGC * | 92 | 50 | 3.83 | 42 | 206 |
| 31 | CACCCC | 77 | 40 | 3.75 | 40 | 207 |
| 32 | GCGCCA | 30 | 10 | 3.58 | 23 | 208 |
| 33 | AGGGGC | 70 | 35 | 3.55 | 34 | 209 |
| 34 | GAGGGC | 66 | 32 | 3.5 | 40 | 210 |
| 35 | GCGAAC | 14 | 2 | 3.37 | 13 | 211 |
| 36 | CCGGCG | 17 | 4 | 3.33 | 12 | 212 |
| 37 | AGCCGG | 34 | 12 | 3.29 | 25 | 213 |
| 38 | GGAGCC | 67 | 34 | 3.27 | 40 | 214 |
| 39 | CCCCAG | 103 | 60 | 3.23 | 51 | 215 |
| 40 | CCGCTC | 24 | 7 | 3.19 | 19 | 216 |
| 41 | CCCCTC | 81 | 44 | 3.19 | 43 | 217 |
| 42 | CACCGC | 33 | 12 | 3.14 | 22 | 218 |
| 43 | CTGCCC | 96 | 55 | 3.01 | 42 | 219 |
| 44 | GGGCCA | 68 | 35 | 2.99 | 39 | 220 |
| 45 | CGCTGC | 28 | 9 | 2.88 | 22 | 221 |
| 46 | CAGCGC | 25 | 8 | 2.77 | 19 | 222 |
| 47 | CGGCCC | 28 | 10 | 2.73 | 19 | 223 |
| 48 | CCGCCG | 19 | 5 | 2.56 | 9 | 224 |
| 49 | CCCCGG | 30 | 11 | 2.41 | 17 | 225 |
| 50 | AGCCGC | 23 | 7 | 2.34 | 17 | 226 |
| 51 | GCACCC | 55 | 27 | 2.31 | 38 | 227 |
| 52 | AGGACC | 54 | 27 | 2.22 | 33 | 228 |
| 53 | AGGGCG | 24 | 8 | 2.2 | 18 | 229 |

TABLE 6-continued

Oligonucleotide patterns (6 base pairs) over-represented in STAR elements.

| Number | Oligonucleotide sequence | Observed occurrences | Expected occurrences | Significance coefficient | Number of matching STARs | SEQ ID NO: |
|---|---|---|---|---|---|---|
| 54 | CAGGGC | 81 | 47 | 2.18 | 42 | 230 |
| 55 | CCCGCC | 45 | 21 | 2.15 | 20 | 231 |
| 56 | GCCAGC | 66 | 36 | 2.09 | 39 | 232 |
| 57 | AGCGCC | 21 | 6 | 2.09 | 18 | 233 |
| 58 | AGGCCC | 64 | 34 | 2.08 | 32 | 234 |
| 59 | CCCACC | 101 | 62 | 2.05 | 54 | 235 |
| 60 | CGCTCA | 21 | 6 | 2.03 | 17 | 236 |
| 61 | AACGCG | 9 | 1 | 1.96 | 9 | 237 |
| 62 | GCGGCA | 21 | 7 | 1.92 | 14 | 238 |
| 63 | AGGTCC | 49 | 24 | 1.87 | 36 | 239 |
| 64 | CCGTCA | 19 | 6 | 1.78 | 14 | 240 |
| 65 | CAGAGG | 107 | 68 | 1.77 | 47 | 241 |
| 66 | CCCGAG | 33 | 14 | 1.77 | 22 | 242 |
| 67 | CCGAGG | 36 | 16 | 1.76 | 25 | 243 |
| 68 | CGCGGA | 11 | 2 | 1.75 | 8 | 244 |
| 69 | CCACCC | 87 | 53 | 1.71 | 45 | 245 |
| 70 | CCTCGC | 23 | 8 | 1.71 | 20 | 246 |
| 71 | CAAGCC | 59 | 32 | 1.69 | 40 | 247 |
| 72 | TCCGCA | 18 | 5 | 1.68 | 17 | 248 |
| 73 | CGCCGC | 18 | 5 | 1.67 | 9 | 249 |
| 74 | GGGAAC | 55 | 29 | 1.63 | 39 | 250 |
| 75 | CCAGAG | 93 | 58 | 1.57 | 49 | 251 |
| 76 | CGTTCC | 19 | 6 | 1.53 | 16 | 252 |
| 77 | CGAGGA | 23 | 8 | 1.5 | 19 | 253 |
| 78 | GGGACC | 48 | 24 | 1.48 | 31 | 254 |
| 79 | CCGCGA | 10 | 2 | 1.48 | 8 | 255 |
| 80 | CCTGCG | 24 | 9 | 1.45 | 17 | 256 |
| 81 | CTGCGC | 23 | 8 | 1.32 | 14 | 257 |
| 82 | GACCCC | 47 | 24 | 1.31 | 33 | 258 |
| 83 | GCTCCA | 66 | 38 | 1.25 | 39 | 259 |
| 84 | CGCCAC | 33 | 15 | 1.19 | 21 | 260 |
| 85 | GCGGGA | 23 | 9 | 1.17 | 18 | 261 |
| 86 | CTGCGA | 18 | 6 | 1.15 | 15 | 262 |
| 87 | CTGCTC | 80 | 49 | 1.14 | 50 | 263 |
| 88 | CAGACG | 23 | 9 | 1.13 | 19 | 264 |
| 89 | CGAGAG | 21 | 8 | 1.09 | 17 | 265 |

TABLE 6-continued

Oligonucleotide patterns (6 base pairs) over-represented in STAR elements.

| Number | Oligonucleotide sequence | Observed occurrences | Expected occurrences | Significance coefficient | Number of matching STARs | SEQ ID NO: |
|---|---|---|---|---|---|---|
| 90 | CGGTGC | 18 | 6 | 1.06 | 16 | 266 |
| 91 | CTCCCC | 84 | 53 | 1.05 | 47 | 267 |
| 92 | GCGGCC | 22 | 8 | 1.04 | 14 | 268 |
| 93 | CGGCGC | 14 | 4 | 1.04 | 13 | 269 |
| 94 | AAGCCC * | 60 | 34 | 1.03 | 42 | 270 |
| 95 | CCGCAG | 24 | 9 | 1.03 | 17 | 271 |
| 96 | GCCCAC | 59 | 34 | 0.95 | 35 | 272 |
| 97 | CACCCA | 92 | 60 | 0.93 | 49 | 273 |
| 98 | GCGCCC | 27 | 11 | 0.93 | 18 | 274 |
| 99 | ACCGGC | 15 | 4 | 0.92 | 13 | 275 |
| 100 | CTCGCA | 16 | 5 | 0.89 | 14 | 276 |
| 101 | ACGCTC | 16 | 5 | 0.88 | 12 | 277 |
| 102 | CTGGAC | 58 | 33 | 0.88 | 32 | 278 |
| 103 | GCCCCA | 67 | 40 | 0.87 | 38 | 279 |
| 104 | ACCGTC | 15 | 4 | 0.86 | 11 | 280 |
| 105 | CCCTCG | 21 | 8 | 0.8 | 18 | 281 |
| 106 | AGCCCG | 22 | 8 | 0.79 | 14 | 282 |
| 107 | ACCCGA | 16 | 5 | 0.78 | 13 | 283 |
| 108 | AGCAGC | 79 | 50 | 0.75 | 41 | 284 |
| 109 | ACCGCG | 14 | 4 | 0.69 | 7 | 285 |
| 110 | CGAGGC | 29 | 13 | 0.69 | 24 | 286 |
| 111 | AGCTGC | 70 | 43 | 0.64 | 36 | 287 |
| 112 | GGGGAC | 49 | 27 | 0.64 | 34 | 288 |
| 113 | CCGCAA | 16 | 5 | 0.64 | 12 | 289 |
| 114 | CGTCGC | 8 | 1 | 0.62 | 6 | 290 |
| 115 | CGTGAC | 17 | 6 | 0.57 | 15 | 291 |
| 116 | CGCCCA | 33 | 16 | 0.56 | 22 | 292 |
| 117 | CTCTGC | 97 | 65 | 0.54 | 47 | 293 |
| 118 | AGCGGG | 21 | 8 | 0.52 | 17 | 294 |
| 119 | ACCGCT | 15 | 5 | 0.5 | 11 | 295 |
| 120 | CCCAGG | 133 | 95 | 0.49 | 58 | 296 |
| 121 | CCCTCA | 71 | 45 | 0.49 | 39 | 297 |
| 122 | CCCCCA * | 77 | 49 | 0.49 | 42 | 298 |
| 123 | GGCGAA | 16 | 5 | 0.48 | 14 | 299 |
| 124 | CGGCTC | 29 | 13 | 0.47 | 19 | 300 |
| 125 | CTCGCC | 20 | 8 | 0.46 | 17 | 301 |

TABLE 6-continued

Oligonucleotide patterns (6 base pairs) over-represented in STAR elements.

| Number | Oligonucleotide sequence | Observed occurrences | Expected occurrences | Significance coefficient | Number of matching STARs | SEQ ID NO: |
|---|---|---|---|---|---|---|
| 126 | CGGAGA | 20 | 8 | 0.45 | 14 | 302 |
| 127 | TCCCCA | 95 | 64 | 0.43 | 52 | 303 |
| 128 | GACACC | 44 | 24 | 0.42 | 33 | 304 |
| 129 | CTCCGA | 17 | 6 | 0.42 | 13 | 305 |
| 130 | CTCGTC | 17 | 6 | 0.42 | 14 | 306 |
| 131 | CGACCA | 13 | 4 | 0.39 | 11 | 307 |
| 132 | ATGACG | 17 | 6 | 0.37 | 12 | 308 |
| 133 | CCATCG | 17 | 6 | 0.37 | 13 | 309 |
| 134 | AGGGGA | 78 | 51 | 0.36 | 44 | 310 |
| 135 | GCTGCA | 77 | 50 | 0.35 | 43 | 311 |
| 136 | ACCCCA | 76 | 49 | 0.33 | 40 | 312 |
| 137 | CGGAGC | 21 | 9 | 0.33 | 16 | 313 |
| 138 | CCTCCG | 28 | 13 | 0.32 | 19 | 314 |
| 139 | CGGGAC | 16 | 6 | 0.3 | 10 | 315 |
| 140 | CCTGGA | 88 | 59 | 0.3 | 45 | 316 |
| 141 | AGGCGA | 18 | 7 | 0.29 | 17 | 317 |
| 142 | ACCCCT | 54 | 32 | 0.28 | 36 | 318 |
| 143 | GCTCCC | 56 | 34 | 0.27 | 36 | 319 |
| 144 | CGTCAC | 16 | 6 | 0.27 | 15 | 320 |
| 145 | AGCGCA | 16 | 6 | 0.26 | 11 | 321 |
| 146 | GAAGCC | 62 | 38 | 0.25 | 39 | 322 |
| 147 | GAGGCC | 79 | 52 | 0.22 | 42 | 323 |
| 148 | ACCCTC | 54 | 32 | 0.22 | 33 | 324 |
| 149 | CCCGGC | 37 | 20 | 0.21 | 21 | 325 |
| 150 | CGAGAA | 20 | 8 | 0.2 | 17 | 326 |
| 151 | CCACCG | 29 | 14 | 0.18 | 20 | 327 |
| 152 | ACTTCG | 16 | 6 | 0.17 | 14 | 328 |
| 153 | GATGAC | 48 | 28 | 0.17 | 35 | 329 |
| 154 | ACGAGG | 23 | 10 | 0.16 | 18 | 330 |
| 155 | CCGGAG | 20 | 8 | 0.15 | 18 | 331 |
| 156 | ACCCAC | 60 | 37 | 0.12 | 41 | 332 |
| 157 | CTGGGC | 105 | 74 | 0.11 | 50 | 333 |
| 158 | CCACGG | 23 | 10 | 0.09 | 19 | 334 |
| 159 | CGGTCC | 13 | 4 | 0.09 | 12 | 335 |
| 160 | AGCACC * | 54 | 33 | 0.09 | 40 | 336 |
| 161 | ACACCC | 53 | 32 | 0.08 | 38 | 337 |

TABLE 6-continued

Oligonucleotide patterns (6 base pairs) over-represented in STAR elements.

| Number | Oligonucleotide sequence | Observed occurrences | Expected occurrences | Significance coefficient | Number of matching STARs | SEQ ID NO: |
|---|---|---|---|---|---|---|
| 162 | AGGGCC | 54 | 33 | 0.08 | 30 | 338 |
| 163 | CGCGAA | 6 | 1 | 0.02 | 6 | 339 |
| 164 | GAGCCC | 58 | 36 | 0.02 | 36 | 340 |
| 165 | CTGAGC | 71 | 46 | 0.02 | 45 | 341 |
| 166 | AATCGG | 13 | 4 | 0.02 | 11 | 342 |

The patterns are ranked according to significance coefficient. These were determined using RSA-Tools with the random sequence from the human genome as reference. Patterns that comprise the most discriminant variables in Linear Discriminant Analysis are indicated with an asterisk. (SEQ ID NOS:343-1072)

TABLE 7

Dyad patterns over-represented in STAR elements.

| Number | Dyad sequence | Observed occurrences | Expected occurrences | Significance coefficient | SEQ ID NO: |
|---|---|---|---|---|---|
| 1 | CCCN{2}CGG | 36 | 7 | 9.31 | 343 |
| 2 | CCGN{6}CCC | 40 | 10 | 7.3 | 344 |
| 3 | CAGN{0}CGG | 36 | 8 | 7.13 | 345 |
| 4 | CGCN{15}CCC | 34 | 8 | 6.88 | 346 |
| 5 | CGGN{9}GCC | 33 | 7 | 6.82 | 347 |
| 6 | CCCN{9}CGC | 35 | 8 | 6.72 | 348 |
| 7 | CCCN{1}GCG | 34 | 8 | 6.64 | 349 |
| 8 | CCCN{0}CAC | 103 | 48 | 6.61 | 350 |
| 9 | AGCN{16}CCG | 29 | 6 | 5.96 | 351 |
| 10 | CCCN{4}CGC | 34 | 8 | 5.8 | 352 |
| 11 | CGCN{13}GGA | 26 | 5 | 5.77 | 353 |
| 12 | GCGN{16}CCC | 30 | 7 | 5.74 | 354 |
| 13 | CGCN{5}GCA | 25 | 5 | 5.49 | 355 |
| 14 | CCCN{14}CCC | 101 | 49 | 5.43 | 356 |
| 15 | CTGN{4}CGC | 34 | 9 | 5.41 | 357 |
| 16 | CCAN{12}GCG | 28 | 6 | 5.37 | 358 |
| 17 | CGGN{11}CAG | 36 | 10 | 5.25 | 359 |
| 18 | CCCN{5}GCC | 75 | 33 | 4.87 | 360 |
| 19 | GCCN{0}CCC | 64 | 26 | 4.81 | 361 |
| 20 | CGCN{4}GAC | 19 | 3 | 4.78 | 362 |
| 21 | CGGN{0}CAG | 33 | 9 | 4.76 | 363 |
| 22 | CCCN{3}CGC | 32 | 8 | 4.67 | 364 |
| 23 | CGCN{1}GAC | 20 | 3 | 4.58 | 365 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 24 | GCGN{2}GCC | 29 | 7 | 4.54 | 366 |
| 25 | CCCN{4}GCC | 76 | 34 | 4.53 | 367 |
| 26 | CCCN{1}CCC | 103 | 52 | 4.53 | 368 |
| 27 | CCGN{13}CAG | 33 | 9 | 4.5 | 369 |
| 28 | GCCN{4}GGA | 64 | 27 | 4.48 | 370 |
| 29 | CCGN{3}GGA | 26 | 6 | 4.46 | 371 |
| 30 | AGGN{2}GGG | 118 | 63 | 4.44 | 372 |
| 31 | CACN{5}GCG | 22 | 4 | 4.42 | 373 |
| 32 | CGCN{17}CCA | 27 | 6 | 4.39 | 374 |
| 33 | CCCN{9}GGC | 69 | 30 | 4.38 | 375 |
| 34 | CCTN{5}GCG | 28 | 7 | 4.37 | 376 |
| 35 | GCGN{0}GAC | 19 | 3 | 4.32 | 377 |
| 36 | GCCN{0}GGC | 40 | 7 | 4.28 | 378 |
| 37 | GCGN{2}CCC | 26 | 6 | 4.27 | 379 |
| 38 | CCGN{11}CCC | 32 | 9 | 4.17 | 380 |
| 39 | CCCN{8}TCG | 23 | 5 | 4.12 | 381 |
| 40 | CCGN{17}GCC | 30 | 8 | 4.12 | 382 |
| 41 | GGGN{5}GGA | 101 | 52 | 4.11 | 383 |
| 42 | GGCN{6}GGA | 71 | 32 | 4.1 | 384 |
| 43 | CCAN{4}CCC | 96 | 48 | 4.1 | 385 |
| 44 | CCTN{14}CCG | 32 | 9 | 4.09 | 386 |
| 45 | GACN{12}GGC | 45 | 16 | 4.07 | 387 |
| 46 | CGCN{13}CCC | 30 | 8 | 4.04 | 388 |
| 47 | CAGN{16}CCC | 92 | 46 | 4.02 | 389 |
| 48 | AGCN{10}GGG | 75 | 35 | 3.94 | 390 |
| 49 | CGGN{13}GGC | 30 | 8 | 3.93 | 391 |
| 50 | CGGN{1}GCC | 30 | 8 | 3.92 | 392 |
| 51 | AGCN{0}GGC | 26 | 6 | 3.9 | 393 |
| 52 | CCCN{16}GGC | 64 | 28 | 3.89 | 394 |
| 53 | GCTN{19}CCC | 67 | 29 | 3.87 | 395 |
| 54 | CCCN{16}GGG | 88 | 31 | 3.81 | 396 |
| 55 | CCCN{9}CGG | 30 | 8 | 3.77 | 397 |
| 56 | CCCN{10}CGG | 30 | 8 | 3.76 | 398 |
| 57 | CCAN{0}GCG | 32 | 9 | 3.75 | 399 |
| 58 | GCCN{17}CGC | 26 | 6 | 3.74 | 400 |
| 59 | CCTN{6}CGC | 27 | 7 | 3.73 | 401 |
| 60 | GGAN{1}CCC | 63 | 27 | 3.71 | 402 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 61 | CGCN{18}CAC | 24 | 5 | 3.7 | 403 |
| 62 | CGCN{20}CCG | 21 | 4 | 3.69 | 404 |
| 63 | CCGN{0}GCA | 26 | 6 | 3.69 | 405 |
| 64 | CGCN{20}CCC | 28 | 7 | 3.69 | 406 |
| 65 | AGCN{15}CCC | 67 | 30 | 3.65 | 407 |
| 66 | CCTN{7}GGC | 69 | 31 | 3.63 | 408 |
| 67 | GCCN{5}CGC | 32 | 9 | 3.61 | 409 |
| 68 | GCCN{14}CGC | 28 | 7 | 3.59 | 410 |
| 69 | CAGN{11}CCC | 89 | 45 | 3.58 | 411 |
| 70 | GGGN{16}GAC | 53 | 21 | 3.57 | 412 |
| 71 | CCCN{15}GCG | 25 | 6 | 3.57 | 413 |
| 72 | CCCN{0}CGC | 37 | 12 | 3.54 | 414 |
| 73 | CCCN{16}AGC * | 67 | 30 | 3.54 | 415 |
| 74 | AGGN{9}GGG | 96 | 50 | 3.52 | 416 |
| 75 | CGCN{12}CTC | 28 | 7 | 3.46 | 417 |
| 76 | CACN{8}CGC | 23 | 5 | 3.43 | 418 |
| 77 | CCAN{7}CCG | 31 | 9 | 3.42 | 419 |
| 78 | CGGN{1}GCA | 25 | 6 | 3.41 | 420 |
| 79 | CGCN{14}CCC | 29 | 8 | 3.4 | 421 |
| 80 | AGCN{0}CCC | 76 | 36 | 3.4 | 422 |
| 81 | CGCN{13}GTC | 18 | 3 | 3.37 | 423 |
| 82 | GCGN{3}GCA | 26 | 7 | 3.35 | 424 |
| 83 | CGGN{0}GGC | 34 | 11 | 3.35 | 425 |
| 84 | GCCN{14}CCC | 68 | 31 | 3.33 | 426 |
| 85 | ACCN{7}CGC | 21 | 4 | 3.32 | 427 |
| 86 | AGGN{7}CGG | 33 | 10 | 3.31 | 428 |
| 87 | CCCN{16}CGA | 22 | 5 | 3.3 | 429 |
| 88 | CGCN{6}CAG | 31 | 9 | 3.29 | 430 |
| 89 | CAGN{11}GCG | 29 | 8 | 3.29 | 431 |
| 90 | CCGN{12}CCG | 19 | 4 | 3.26 | 432 |
| 91 | CGCN{18}CAG | 27 | 7 | 3.24 | 433 |
| 92 | CAGN{1}GGG | 80 | 39 | 3.21 | 434 |
| 93 | CGCN{0}CCC | 32 | 10 | 3.2 | 435 |
| 94 | GCNN{18}GCC | 26 | 7 | 3.18 | 436 |
| 95 | CGGN{15}GGC | 27 | 7 | 3.15 | 437 |
| 96 | CCCN{15}AGG | 72 | 34 | 3.14 | 438 |
| 97 | AGGN{20}GCG | 26 | 7 | 3.14 | 439 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 98 | CGGN{5}CTC | 26 | 7 | 3.13 | 440 |
| 99 | TCCN{17}CGA | 23 | 5 | 3.12 | 441 |
| 100 | GCGN{4}CCC | 30 | 9 | 3.08 | 442 |
| 101 | CCCN{2}CGC | 30 | 9 | 3.07 | 443 |
| 102 | CGTN{3}CAG | 28 | 8 | 3.06 | 444 |
| 103 | CCGN{13}GAG | 27 | 7 | 3.05 | 445 |
| 104 | CTCN{6}CGC | 28 | 8 | 3.04 | 446 |
| 105 | CGCN{4}GAG | 21 | 5 | 3.03 | 447 |
| 106 | GCGN{5}GGA | 24 | 6 | 3.03 | 448 |
| 107 | CCGN{1}CAG | 27 | 7 | 3.01 | 449 |
| 108 | CGCN{11}CCG | 18 | 3 | 2.99 | 450 |
| 109 | GCGN{19}CCC | 26 | 7 | 2.98 | 451 |
| 110 | CGCN{18}GAA | 21 | 5 | 2.98 | 452 |
| 111 | GGGN{19}GGA | 78 | 39 | 2.95 | 453 |
| 112 | CCAN{1}CGG | 24 | 6 | 2.94 | 454 |
| 113 | CCCN{7}GCG | 25 | 6 | 2.94 | 455 |
| 114 | AGGN{10}CCC | 84 | 43 | 2.92 | 456 |
| 115 | CCAN{0}GGG | 97 | 52 | 2.88 | 457 |
| 116 | CAGN{10}CCC | 82 | 41 | 2.87 | 458 |
| 117 | CCGN{18}CCG | 19 | 4 | 2.86 | 459 |
| 118 | CCGN{18}GGC | 26 | 7 | 2.85 | 460 |
| 119 | CCCN{2}GCG | 24 | 6 | 2.84 | 461 |
| 120 | CGCN{1}GGC | 25 | 7 | 2.83 | 462 |
| 121 | CCGN{5}GAC | 19 | 4 | 2.81 | 463 |
| 122 | GGAN{0}CCC | 52 | 22 | 2.8 | 464 |
| 123 | CCCN{1}CCG | 29 | 9 | 2.78 | 465 |
| 124 | CCCN{15}ACG | 23 | 6 | 2.75 | 466 |
| 125 | AGCN{8}CCC | 66 | 31 | 2.73 | 467 |
| 126 | CCCN{3}GGC | 60 | 27 | 2.71 | 468 |
| 127 | AGGN{9}CGG | 31 | 10 | 2.7 | 469 |
| 128 | CCCN{14}CGC | 27 | 8 | 2.7 | 470 |
| 129 | CCGN{0}CCG | 19 | 4 | 2.7 | 471 |
| 130 | CGCN{8}AGC | 23 | 6 | 2.69 | 472 |
| 131 | CGCN{19}ACC | 21 | 5 | 2.68 | 473 |
| 132 | GCGN{17}GAC | 17 | 3 | 2.66 | 474 |
| 133 | AGCN{1}GCG | 24 | 6 | 2.63 | 475 |
| 134 | CCGN{11}GGC | 31 | 10 | 2.63 | 476 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 135 | CGGN{4}AGA | 26 | 7 | 2.63 | 477 |
| 136 | CGCN{14}CCG | 17 | 3 | 2.62 | 478 |
| 137 | CCTN{20}GCG | 24 | 6 | 2.62 | 479 |
| 138 | CCAN{10}CGC | 26 | 7 | 2.61 | 480 |
| 139 | CCCN{20}CAC | 69 | 33 | 2.6 | 481 |
| 140 | CCGN{11}GCC | 27 | 8 | 2.6 | 482 |
| 141 | CGCN{18}CCC | 26 | 7 | 2.59 | 483 |
| 142 | CGGN{15}CGC | 16 | 3 | 2.57 | 484 |
| 143 | CGCN{16}GCC | 24 | 6 | 2.55 | 485 |
| 144 | CGCN{20}GGC | 23 | 6 | 2.54 | 486 |
| 145 | CGCN{19}CCG | 18 | 4 | 2.52 | 487 |
| 146 | CGGN{10}CCA | 28 | 8 | 2.51 | 488 |
| 147 | CGCN{17}CCC | 26 | 7 | 2.51 | 489 |
| 148 | CGCN{11}ACA | 23 | 6 | 2.51 | 490 |
| 149 | CGGN{0}ACC | 17 | 3 | 2.5 | 491 |
| 150 | GCGN{10}GCC | 24 | 6 | 2.49 | 492 |
| 151 | GCGN{8}GAC | 17 | 3 | 2.49 | 493 |
| 152 | CCCN{15}GGG | 84 | 32 | 2.44 | 494 |
| 153 | CGGN{16}GGC | 27 | 8 | 2.44 | 495 |
| 154 | CGCN{16}CCA | 23 | 6 | 2.42 | 496 |
| 155 | GCCN{3}CCC | 73 | 36 | 2.4 | 497 |
| 156 | CAGN{4}GGG | 94 | 51 | 2.4 | 498 |
| 157 | CCCN{6}GCG | 23 | 6 | 2.38 | 499 |
| 158 | CCGN{16}CGC | 17 | 3 | 2.38 | 500 |
| 159 | CCCN{17}GCA | 61 | 28 | 2.37 | 501 |
| 160 | CGCN{13}TCC | 24 | 6 | 2.37 | 502 |
| 161 | GCCN{1}CGC | 29 | 9 | 2.36 | 503 |
| 162 | CCGN{19}GAG | 26 | 7 | 2.35 | 504 |
| 163 | GGGN{10}GGA | 89 | 48 | 2.35 | 505 |
| 164 | CAGN{5}CCG | 32 | 11 | 2.35 | 506 |
| 165 | CGCN{3}AGA | 19 | 4 | 2.32 | 507 |
| 166 | GCCN{0}GCC | 29 | 9 | 2.32 | 508 |
| 167 | CCCN{8}GGC | 61 | 28 | 2.31 | 509 |
| 168 | CCTN{6}GCG | 22 | 6 | 2.29 | 510 |
| 169 | GACN{6}CCC | 48 | 20 | 2.29 | 511 |
| 170 | CGGN{1}CCC | 26 | 8 | 2.27 | 512 |
| 171 | CCCN{15}CCG | 30 | 10 | 2.27 | 513 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 172 | CAGN{9}CCC | 84 | 44 | 2.26 | 514 |
| 173 | CGGN{10}GGC | 27 | 8 | 2.26 | 515 |
| 174 | CGAN{10}ACG | 10 | 1 | 2.26 | 516 |
| 175 | GCGN{3}TCC | 21 | 5 | 2.26 | 517 |
| 176 | CCCN{3}GCC | 75 | 38 | 2.24 | 518 |
| 177 | GCGN{1}ACC | 17 | 3 | 2.24 | 519 |
| 178 | CCGN{9}AGG | 27 | 8 | 2.23 | 520 |
| 179 | CGCN{16}CAG | 26 | 8 | 2.23 | 521 |
| 180 | GGCN{0}CCC | 62 | 29 | 2.22 | 522 |
| 181 | AGGN{12}CCG | 26 | 8 | 2.19 | 523 |
| 182 | CCGN{0}GCG | 16 | 3 | 2.19 | 524 |
| 183 | CCGN{2}GCC | 30 | 10 | 2.18 | 525 |
| 184 | CCGN{11}GTC | 19 | 4 | 2.17 | 526 |
| 185 | CAGN{0}CCC | 88 | 47 | 2.17 | 527 |
| 186 | CCCN{5}CCG | 32 | 11 | 2.17 | 528 |
| 187 | GCCN{20}CCC | 66 | 32 | 2.15 | 529 |
| 188 | GACN{2}CGC | 18 | 4 | 2.14 | 530 |
| 189 | CGCN{6}CAC | 23 | 6 | 2.13 | 531 |
| 190 | AGGN{14}GCG | 25 | 7 | 2.1 | 532 |
| 191 | GACN{5}CGC | 17 | 3 | 2.1 | 533 |
| 192 | CCTN{19}CCG | 29 | 9 | 2.1 | 534 |
| 193 | CCGN{12}GGA | 24 | 7 | 2.08 | 535 |
| 194 | GGCN{9}GAC * | 44 | 18 | 2.08 | 536 |
| 195 | AGGN{10}GGG | 94 | 52 | 2.07 | 537 |
| 196 | CCGN{10}GAG | 25 | 7 | 2.07 | 538 |
| 197 | CGCN{6}GGA | 20 | 5 | 2.06 | 539 |
| 198 | CGCN{7}AGC | 23 | 6 | 2.04 | 540 |
| 199 | CCAN{13}CGG | 26 | 8 | 2.03 | 541 |
| 200 | CGGN{6}GGA | 25 | 7 | 2.03 | 542 |
| 201 | CGCN{19}GCC | 24 | 7 | 2.03 | 543 |
| 202 | CCAN{12}CGC | 24 | 7 | 2.02 | 544 |
| 203 | CGGN{1}GGC | 41 | 16 | 2.02 | 545 |
| 204 | GCGN{3}CCA | 25 | 7 | 2.01 | 546 |
| 205 | AGGN{1}CGC | 21 | 5 | 2 | 547 |
| 206 | CTCN{5}CGC | 24 | 7 | 1.98 | 548 |
| 207 | CCCN{0}ACG | 30 | 10 | 1.97 | 549 |
| 208 | CAGN{17}CCG | 29 | 9 | 1.96 | 550 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 209 | GGCN{4}CCC | 62 | 30 | 1.96 | 551 |
| 210 | AGGN{8}GCG | 26 | 8 | 1.96 | 552 |
| 211 | CTGN{1}CCC | 88 | 48 | 1.94 | 553 |
| 212 | CCCN{16}CAG | 85 | 46 | 1.94 | 554 |
| 213 | CGCN{9}GAC | 16 | 3 | 1.93 | 555 |
| 214 | CAGN{6}CCG | 29 | 9 | 1.92 | 556 |
| 215 | CGTN{12}CGC | 11 | 1 | 1.92 | 557 |
| 216 | CTCN{7}GCC | 69 | 35 | 1.92 | 558 |
| 217 | CGCN{19}TCC | 22 | 6 | 1.92 | 559 |
| 218 | CCCN{7}GCC | 67 | 33 | 1.91 | 560 |
| 219 | CAGN{13}CGG | 30 | 10 | 1.9 | 561 |
| 220 | CGCN{1}GCC | 27 | 8 | 1.9 | 562 |
| 221 | CGCN{17}CCG | 17 | 4 | 1.89 | 563 |
| 222 | AGGN{4}CCC | 63 | 31 | 1.89 | 564 |
| 223 | AGCN{10}CGC | 21 | 5 | 1.89 | 565 |
| 224 | CCCN{11}CGG | 30 | 10 | 1.88 | 566 |
| 225 | CCCN{8}GCC | 75 | 39 | 1.86 | 567 |
| 226 | CCGN{1}CGG | 22 | 3 | 1.86 | 568 |
| 227 | CCCN{1}ACC | 71 | 36 | 1.85 | 569 |
| 228 | CGCN{0}CAG | 25 | 7 | 1.85 | 570 |
| 229 | CCGN{19}TGC | 23 | 6 | 1.82 | 571 |
| 230 | GCGN{4}CGA | 12 | 2 | 1.82 | 572 |
| 231 | CCGN{19}GCC | 30 | 10 | 1.82 | 573 |
| 232 | CCAN{10}CCC | 85 | 46 | 1.81 | 574 |
| 233 | CAGN{13}GGG | 91 | 51 | 1.81 | 575 |
| 234 | AGCN{18}CGG | 23 | 6 | 1.81 | 576 |
| 235 | CGAN{8}CGC | 11 | 1 | 1.81 | 577 |
| 236 | AGCN{4}CCC | 63 | 31 | 1.8 | 578 |
| 237 | GGAN{6}CCC | 61 | 30 | 1.8 | 579 |
| 238 | CGGN{13}AAG | 23 | 6 | 1.8 | 580 |
| 239 | ACCN{11}CGC | 19 | 5 | 1.79 | 581 |
| 240 | CCGN{12}CAG | 28 | 9 | 1.78 | 582 |
| 241 | CCCN{12}GGG | 76 | 29 | 1.77 | 583 |
| 242 | CACN{17}ACG | 22 | 6 | 1.76 | 584 |
| 243 | CAGN{18}CCC | 82 | 44 | 1.76 | 585 |
| 244 | CGTN{10}GTC | 19 | 5 | 1.75 | 586 |
| 245 | CCCN{13}GCG | 23 | 6 | 1.75 | 587 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 246 | GCAN{1}CGC | 20 | 5 | 1.73 | 588 |
| 247 | AGAN{4}CCG | 24 | 7 | 1.73 | 589 |
| 248 | GCGN{10}AGC | 22 | 6 | 1.72 | 590 |
| 249 | CGCN{0}GGA | 12 | 2 | 1.72 | 591 |
| 250 | CGGN{4}GAC | 17 | 4 | 1.69 | 592 |
| 251 | CCCN{12}CGC | 26 | 8 | 1.68 | 593 |
| 252 | GCCN{15}CCC | 65 | 33 | 1.68 | 594 |
| 253 | GCGN{6}TCC | 20 | 5 | 1.66 | 595 |
| 254 | CGGN{3}CAG | 33 | 12 | 1.65 | 596 |
| 255 | CCCN{3}CCA | 88 | 49 | 1.65 | 597 |
| 256 | AGCN{3}CCC | 59 | 28 | 1.65 | 598 |
| 257 | GGGN{16}GCA | 65 | 33 | 1.65 | 599 |
| 258 | AGGN{8}CCG | 28 | 9 | 1.64 | 600 |
| 259 | CCCN{0}CCG | 29 | 10 | 1.64 | 601 |
| 260 | GCGN{5}GAC | 16 | 3 | 1.64 | 602 |
| 261 | CCCN{9}ACC | 60 | 29 | 1.64 | 603 |
| 262 | CTGN{5}CGC | 25 | 8 | 1.64 | 604 |
| 263 | CGCN{14}CTC | 23 | 7 | 1.64 | 605 |
| 264 | CGGN{14}GCA | 23 | 7 | 1.63 | 606 |
| 265 | CCGN{8}GCC | 26 | 8 | 1.62 | 607 |
| 266 | CCGN{7}CAC | 23 | 7 | 1.62 | 608 |
| 267 | AGCN{8}GCG | 21 | 6 | 1.61 | 609 |
| 268 | CGGN{16}GGA | 29 | 10 | 1.61 | 610 |
| 269 | CCAN{12}CCG | 26 | 8 | 1.61 | 611 |
| 270 | CGGN{2}CCC | 26 | 8 | 1.6 | 612 |
| 271 | CCAN{13}GGG | 71 | 37 | 1.6 | 613 |
| 272 | CGGN{15}GCA | 21 | 6 | 1.6 | 614 |
| 273 | CGCN{9}GCA | 20 | 5 | 1.58 | 615 |
| 274 | CGGN{19}CCA | 26 | 8 | 1.58 | 616 |
| 275 | GGGN{15}CGA | 20 | 5 | 1.57 | 617 |
| 276 | CCCN{10}CGC | 26 | 8 | 1.57 | 618 |
| 277 | CTCN{14}CGC | 26 | 8 | 1.55 | 619 |
| 278 | CACN{11}GCG | 20 | 5 | 1.55 | 620 |
| 279 | CCGN{2}GGC | 24 | 7 | 1.55 | 621 |
| 280 | CTGN{18}CCC | 85 | 47 | 1.54 | 622 |
| 281 | GGGN{13}CAC | 58 | 28 | 1.54 | 623 |
| 282 | CCTN{15}GGC | 62 | 31 | 1.54 | 624 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 283 | CCCN{20}CGA | 20 | 5 | 1.54 | 625 |
| 284 | CCCN{8}CGA | 20 | 5 | 1.53 | 626 |
| 285 | GAGN{7}CCC | 61 | 30 | 1.53 | 627 |
| 286 | CGCN{2}CCG | 22 | 6 | 1.53 | 628 |
| 287 | CCCN{0}TCC | 98 | 57 | 1.52 | 629 |
| 288 | AGCN{0}GCC | 21 | 6 | 1.52 | 630 |
| 289 | CCCN{2}TCC | 82 | 45 | 1.52 | 631 |
| 290 | CCGN{5}CCC | 30 | 10 | 1.52 | 632 |
| 291 | CGCN{13}CGC | 16 | 3 | 1.51 | 633 |
| 292 | CCCN{1}CGC | 28 | 9 | 1.51 | 634 |
| 293 | GCCN{16}GCA | 53 | 25 | 1.51 | 635 |
| 294 | CCCN{16}CCA | 84 | 46 | 1.5 | 636 |
| 295 | CCGN{13}CGC | 19 | 5 | 1.5 | 637 |
| 296 | CCGN{17}CAG | 28 | 9 | 1.49 | 638 |
| 297 | CGGN{18}GGC | 26 | 8 | 1.49 | 639 |
| 298 | CCGN{14}AGG | 23 | 7 | 1.49 | 640 |
| 299 | CCCN{5}CGG | 26 | 8 | 1.49 | 641 |
| 300 | CCCN{6}GGA | 58 | 28 | 1.49 | 642 |
| 301 | ACGN{2}CCC | 20 | 5 | 1.49 | 643 |
| 302 | CCAN{9}CCG | 27 | 9 | 1.48 | 644 |
| 303 | CCCN{19}CCA | 78 | 42 | 1.48 | 645 |
| 304 | CAGN{0}GGG | 77 | 41 | 1.48 | 646 |
| 305 | AGCN{1}CCC | 58 | 28 | 1.47 | 647 |
| 306 | GCGN{7}TCC | 27 | 9 | 1.46 | 648 |
| 307 | ACGN{18}CCA | 25 | 8 | 1.46 | 649 |
| 308 | GCTN{14}CCC | 61 | 30 | 1.46 | 650 |
| 309 | GCGN{14}CCC | 23 | 7 | 1.46 | 651 |
| 310 | GCGN{19}AGC | 20 | 5 | 1.45 | 652 |
| 311 | CCGN{8}CAG | 29 | 10 | 1.45 | 653 |
| 312 | GCGN{6}GCC | 22 | 6 | 1.45 | 654 |
| 313 | GCGN{10}GCA | 20 | 5 | 1.44 | 655 |
| 314 | CCTN{7}GCC | 69 | 36 | 1.44 | 656 |
| 315 | GCCN{13}GCC | 54 | 26 | 1.42 | 657 |
| 316 | CCCN{14}GCC | 63 | 32 | 1.42 | 658 |
| 317 | CCCN{15}CGG | 26 | 8 | 1.42 | 659 |
| 318 | CCAN{13}CGC | 23 | 7 | 1.42 | 660 |
| 319 | AGCN{11}GGG | 67 | 35 | 1.41 | 661 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 320 | GGAN{0}GCC | 64 | 32 | 1.4 | 662 |
| 321 | GCCN{3}TCC | 61 | 30 | 1.4 | 663 |
| 322 | CCTN{5}GCC | 69 | 36 | 1.39 | 664 |
| 323 | CGGN{18}CCC | 25 | 8 | 1.39 | 665 |
| 324 | CCTN{3}GGC | 59 | 29 | 1.38 | 666 |
| 325 | CCGN{0}CTC | 22 | 6 | 1.38 | 667 |
| 326 | AGCN{17}GCG | 19 | 5 | 1.37 | 668 |
| 327 | ACGN{14}GGG | 20 | 5 | 1.37 | 669 |
| 328 | CGAN{12}GGC | 19 | 5 | 1.37 | 670 |
| 329 | CCCN{20}CGC | 24 | 7 | 1.37 | 671 |
| 330 | ACGN{12}CTG | 24 | 7 | 1.36 | 672 |
| 331 | CCGN{0}CCC | 36 | 14 | 1.36 | 673 |
| 332 | CCGN{10}GGA | 23 | 7 | 1.36 | 674 |
| 333 | CCCN{3}GCG | 21 | 6 | 1.36 | 675 |
| 334 | GCGN{14}CGC | 22 | 3 | 1.35 | 676 |
| 335 | CCGN{8}CGC | 16 | 4 | 1.35 | 677 |
| 336 | CGCN{10}ACA | 22 | 6 | 1.34 | 678 |
| 337 | CCCN{19}CCG | 28 | 10 | 1.33 | 679 |
| 338 | CACN{14}CGC | 20 | 5 | 1.32 | 680 |
| 339 | GACN{3}GGC | 46 | 21 | 1.32 | 681 |
| 340 | GAAN{7}CGC | 19 | 5 | 1.32 | 682 |
| 341 | CGCN{16}GGC | 21 | 6 | 1.31 | 683 |
| 342 | GGCN{9}CCC | 64 | 33 | 1.31 | 684 |
| 343 | CCCN{9}GCC | 64 | 33 | 1.31 | 685 |
| 344 | CGCN{0}TGC | 26 | 9 | 1.3 | 686 |
| 345 | CCTN{8}GGC | 67 | 35 | 1.3 | 687 |
| 346 | CCAN{8}CCC | 82 | 46 | 1.29 | 688 |
| 347 | GACN{2}CCC | 42 | 18 | 1.28 | 689 |
| 348 | GGCN{1}CCC | 54 | 26 | 1.27 | 690 |
| 349 | CGCN{0}AGC | 24 | 7 | 1.26 | 691 |
| 350 | AGGN{4}GCG | 28 | 10 | 1.26 | 692 |
| 351 | CGGN{6}TCC | 22 | 6 | 1.25 | 693 |
| 352 | ACGN{19}GGC | 20 | 5 | 1.25 | 694 |
| 353 | CCCN{8}ACG | 21 | 6 | 1.24 | 695 |
| 354 | CCCN{18}GCC | 62 | 31 | 1.24 | 696 |
| 355 | GCCN{2}CGA | 19 | 5 | 1.24 | 697 |
| 356 | CCCN{8}GCG | 28 | 10 | 1.23 | 698 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 357 | CCCN{0}CTC | 76 | 41 | 1.23 | 699 |
| 358 | GCCN{11}CGC | 27 | 9 | 1.22 | 700 |
| 359 | AGCN{9}CCC | 59 | 29 | 1.22 | 701 |
| 360 | GCTN{0}GCC | 71 | 38 | 1.21 | 702 |
| 361 | CGCN{3}CCC | 26 | 9 | 1.21 | 703 |
| 362 | CCCN{2}CCC | 117 | 72 | 1.19 | 704 |
| 363 | GCCN{9}CGC | 23 | 7 | 1.19 | 705 |
| 364 | GCAN{19}CGC | 19 | 5 | 1.19 | 706 |
| 365 | CAGN{4}CGG | 32 | 12 | 1.18 | 707 |
| 366 | CAGN{2}GGG | 80 | 44 | 1.17 | 708 |
| 367 | GCCN{16}CCC | 67 | 35 | 1.16 | 709 |
| 368 | GAGN{5}CCC | 60 | 30 | 1.16 | 710 |
| 369 | CCTN{16}TCG | 20 | 6 | 1.16 | 711 |
| 370 | CCCN{2}GGC | 62 | 32 | 1.15 | 712 |
| 371 | GCGN{13}GGA | 24 | 8 | 1.15 | 713 |
| 372 | GCCN{17}GGC | 66 | 25 | 1.15 | 714 |
| 373 | CCCN{14}GGC | 58 | 29 | 1.14 | 715 |
| 374 | AGGN{3}CCG | 31 | 12 | 1.14 | 716 |
| 375 | CACN{0}CGC | 32 | 12 | 1.14 | 717 |
| 376 | CGGN{18}CAG | 28 | 10 | 1.14 | 718 |
| 377 | AGCN{1}GCC | 57 | 28 | 1.13 | 719 |
| 378 | CGCN{18}GGC | 23 | 7 | 1.13 | 720 |
| 379 | CCCN{5}AGG | 64 | 33 | 1.11 | 721 |
| 380 | AACN{0}GCG | 9 | 1 | 1.11 | 722 |
| 381 | CCCN{10}CCA | 88 | 50 | 1.09 | 723 |
| 382 | CGCN{13}GAG | 20 | 6 | 1.09 | 724 |
| 383 | CGCN{7}GCC | 25 | 8 | 1.08 | 725 |
| 384 | CCCN{9}CCG | 28 | 10 | 1.07 | 726 |
| 385 | CGCN{16}CCC | 24 | 8 | 1.05 | 727 |
| 386 | GAAN{13}CGC | 18 | 5 | 1.05 | 728 |
| 387 | GGCN{3}CCC | 49 | 23 | 1.03 | 729 |
| 388 | TCCN{11}CCA | 87 | 50 | 1.03 | 730 |
| 389 | CACN{0}CCC | 70 | 38 | 1.02 | 731 |
| 390 | CGCN{16}CCG | 15 | 3 | 1.02 | 732 |
| 391 | CGGN{15}AGC | 21 | 6 | 1.02 | 733 |
| 392 | CCCN{12}GCG | 21 | 6 | 1.02 | 734 |
| 393 | CCCN{9}GAG | 59 | 30 | 1.01 | 735 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 394 | CCGN{20}TCC | 24 | 8 | 1.01 | 736 |
| 395 | CGCN{0}CGC | 17 | 4 | 1.01 | 737 |
| 396 | ATGN{7}CGG | 20 | 6 | 1 | 738 |
| 397 | GGGN{20}GCA | 59 | 30 | 1 | 739 |
| 398 | CGGN{4}GGC | 26 | 9 | 0.99 | 740 |
| 399 | CGGN{16}AGC | 22 | 7 | 0.99 | 741 |
| 400 | CGGN{5}GGC | 25 | 8 | 0.99 | 742 |
| 401 | GCGN{0}GGA | 25 | 8 | 0.98 | 743 |
| 402 | GGCN{20}CAC | 52 | 25 | 0.98 | 744 |
| 403 | CCCN{9}CCC | 97 | 58 | 0.97 | 745 |
| 404 | ACCN{17}GGC | 44 | 20 | 0.97 | 746 |
| 405 | CCCN{6}CGA | 18 | 5 | 0.96 | 747 |
| 406 | AAGN{10}CGG | 26 | 9 | 0.96 | 748 |
| 407 | CGCN{17}CAC | 21 | 6 | 0.95 | 749 |
| 408 | CCCN{16}CGG | 25 | 8 | 0.94 | 750 |
| 409 | GACN{18}GGC | 39 | 17 | 0.94 | 751 |
| 410 | GGGN{15}GAC | 47 | 22 | 0.92 | 752 |
| 411 | GCCN{4}TCC | 66 | 35 | 0.92 | 753 |
| 412 | GGCN{15}CCC | 56 | 28 | 0.92 | 754 |
| 413 | CAGN{12}CGC | 24 | 8 | 0.92 | 755 |
| 414 | CCAN{3}GCG | 22 | 7 | 0.91 | 756 |
| 415 | CCGN{16}GAG | 22 | 7 | 0.9 | 757 |
| 416 | AGCN{2}CGC | 24 | 8 | 0.89 | 758 |
| 417 | GAGN{4}CCC | 54 | 27 | 0.89 | 759 |
| 418 | AGGN{3}CGC | 23 | 7 | 0.88 | 760 |
| 419 | CACN{13}AGG * | 67 | 36 | 0.88 | 761 |
| 420 | CCCN{4}CAG | 88 | 51 | 0.88 | 762 |
| 421 | CCCN{2}GAA | 63 | 33 | 0.87 | 763 |
| 422 | CGCN{19}GAG | 21 | 6 | 0.87 | 764 |
| 423 | ACGN{18}GGG | 21 | 6 | 0.87 | 765 |
| 424 | CCCN{4}GGC | 62 | 32 | 0.87 | 766 |
| 425 | CGGN{9}GAG | 28 | 10 | 0.86 | 767 |
| 426 | CCCN{3}GGG | 66 | 26 | 0.86 | 768 |
| 427 | GAGN{4}GGC | 66 | 35 | 0.85 | 769 |
| 428 | CGCN{5}GAG | 18 | 5 | 0.84 | 770 |
| 429 | CCGN{20}AGG | 24 | 8 | 0.84 | 771 |
| 430 | CCCN{15}CCC | 88 | 51 | 0.83 | 772 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 431 | AGGN{17}CCG | 25 | 8 | 0.82 | 773 |
| 432 | AGGN{6}GGG | 89 | 52 | 0.82 | 774 |
| 433 | GGCN{20}CCC | 57 | 29 | 0.82 | 775 |
| 434 | GCAN{17}CGC | 19 | 5 | 0.82 | 776 |
| 435 | CGAN{11}ACG | 9 | 1 | 0.81 | 777 |
| 436 | CGCN{2}GGA | 19 | 5 | 0.81 | 778 |
| 437 | CTGN{5}CCC | 79 | 45 | 0.8 | 779 |
| 438 | TCCN{20}CCA | 77 | 43 | 0.8 | 780 |
| 439 | CCAN{2}GGG | 59 | 30 | 0.8 | 781 |
| 440 | CCGN{15}GCG | 14 | 3 | 0.8 | 782 |
| 441 | CCAN{5}GGG | 69 | 38 | 0.79 | 783 |
| 442 | CGGN{1}TGC | 24 | 8 | 0.79 | 784 |
| 443 | CCCN{14}GCG | 21 | 6 | 0.79 | 785 |
| 444 | CAGN{0}CCG | 27 | 10 | 0.79 | 786 |
| 445 | GCCN{9}TCC | 60 | 31 | 0.78 | 787 |
| 446 | AGGN{20}CGC | 22 | 7 | 0.78 | 788 |
| 447 | CCCN{6}GAC | 42 | 19 | 0.77 | 789 |
| 448 | CGGN{11}CCA | 23 | 7 | 0.76 | 790 |
| 449 | GGGN{14}CAC | 57 | 29 | 0.75 | 791 |
| 450 | GCAN{15}CGC | 19 | 5 | 0.74 | 792 |
| 451 | CGCN{2}ACA | 20 | 6 | 0.74 | 793 |
| 452 | ACCN{9}CCC | 57 | 29 | 0.73 | 794 |
| 453 | GCGN{9}CGC | 20 | 3 | 0.73 | 795 |
| 454 | CAGN{15}GCG | 23 | 7 | 0.73 | 796 |
| 455 | CCCN{18}GTC | 45 | 21 | 0.72 | 797 |
| 456 | GCGN{3}CCC | 24 | 8 | 0.72 | 798 |
| 457 | CGGN{11}GCC | 23 | 8 | 0.72 | 799 |
| 458 | CCCN{1}CGG | 24 | 8 | 0.71 | 800 |
| 459 | GCCN{4}CCA | 70 | 38 | 0.71 | 801 |
| 460 | CCCN{4}CCG | 30 | 12 | 0.7 | 802 |
| 461 | CGTN{2}GCA | 21 | 6 | 0.7 | 803 |
| 462 | AGCN{7}TCG | 18 | 5 | 0.69 | 804 |
| 463 | CCGN{15}GAA | 20 | 6 | 0.69 | 805 |
| 464 | ACCN{5}CCC | 62 | 33 | 0.69 | 806 |
| 465 | CGCN{14}GAG | 19 | 5 | 0.68 | 807 |
| 466 | CCCN{7}CGC | 30 | 12 | 0.68 | 808 |
| 467 | GAGN{12}CGC | 21 | 6 | 0.68 | 809 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 468 | GGCN{17}CCC | 58 | 30 | 0.67 | 810 |
| 469 | ACGN{11}CTC | 21 | 7 | 0.65 | 811 |
| 470 | ACAN{9}CGG | 24 | 8 | 0.65 | 812 |
| 471 | CTGN{7}CCC | 82 | 47 | 0.65 | 813 |
| 472 | CCCN{2}GCC | 72 | 40 | 0.65 | 814 |
| 473 | CGGN{2}GCA | 24 | 8 | 0.64 | 815 |
| 474 | CCCN{0}TGC | 83 | 48 | 0.64 | 816 |
| 475 | CGCN{7}ACC | 18 | 5 | 0.63 | 817 |
| 476 | GCAN{2}GCC | 54 | 27 | 0.63 | 818 |
| 477 | GCGN{8}CCA | 20 | 6 | 0.63 | 819 |
| 478 | AGCN{0}CGC | 22 | 7 | 0.63 | 820 |
| 479 | GCGN{2}GCA | 18 | 5 | 0.63 | 821 |
| 480 | CCGN{2}GTC | 18 | 5 | 0.62 | 822 |
| 481 | CCGN{3}ACA | 21 | 7 | 0.62 | 823 |
| 482 | ACGN{13}TGG | 21 | 7 | 0.62 | 824 |
| 483 | CCAN{8}CGC | 23 | 8 | 0.62 | 825 |
| 484 | CCGN{9}GGC | 23 | 8 | 0.61 | 826 |
| 485 | CCAN{5}CCG | 25 | 9 | 0.61 | 827 |
| 486 | AGGN{3}GGG | 97 | 59 | 0.61 | 828 |
| 487 | CAGN{2}GGC | 78 | 45 | 0.61 | 829 |
| 488 | CCCN{8}CAG | 81 | 47 | 0.61 | 830 |
| 489 | AGCN{5}CAG | 80 | 46 | 0.6 | 831 |
| 490 | CGGN{16}GCC | 22 | 7 | 0.6 | 832 |
| 491 | GCGN{15}CCC | 23 | 8 | 0.6 | 833 |
| 492 | CCCN{11}GCC | 59 | 31 | 0.59 | 834 |
| 493 | CGAN{2}ACG | 9 | 1 | 0.59 | 835 |
| 494 | CGGN{4}GCC | 22 | 7 | 0.59 | 836 |
| 495 | CACN{6}CGC | 19 | 6 | 0.59 | 837 |
| 496 | CGGN{5}ACG | 11 | 2 | 0.59 | 838 |
| 497 | CTGN{4}GCC * | 66 | 36 | 0.59 | 839 |
| 498 | GGGN{18}CGA | 18 | 5 | 0.59 | 840 |
| 499 | CCTN{8}CGC | 22 | 7 | 0.59 | 841 |
| 500 | GCCN{4}CCC | 67 | 37 | 0.58 | 842 |
| 501 | CGGN{10}GCC | 22 | 7 | 0.58 | 843 |
| 502 | GCCN{5}GGA | 54 | 27 | 0.57 | 844 |
| 503 | ACCN{7}GCG | 15 | 4 | 0.57 | 845 |
| 504 | CCCN{8}CGC | 24 | 8 | 0.57 | 846 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 505 | CAGN{5}CCC | 77 | 44 | 0.56 | 847 |
| 506 | CACN{14}GGA | 63 | 34 | 0.56 | 848 |
| 507 | CCCN{1}GCC | 94 | 57 | 0.55 | 849 |
| 508 | CCCN{5}AGC | 67 | 37 | 0.55 | 850 |
| 509 | GGCN{5}GGA | 59 | 31 | 0.55 | 851 |
| 510 | CGAN{17}GAG | 19 | 6 | 0.55 | 852 |
| 511 | CGCN{7}ACA | 18 | 5 | 0.54 | 853 |
| 512 | CCAN{13}CCC | 87 | 52 | 0.54 | 854 |
| 513 | CGGN{20}GGC | 24 | 8 | 0.54 | 855 |
| 514 | CCCN{17}GCC | 58 | 30 | 0.53 | 856 |
| 515 | CCTN{10}CCG | 30 | 12 | 0.53 | 857 |
| 516 | CCCN{8}CCG | 27 | 10 | 0.53 | 858 |
| 517 | CGCN{3}GAG | 18 | 5 | 0.52 | 859 |
| 518 | CGCN{7}AAG | 17 | 5 | 0.51 | 860 |
| 519 | CGGN{11}GGA | 23 | 8 | 0.51 | 861 |
| 520 | CCGN{15}CCG | 15 | 4 | 0.51 | 862 |
| 521 | CCCN{3}GCA | 57 | 30 | 0.51 | 863 |
| 522 | CGGN{2}CAG | 24 | 8 | 0.5 | 864 |
| 523 | AGGN{2}CCG | 24 | 8 | 0.5 | 865 |
| 524 | CCCN{4}CAC | 69 | 38 | 0.5 | 866 |
| 525 | GGAN{19}CCC | 56 | 29 | 0.49 | 867 |
| 526 | CCCN{8}CAC | 68 | 38 | 0.49 | 868 |
| 527 | ACCN{6}CCG | 18 | 5 | 0.49 | 869 |
| 528 | CCCN{6}GGC | 54 | 28 | 0.49 | 870 |
| 529 | CCCN{6}CCG | 29 | 11 | 0.48 | 871 |
| 530 | CGCN{14}GCC | 26 | 9 | 0.47 | 872 |
| 531 | CCGN{5}TCC | 25 | 9 | 0.46 | 873 |
| 532 | GCCN{6}GCC | 55 | 28 | 0.46 | 874 |
| 533 | CGGN{7}GGA | 24 | 8 | 0.45 | 875 |
| 534 | GGGN{6}GGA | 87 | 52 | 0.44 | 876 |
| 535 | GCCN{12}TCC | 60 | 32 | 0.44 | 877 |
| 536 | AGTN{16}CCG | 17 | 5 | 0.44 | 878 |
| 537 | GGCN{19}GCC | 68 | 29 | 0.44 | 879 |
| 538 | CCGN{3}CCG | 22 | 7 | 0.44 | 880 |
| 539 | CCCN{8}ACC | 58 | 31 | 0.44 | 881 |
| 540 | CAGN{15}GCC | 77 | 44 | 0.44 | 882 |
| 541 | CCCN{17}CGG | 24 | 8 | 0.44 | 883 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 542 | GCGN{1}CCA | 22 | 7 | 0.44 | 884 |
| 543 | CCCN{14}CAG | 79 | 46 | 0.44 | 885 |
| 544 | CCCN{8}CCC | 89 | 53 | 0.44 | 886 |
| 545 | ACAN{12}GCG | 23 | 8 | 0.43 | 887 |
| 546 | AGGN{4}CCG | 23 | 8 | 0.43 | 888 |
| 547 | CGCN{13}GCC | 23 | 8 | 0.43 | 889 |
| 548 | GAGN{2}CGC | 23 | 8 | 0.42 | 890 |
| 549 | CCCN{9}GCG | 21 | 7 | 0.42 | 891 |
| 550 | CGCN{17}ACA | 17 | 5 | 0.42 | 892 |
| 551 | GCGN{17}CCA | 23 | 8 | 0.42 | 893 |
| 552 | AAGN{18}CCG | 20 | 6 | 0.42 | 894 |
| 553 | CGCN{1}GGA | 18 | 5 | 0.41 | 895 |
| 554 | CCAN{1}CCC | 90 | 54 | 0.41 | 896 |
| 555 | CGTN{18}TGC | 20 | 6 | 0.41 | 897 |
| 556 | TCCN{14}CGA | 17 | 5 | 0.41 | 898 |
| 557 | CACN{5}GGG | 56 | 29 | 0.4 | 899 |
| 558 | CCGN{12}GCA | 21 | 7 | 0.4 | 900 |
| 559 | CTGN{6}CCC | 77 | 44 | 0.4 | 901 |
| 560 | CGGN{8}GGC | 32 | 13 | 0.4 | 902 |
| 561 | CCAN{11}GGG | 68 | 38 | 0.4 | 903 |
| 562 | ACGN{19}CAA | 21 | 7 | 0.39 | 904 |
| 563 | GGGN{20}CCC | 72 | 31 | 0.39 | 905 |
| 564 | CGCN{3}CAG | 23 | 8 | 0.39 | 906 |
| 565 | AGCN{17}GGG | 58 | 31 | 0.37 | 907 |
| 566 | CACN{20}CCG | 21 | 7 | 0.37 | 908 |
| 567 | ACGN{17}CAG | 24 | 8 | 0.37 | 909 |
| 568 | AGGN{1}CCC | 60 | 32 | 0.37 | 910 |
| 569 | CGTN{12}CAC | 20 | 6 | 0.37 | 911 |
| 570 | CGGN{9}GGC | 23 | 8 | 0.37 | 912 |
| 571 | CGCN{10}GCG | 18 | 3 | 0.37 | 913 |
| 572 | CCCN{6}CTC | 80 | 47 | 0.36 | 914 |
| 573 | CCGN{10}AGG | 23 | 8 | 0.36 | 915 |
| 574 | CCCN{18}CAG | 79 | 46 | 0.36 | 916 |
| 575 | AGCN{17}CCG | 21 | 7 | 0.36 | 917 |
| 576 | AGCN{9}GCG | 18 | 5 | 0.36 | 918 |
| 577 | CCAN{3}GGC | 62 | 34 | 0.36 | 919 |
| 578 | CCCN{11}GGC | 57 | 30 | 0.35 | 920 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 579 | ACGN{5}GCA | 23 | 8 | 0.35 | 921 |
| 580 | CCCN{14}CGG | 23 | 8 | 0.35 | 922 |
| 581 | CCCN{5}CCA | 91 | 55 | 0.35 | 923 |
| 582 | CCGN{1}AGG | 22 | 7 | 0.34 | 924 |
| 583 | GGGN{10}GAC | 45 | 22 | 0.34 | 925 |
| 584 | CGCN{15}CCA | 20 | 6 | 0.34 | 926 |
| 585 | CCTN{19}CGC | 22 | 7 | 0.34 | 927 |
| 586 | CGTN{3}CGC | 10 | 2 | 0.33 | 928 |
| 587 | AGCN{14}CCG | 21 | 7 | 0.33 | 929 |
| 588 | GGCN{2}CGA | 17 | 5 | 0.33 | 930 |
| 589 | CAGN{8}CCC | 79 | 46 | 0.33 | 931 |
| 590 | CCGN{2}GAC | 16 | 4 | 0.33 | 932 |
| 591 | AGCN{19}AGG | 70 | 40 | 0.32 | 933 |
| 592 | CCTN{4}GGC | 64 | 35 | 0.32 | 934 |
| 593 | CCGN{11}AGC | 22 | 7 | 0.32 | 935 |
| 594 | CACN{4}CGC | 18 | 5 | 0.32 | 936 |
| 595 | CCGN{1}CCC | 30 | 12 | 0.31 | 937 |
| 596 | CTGN{13}GGC | 73 | 42 | 0.31 | 938 |
| 597 | CGCN{16}ACC | 15 | 4 | 0.31 | 939 |
| 598 | CACN{18}CAG | 79 | 46 | 0.31 | 940 |
| 599 | GGCN{8}GCC | 68 | 29 | 0.29 | 941 |
| 600 | GGGN{15}GGA | 78 | 46 | 0.29 | 942 |
| 601 | CCGN{16}GCC | 22 | 7 | 0.29 | 943 |
| 602 | CCGN{20}ACC | 18 | 5 | 0.29 | 944 |
| 603 | CGAN{7}CCC | 17 | 5 | 0.28 | 945 |
| 604 | CCGN{6}CTC | 23 | 8 | 0.28 | 946 |
| 605 | CGGN{10}CTC | 22 | 7 | 0.28 | 947 |
| 606 | CAGN{16}CGC | 23 | 8 | 0.28 | 948 |
| 607 | CCAN{3}AGG | 77 | 45 | 0.27 | 949 |
| 608 | GCCN{18}GCC | 52 | 27 | 0.27 | 950 |
| 609 | CGCN{18}GGA | 19 | 6 | 0.26 | 951 |
| 610 | CCGN{20}GGC | 22 | 7 | 0.26 | 952 |
| 611 | ACAN{10}GCG | 17 | 5 | 0.26 | 953 |
| 612 | CGGN{5}CCC | 25 | 9 | 0.25 | 954 |
| 613 | CCCN{7}TCC | 75 | 43 | 0.25 | 955 |
| 614 | ACGN{10}CGC | 10 | 2 | 0.25 | 956 |
| 615 | CCCN{3}TCC | 81 | 48 | 0.25 | 957 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 616 | CCGN{8}CGG | 20 | 3 | 0.24 | 958 |
| 617 | CCAN{15}CGG | 22 | 7 | 0.24 | 959 |
| 618 | CCGN{6}CCG | 17 | 5 | 0.24 | 960 |
| 619 | CAGN{3}GCG | 25 | 9 | 0.24 | 961 |
| 620 | GAGN{1}CCC | 62 | 34 | 0.24 | 962 |
| 621 | CCGN{18}TGC | 22 | 7 | 0.23 | 963 |
| 622 | CCCN{7}CCA | 85 | 51 | 0.23 | 964 |
| 623 | CGGN{3}CCA | 24 | 9 | 0.23 | 965 |
| 624 | ACGN{1}CCC | 18 | 5 | 0.23 | 966 |
| 625 | CGGN{13}TGA | 21 | 7 | 0.22 | 967 |
| 626 | CTCN{6}GGC | 53 | 28 | 0.22 | 968 |
| 627 | GCGN{2}GAC | 15 | 4 | 0.22 | 969 |
| 628 | GGGN{11}ACC | 49 | 25 | 0.22 | 970 |
| 629 | CGCN{4}GGA | 17 | 5 | 0.22 | 971 |
| 630 | CCCN{11}CCG | 27 | 10 | 0.22 | 972 |
| 631 | CCGN{19}GCA | 20 | 6 | 0.22 | 973 |
| 632 | GCGN{0}GCA | 20 | 6 | 0.21 | 974 |
| 633 | AGAN{7}CCC | 61 | 33 | 0.21 | 975 |
| 634 | CGGN{2}CCA | 21 | 7 | 0.21 | 976 |
| 635 | CCCN{7}CCC | 89 | 54 | 0.21 | 977 |
| 636 | ACCN{4}GCG | 15 | 4 | 0.2 | 978 |
| 637 | CCTN{15}CGC | 20 | 6 | 0.2 | 979 |
| 638 | AGCN{9}GTC | 44 | 21 | 0.2 | 980 |
| 639 | CCCN{18}CTC | 74 | 43 | 0.2 | 981 |
| 640 | CGCN{18}CGA | 9 | 1 | 0.19 | 982 |
| 641 | CCCN{15}GCC | 62 | 34 | 0.18 | 983 |
| 642 | ACCN{11}GGC | 45 | 22 | 0.18 | 984 |
| 643 | AGGN{15}CGC | 29 | 12 | 0.18 | 985 |
| 644 | GCGN{0}CCA | 27 | 10 | 0.18 | 986 |
| 645 | GCGN{9}AGC | 18 | 5 | 0.17 | 987 |
| 646 | GGGN{18}GCA | 59 | 32 | 0.17 | 988 |
| 647 | CCCN{17}CAG | 77 | 45 | 0.17 | 989 |
| 648 | CCAN{8}CGG | 22 | 8 | 0.16 | 990 |
| 649 | CCGN{10}GGC | 21 | 7 | 0.16 | 991 |
| 650 | GCAN{0}GCC | 76 | 44 | 0.16 | 992 |
| 651 | CAGN{2}CGC | 20 | 6 | 0.16 | 993 |
| 652 | CGCN{8}GGC | 19 | 6 | 0.16 | 994 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 653 | CTGN{17}GGC | 65 | 36 | 0.16 | 995 |
| 654 | GGGN{14}ACC | 46 | 23 | 0.16 | 996 |
| 655 | CCGN{1}TGC | 20 | 6 | 0.16 | 997 |
| 656 | CAGN{8}CGC | 22 | 8 | 0.15 | 998 |
| 657 | AAGN{11}CGC | 17 | 5 | 0.15 | 999 |
| 658 | CCGN{6}TCC | 22 | 8 | 0.14 | 1000 |
| 659 | CCAN{18}CCC | 72 | 42 | 0.14 | 1001 |
| 660 | CCAN{0}CCC | 84 | 51 | 0.14 | 1002 |
| 661 | GAGN{6}CCC | 53 | 28 | 0.14 | 1003 |
| 662 | AGCN{20}GGC | 52 | 27 | 0.14 | 1004 |
| 663 | CAGN{0}CGC | 21 | 7 | 0.14 | 1005 |
| 664 | CCGN{12}CTC | 22 | 8 | 0.14 | 1006 |
| 665 | CGCN{15}ACG | 9 | 1 | 0.13 | 1007 |
| 666 | GGCN{17}CGA | 15 | 4 | 0.13 | 1008 |
| 667 | CCGN{16}AAG | 19 | 6 | 0.13 | 1009 |
| 668 | CGCN{14}TCC | 19 | 6 | 0.12 | 1010 |
| 669 | AGGN{7}CGC | 20 | 7 | 0.12 | 1011 |
| 670 | CGGN{7}CCC | 22 | 8 | 0.12 | 1012 |
| 671 | CGCN{4}GCC | 34 | 15 | 0.12 | 1013 |
| 672 | CGAN{6}CCC | 17 | 5 | 0.12 | 1014 |
| 673 | CCCN{19}GGA | 60 | 33 | 0.11 | 1015 |
| 674 | CCCN{16}GCG | 28 | 11 | 0.11 | 1016 |
| 675 | CCAN{7}CGC | 20 | 7 | 0.11 | 1017 |
| 676 | CCCN{6}GCC | 80 | 48 | 0.11 | 1018 |
| 677 | GCCN{14}TCC | 55 | 29 | 0.11 | 1019 |
| 678 | AGGN{14}GCC | 64 | 36 | 0.1 | 1020 |
| 679 | CGCN{11}GCC | 20 | 7 | 0.1 | 1021 |
| 680 | TCCN{0}GCA | 17 | 5 | 0.09 | 1022 |
| 681 | GCGN{8}CCC | 27 | 11 | 0.09 | 1023 |
| 682 | CCAN{11}GCG | 19 | 6 | 0.09 | 1024 |
| 683 | CACN{4}GGG | 51 | 26 | 0.09 | 1025 |
| 684 | CGGN{7}TCC | 20 | 7 | 0.09 | 1026 |
| 685 | GCGN{5}GCC | 20 | 7 | 0.09 | 1027 |
| 686 | ACGN{12}CAG | 26 | 10 | 0.09 | 1028 |
| 687 | CCGN{19}CGC | 14 | 4 | 0.08 | 1029 |
| 688 | CGGN{8}TGC | 18 | 5 | 0.08 | 1030 |
| 689 | CCCN{1}GAG | 65 | 37 | 0.07 | 1031 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 690 | GCGN{19}TGA | 18 | 6 | 0.07 | 1032 |
| 691 | GGCN{15}GCC | 70 | 31 | 0.07 | 1033 |
| 692 | CCGN{7}CCC | 27 | 11 | 0.07 | 1034 |
| 693 | ACAN{19}CCC | 63 | 35 | 0.07 | 1035 |
| 694 | ACCN{16}GGG | 47 | 24 | 0.07 | 1036 |
| 695 | AGAN{1}GGC | 64 | 36 | 0.07 | 1037 |
| 696 | GGGN{17}TGA | 64 | 36 | 0.06 | 1038 |
| 697 | CAGN{5}GGG | 83 | 50 | 0.06 | 1039 |
| 698 | GCCN{13}CGC | 22 | 8 | 0.06 | 1040 |
| 699 | GCGN{7}GGA | 19 | 6 | 0.06 | 1041 |
| 700 | CAGN{14}CCA | 94 | 58 | 0.06 | 1042 |
| 701 | CCGN{4}GTC | 16 | 4 | 0.06 | 1043 |
| 702 | CCCN{13}CGC | 22 | 8 | 0.06 | 1044 |
| 703 | GCGN{14}ACC | 15 | 4 | 0.05 | 1045 |
| 704 | CAGN{20}GGG | 81 | 49 | 0.05 | 1046 |
| 705 | CCGN{4}CCC | 27 | 11 | 0.05 | 1047 |
| 706 | CGCN{5}GGC | 18 | 6 | 0.05 | 1048 |
| 707 | CCTN{6}GGC | 57 | 31 | 0.05 | 1049 |
| 708 | AGGN{3}GGC | 67 | 38 | 0.05 | 1050 |
| 709 | CGGN{11}CGC | 14 | 4 | 0.05 | 1051 |
| 710 | CTGN{18}GGA | 77 | 46 | 0.04 | 1052 |
| 711 | CACN{17}CCA | 74 | 43 | 0.04 | 1053 |
| 712 | CGGN{3}GAG | 22 | 8 | 0.04 | 1054 |
| 713 | CCCN{9}CCA | 82 | 49 | 0.03 | 1055 |
| 714 | CCCN{1}ACG | 18 | 6 | 0.03 | 1056 |
| 715 | CAGN{1}GCC | 72 | 42 | 0.03 | 1057 |
| 716 | AGGN{6}CCG | 23 | 8 | 0.03 | 1058 |
| 717 | AGCN{9}GGG | 57 | 31 | 0.03 | 1059 |
| 718 | CCCN{7}GGC | 54 | 29 | 0.02 | 1060 |
| 719 | CCTN{13}CCC | 88 | 54 | 0.02 | 1061 |
| 720 | CCGN{19}TTC | 20 | 7 | 0.02 | 1062 |
| 721 | CCCN{7}CCG | 27 | 11 | 0.02 | 1063 |
| 722 | CGAN{6}GGC | 17 | 5 | 0.01 | 1064 |
| 723 | CGGN{4}CTC | 21 | 7 | 0.01 | 1065 |
| 724 | CGGN{0}CGC | 13 | 3 | 0.01 | 1066 |
| 725 | CCTN{13}ACG | 19 | 6 | 0.01 | 1067 |
| 726 | GGGN{6}CAC | 53 | 28 | 0.01 | 1068 |

TABLE 7-continued

Dyad patterns over-represented in STAR elements.

| Number | Dyad sequence | Observed occurrences | Expected occurrences | Significance coefficient | SEQ ID NO: |
|---|---|---|---|---|---|
| 727 | CCCN{16}CGC | 21 | 7 | 0.01 | 1069 |
| 728 | CCCN{10}CTC | 76 | 45 | 0 | 1070 |
| 729 | CCCN{0}CAG | 92 | 57 | 0 | 1071 |
| 730 | GCCN{5}CCC | 65 | 37 | 0 | 1072 |

TABLE 8

Candidate STAR elements tested by Linear Discriminant Analysis
(SEQ ID NOS: 66-84)

| SEQ ID NO: | Candidate STAR | Location[1] | Length |
|---|---|---|---|
| 66 | T2 F | 20q13.33 | ~2800 |
| 67 | T2 R | 6q14.1 | ~2800 |
| 68 | T3 F | 15q12 | ~2900 |
| 69 | T3 R | 7q31.2 | ~2900 |
| 70 | T5 F | 9q34.13 | ND[2] |
| 71 | T5 R | 9q34.13 | ND |
| 72 | T7 | 22q12.3 | ~1200 |
| 73 | T9 F | 21q22.2 | ~1600 |
| 74 | T9 R | 22q11.22 | ~1600 |
| 75 | T10 F | 7q22.2 | ~1300 |
| 76 | T10 R | 6q14.1 | ~1300 |
| 77 | T11 F | 17q23.3 | ~2000 |
| 78 | T11 R | 16q23.1 | ~2000 |
| 79 | T12 | 4p15.1 | ~2100 |
| 80 | T13 F | 20p13 | ~1700 |
| 81 | T13 R | 1p13.3 | ~1700 |
| 82 | T14 R | 11q25 | ~1500 |
| 83 | T17 | 2q31.3 | ND |
| 84 | T18 | 2q31.1 | ND |

[1]Chromosomal location is determined by BLAT search of DNA sequence data from the STAR elements against the human genome database. The location is given according to standard nomenclature referring to the cytogenetic ideogram of each chromosome; e.g., 1p2.3 is the third cytogenetic sub-band of the second cytogenetic band of the short arm of chromosome 1 (http://www.ncbi.nlm.nih.gov/Class/MLACourse/Genetics/chrombanding-.html). F, forward sequencing reaction result; R, reverse sequencing reaction result. When the forward and reverse sequencing results mapped to different genomic locations, each sequence was extended to the full length of the original clone (as determined by restriction mapping) based on sequence information from the human genome database.
[2]ND: Not Determined.

TABLE 9

*Arabidopsis* STAR elements of the invention, including chromosome location and length (SEQ ID NOS: 85-119)

| STAR | Chromosome | Length, kb | SEQ ID NO: |
|---|---|---|---|
| A1 | I | 1.2 | 85 |
| A2 | I | 0.9 | 86 |
| A3 | I | 0.9 | 87 |
| A4 | I | 0.8 | 88 |
| A5 | I | 1.3 | 89 |
| A6 | I | 1.4 | 90 |
| A7 | II | 1.2 | 91 |
| A8 | II | 0.8 | 92 |
| A9 | II | 0.9 | 93 |
| A10 | II | 1.7 | 94 |
| A11 | II | 1.9 | 95 |
| A12 | II | 1.4 | 96 |
| A13 | II | 1.2 | 97 |
| A14 | II | 2.1 | 98 |
| A15 | II | 1.4 | 99 |
| A16 | II | 0.7 | 100 |
| A17 | II | 1.5 | 101 |
| A18 | III | 1.5 | 102 |
| A19 | III | 0.7 | 103 |
| A20 | III | 2.0 | 104 |
| A21 | IV | 1.8 | 105 |
| A22 | IV | 0.8 | 106 |
| A23 | IV | 0.6 | 107 |
| A24 | IV | 0.5 | 108 |
| A25 | V | 0.9 | 109 |
| A26 | V | 1.9 | 110 |
| A27 | V | 1.1 | 111 |
| A28 | V | 1.6 | 112 |
| A29 | V | 0.9 | 113 |
| A30 | V | 2.0 | 114 |
| A31 | V | 2.0 | 115 |
| A32 | V | 1.3 | 116 |
| A33 | V | 0.9 | 117 |
| A34 | I | 0.9 | 118 |
| A35 | II | 1.1 | 119 |

REFERENCES

Altschul S. F., Gish W., Miller W., Myers E. W. and Lipman D. J. (1990) Basic local alignment search tool. *J. Mol. Biol.* 215, 403-10.

Bell A. C., West A. G. and Felsenfeld G. (2001) Insulators and boundaries: versatile regulatory elements in the eukaryotic genome. *Science* 291, 447-50.

Berger J., Hauber J., Hauber R., Geiger R. and Cullen B. R. (1988) Secreted placental alkaline phosphatase: a powerful new quantitative indicator of gene expression in eukaryotic cells. *Gene* 66, 1-10.

Bevan M., Mayer K., White O., Eisen J. A., Preuss D., Bureau T., Salzberg S. L. and Mewes H. W. (2001) Sequence and analysis of the *Arabidopsis* genome. *Curr. Opin. Plant Biol.* 4, 105-10.

Bibel M. and Barde Y. A. (2000) Neurotrophins: key regulators of cell fate and cell shape in the vertebrate nervous system. *Genes Dev.* 14, 2919-37.

Boivin A. and Dura J. M. (1998) In vivo chromatin accessibility correlates with gene silencing in *Drosophila*. *Genetics* 150, 1539-49.

Boshart M., Weber F., Jahn G., Dorsch-Hasler K., Fleckenstein B. and Schaffner W. (1985) A very strong enhancer is located upstream of an immediate early gene of human cytomegalovirus. *Cell* 41, 521-30.

Bunker C. A. and Kingston R. E. (1994) Transcriptional repression by *Drosophila* and mammalian Polycomb group proteins in transfected mammalian cells. *Mol. Cell. Biol.* 14, 1721-32.

Chung J. H, Whiteley M. and Felsenfeld G. (1993) A 5' element of the chicken beta-globin domain serves as an insulator in human erythroid cells and protects against position effect in *Drosophila*. *Cell* 74, 505-14.

Deuschle U., Meyer W. K. and Thiesen H. J. (1995) Tetracycline-reversible silencing of eukaryotic promoters. *Mol. Cell. Biol.* 15, 1907-14.

Doll R. F., Crandall J. E., Dyer C. A., Aucoin J. M. and Smith F. I. (1996) Comparison of promoter strengths on gene delivery into mammalian brain cells using AAV vectors. *Gene Ther.* 3, 437-447.

Foecking M. K. and Hofstetter H. (1986) Powerful and versatile enhancer-promoter unit for mammalian expression vectors. *Gene* 45, 101-5.

Garrick D., Fiering S., Martin D. I. and Whitelaw E. (1998) Repeat-induced gene silencing in mammals. *Nat. Genet.* 18, 56-9.

Gerasimova T. I. and Corces V. G. (2001) Chromatin insulators and boundaries: effects on transcription and nuclear organization. *Annu. Rev. Genet.* 35, 193-208.

Gossen M. and Bujard H. (1992) Tight control of gene expression in mammalian cells by tetracycline-responsive promoters. *Proc. Natl. Acad. Sci. U.S.A.* 89, 5547-51.

Graham F. L. and van der Eb A. J. (1973) Transformation of rat cells by DNA of human adenovirus 5. *Virology* 54, 536-9.

Henthorn P., Zervos P., Raducha M., Harris H. and Kadesch T. (1988) Expression of a human placental alkaline phosphatase gene in transfected cells: use as a reporter for studies of gene expression. *Proc. Natl. Acad. Sci. U.S.A.* 85, 6342-6.

Himes S. R. and Shannon M. F. (2000) Assays for transcriptional activity based on the luciferase reporter gene. *Methods Mol. Biol.* 130, 165-74.

Huberty C. J. (1994) Applied discriminant analysis, Wiley and Sons, New York.

Initiative A. G. (2000) Analysis of the genome sequence of the flowering plant *Arabidopsis thaliana*. *Nature* 408, 796-815.

Izumi M. and Gilbert D. M. (1999) Homogeneous tetracycline-regulatable gene expression in mammalian fibroblasts. *J. Cell. Biochem.* 76, 280-9.

Kain S. R. (1997) Use of secreted alkaline phosphatase as a reporter of gene expression in mammalian cells. *Methods Mol. Biol.* 63, 49-60.

Kaufman R. J. (1990) Selection and coamplification of heterologous genes in mammalian cells. *Methods in Enzymology* 185, 536-566.

Kellum R. and Schedl P. (1992) A group of scs elements function as domain boundaries in an enhancer-blocking assay. *Mol. Cell. Biol.* 12, 2424-2431.

Kent W. J. (2002) BLAT—the BLAST-like alignment tool. *Genome Res.* 12, 656-64.

Knofler M., Meinhardt G., Bauer S., Loregger T., Vasicek R., Bloor D. J., Kimber S. J. and Husslein P. (2002) Human Hand1 basic helix-loop-helix (bHLH) protein: extra-embryonic expression pattern, interaction partners and identification of its transcriptional repressor domains. *Biochem J.* 361, 641-51.

Meyer P. (2000) Transcriptional transgene silencing and chromatin components. *Plant Mol. Biol.* 43, 221-34.

Mercenier A., Wiedermann U. and Breiteneder H. (2001) Edible genetically modified microorganisms and plants for improved health. *Curr. Opin. Biotechnol.* 12, 510-5.

Morgenstern J. P. and Land H. (1990) Advanced mammalian gene transfer: high titre retroviral vectors with multiple drug selection markers and a complementary helper-free packaging cell line. *Nucleic Acids Res.* 18, 3587-96.

Sambrook J., Fritsch E. F. and Maniatis T. (1989) *Molecular Cloning: A Laboratory Manual*, Second ed., Cold Spring Harbor Laboratory Press, Plainview N.Y.

Sanger F., Nicklen S, and Coulson A. R. (1977) DNA sequencing with chain-terminating inhibitors. *Proc. Natl. Acad. Sci. U.S.A.* 74, 5463-7.

Stam M., Viterbo A., Mol. J. N. and Kooter J. M. (1998) Position-dependent methylation and transcriptional silencing of transgenes in inverted T-DNA repeats: implications for posttranscriptional silencing of homologous host genes in plants. *Mol. Cell. Biol.* 18, 6165-77.

Umana P., Jean-Mairet J. and Bailey J. E. (1999) Tetracycline-regulated overexpression of glycosyltransferases in Chinese hamster ovary cells. *Biotechnol. Bioeng.* 65, 542-9.

Van der Vlag J., den Blaauwen J. L., Sewalt R. G., van Driel R. and Otte A. P. (2000) Transcriptional repression mediated by polycomb group proteins and other chromatin-associated repressors is selectively blocked by insulators. *J. Biol. Chem.* 275, 697-704.

van Helden J., Andre B. and Collado-Vides J. (1998) Extracting regulatory sites from the upstream region of yeast genes by computational analysis of oligonucleotide frequencies *J. Mol. Biol.* 281, 827-42.

van Helden J., Andre B. and Collado-Vides J. (2000) A web site for the computational analysis of yeast regulatory sequences. *Yeast* 16, 177-87.

van Helden J., Rios A. F. and Collado-Vides J. (2000) Discovering regulatory elements in non-coding sequences by analysis of spaced dyads. *Nucleic Acids Res.* 28, 1808-18.

Vance V. and Vaucheret H. (2001) RNA silencing in plants—defense and counterdefense. *Science* 292, 2277-80.

Wigler M., Pellicer A., Silverstein S, and Axel R. (1978) Biochemical transfer of single-copy eucaryotic genes using total cellular DNA as donor. *Cell* 14, 725-31.

Yang T. T., Sinai P., Kitts P. A. and Kain S. R. (1997) Quantification of gene expression with a secreted alkaline phosphatase reporter system. *Biotechniques* 23, 1110-4.

Zink D. and Paro R. (1995) *Drosophila* Polycomb-group regulated chromatin inhibits the accessibility of a transactivator to its target DNA. *Embo. J.* 14, 5660-71.

What is claimed is:

1. A method for producing a proteinaceous molecule in a cell comprising:
   providing a cell selected from the group consisting of: a cell having an adenovirus Early Region 1 (E1) sequence, a HuNS-1 myeloma cell, a 293 cell, a CHO cell, a Vero cell, a WERI-Rb-1 retinoblastoma cell, a BHK cell, a non-secreting mouse myeloma Sp2/0-Ag 14 cell, a non-secreting mouse myeloma NSO cell, and an NCI-H295R adrenal gland carcinoma cell;
   wherein said cell comprises an anti-repressor activity sequence operably linked to a nucleic acid sequence encoding a heterologous proteinaceous molecule, wherein said anti-repressor activity sequence comprises SEQ ID NO:44;
   expressing the proteinaceous molecule in said cell; and
   isolating said proteinaceous molecule.

2. The method of claim 1, wherein said anti-repressor activity sequence is SEQ ID NO:44.

3. The method of claim 1, wherein said cell comprises an adenovirus Early Region 1 (E1) sequence.

4. The method of claim 1, wherein said proteinaceous molecule is secreted by said cell.

5. The method of claim 2, wherein said proteinaceous molecule is secreted by said cell.

6. The method of claim 1, wherein said cell comprises a plurality of the anti-repressor activity sequence operably linked to said nucleic acid sequence encoding the heterologous proteinaceous molecule.

7. The method of claim 6, wherein at least one anti-repressor activity sequence is positioned 5' of the sequence encoding the proteinaceous molecule and at least one anti-repressor activity sequence is positioned 3' of the sequence encoding the proteinaceous molecule.

8. The method of claim 1, wherein said cell is a CHO cell.

9. The method of claim 6, wherein said cell is a CHO cell.

10. The method of claim 7, wherein said cell is a CHO cell.

11. A recombinant host cell line, comprising:
   a cell selected from the group consisting of: a cell line comprising an adenovirus Early Region 1 (E1) sequence, a HuNS-1 myeloma cell line, a 293 cell line, a CHO cell line, a Vero cell line, a WERI-Rb-1 retinoblastoma cell line, a BHK cell line, a non-secreting mouse myeloma Sp2/0-Ag 14 cell line, a non-secreting mouse myeloma NSO cell line, and an NCI-H295R adrenal gland carcinoma cell line;
   said cell comprising an anti-repressor activity sequence operably linked to a nucleic acid sequence encoding a heterologous proteinaceous molecule, wherein said anti-repressor activity sequence comprises SEQ ID NO:44.

12. The cell line of claim 11, wherein said anti-repressor activity sequence is SEQ ID NO:44.

13. The cell line of claim 11, wherein said cell line comprises an adenovirus Early Region 1 sequence.

14. The cell line of claim 11, wherein said cell comprises a plurality of the anti-repressor activity sequence operably linked to said nucleic acid sequence encoding the heterologous proteinaceous molecule.

15. The cell line of claim 11, wherein at least one anti-repressor activity sequence is positioned 5' of the sequence encoding the proteinaceous molecule and at least one anti-repressor activity sequence is positioned 3' of the sequence encoding the proteinaceous molecule.

16. The cell line of claim 11, wherein said cell line is a CHO cell line.

17. The cell line of claim 14, wherein said cell line is a CHO cell line.

18. The cell line of claim 15, wherein said cell line is a CHO cell line.

* * * * *

SEQUENCE LISTING

<160> NUMBER OF SEQ ID NOS: 1072

<210> SEQ ID NO 1
<211> LENGTH: 749
<212> TYPE: DNA
<213> ORGANISM: Artificial Sequence

```
<220> FEATURE:
<223> OTHER INFORMATION: sequence of STAR1

<400> SEQUENCE: 1
atgcggtggg ggcgcgccag agactcgtgg gatccttggc ttggatgttt ggatctttct      60
gagttgcctg tgccgcgaaa gacaggtaca tttctgatta ggcctgtgaa gcctcctgga     120
ggaccatctc attaagacga tggtattgga gggagagtca cagaaagaac tgtgcccct      180
ccctcactgc aaaacggaag tgattttatt ttaatgggag ttggaatatg tgagggctgc     240
aggaaccagt ctccctcctt cttggttgga aaagctgggg ctggcctcag agacaggttt     300
tttggccccg ctgggctggg cagtctagtc gaccctttgt agactgtgca caccctaga     360
agagcaacta cccctataca ccaggctggc tcaagtgaaa ggggctctgg gctccagtct     420
ggaaaatctg gtgtcctggg gacctctggt cttgcttctc tcctcccctg cactggctct     480
gggtgcttat ctctgcagaa gcttctcgct agcaaaccca cattcagcgc cctgtagctg     540
aacacagcac aaaaagccct agagatcaaa agcattagta tgggcagttg agcgggaggt     600
gaatatttaa cgcttttgtt catcaataac tcgttggctt tgacctgtct gaacaagtcg     660
agcaataagg tgaaatgcag gtcacagcgt ctaacaaata tgaaaatgtg tatattcacc     720
ccggtctcca gccggcgcgc caggctccc                                      749

<210> SEQ ID NO 2
<211> LENGTH: 883
<212> TYPE: DNA
<213> ORGANISM: Artificial Sequence
<220> FEATURE:
<223> OTHER INFORMATION: sequence of STAR2

<400> SEQUENCE: 2
gggtgcttcc tgaattcttc cctgagaagg atggtggccg gtaaggtccg tgtaggtggg      60
gtgcggctcc ccaggccccg gcccgtggtg gtggccgctg cccagcggcc cggcaccccc     120
atagtccatg gcgcccgagg cagcgtgggg gaggtgagtt agaccaaaga gggctggccc     180
ggagttgctc atgggctcca catagctgcc ccccacgaag acggggcttc cctgtatgtg     240
tggggtccca tagctgccgt tgccctgcag gccatgagcg tgcgggtcat agtcggggt      300
gccccctgcg cccgccctg ccgccgtgta gcgcttctgt gggggtggcg ggggtgcgca     360
gctgggcagg gacgcagggt aggaggcggg gggcagcccg taggtaccct gggggggctt     420
ggagaagggc gggggcgact gggggctcata cgggacgctg ttgaccagcg aatgcataga     480
gttcagatag ccaccggctc cgggggcac ggggctgcga cttggagact ggccccccga     540
tgacgttagc atgcccttgc ccttctgatc ctttttgtac ttcatgcggc gattctggaa     600
ccagatcttg atctggcgct cagtgaggtt cagcagattg gccatctcca cccggcgcgg     660
ccggcacagg tagcggttga agtggaactc tttctccagc tccaccagct gcgcgctcgt     720
gtaggccgtg cgcgcgcgct tggacgaagc ctgccccggc gggctcttgt cgccagcgca     780
gctttcgcct gcgaggacag agagaggaag agcggcgtca ggggctgccg cggccccgcc     840
cagcccctga cccagcccgg cccctccttc caccaggccc caa                      883

<210> SEQ ID NO 3
<211> LENGTH: 2126
<212> TYPE: DNA
<213> ORGANISM: Artificial Sequence
<220> FEATURE:
<223> OTHER INFORMATION: sequence of STAR3
```

<400> SEQUENCE: 3

```
atctcgagta ctgaaatagg agtaaatctg aagagcaaat aagatgagcc agaaaaccat      60
gaaaagaaca gggactacca gttgattcca caaggacatt cccaaggtga gaaggccata     120
tacctccact acctgaacca attctctgta tgcagattta gcaaggttat aaggtagcaa     180
aagattagac ccaagaaaat agagaacttc caatccagta aaaatcatag caaatttatt     240
gatgataaca attgtctcca aaggaacaag gcagagtcgt gctagcagag gaagcacgtg     300
agctgaaaac agccaaatct gctttgtttt catgacacag gagcataaag tacacaccac     360
caactgacct attaaggctg tggtaaaccg attcatagag agaggttcta aatacattgg     420
tccctcacag gcaaactgca gttcgctccg aacgtagtcc ctggaaattt gatgtccagt     480
atagaaaagc agagcagtca aaaaatatag ataaagctga accagatgtt gcctgggcaa     540
tgttagcagc accacactta agatataacc tcaggctgtg gactccctcc ctggggagcg     600
gtgctgccgg cggcgggcgg gctccgcaac tccccggctc tctcgcccgc cctcccgttc     660
tcctcgggcg gcggcggggg ccgggactgc gccgctcaca gcggcggctc ttctgcgccc     720
ggcctcggag gcagtggcgg tggcggccat ggcctcctgc gttcgccgat gtcagcattt     780
cgaactgagg gtcatctcct tgggactggt tagacagtgg gtgcagccca cggagggcga     840
gttgaagcag ggtggggtgt cacctccccc aggaagtcca gtgggtcagg gaactccctc     900
ccctagccaa gggaggccgt gagggactgt gcccggtgag agactgtgcc ctgaggaaag     960
gtgcactctg gcccagatac tacactttc ccacggtctt caaaacccgc agaccaggag    1020
attccctcgg gttcctacac caccaggacc ctgggtttca accacaaaac cgggccattt    1080
gggcagacac ccagctagct gcaagagttg ttttttttttt tatactcctg tggcacctgg    1140
aacgccagcg agagagcacc tttcactccc ctggaaaggg ggctgaaggc agggaccttt    1200
agctgcgggc taggggggttt ggggttgagt ggggggaggg agagggaaaa ggcctcgtca    1260
ttggcgtcgt ctgcagccaa taaggctacg ctcctctgct gcgagtagac ccaatccttt    1320
cctagaggtg gaggggggcgg gtaggtggaa gtagaggtgg cgcggtatct aggagagaga    1380
aaaagggctg gaccaatagg tgcccggaag aggcggaccc agcggtctgt tgattggtat    1440
tggcagtgga ccctcccccg gggtggtgcc ggaggggggg atgatgggtc gaggggtgtg    1500
tttatgtgga agcgagatga ccggcaggaa cctgccccaa tgggctgcag agtggttagt    1560
gagtgggtga cagacagacc cgtaggccaa cgggtggcct taagtgtctt tggtctcctc    1620
caatggagca gcggcggggc gggaccgcga ctcgggttta atgagactcc attgggctgt    1680
aatcagtgtc atgtcggatt catgtcaacg acaacaacag ggggacacaa aatggcggcg    1740
gcttagtcct acccctggcg gcggcggcag cggtggcgga ggcgacggca ctcctccagg    1800
cggcagccgc agtttctcag gcagcggcag cgccccggc aggcgcggtg gcggtggcgc    1860
gcagccaggt ctgtcaccca ccccgcgcgt tccaggggg aggagactgg gcgggagggg    1920
ggaacagacg gggggggatt caggggcttg cgacgcccct cccacaggcc tctgcgcgag    1980
ggtcaccgcg gggccgctcg gggtcaggct gcccctgagc gtgacggtag ggggcggggg    2040
aaagggagg agggacaggc cccgcccctc ggcagggcct ctagggcaag ggggcggggc    2100
tcgaggagcg gagggggggcg gggcgg                                        2126
```

<210> SEQ ID NO 4
<211> LENGTH: 1625
<212> TYPE: DNA
<213> ORGANISM: Artificial Sequence
<220> FEATURE:
<223> OTHER INFORMATION: sequence of STAR4

<400> SEQUENCE: 4

```
gatctgagtc atgttttaag gggaggattc ttttggctgc tgagttgaga ttaggttgag      60
ggtagtgaag gtaaaggcag tgagaccacg taggggtcat tgcagtaatc caggctggag     120
atgatggtgg ttcagttgga atagcagtgc atgtgctgta acaacctcag ctgggaagca     180
gtatatgtgg cgttatgacc tcagctggaa cagcaatgca tgtggtggtg taatgacccc     240
agctgggtag ggtgcatgtg gtgtaacgac ctcagctggg tagcagtgtg tgtgatgtaa     300
caacctcagc tgggtagcag tgtacttgat aaaatgttgg catactctag atttgttatg     360
agggtagtgc cattaaattt ctccacaaat tggttgtcac gtatgagtga aagaggaag      420
tgatggaaga cttcagtgct tttggcctga ataaatagaa gacgtcattt ccagttaatg     480
gagacaggga agactaaagg tagggtggga ttcagtagag caggtgttca gttttgaata     540
tgatgaactc tgagagagga aaaactttt ctacctctta gttttgtga ctggacttaa      600
gaattaaagt gacataagac agagtaacaa gacaaaaata tgcgaggtta tttaatattt     660
ttacttgcag aggggaatct tcaaaagaaa aatgaagacc caaagaagcc attagggtca     720
aaagctcata tgccttttta agtagaaaat gataaatttt aacaatgtga aagacaaag      780
gtgtttgagc tgagggcaat aaattgtggg acagtgatta agaaatatat gggggaaatg     840
aaatgataag ttattttagt agatttattc ttcatatcta ttttggcttc aacttccagt     900
ctctagtgat aagaatgttc ttctcttcct ggtacagaga gagcaccttt ctcatgggaa     960
attttatgac cttgctgtaa gtagaaaggg gaagatcgat ctcctgtttc ccagcatcag    1020
gatgcaaaca tttccctcca ttccagttct caaccccatg gctgggcctc atggcattcc    1080
agcatcgcta tgagtgcacc tttcctgcag gctgcctcgg gtagctggtg cactgctagg    1140
tcagtctatg tgaccaggag ctgggcctct gggcaatgcc agttggcagc ccccatcct     1200
ccactgctgg gggcctccta tccagaaggg cttggtgtgc agaacgatgg tgcaccatca    1260
tcattcccca cttgccatct ttcagggac agccagctgc tttgggcgcg caaaaaaca     1320
cccaactcac tcctcttcag gggcctctgg tctgatgcca ccacaggaca tccttgagtg    1380
ctgggcagtc tgaggacagg gaaggagtga tgaccacaaa acaggaatgg cagcagcagt    1440
gacaggagga agtcaaaggc ttgtgtgtcc tggccctgct gagggctggc gagggccctg    1500
ggatggcgct cagtgcctgg tcggctgcaa gaggccagcc ctctgcccat gagggggagct    1560
ggcagtgacc aagctgcact gccctggtgg tgcatttcct gccccactct ttccttctaa    1620
gatcc                                                                 1625
```

<210> SEQ ID NO 5
<211> LENGTH: 1571
<212> TYPE: DNA
<213> ORGANISM: Artificial Sequence
<220> FEATURE:
<223> OTHER INFORMATION: sequence of STAR5

<400> SEQUENCE: 5

```
agcagagatc ttatttcccg tattcccttg tggcacagca cctcccacgc caaagcaaac      60
caaagcaaag gagcccttga tgaggagggg ccttccccca acctggtctc ccacaggtcc     120
tacatacgta cccaccccag acacacagag ctgcttcctg ctctcacacc agactgagct     180
gtgcccagac atttccccta gcactaacca actctttcaa aaatacattt ttctctaaaa     240
```

```
agaacaagtt taaacaaagt tgactcattt taagaactgt ttagaagata accttgtgtt      300
tattaattat gtatttgcag aaattggagg cagaaggtta ccaacattgc ctggtgtcca      360
gccaggaggt agagcgtggt ggcatccaga accttcctcc aactcctgcc tggcgtggtt      420
tttattcatc tttgtattcc caagaaactt ctcagtgtct caggagtgtt aggcactcag      480
tacgtgtttg gtagttacat gaatgaatgc ataatgacta agtgagttaa tggatgaagc      540
taattgtctc tcccttttgc ttttccagag ctttccaagg tgaaagtgtt ggacactctt      600
tcttcatctc agatttaatc aactaagaat gctgcaaatt gaacaccagt ccacaaaact      660
caggaataca tgaaaagcat tgtgccttat ttttaactaa ctcaaattct atgtcagtct      720
cccttttatg ctggatgttg cgctaaatc tcagtgggtt cctcattctg ccagacctgt      780
gtccagtttg ggggcttcac atagagccac cccatcacag gagagggaag ggtcttgctc      840
ttggttgcca tcactccacc ctcttgtctt ccgagctttg atgttcactt tccttttcac      900
cactcggaag cttcctgcca tgatacattg agacctcaat gttaatgcca attgggttt       960 ggggttctca taaactcaga agtccaggaa aatcgcctgc tgcctcccac aacactctga    1020
gggcattctg gaatcctacc acttacctgg agcctgctgg cctcaactgt tttgaagtct    1080
gtgtctgggc catgcaggta aatgggagga tgttctgtgg ccataaaaat acccgaagtc    1140
ccacctaaag ttgatgcagg gtcttctgca tttcattgca aaattgttct atcatttcta    1200
tagttttcag cctacagtca ggggccagga ctttgcaccc ttggtaaacc tcaatctctt    1260
ctccttcctg gcttctactc ctttctccct caatcccaaa tcaaggccct tgattgtctg    1320
gaggtaggaa agcctggttc tggctcatga tatagtctac atcatagcct ttgtcatctc    1380
atggattcac tcaacaaccg tgtgtggatg gggccaccca atatgtgcca ggagttgagg    1440
acacgcaggg ttatgatgat gaaatagata aggggcccac actcacggac cctgcaggac    1500
agtggagctg tggacccagc atgcgagtaa agaccccagtg agctcaccag acagatcatt    1560
taaatcaggt g                                                         1571
```

```
<210> SEQ ID NO 6
<211> LENGTH: 1173
<212> TYPE: DNA
<213> ORGANISM: Artificial Sequence
<220> FEATURE:
<223> OTHER INFORMATION: sequence of STAR6

<400> SEQUENCE: 6
```

```
tgacccacca cagacatccc ctctggcctc ctgagtggtt tcttcagcac agcttccaga       60
gccaaattaa acgttcactc tatgtctata gacaaaaagg ttttgactaa aactctgtgt      120
tttagagagg gagttaaatg ctgttaactt tttaggggtg ggcgagaggg atgacaaata      180
acaacttgtc tgaatgtttt acatttctcc ccactgcctc aagaaggttc acaacgaggt      240
catccatgat aaggagtaag acctcccagc cggactgtcc ctcggcccccc agaggacact    300 ccacagagat atgctaactg gacttggaga ctggctcaca ctccagagaa agcatggag       360 cacgagcgca cagagcaggg ccaaggtccc aggacagaa tgtctaggag ggagattggg      420
gtgagggtaa tctgatgcaa ttactgtggc agctcaacat tcaagggagg gggaagaaag     480
aaacagtccc tgtcaagtaa gttgtgcagc agagatggta agctccaaaa tttgaaactt     540
tggctgctgg aaagttttag ggggcagaga taagaagaca taagagactt tgagggttta    600
ctacacacta gacgctctat gcattttattt atttattatc tcttatttat tactttgtat   660
aactcttata ataatcttat gaaaacggaa accctcatat acccattta cagatgagaa      720
```

```
aagtgacaat tttgagagca tagctaagaa tagctagtaa gtaaaggagc tgggacctaa      780
accaaaccct atctcaccag agtacacact cttttttttt ttccagtgta attttttta       840 attttattt tactttaagt tctgggatac atgtgcagaa ggtatggttt gttacatagg       900
tatatgtgtg ccatagtgga ttgctgcacc tatcaacccg tcatctaggt ttaagcccca     960
catgcattag ctatttgtcc tgatgctctc cctcccctcc ccacaccaga caggccttgg    1020
tgtgtgatgt tcccctccct gtgtccatgt gttctcactg ttcagctccc acttatgagt   1080
gagaacgtgt ggtatttggt tttctgttcc tgtgttagtt tgctgaggat gatggcttcc   1140
agcttcatcc atgtccctgc aaaggacacg atc                                 1173
```

<210> SEQ ID NO 7
<211> LENGTH: 2101
<212> TYPE: DNA
<213> ORGANISM: Artificial Sequence
<220> FEATURE:
<223> OTHER INFORMATION: sequence of STAR7

<400> SEQUENCE: 7

```
atcatgccag cttaggcgac agagtgagac tggacataat aacaataata ataaaaataa     60
ataaataaaa caattatctg agaggaaaaa tttgattcat aataaagaga ataaggtttt    120
ttggcgtgtt tgttttgttt tcacctaaga acagctgttc ccctcattgg gttagtttta   180
tttgcaagca gaaatcatct ccgcatgatt tccagggtga tggaaaactg aatatgaatc   240
caccttctgc catctattca cttgtcacat ttaataagac actcatgcct attttagcat   300
gttttcttcc ctaccaaatg agttagtaac atcaagagat taaataaca caaataagaa   360 cattgaaggt attcaaatgt tacatacaaa tattaaacac aatattatta taattattcc   420
tggaaatgac attgcctcta ctctcaaggt aaaggtcatt tttcttgatt taaacttttt   480
tctcaagttt gaaatctcta agtttcaacc cgtaatctat ttgcaagttt gtgcaaattt   540
tagggattga atccatagta attagtgatt tattgtggtg tagggagaca agtcaaaaga   600
atcaggactg ctaggtagat gactaaggaa aggatggttc acgaggtgac ataaagcact   660
cagaagaaaa aggtcaggaa acggaggaca gaaaaaaacc taagttctgc tgggtgatgc   720
tgaatttgtc atcacaaaat ctgcattgtg gaagctttag ctattgagga gattgctcaa   780
gtgtagaact gagaacaata ggcagtgaac ccgagagaac atcaagagac tgagagaaaa   840
tgaaccagac ttccaggtgc tccatgttcc aaccaacatt ttgtattgtc agaaggaatt   900
gagaggcaaa aggaaaccca ataaaaaata aaacaggaaa gggcatacat gattaccacc    960
ccttttctca ccagctgctc atggaccagc tttctcctag tgctatttc ttggtcactg   1020 catcactctg ctaacatagt ttccccacta gctctgaggc tgtcccagag gggaagccag   1080
ctgtcatctc cttcttccac actctgttgg aggaacctgt cattagcagc tccctactaa   1140
acgcatttat gacaaacagg caggagataa ttaactagaa agtgaacaaa ctcaaacttc   1200
agagcctctc atttgtatga atgcccttgt aaggtcttgg gcctatttta atatttataa   1260
atgtgttatt ttcttctaaa gaaaaccacc aaattgtata agctacagaa tctgcaaaac   1320
tgaggtccat ccatgcactc aggatacatt catagcatct ctgagctgga aaatatctta   1380
aaggtcatat atgtcctcca acactgcaag aatctctctg gcagcattct tttaaaatca   1440
tcatctaaaa gagggaaatc cccagctgtg tttggatttt gctctgtcac ttgtccagtt   1500
tccccatcca taaagggca acaatatgaa tttcctgata aggtagttgt taatataaat   1560
```

| | |
|---|---|
| acaaagtgcg tagccacttc cctaagaaaa atatggggtt tctgcttcac agtctaggga | 1620 |
| gaggaaaaaa aagggggtc agaagtgatt attattatca ttctatattg gaatgttttc | 1680 |
| agacataaaa agctcaccac gtcttaggcc agacagatgc attatgaaag ttaagctaag | 1740 |
| tcttcctcat catgagctgc acctatatcc ccattacttc ttctagaact gcataattta | 1800 |
| tttattcttt cttcaaaagt ttgagagagc cattcttgtc ctctaagatt ttttttttt | 1860 |
| tttttggaga cagagtctcc gtctgttgcc caggctggag tgcaatggca ctatctcagc | 1920 |
| tcactgcaac ctctgcctcc cagattcaag tgattctcct gcctcagcct cccgagtagc | 1980 |
| tgggattaca agcacgcacc accacaacca gctaatttttt cgtattttttt agtagagacg | 2040 |
| aggttttacc atgttggcca ggctggtctt gaactcctga cctcgggtga tccacccacc | 2100 |
| t | 2101 |

<210> SEQ ID NO 8
<211> LENGTH: 1821
<212> TYPE: DNA
<213> ORGANISM: Artificial Sequence
<220> FEATURE:
<223> OTHER INFORMATION: sequence of STAR8

<400> SEQUENCE: 8

| | |
|---|---|
| gagatcacct cgaagagagt ctaacgtccg taggaacgct ctcgggttca caaggattga | 60 |
| ccgaacccca ggatacgtcg ctctccatct gaggcttgct ccaaatggcc ctccactatt | 120 |
| ccaggcacgt gggtgtctcc cctaactctc cctgctctcc tgagcccatg ctgcctatca | 180 |
| cccatcggtg caggtccttt ctgaagagct cgggtggatt ctctccatcc cacttccttt | 240 |
| cccaagaaag aagccaccgt tccaagacac ccaatgggac attccccttc cacctccttc | 300 |
| tccaaagttg cccaggtgtt catcacaggt tagggagaga agcccccagg tttcagttac | 360 |
| aaggcatagg acgctggcat gaacacacac acacacacac acacacacac acacacacac | 420 |
| acacgactcg aagaggtagc cacaagggtc attaaacact tgacgactgt tttccaaaaa | 480 |
| cgtggatgca gttcatccac gccaaagcca agggtgcaaa gcaaacacgg aatggtggag | 540 |
| agattccaga ggctcaccaa accctctcag gaatattttc ctgaccctgg gggcagaggt | 600 |
| tggaaacatt gaggacattt cttgggacac acggagaagc tgaccgacca ggcattttcc | 660 |
| tttccactgc aaatgaccta tggcgggggc atttcacttt cccctgcaaa tcacctatgg | 720 |
| cgaggtacct ccccaagccc caccccccac ttccgcgaat cggcatggct cggcctctat | 780 |
| ccgggtgtca ctccaggtag gcttctcaac gctctcggct caaagaagga caatcacagg | 840 |
| tccaagccca agcccacac ctcttccttt tgttataccc acagaagtta gagaaaacgc | 900 |
| cacactttga gacaaattaa gagtccttta tttaagccgg cggccaaaga gatggctaac | 960 |
| gctcaaaatt ctctgggccc cgaggaaggg gcttgactaa cttctatacc ttggtttagg | 1020 |
| aagggggggg gaactcaaat gcggtaattc tacagaagta aaaacatgca ggaatcaaaa | 1080 |
| gaagcaaatg gttatagaga gataaacagt tttaaaggc aaatggttac aaaaggcaac | 1140 |
| ggtaccaggt gcgggctct aaatccttca tgacacttag ataggtgc tatgctggac | 1200 |
| acgaactcaa ggctttatgt tgttatctct tcgagaaaaa tcctgggaac ttcatgcact | 1260 |
| gtttgtgcca gtatcttatc agttgattgg gctcccttga aatgctgagt atctgcttac | 1320 |
| acaggtcaac tccttgcgga aggggttgg gtaaggagcc cttcgtgtct cgtaaattaa | 1380 |
| ggggtcgatt ggagtttgtc cagcattccc agctacagag agccttattt acatgagaag | 1440 |
| caaggctagg tgattaaaga gaccaacagg gaagattcaa agtagcgact tagagtaaaa | 1500 |

```
acaaggttag gcatttcact ttcccagaga acgcgcaaac attcaatggg agagaggtcc    1560
cgagtcgtca aagtcccaga tgtggcgagc ccccgggagg aaaaaccgtg tcttccttag    1620
gatgcccgga acaagagcta ggcttccgga gctaggcagc catctatgtc cgtgagccgg    1680
cgggagggag accgccggga ggcgaagtgg ggcggggcca tccttctttc tgctctgctg    1740
ctgccgggga gctcctggct ggcgtccaag cggcaggagg ccgccgtcct gcagggcgcc    1800
gtagagtttg cggtgcagag t                                              1821
```

<210> SEQ ID NO 9
<211> LENGTH: 1929
<212> TYPE: DNA
<213> ORGANISM: Artificial Sequence
<220> FEATURE:
<223> OTHER INFORMATION: sequence of STAR9

<400> SEQUENCE: 9

```
atgagccccc aaaaatgatc ctctggctta tgacaacctg atgcagccca ggaaatgcct      60
gcaacatgcc cactagcagc tgggaacccc tctgtgagga agagaacgtt ttacattaag     120 aaacccttg ttttgcagca gagactattc aggtcacaca tgtgtggcct ctcagttctt      180
tgagccattt gaagttctct atccttgctg ggaggctgag ctctccatgg aaacctggtc     240
cgatagtgag aggagcagac cctctggaaa caccttttta cacctgacca agcagccag     300 tcatgggcca gtgatgcaac aaggtcaacc ggtgcattct ggcccctcag aaaagcagcc    360
cccgggaagg tcaggaggag gctgctgact ccctcttccc ctgcagccgc ccaagcaca    420 cccaggagcc ctgcaggttt gggttcacca ggtgccagca ggtcccacga tgctgcattt    480
cttacgagct cctggaggat gcagatggtc ctggtcagag gctgcattct gagtatcagg    540
agccatgggg caacgtttct gcgattgagg aagggggcatt tctggggtgg gcagaacaaa   600
ggtctttggc tgagctggag catccgcctc atcagtgtt ttccggcaac tgtactatcc    660
atcgtcttcc cttcccacag ctgaccatgg cttttggaaaa tgctctgaaa cttctttttc    720
agaagagttg actcccaact ccacacttag gggaagtcaa gcctacttct cagaattcag    780
agaaggcata aaaagaatt catttctaaa ggccctttag aagtaacttc aggtctgaca    840
gcggccagct aatttctggt cgccttccag gaatcttctg actgcaaaaa aaagcatttt    900
accacctgaa cacaaaccca gttacagata gaaaaacata gtcatttaaa tagaatataa    960
gcatctggcc tctgcccatc ataatggagt aacacaaaaa tctatttttca aaaggaaact  1020 aaatattatt gaccaaaaca tgaatgggga gacctcaggg tgatacagct cttgcctgga  1080
tggaatttgt aatcaagagg atgagacagg attgtaactt gtgccaatgt gaaagggttt  1140
gctcaggtat cattcatttt gcttaaatgc atgggtaatt tccaaagttc tttggagctg  1200
aatttcacaa tttagtgcag gtcctggtga gcccaccttg acttatctca cagtacaatg  1260
cagtggcgtg gctacaatgc tgggcaagag aagccaatgt caacagccca ggagtggctg  1320
ggtccttacc aggctcccag gcatgcttca tggtgggccc tggctgggag gaacagcac    1380 ctttgcctgg tccatgagta tctgggtcaa actctcctgt ggacacagaa ggccatggcg  1440
acaggcattc ccaggaaaag aaagggcag cagctgaaat cgtcaggtgg agaaggcagt    1500
catccttgct cagtcaactc taatccggct gcctcctcct cagcttcagg gtgaacctct  1560
cctaagctgt gtcttggta tctgatgggc attaggtgct ggtgaaaaag ctggagggtc  1620
ctttgggata ttacagaagc ccaatctagc cttgtattca atatctaggc actctcaccc  1680
```

```
ctgaagttct acgtttccag atttctgaaa acatgggaaa gcatgtgtgt gatgtctgag    1740
gtccccctca gcctctggtg tagggttagg agggctctaa agggtggcag ctccagtgtc    1800 ccagtgggc ctgaagttgg tcccttccct tcccagctcc catccatggt ttagcccaat     1860
cccttccgta cctaagagta ctgcacatgg atgctccacg cagagcctct gctccactcc    1920
caggaagtg                                                            1929

<210> SEQ ID NO 10
<211> LENGTH: 1167
<212> TYPE: DNA
<213> ORGANISM: Artificial Sequence
<220> FEATURE:
<223> OTHER INFORMATION: sequence of STAR10
<220> FEATURE:
<221> NAME/KEY: misc_feature
<222> LOCATION: (452)..(1143)
<223> OTHER INFORMATION: "N" stands for any nucleotide on various
      positions

<400> SEQUENCE: 10
aggtcaggag ttcaagacca gcctggccaa catggtgaaa ccctgtccct acaaaaaata    60
caaaaattag ccgggcgtgg tggggggcgc ctataatccc agctactcag gatgctgaga    120
caggagaatt gtttgaaccc gggaggtgga ggttgcagtg aactgagatc gcgccactgc    180
actccagcct ggtgacagag agagactccg tctcaacaac agacaaacaa acaaacaaac    240
aacaacaaaa atgtttactg acagctttat tgagataaaa ttcacatgcc ataaaggtca    300
ccttctacag tatacaattc agtggattta gtatgttcac aaagttgtac gttgttcacc    360
atctactcca gaacatttac atcaccccta aaagaagctc tttagcagtc acttctcatt    420
ctccccagcc cctgccaacc acgaatctac tntctgtctc tattctgaat atttcatata    480
aaggagtcct atcatatggg cctttacgt ctaccttctt tcacttagca tcatgttttt     540
aagattcatc cacagtgtag cacgtgtcag ttaattcatt tcatcttatg ctggataat     600 gctctattgt atgcatatcc ctcactttgc ttatccattc atcaactgat tgacatttgg    660
gttatttcta cttttttgact attatgagta atgctgctat gaacattcct gtaccaatcg   720
ttacgtggac atatgctttc aattctcctg agtatgtaac tagggttgga gttgctgggt    780
catatgttaa ctcagtgttt cattttttg aagaactacc aaatggtttt ccaaagtgga     840
tgcaacactt tacattccca ccagcaagat atgaaggttc caatgtctct acatttttgc    900
caacacttgt gattttcttt tatttattta tttatttatt tatttttgag atggagtctc    960
actctgtcac ccaggctgga gtgcagtggc acaatttcag ctcactgcaa tctccacctc    1020
tcgggctcaa gcgatactcc tgcctcaacc tcccgagtaa ctgggattac aggcgcccac    1080
caccacacca agctaatttt ttgtattttt agtagagacg gggtttcatc atgtcggcca    1140
ggntgtactc gaactctgac ctcaagt                                        1167

<210> SEQ ID NO 11
<211> LENGTH: 1377
<212> TYPE: DNA
<213> ORGANISM: Artificial Sequence
<220> FEATURE:
<223> OTHER INFORMATION: sequence of STAR11

<400> SEQUENCE: 11
gattctgggt gggtttgatg atctgagagt cccttgaata aaagaattc tagaaaagct     60 gtgaaacttc acctttcccc tattcttaac cttacttgcc tttgggaggc tgaggcagga    120
```

```
ggatgactta aggccaggag tttgagaatg tagtgagcta tgaccacacc ggttacactc      180
aagcctgggc gagaccacaa caaaaacctt acctgccaac tgctccatgc tggaaattta      240
tttcgtttct tggattgtgg aaagaactgg cttactgaaa accacacttc tctaaaaccc      300
ttcttccagt taggtgttaa gattttaaca gcctttccta tctgaataaa aactgcacac      360
aaagtaaact taagagatgt caacaactca tctgtttgtt acaagatgag tctccatgct      420
tcatcgcctg tggggaatcc tcatcagcgt ctagtggcaa agactcctgt gtgctcaccg      480
aaacgctccc cttcctccag ggcacacagt cacatggatt tcccatgcac cctggcagct      540
cagcaggagt ccatgactta agaaggccaa tggactgtgg gtgaagtctg tggacgggga      600
agccacatgc gtcacttcca ggcctgggcg tgtgcatcct ccactctctt ccctgtggg       660 tgcagaaggc ggggcagagg gccctgaaac cttggaggtc ggtggagccc aaaatgaagg      720
agcgtgggcc tctgggtctt catgtaaatt taggtaacac tgaactgtca ggtgaacaag      780
aaataaacgt caaatgtatt cagtcgatta gatttggtga tggttgttac agcggttacc      840
ctccctcaac ataataaatt ttcaaacaac tcataatggc tcactcatgt ataaaatatt      900
ccatatgaaa tcccgggata acatgcttat tctagctcaa gcttaatcag agtagtccat      960
ctgagggagg agatagtaga gggcagcaag gggttgtcac tgaagataac tagccttgct     1020
aaaagaatgg ttgaagaagt gagctacaga tagggtaaat ccacatctca gacattctgt     1080
gatggtcctg atattatcct aaagtaaaat gtagagttga accatttaa ttagattcta      1140 gaattctatt aatttataag atgggcattt ccacaaagga ctaaacaaag tacaagagga     1200
ttaaataatc atccacatgg gaggcaccgc cttgcacttt aaaatgatgg agcttatcaa     1260
gactggctgt ggatatctgt ccctgggagg gttttttccc ccatttttt ccttttgag      1320 acatgttctc gctatgttgc ccaggctggt cttgaactcc tgggctcaag tgatcct        1377
```

<210> SEQ ID NO 12
<211> LENGTH: 1051
<212> TYPE: DNA
<213> ORGANISM: Artificial Sequence
<220> FEATURE:
<223> OTHER INFORMATION: sequence of STAR12

<400> SEQUENCE: 12

```
atcctgcttc tgggaagaga gtggcctccc ttgtgcaggt gactttggca ggaccagcag       60
aaacccaggt ttcctgtcag gaggaagtgc tcagcttatc tctgtgaagg gtcgtgataa      120
ggcacgagga ggcaggggct tgccaggatg ttgccttcct gtgccatatg ggacatctca      180
gcttacgttg ttaagaaata tttggcaaga agatgcacac agaatttctg taacgaatag      240
gatggagttt taagggttac tacgaaaaaa agaaaactac tggagaagag ggaagccaaa      300
caccaccaag tttgaaatcg attttattgg acgaatgtct cactttaaat ttaaatggag      360
tccaacttcc ttttctcacc cagacgtcga gaaggtggca ttcaaaatgt ttacacttgt      420
ttcatctgcc tttttgctaa gtcctggtcc cctacctcct ttccctcact tcacatttgt      480
cgtttcatcg cacacatatg ctcatctttta tatttacata tatataattt ttatatatgg      540
cttgtgaaat atgccagacg agggatgaaa tagtcctgaa aacagctgga aaattatgca      600
acagtgggga gattgggcac atgtacattc tgtactgcaa agttgcacaa cagaccaagt      660
ttgttataag tgaggctggg tggttttttat ttttctcta ggacaacagc ttgcctggtg       720
gagtaggcct cctgcagaag gcatttcctt aggagcctca acttcccaa gaagaggaga      780 gggcgagact ggagttgtgc tggcagcaca gagacaaggg ggcacggcag gactgcagcc      840
```

```
tgcagagggg ctggagaagc ggaggctggc acccagtggc cagcgaggcc caggtccaag        900
tccagcgagg tcgaggtcta gagtacagca aggccaaggt ccaaggtcag tgagtctaag        960
gtccatggtc agtgaggctg agacccaggt tccaatgagg ccaaggtcca gagtccagta       1020
aggccgagat ccagggtcca gggaggtcaa g                                      1051
```

<210> SEQ ID NO 13
<211> LENGTH: 1291
<212> TYPE: DNA
<213> ORGANISM: Artificial Sequence
<220> FEATURE:
<223> OTHER INFORMATION: sequence of STAR13

<400> SEQUENCE: 13

```
ctgccctgat cccttaatgc ttttggccca gagcaccccg ctaagtccaa ccccagaggg         60
gcctcatccg caaagcctcg ggaagaggac agtgacggag gcggctgccc tgtgagctgc        120
acggggcaga atgtcctttt ggcgtcatgt tggatgtcca cacatccata tggggtcagt        180
tctattagga ttccttcggg aagaggtaga gggtaggagg ggttaagcca cgagacgagg        240
catgcagagg ggtggcctgg atgggtctgc actgctgtcc atgcacacgg ggagcgttgc        300
aaattgtgct tcccagccca tagtgccccc acagaggagc ccgggagtcc ctggtgggcg        360
tctgtgttcc tgcaaggagc cagtggagat ggccccgtga actctcatcc cccttgcctt        420
ggtggggtct ctggcaggtt tatggagccg tacatctttg ggagccgcct ggaccacgac        480
atcatcgacc tggaacagac agccacgcac ctccagctgg ccttgaactt caccgcccac        540
atggcctacc gcaagggcat catcttgttt ataagccgca accggcagtt ctcgtacctg        600
attgagaaca tggcccgtga ctgtggcgag tacgcccaca ctcgctactt caggggcggc        660
atgctgacca acgcgcgcct cctctttggc cccacggtcc gcctgccgga cctcatcatc        720
ttcctgcaca cgctcaacaa catctttgag ccacacgtgg ccgtgagaga cgcagccaag        780
atgaacatcc ccacagtggg catcgtggac accaactgca cccctgcct catcacctac        840 cctgtacccg gcaatgacga ctctccgctg gctgtgcacc tctactgcag gctcttccag        900
acggccatca cccgggccaa ggagaagcgg cagcaggttg aggctctcta tcgcctgcag        960
ggccagaagg agcccgggga ccaggggcca gccaccctc ctgggctga catgagccat       1020 tccctgtgat gttcactctc ctcccaaagc aaaccacagc caagcctgtc tgagctggga       1080
gtccccttcc ccagccctgg gtcagcggca tcctcagtcg ttgttactta ctcagctgat       1140
gtcacagtgc agacatccac cgttccacca cagaaccagt ggctgagcgg accaacgttg       1200
ccatgtgcgt ttgctctgtg gggaacagag cacagagggt gagcgacatg tgcagaacgg       1260
ccccttggct gcagttagga cctcagtggc t                                     1291
```

<210> SEQ ID NO 14
<211> LENGTH: 711
<212> TYPE: DNA
<213> ORGANISM: Artificial Sequence
<220> FEATURE:
<223> OTHER INFORMATION: sequence of STAR14

<400> SEQUENCE: 14

```
agcaaggacc agggctctgc ctccccagtc agcatgagca gagcagactc ctttgagcag         60
agcatcaggg cagaaataga acagtttctg aatgagaaaa gacagcatga gacccaaaaa        120
tgtgatgggt cagtggagaa gaaaccagac acacatgaaa attcggcgaa gtcactctcg        180
```

```
aaatcccacc aagagccggc tacaaaggtg gtgcaccggc agggcctgat gggcgtccag    240
aaggagttcg ccttctgcag acctcccccg gttagcaaag acaaacgtgc agcccagaag    300
cctcaggtcc aaggtcacga ccacgaccac gcaggagaag gagggcagca caaagccagc    360 aaccccacc gcccttcaga agcagtacag aataaaagtg ggattaaaag gaacgccagc     420
accgcaagga ggggaaagcg agtcacgagc gccgtacagg cgcccgaggc gtccgactcc    480
agcagcgacg acggcattga ggaggccatc cagctgtacc aggtgcagaa acacacaag     540 gaggccgacg ggacccgcc ccagagggtc cagctccaag aggaaagagc acctgcccct     600
cccgcacaca gcacaagcag cgccacaaaa agtgccttgc cagagaccca caggaaaaca    660
cccagcaaga agaagccagt gcccaccaag accacggacc ctggtccagg g             711
```

<210> SEQ ID NO 15
<211> LENGTH: 1876
<212> TYPE: DNA
<213> ORGANISM: Artificial Sequence
<220> FEATURE:
<223> OTHER INFORMATION: sequence of STAR15

<400> SEQUENCE: 15

```
cagtacatgc agaactgagt ccaaacgaga cggacagcaa acccggcagt gggctcccag     60
acattcctgg gggaaaggga tcctaaccac aggcagttaa agtcatctcc tccaaccctc    120
tatgacacag gctgtgcgct gtcatttaaa agctgagtga aatttaaccc ttttcccatt    180
tagaaaaaca aagcgcagct ggctgccagc actcatttaa ttttacataa acgtgctctt    240
tgaggctgaa gcaaatctga ctgattttca atgtgaaaat aaaatgtaaa aactgttctt    300
ggaattattt ctaaacagaa catcagaatc gtctgaatca tcagaatcgg ctattttgga    360
aaaatcggat tcatcaaacg aatcttcggc caacaactgt tagagaacga tgttaacacc    420
acgcatagga atgttacatt ttctagaatt tgacattttc attgacggaa aattactgta    480
tcttgtatat ggaaatacca ctactaaaaa cataatgcta taaatagaat gatgtctttt    540
gtttccaaag tcaatatact cgagcaatgc aaaaataata ataaagtga gatacttcat    600 ggcaaagctg ccgcaggata acattgcag ccacaagtgc ccccagtatt ctcggggcaa     660
actggaaaag gctaacagg caacattttc atgttattct actgagtgca gtaattattt     720 ttaaaatat acatgaataa tgaaaaaact gtggtatggt tttaagaaa tttccataac      780 ctggtgaaac tcttcacaca gggtaatagg ttcataaagc cttggtcctc tgcaaaacaa    840
gcatcaactt gacaatgact aaaagaagca acagcaaaac tgtcacgcat ttggagccat    900
ggcctgggtt gggccggtgt aaagctctcc gccctctgga gcaagtctgg gcccagcgg    960 ctggcatgtg ggcactgcag ggcctgggtt gggcaggtgt gcagctctcc gtcatctgag   1020
cctagtctga ggcctggtgg ctggcacgtg ggcctgcag ggcctctact tctcacccca    1080
gctccacttc cctccctgcc ctcactgggt ctcacagagc caatgaacac tggggtcaga   1140
ttcagggccc agcatccact gcagtgggca ctgcccttcc acaaggcctg gctccaggaa   1200
gcaaccccca cctcagccac acagtagggc aacaggaaat cccattcccc catgccagtg   1260
actacaccag ggaaggggct cacgtgaggc tggcccagg cctgctgtga accgcgttg     1320 tctatgagct tggatttaag gaacttggga gcaagaagct ttctttcatt acgggccacc   1380
agcagggaaa aaagttagcc caacgcagtt gacagtcaca cccccaccag gaccccaggg   1440
cacagaagga gggaagagga caacagagga tgaggtgggg ccagcagagg gacagagaag   1500
agctgcctgc cctggaacag gcagaaagca tcccacgtgc aagaaaaagt aggccagcta   1560
```

```
gacttaaaat cagaactacc gctcatcaaa agatagtgta acatttgggg tgctataatt      1620
ttaacatgtc ccccaaaagg catgtgttgg aaatttaatc cccaacaaac cagggctggg      1680
aggtggagcc tcatgagagg tggtgaggcc atgagggtgg agtgaatgga tgaatgccat      1740
tgtctcggga atgggcctct tctacaagga cgagttcagc ccccctttct cttgctcacc      1800
ctctctttgc cctttcgcta gggagtgacg taacaagaag ccctcacaa  gatgctggca      1860 ccttgatctt ggactc                                                      1876

<210> SEQ ID NO 16
<211> LENGTH: 1282
<212> TYPE: DNA
<213> ORGANISM: Artificial Sequence
<220> FEATURE:
<223> OTHER INFORMATION: sequence of STAR16

<400> SEQUENCE: 16
cgcccacctc ggctttccaa agtgctggga ttacaggcat gagtcactgc gcccatcctg        60
attccaagtc tttagataat aacttaactt tttcgaccaa ttgccaatca ggcaatcttt       120
gaatctgcct atgacctagg acatccctct ccctacaagt tgccccgcgt ttccagacca       180
aaccaatgta catcttacat gtattgattg aagttttaca tctccctaaa acatataaaa       240
ccaagctata gtctgaccac ctcaggcacg tgttctcagg acctccctgg ggctatggca       300
tgggtcctgg tcctcagatt tggctcagaa taaatctctt caaatatttt ccagaatttt       360
actcttttca tcaccattac ctatcaccca taagtcagag ttttccacaa ccccttcctc       420
agattcagta atttgctaga atggccacca aactcaggaa agtatttac  ttacaattac       480 caatttatta tgaagaactc aaatcaggaa tagccaaatg gaagaggcat agggaaaggt       540
atggaggaag gggcacaaag cttccatgcc ctgtgtgcac accaccctct cagcatcttc       600
atgtgttcac caactcagaa gctcttcaaa ctttgtcatt taggggtttt tatggcagtt       660
ccactatgta ggcatggttg ataaatcact ggtcatcggt gatagaactc tgtctccagc       720
tcctctctct ctcctcccca gaagtcctga ggtggggctg aaagtttcac aaggttagtt       780
gctctgacaa ccagccccta tcctgaagct attgagggt  ccccaaaaag ttaccttagt       840
atggttggaa gaggcttatt atgaataaca aagatgctc  ctattttac  cactagggag       900 catatccaag tcttgcggga acaaagcatg ttactggtag caaattcata caggtagata       960
gcaatctcaa ttcttgcctt ctcagaagaa agaatttgac caaggggca  taaggcagag      1020 tgagggacca agataagttt tagagcagga gtgaaagttt attaaaaagt tttaggcagg      1080
aatgaaagaa agtaaagtac atttggaaga gggccaagtg ggcgacatga gagagtcaaa      1140
caccatgccc tgtttgatgt ttggcttggg gtcttatatg atgacatgct tctgagggtt      1200
gcatccttct cccctgattc ttcccttggg gtgggctgtc cgcatgcaca atggcctgcc      1260
agcagtaggg aggggccgca tg                                              1282

<210> SEQ ID NO 17
<211> LENGTH: 793
<212> TYPE: DNA
<213> ORGANISM: Artificial Sequence
<220> FEATURE:
<223> OTHER INFORMATION: sequence of STAR17

<400> SEQUENCE: 17
atccgagggg aggaggagaa gaggaaggcg agcagggcgc cggagcccga ggtgtctgcg        60
```

```
agaactgttt taaatggttg gcttgaaaat gtcactagtg ctaagtggct tttcggattg    120
tcttatttat tactttgtca ggtttcctta aggagagggt gtgttggggg tgggggagga    180
ggtggactgg ggaaacctct gcgtttctcc tcctcggctg cacagggtga gtaggaaacg    240
cctcgctgcc acttaacaat ccctctatta gtaaatctac gcggagactc tatgggaagc    300
cgagaaccag tgtcttcttc cagggcagaa gtcacctgtt gggaacggcc cccgggtccc    360
cctgctgggc tttccggctc ttctaggcgg cctgatttct cctcagccct ccacccagcg    420
tccctcaggg acttttcaca cctccccacc cccatttcca ctacagtctc ccagggcaca    480
gcacttcatt gacagccaca cgagccttct cgttctcttc cctctgttc cttctctttc     540 tcttctcctc tgttccttct ctttctctgt cataatttcc ttggtgcttt cgccacctta    600
aacaaaaaag agaaaaaaat aaaataaaaa aaacccattc tgagccaaag tattttaaga    660
tgaatccaag aaagcgaccc acatagccct ccccacccac ggagtgcgcc aagacgcacc    720
caggctccat cacagggccg agagcagcgc cactctggtc gtactttgg gtcaagagat      780 cttgcaaaag agg                                                       793

<210> SEQ ID NO 18
<211> LENGTH: 492
<212> TYPE: DNA
<213> ORGANISM: Artificial Sequence
<220> FEATURE:
<223> OTHER INFORMATION: sequence of STAR18

<400> SEQUENCE: 18 atcttttgc tctctaaatg tattgatggg ttgtgttttt tttcccacct gctaataaat      60
attacattgc aacattcttc cctcaacttc aaaactgctg aactgaaaca atatgcataa    120
aagaaaatcc tttgcagaag aaaaaaagct attttctccc actgattttg aatggcactt    180
gcggatgcag ttcgcaaatc ctattgccta ttccctcatg aacattgtga atgaaaacct    240
ttggacagtc tgccgcattg cgcatgagac tgcctgcgca aggcaagggt atggttccca    300
aagcacccag tggtaaatcc taacttatta ttcccttaaa attccaatgt aacaacgtgg    360
gccataaaag agtttctgaa caaaacatgt catctttgtg gaaggtgtt tttcgtaatt     420 aatgatggaa tcatgctcat ttcaaaatgg aggtccacga tttgtggcca gctgatgcct    480
gcaaattatc ct                                                        492

<210> SEQ ID NO 19
<211> LENGTH: 1840
<212> TYPE: DNA
<213> ORGANISM: Artificial Sequence
<220> FEATURE:
<223> OTHER INFORMATION: sequence of STAR19

<400> SEQUENCE: 19
tcacttcctg atattttaca ttcaaggcta gctttatgca tatgcaacct gtgcagttgc     60
acagggcttt gtgttcagaa agactagctc ttggtttaat actctgttgt tgccatcttg    120
agattcatta taatataatt tttgaatttg tgttttgaac gtgatgtcca atgggacaat    180
ggaacattca cataacagag gagacaggtc aggtggcagc ctcaattcct gccacccttt    240
ttcacataca gcattggcaa tgccccatga gcacaaaatt tggggaacc atgatgctaa     300 gactcaaagc acatataaac atgttacctc tgtgactaaa agaagtggag gtgctgacag    360
cccccagagg ccacagttta tgttcaaacc aaaaacttgct tagggtgcag aaagaaggca    420
atggcagggt ctaagaaaca gcccatcata tccttgttta ttcatgttac gtccctgcat    480
```

```
gaactaatca cttacactga aaatattgac agaggaggaa atggaaagat agggcaaccc    540
atagttcttt ttccttttag tctttcctta tcagtaaacc aaagatagta ttggtaaaat    600
gtgtgtgagt taattaatga gttagtttta ggcagtgttt ccactgttgg ggtaagaaca    660
aaatatatag gcttgtattg agctattaaa tgtaaattgt ggaatgtcag tgattccaag    720
tatgaattaa atatccttgt atttgcattt aaaattggca ctgaacaaca aagattaaca    780
gtaaaattaa taatgtaaaa gtttaatttt tacttagaat gacattaaat agcaaataaa    840
agcaccatga taaatcaaga gagagactgt ggaaagaagg aaaacgtttt tattttagta    900
tatttaatgg gactttcttc ctgatgtttt gttttgtttt gagagagagg gatgtggggg    960
cagggaggtc tcattttgtt gcccaggctg gacttgaact cctgggctcc agctatcctg   1020
ccttagcttc ttgagtagct gggactacag gcacacacca cagtgtctga cattttctgg   1080 atttttttt ttttttattt ttttttgtga gacaggttct ggctctgtta ctcaggttgc   1140
agtgcagtgg catgatagcg gctcactgca gcctcaacct cctcagctta agctactctc   1200
ccacttcagc ctcctgagta gccaggacta cagttgtgtg ccaccacacc tgtggctaat   1260
ttttgtagag atggggtctc tccacgttgc cgaggctggt ctccaactcc tggtctcaag   1320
cgaacctcct gacttggcct cccgaagtgc tgggattaca ggcttgagcc actgcatcca   1380
gcctgtcctc tgtgttaaac ctactccaat ttgtctttca tctctacata aacggctctt   1440
ttcaaagttc ccatagacct cactgttgct aatctaataa taaattatct gccttttctt   1500
acatggttca tcagtagcag cattagattg ggctgctcaa ttcttcttgg tatattttct   1560
tcatttggct tctgggcat cacactctct ttgagttact cattcctcat tgatagcttc   1620
ttcctagtct tctttactgg ttcttcctct tctccctgac tccttaatat tgttttctc   1680 cccaggcttt agttcttagt cctcttctgt tatctattta cacccaattc tttcagagtc   1740
tcatccagag tcatgaactt aaacctgttt ctgtgcagat aattcacatt attatatctc   1800
cagcccagac tctcccgcaa actgcagact gatcctactg                         1840
```

<210> SEQ ID NO 20  
<211> LENGTH: 780  
<212> TYPE: DNA  
<213> ORGANISM: Artificial Sequence  
<220> FEATURE:  
<223> OTHER INFORMATION: sequence of STAR20

<400> SEQUENCE: 20

```
gatctcaagt ttcaatatca tgttttggca aaacattcga tgctcccaca tccttaccta     60
aagctaccag aaaggctttg ggaactgtca acagagctac agaaaagtca gtaaagacca    120
atggacccct caaacaaaaa cagccaagct tttctgccaa aaagatgact gagaagactg    180
ttaaagcaaa aaactctgtt cctgcctcag atgatggcta tccagaaata gaaaaattat    240
ttcccttcaa tcctctaggc ttcgagagtt ttgacctgcc tgaagagcac cagattgcac    300 atctccccctt gagtgaagtg cctctcatga tacttgatga ggagagagag cttgaaaagc    360
tgtttcagct gggccccccct tcacctttga agatgccctc tccaccatgg aaatccaatc    420
tgttgcagtc tcctttaagc attctgttga ccctggatgt tgaattgcca cctgtttgct    480
ctgacataga tatttaaatt tcttagtgct ttagagtttg tgtatatttc tattaataaa    540
gcattatttg tttaacagaa aaaaagatat atacttaaat cctaaaataa aataaccatt    600
aaaaggaaaa acaggagtta taactaataa gggaacaaag gacataaaat gggataataa    660
```

<210> SEQ ID NO 21
<211> LENGTH: 607
<212> TYPE: DNA
<213> ORGANISM: Artificial Sequence
<220> FEATURE:
<223> OTHER INFORMATION: sequence of STAR21

<400> SEQUENCE: 21

```
tgcttaatcc aaaataaagc agaaaatgaa gaaaaatgaa atgaagaaca gataaataga      720
aaacaaatag caatatgaaa gacaaacttg accgggtgtg gtggctgatg cctgtaatcc      780
```

<210> SEQ ID NO 21
<211> LENGTH: 607
<212> TYPE: DNA
<213> ORGANISM: Artificial Sequence
<220> FEATURE:
<223> OTHER INFORMATION: sequence of STAR21

<400> SEQUENCE: 21

```
gatcaataat ttgtaatagt cagtgaatac aaaggggtat atactaaatg ctacagaaat       60
tccattcctg ggtataaatc ctagacatat ttatgcatat gtacaccaag atatatctgc      120
aagaatgttc acagcaaatc tctttgtagt agcaaaaggc caaaaggtct atcaacaaga      180
aaattaatac attgtggcac ataatggcat ccttatgcca ataaaaatgg atgaaattat      240
agttaggttc aaaaggcaag cctccagata atttatatca taattccca tgtacaacat       300
tcaacaacaa gcaaaactaa acatatacaa atgtcaggga aatgatgaa caaggttaga      360
aaatgattaa tataaaaata ctgcacagtg ataacattta atgagaaaaa aagaaggaag      420
ggcttaggga gggacctaca gggaactcca aagttcatgg taagtactaa atacataatc      480
aaagcactca aaatagaaaa tattttagta atgttttagc tagttaatat cttacttaaa      540
acaaggtcta ggccaggcac ggtggctcac acctgtaatc ccagcacttt gggaggctga      600
ggcgggt                                                               607
```

<210> SEQ ID NO 22
<211> LENGTH: 1380
<212> TYPE: DNA
<213> ORGANISM: Artificial Sequence
<220> FEATURE:
<223> OTHER INFORMATION: sequence of STAR22

<400> SEQUENCE: 22

```
cccttgtgat ccacccgcct tggcctccca aagtgctggg attacaggcg tgagtcacta       60
cgcccggcca ccctccctgt atattatttc taagtatact attatgttaa aaaagtttta      120
aaaatattga tttaatgaat tcccagaaac taggatttta catgtcacgt tttcttatta      180
taaaaataaa aatcaacaat aaatatatgg taaaagtaaa aagaaaaaca aaacaaaaa       240
gtgaaaaaaa taacaacac tcctgtcaaa aaacaacagt tgtgataaaa cttaagtgcc       300
tgaaaattta gaaacatcct tctaaagaag ttctgaataa aataaggaat aaaataatca      360
catagttttg gtcattggtt ctgtttatgt gatggattat gtttattgat ttgtgtatgt      420
tgaacttatc tcaatagatg cagacaaggc cttgataaaa gttttaaca ccttttcatg        480
ttgaaaactc tcaatagact aggtattgat gaaacatatc tcaaaataat agaagctatt      540
tatgataaac ccatagccaa tatcatactg agtgggcaaa agctggaagc attccctttg      600
aaaactggca caagacaagg atgccctctc tcaccactcc tattaaatgt agtattggaa      660
gttctggcca gagcaatcag gcaggagaaa gaaaaggtat taaaatagga agagaggaag      720
tcaaattgtc tctgtttgca gtaaacatga ttgtatattt agaaaacccc attgtctcat       780
cctaaaaact ccttaagctg ataaacaact tcagcaaagt ctcaggatac aaaatcaatg      840
tgcaaaaatc acaagcattc ctatacaccg ataatagaca gcagagagcc aaatcatgag      900
tgaagtccca ttcacaattg cttcaaagaa aataaaatac ttaggaatac aactttcacg      960
ggacatgaag gacattttca aggacaacta aaaaccactg ctcaaggaaa tgagagagga     1020
```

```
cacaaagaaa tggaaaaaca ttccatgctc atggaagaat caatatcatg aaaatggcca    1080
tactgcccaa agtaatttat agattcaatg ctaaccccat caagccacca ttgactttct    1140
tcacagaact agaaaaaaac tattttaaaa ctcatatgta gtcaaaaaga gtcggtatag    1200
ccaagacaat cctaagcata aagaacaaag ctggatgcat cacgctgact tcaaaccata    1260
ctacaaggct acagtaacca aaacagcatg gtactggtac caaaacagat agatagaccg    1320
atagaacaga acagaggcct cggaaataac accacacatc tacaacccctt tgatcttcaa    1380
```

<210> SEQ ID NO 23
<211> LENGTH: 1246
<212> TYPE: DNA
<213> ORGANISM: Artificial Sequence
<220> FEATURE:
<223> OTHER INFORMATION: sequence of STAR23

<400> SEQUENCE: 23

```
atcccctcat ccttcagggc agctgagcag ggcctcgagc agctggggga gcctcactta      60
atgctcctgg gagggcagcc agggagcatg gggtctgcag gcatggtcca gggtcctgca     120
ggcggcacgc accatgtgca gccgccccca cctgttgctc tgcctccgcc acctggccat     180
gggcttcagc agccagccac aaagtctgca gctgctgtac atggacaaga agcccacaag     240
cagctagagg accttgtgtt ccacgtgccc agggagcatg gcccacagcc caaagaccag     300
tcaggagcag gcaggggctt ctggcaggcc cagctctacc tctgtcttca cacagatggg     360
agatttctgt tgtgattttg agtgatgtgc ccctttggtg acatccaaga tagttgctga     420
agcaccgctc taacaatgtg tgtgtattct gaaaacgaga acttctttat tctgaaataa     480
ttgatgcaaa ataaattagt ttggatttga aattctattc atgtaggcat gcacacaaaa     540
gtccaacatt gcatatgaca caaagaaaag aaaaagcttg cattccttaa atacaaatat     600
ctgttaacta tatttgcaaa tatatttgaa tacacttcta ttatgttaca tataatatta     660
tatgtatatg tatatataat atacatatat atgttacata taatatactt ctattatgtt     720
acatataata tttatctata agtaaataca taaatataaa gatttgagta gctgtagaac     780
attgtcttat gtgttatcag ctactactac aaaaatatct cttccactta tgccagtttg     840
ccatataaat atgatcttct cattgatggc ccagggcaag agtgcagtgg gtacttattc     900
tctgtgagga gggaggagaa aagggaacaa ggagaaagtc acaaagggaa aactctggtg     960
ttgccaaaat gtcaagtttc acatattccg agacggaaaa tgacatgtcc cacagaagga    1020
ccctgcccag ctaatgtgtc acagatatct caggaagctt aaatgatttt tttaaaagaa    1080
aagagatggc attgtcactt gtttcttgta gctgaggctg tgggatgatg cagatttctg    1140
gaaggcaaag agctcctgct ttttccacac cgagggactt tcaggaatga ggccagggtg    1200
ctgagcacta caccaggaaa tccctggaga gtgttttcct tactta                   1246
```

<210> SEQ ID NO 24
<211> LENGTH: 939
<212> TYPE: DNA
<213> ORGANISM: Artificial Sequence
<220> FEATURE:
<223> OTHER INFORMATION: sequence of STAR24

<400> SEQUENCE: 24

```
acgaggtcac gagttcgaga ccagcctggc caagatggtg aagccctgtc tctactaaaa      60
atacaacaag tagccgggcg cggtgacggg cgcctgtaat cccagctact caggaggctg     120
```

```
aagcaggaga atctctagaa cccaggaggc ggaggtgcag tgagctgaga ctgccccgct      180
gcactctagc ctgggcaaca cagcaagact ctgtctcaaa taaataaata aataaataaa      240
taaataaata aataaataaa tagaaaggga gagttggaag tagatgaaag agaagaaaag      300
aaatcctaga tttcctatct gaaggcacca tgaagatgaa ggccacctct tctgggccag      360
gtcctcccgt tgcaggtgaa ccgagttctg gcctccattg gagaccaaag gagatgactt      420
tggcctggct cctagtgagg aagccatgcc tagtcctgtt ctgtttgggc ttgatcctgt      480
atcacttgat tgtctctcct ggactttcca tggattccag ggatgcaact gagaagttta      540
tttttaatgc acttacttga agtaagagtt attttaaaac attttagcaa aggaaatgaa      600
ttctgacagg ttttgcactg aagacattca catgtgagga aaacaggaaa accactatgc      660
tagaaaaagc aaatgctgtt gagattgtct cacaaacaca aattgcgtgc cagcaggtag      720
gtttgagcct caggttgggc acattttacc ttaagcgcac tgttggtgga acttaaggtg      780
actgtaggac ttatatatac atacatacat ataatatata tacatattta tgtgtatata      840
cacacacaca cacacacaca cacacagggt cttgctatct tgcccagggt ggtctccaac      900
tctgggtctc aagcgatcct ctgcctcccc ttcccaaag                             939
```

<210> SEQ ID NO 25
<211> LENGTH: 1067
<212> TYPE: DNA
<213> ORGANISM: Artificial Sequence
<220> FEATURE:
<223> OTHER INFORMATION: sequence of STAR25

<400> SEQUENCE: 25

```
ataaaaaaat aaaaaacccct gctctaattt gcaaaggctc tatctttcct cccaaccacc       60
tgaaatttta gtgaaaacgg ggcttcctgt aggaaggagt agctagctat cccggtccgc      120
tacaggttat cagtgcgtga ataccctgac tcctaaggct caggatttga ctgggtcgcc      180
tcgtccgact gccccgcccc caacgcggac ccacgtcacc gcgcgccagc ctgcggccgt      240
cctgacctcg cgggatttga gcttcggtgc caacaaacac tcccaccgcg gctgcgtcca      300 cttacctgc cggcggcgac cagcttctga agaaaagtgt ccaccatggt gtcgaggagc      360
ttcaccctcg aaatggtagt gccgggtggc acagattccg aagacgaccc ctcatgcctt      420
ttttcctcac agccgctgcc tagattggcg ctacttgctt cggccatgtt gaagttgaac      480
ctccaaatct aactggcccg gcctccccgc ctgccggagc tcccgattgg ccgctcccgc      540
gaagggtgcc tccgattgga agcagtagaa cgtctgtcac cgagcagggc gggggcgggg      600
aagtcatcgg aggctgaggg cagcggggag gcgaggctct gcgcggtggg atgtccgcga      660
ccggaaaaat acgcgcaagc caaagctcgg gggctcaata aaaactttta attacatttc      720
agagacttcg tacagtgcaa cagtgaatat tcactgttaa ttttcacaag agtccatttc      780
atcaaacgtt cagagagtct gccttttcat tccctgttc ctcagtgctc caatcaggtt      840
tccagtctcc cagaggtttc ttttagtttt gattaccgac caaaactcca gtttagggag      900
aatgaaagtc caccgtccca tccccaccaa aacatatttc agtcaaaccc aatcccagtc      960
cctaaagaat taggaaagta tgggccaagg gtccttttaa ttatacacac atcacccttaa     1020 aaactgcgtg tgtgtacgag aaataaagaa aaacacaaga ggggctg                   1067
```

<210> SEQ ID NO 26
<211> LENGTH: 540
<212> TYPE: DNA
<213> ORGANISM: Artificial Sequence
<220> FEATURE:
<223> OTHER INFORMATION: sequence of STAR26

<400> SEQUENCE: 26

| | | | | | |
|---|---|---|---|---|---|
| cccctgaca | agcccagtg | tgtgatgttc | cccactctgt | gtccatgcat | tctcattgtt | 60 |
| caactcccat | ctgtgagtga | aacatgcag | tgtttggttt | tctgtccttg | agatagtttg | 120 |
| ctgagaatga | tggtttccag | cttcatccat | gtccttgcaa | aggaagtgaa | cttatccttt | 180 |
| tttatggctt | catagtattc | catggcacat | atgtgccaca | ttttttttaat | ccagtctatc | 240 |
| attgatggac | atttgggttg | gttccaagtc | tttgctattg | tgaatagcac | acaattaac | 300 |
| atatgtgtgc | atgtatacat | ctttatagta | gcatgattta | taatccttcg | ggtatatacc | 360 |
| ctgtaatggg | atcgctgggt | caaatggtat | ttctagttct | agatccttga | ggaatcacca | 420 |
| cactgctttc | cacaatggtt | gaactaattt | acgctcccac | cagcagtgta | aaagcattcc | 480 |
| tatttctcca | cgtcctctcc | agtatctgtt | gtttcctgac | ttttaatga | tcatcattct | 540 |

<210> SEQ ID NO 27
<211> LENGTH: 1520
<212> TYPE: DNA
<213> ORGANISM: Artificial Sequence
<220> FEATURE:
<223> OTHER INFORMATION: sequence of STAR27

<400> SEQUENCE: 27

| | | | | | |
|---|---|---|---|---|---|
| cttggccctc | acaaagcctg | tggccaggga | acaattagcg | agctgcttat | tttgctttgt | 60 |
| atccccaatg | ctgggcataa | tgcctgccat | tatgagtaat | gccggtagaa | gtatgtgttc | 120 |
| aaggaccaaa | gttgataaat | accaaagaat | ccagagaagg | gagagaacat | tgagtagagg | 180 |
| atagtgacag | aagagatggg | aacttctgac | aagagttgtg | aagatgtact | aggcaggggg | 240 |
| aacagcttaa | ggagagtcac | acaggaccga | gctcttgtca | agccggctgc | catggaggct | 300 |
| gggtggggcc | atggtagctt | tcccttcctt | ctcaggttca | gagtgtcagc | cttgaacttc | 360 |
| taattcccag | aggcatttat | tcaatgtttt | cttctagggg | catacctgcc | ctgctgtgga | 420 |
| agactttctt | ccctgtgggt | cgccccagtc | cccagatgag | acggtttggg | tcagggccag | 480 |
| gtgcaccgtt | gggtgtgtgc | ttatgtctga | tgacagttag | ttactcagtc | attagtcatt | 540 |
| gagggaggtg | tggtaaagat | ggagatgctg | ggtcacatcc | ctagagaggt | gttccagtat | 600 |
| ggcacatgg | gagggctgga | aggataggtt | actgctagac | gtagagaagc | cacatccttt | 660 |
| aacaccctgg | cttttcccac | tgccaagatc | cagaaagtcc | ttgtggtttc | gctgctttct | 720 |
| cctttttttt | tttttttttt | tttctgagat | ggagtctggc | tctgtcgccc | aggctggagt | 780 |
| gcagtggcac | gatttcggct | cactgcaagt | tccgcctcct | aggttcatac | cattctccca | 840 |
| cctcagcctc | ccgagtagct | gggactacag | gcgccaccac | acccagctaa | ttttttgtat | 900 |
| ttttagtaga | gacggcgttt | caccatgtta | gccaggatgg | tcttgatccg | cctgcctcag | 960 |
| cctcccaaag | tgctgggatt | acaggcgtga | gccaccgcgc | ccggcctgct | tcttcttttc | 1020 |
| atgaagcatt | cagctggtga | aaagctcag | ccaggctggt | ctggaactct | tgacctcaag | 1080 |
| tgatctgcct | gcctcagcct | cccaaagtgc | tgagattaca | ggcatgagcc | agtccgaatg | 1140 |
| tggcttttt | tgtttgtttt | tgaaacaagg | tctcactgtt | gcccaggctg | cagtgcagtg | 1200 |
| gcatacctca | gctccactgc | agcctcgacc | tcctgggctc | aagcaatcct | cccaactgag | 1260 |
| cctccccagt | agctgggct | acaagcgcat | gccaccacgc | ctggctattt | tttttttttt | 1320 |
| ttttttttt | gagaaggagt | ttcattcttg | ttgcccaggc | tggagtgcaa | tggcacagtc | 1380 |

<210> SEQ ID NO 28
<211> LENGTH: 961
<212> TYPE: DNA
<213> ORGANISM: Artificial Sequence
<220> FEATURE:
<223> OTHER INFORMATION: sequence of STAR28

<400> SEQUENCE: 28

```
tcagctcact gcagcctccg cctcctgggt tcaagcgatt ctcctgcctc agcctcccga    1440
gtagctggga ttataggcac ctgccaccat gcctggctaa ttttttttgta tttttagtag   1500
ggatggggtt tcaccatgtt                                                1520
```

<210> SEQ ID NO 28
<211> LENGTH: 961
<212> TYPE: DNA
<213> ORGANISM: Artificial Sequence
<220> FEATURE:
<223> OTHER INFORMATION: sequence of STAR28

<400> SEQUENCE: 28

```
aggaggttat tcctgagcaa atggccagcc tagtgaactg gataaatgcc catgtaagat     60
ctgtttaccc tgagaagggc atttcctaac tctccctata aaatgccaag tggagcaccc    120
cagatgaaat agctgatatg ctttctatac aagccatcta ggactggctt tatcatgacc   180
aggatattca cccactgaat atggctatta cccaagttat ggtaaatgct gtagttaagg    240
gggtcccttc cacatggaca ccccaggtta taaccagaaa gggttcccaa tctagactcc    300
aagagagggt tcttagacct catgcaagaa agaacttggg gcaagtacat aaagtgaaag    360
caagtttatt aagaaagtaa agaaacaaaa aaatggctac tccataagca aagttatttc    420
tcacttatat gattaataag agatggatta ttcatgagtt ttctgggaaa ggggtgggca    480
attcctggaa ctgagggttc ctcccacttt tagaccatat agggtatctt cctgatattg    540
ccatggcatt tgtaaactgt catggcactg atgggagtgt cttttagcat tctaatgcat    600
tataattagc atataatgag cagtgaggat gaccagaggt cacttctgtt gccatattgg    660
tttcagtggg gtttggttgg cttttttttt tttttaacca caacctgttt tttatttatt    720
tatttattta tttatttatt tatattttttt atttttttttt agatggagtc ttgctctgtc    780
acccaggtta gagtgcagtg gcaccatctc ggctcactgc aagctctgcc tccttggttc    840
acgccattct gctgcctcag cctcccgagt agctgggact acaggtgcct gccaccatac    900
ccggctaatt ttttctattt ttcagtagag acggggtttc accgtgttag ccaggatggt    960
c                                                                    961
```

<210> SEQ ID NO 29
<211> LENGTH: 2233
<212> TYPE: DNA
<213> ORGANISM: Artificial Sequence
<220> FEATURE:
<223> OTHER INFORMATION: sequence of STAR29

<400> SEQUENCE: 29

```
agcttggaca cttgctgatg ccactttgga tgttgaaggg ccgccctctc ccacaccgct     60
ggccactttt aaatatgtcc cctctgccca gaagggcccc agaggagggg ctggtgaggg    120
tgacaggagt tgactgctct cacagcaggg ggttccggag ggacctttc tccccattgg    180
gcagcataga aggacctaga agggcccccct ccaagcccag ctgggcgtgc agggccagcg    240
attcgatgcc ttcccctgac tcaggtggcg ctgtcctaaa ggtgtgtgtg ttttctgttc    300
gccaggggt ggcggataca gtggagcatc gtgcccgaag tgtctgagcc cgtggtaagt    360
ccctggaggg tgcacggtct cctccgactg tctccatcac gtcaggcctc acagcctgta    420
ggcaccgctc ggggaagcct ctggatgagg ccatgtggtc atcccctgg agtcctggcc    480
tggcctgaag aggaggggag gaggaggcca gcccctccct agcccaagg cctgcgaggc    540
tgcaagcccg gccccacatt ctagtccagg cttggctgtg caagaagcag attgcctggc    600
```

| | |
|---|---|
| cctggccagg cttcccagct aggatgtggt atggcagggg tgggggacat tgagggctg | 660 |
| ctgtagcccc cacaacctcc ccaggtaggg tggtgaacag taggctggac aagtggacct | 720 |
| gttcccatct gagattcaag agcccacctc tcggaggttg cagtgagccg agatccctcc | 780 |
| actgcactcc agcctgggca acagagcaag actctgtctc aaaaaaacag aacaacgaca | 840 |
| acaaaaaacc cacctctggc ccactgccta actttgtaaa taaagtttta ttggcacata | 900 |
| gacacaccca ttcatttaca tactgctgcg gctgcttttg cattacccct gagtagacga | 960 |
| cagaccacgt ggccatggaa gccaaaaata tttactgtct ggcccttttac agaagtctgc | 1020 |
| tctagaggga gaccccggcc catggggcag gaccactggg cgtgggcaga agggaggcct | 1080 |
| cggtgcctcc acgggcctag ttgggtatct cagtgcctgt ttcttgcatg gagcaccagg | 1140 |
| ggtcagggca agtacctgga ggaggcaggc tgttgcccgc ccagcactgg gacccaggag | 1200 |
| accttgagag gctcttaacg aatgggagac aagcaggacc agggctccca ttggctgggc | 1260 |
| ctcagtttcc ctgcctgtaa gtgagggagg gcagctgtga aggtgaactg tgaggcagag | 1320 |
| cctctgctca gccattgcag gggcggctct gccccactcc tgttgtgcac ccagagtgag | 1380 |
| gggcacgggg tgagatgtca ccatcagccc ataggggtgt cctcctggtg ccaggtcccc | 1440 |
| aagggatgtc ccatcccccc tggctgtgtg gggacagcag agtccctggg gctgggaggg | 1500 |
| ctccacactg ttttgtcagt ggtttttctg aactgttaaa tttcagtgga aaattctctt | 1560 |
| tccccttta ctgaaggaac ctccaaagga agacctgact gtgtctgaga agttccagct | 1620 |
| ggtgctggac gtcgcccaga aagcccaggt actgccacgg gcgccggcca ggggtgtgtc | 1680 |
| tgcgccagcc atgggcacca gccaggggtg tgtctacgcc ggccaggggt aggtctccgc | 1740 |
| cggcctccgc tgctgcctgg ggagggccgt gcctgacact gcaggcccgg tttgtccgcg | 1800 |
| gtcagctgac ttgtagtcac cctgcccttg gatggtcgtt acagcaactc tggtggttgg | 1860 |
| ggaagggggcc tcctgattca gcctctgcgg acgtgcgcg agggtggagc tcccctccct | 1920 |
| ccccaccgcc cctggccagg gttgaacgcc cctgggaagg actcaggccc gggtctgctg | 1980 |
| ttgctgtgag cgtggccacc tctgccctag accagagctg ggccttcccc ggcctaggag | 2040 |
| cagccgggca ggaccacagg gctccgagtg acctcagggc tgcccgacct ggaggccctc | 2100 |
| ctggcgtcgc ggtgtgactg acagcccagg agcggggct gttgtaattg ctgtttctcc | 2160 |
| ttcacacaga accttttcgg gaagatggct gacatcctgg agaagatcaa gaagtaagtc | 2220 |
| ccgccccca ccc | 2233 |

<210> SEQ ID NO 30
<211> LENGTH: 1851
<212> TYPE: DNA
<213> ORGANISM: Artificial Sequence
<220> FEATURE:
<223> OTHER INFORMATION: sequence of STAR30

<400> SEQUENCE: 30

| | |
|---|---|
| cctcccctgg agccttcaga aggagcatgg cataggagtc ttgatttcag acgtctggtc | 60 |
| cccagaatga tgggagaatg aatttctgtt atttaagcca cccaacctgt ggtgctttgt | 120 |
| tatagcagcc tcaggaaact aacacactgc acgtgcccac tattcccttt tccagtatct | 180 |
| ttcaggactt gctggcttcc tttgttctgg cgtacaccca tgcatggccc cattccccac | 240 |
| ttcctaaaac aacaaccctg acttagtctg tttgggctgc tagaacaaaa tactatagac | 300 |
| tgggtgactt ataaacaaca gaaattcatt tctcacattc tggaggctgg gaagtccaat | 360 |

| | |
|---|---|
| atcgaggcac catcacattt ggtctctgct gaggccccct tcctagctcc tcactgtgtc | 420 |
| cttacatggc agaaggggca aggcagctct ctggggtccc ttttcaaggc cacaaatccc | 480 |
| attcattagg gctgatgact tcatgactta atcacctcct aatggcccca cctcctaatc | 540 |
| gcattgggcg ttaggattca acataaattt tgggggacac acatattca gaccatagca | 600 |
| aaccccaaca ataaaaaacc ttcactttaa ggttccaaat ggactggcag ttaaatcatg | 660 |
| ttcatattta cataaaagaa ggagtaagtc aacaaattga taaacgcgtg gagatttgtt | 720 |
| cggatggatg ttcaccaaaa tgctggcctt aaagagtgag atgggaaatg gaactatta | 780 |
| cattcttctt catactttt ggtactgcct gcattgttaa aaaaaaaaa aaagagcaca | 840 |
| gagcattttt acaatcagga aaaaacaat gaggttatct tcattctgga aaaaatgga | 900 |
| aaatgaaaca gtggagtcac atcatggaaa atgcttatgg tacaatttca tgtgacataa | 960 |
| aacaatagaa tagaggacct gttttatgac taaagcactg taaaaatgac aggcctggaa | 1020 |
| ggagagatga aaaccactca tttgttaagg tagtcaggtg gcaggtgatt tctcttcttt | 1080 |
| tgaaaatttc cattttcatt atatcgcagt ttgtgcattt actaaaactt tcggttggta | 1140 |
| cacatgcata aatagataga taaataagta gatagatgat agataaatag acggtaggta | 1200 |
| gatagataga tagatatgag aaataagtcc cctgtacttg gccttgcagc cataactagt | 1260 |
| cattcccctt cctctgtcca ttgctatgcc tgatggacaa ggcagtctgt gccctctggc | 1320 |
| cccaattcca atgtgccctc tgctcctggc tgttagtccc tttccacccc aatacaattg | 1380 |
| ctccgaggtc acttctaagt gtgaagcccc cagatcagat ggcttcttct gtgtccttac | 1440 |
| cttacccaat ttctaattat aactaaaaca caatgaggct ctagtaaaat accatgagac | 1500 |
| ttcaggcccct ctgtataact tcactcattt aaacctaaca aggaaaacct accatgaatc | 1560 |
| cgaggcacag agcagctaag gaactcacca aggtcacgca gctattggtg atggaaccat | 1620 |
| gagtcaagct tcacagcctg ttggctctag aatagggttt cccaacctca gcactgtgga | 1680 |
| cattttcagg ctggataatt ctctgttgtg gggggctgtt ctgtgccttg taggatatta | 1740 |
| ggagcatctc tggcctctac ccactagacg cagcagcact cccatgccca gttgtgacaa | 1800 |
| caagcaatgt ctcccaccat tgccaagtgt ccctgggtg gaaatgcacc c | 1851 |

<210> SEQ ID NO 31
<211> LENGTH: 1701
<212> TYPE: DNA
<213> ORGANISM: Artificial Sequence
<220> FEATURE:
<223> OTHER INFORMATION: sequence of STAR31
<220> FEATURE:
<221> NAME/KEY: misc_feature
<222> LOCATION: (159)..(1696)
<223> OTHER INFORMATION: "N" stands for any nucleotide on various positions

<400> SEQUENCE: 31

| | |
|---|---|
| cacccgcctt ggccccccag agtgctggga ttacaagtgt aaaccaccat tcctggctag | 60 |
| atttaatttt ttaaaaaata aagagaagta ggaatagttc attttaggga gagcccctta | 120 |
| actgggacag gggcaggaca ggggtgaggc ttcccttant tcaagctcac ctcaaaccca | 180 |
| cccaggactg tgtgtcacat tctccaataa aggaaaggtt gctgccccg cctgtgagtg | 240 |
| ctgcagtgga gggtagaggg ccgtgggcag agtgcttcat ggactgctca tcaagaaagg | 300 |
| cttcatgaca atcggcccag ctgctgtcat cccacattct acttccagct aggagaaggc | 360 |
| ggcttgccca cagtcaccca gccggcaagt gtcacccctg ggttgacccc agagctatga | 420 |

| | |
|---|---|
| tcctgcccag gggtccagct gagaatcagg cccacgttct aggcagaggg gctcacctac | 480 |
| tgggactcca gtagctgtag tgcatggagg catcatggct gcagcagcct ggacctggtc | 540 |
| tcacactggc tgtccctgtg ggcaggccat cctcaatgcc aggtcaggcc caagcatgta | 600 |
| tcccagacaa tgacaatggg gtggaatcct ctcttgtccc agaagccact cctcactgtt | 660 |
| ctacctgagg aaggcagggg catggtggaa tcctgaagcc tgctgtgagg gtctccagcg | 720 |
| aacttgcaca tggtcagccc tgccttctcc tccctgaact agattgagcg agagcaagaa | 780 |
| ggacattgaa ccagcaccca agaattttg gggaacggcc tctcatccag gtcaggctca | 840 |
| cctccttttt aaaatttaat taattaatta attaattttt ttttagagac agagtcttac | 900 |
| tgtgtggccc aggctgtagt gcagtggcac aatcatagtt cactgcagcc tcaaactccc | 960 |
| cacctcagcc tctggattag ctgagactac aggtgcacca ccaccacacc cagctaatat | 1020 |
| ttttattttt gtagagagag ggtttcacca tcttgcccag gctggtctca aactcctggg | 1080 |
| ctcaagtgat cccgcccagg tctgaaagcc cccaggctgg cctcagactg tggggttttc | 1140 |
| catgcagcca cccgagggcg ccccaagcc agttcatctc ggagtccagg cctggccctg | 1200 |
| ggagacagag tgaaaccagt ggttttatg aacttaactt agagtttaaa agatttctac | 1260 |
| tcgatcactt gtcaagatgc ccctctctg gggagaaggg aacgtgactg gattccctca | 1320 |
| ctgttgtatc ttgaataaac gctgctgctt catcctgtgg gggccgtggc cctgtccctg | 1380 |
| tgtgggtggg gcctcttcca tttccctgac ttagaaacca cagtccacct agaacagggt | 1440 |
| ttgagaggct tagtcagcac tgggtagcgt tttgactcca ttctcggctt tcttcttttt | 1500 |
| cttccagga tttttgtgca gaaatggttc ttttgttgcc gtgttagtcc tccttggaag | 1560 |
| gcagctcaga aggcccgtga atgtcgggg gacaggaccc ccagggaggg aaccccaggc | 1620 |
| tacgcacttt agggttcgtt ctccagggag ggcgacctga ccccgnatc cgtcggngcg | 1680 |
| cgnngnnacn aannnnttcc c | 1701 |

<210> SEQ ID NO 32
<211> LENGTH: 771
<212> TYPE: DNA
<213> ORGANISM: Artificial Sequence
<220> FEATURE:
<223> OTHER INFORMATION: sequence of STAR32

<400> SEQUENCE: 32

| | |
|---|---|
| gatcacacag cttgtatgtg ggagctagga ttggaaccccc agaagtctgg ccccaggttc | 60 |
| atgctctcac ccactgcata caatggcctc tcataaatca atccagtata aaacattaga | 120 |
| atctgcttta aaaccataga attagtagcg taagtaataa atgcagagac catgcagtga | 180 |
| atggcattcc tggaaaaagc ccccagaagg aattttaaat cagctttcgt ctaatcttga | 240 |
| gcagctagtt agcaaatatg agaatacagt tgttcccaga taatgcttta tgtctgacca | 300 |
| tcttaaactg gcgctgtttt tcaaaaactt aaaaacaaaa tccatgactc ttttaattat | 360 |
| aaaagtgata catgtctact tgggaggctg aggtggtggg aggatggctt gagtttgagg | 420 |
| ctgcagtatg ctactatcat gcctataaat agccgctgca ttccagcttg gcaacatac | 480 |
| ccaggcccta tctcaaaaaa ataaaagta atacatctac attgaagaaa attaattta | 540 |
| ttgggttttt ttgcatttt attatacaca gcacacacag cacatatgaa aaatgggta | 600 |
| tgaactcagg cattcaactg gaagaacagt actaaatcaa tgtccatgta gtcagcgtga | 660 |
| ctgaggttgg tttgtttttt cttttttctt ctcttctctt ctcttttctt ttttttgag | 720 |
| acggagcttt gctctttttg cccaggcttg attgcaatgg cgtgatctca g | 771 |

<210> SEQ ID NO 33
<211> LENGTH: 1368
<212> TYPE: DNA
<213> ORGANISM: Artificial Sequence
<220> FEATURE:
<223> OTHER INFORMATION: sequence of STAR33

<400> SEQUENCE: 33

```
gcttttatcc tccattcaca gctagcctgg cccccagagt acccaattct ccctaaaaaa      60
cggtcatgct gtatagatgt gtgtggcttg gtagtgctaa agtggccaca tacagagctc     120
tgacaccaaa cctcaggacc atgttcatgc cttctcactg agttctggct tgttcgtgac     180
acattatgac attatgatta tgatgacttg tgagagcctc agtcttctat agcactttta     240
gaatgcttta taaaaccat ggggatgtca ttatattcta acctgttagc acttctgttc      300
gtattaccca tcacatccca acatcaattc tcatatatgc aggtacctct tgtcacgcgc     360
gtccatgtaa ggagaccaca aaacaggctt tgtttgagca acaaggtttt tatttcacct     420
gggtgcaggt gggctgagtc tgaaaagaga gtcagtgaag ggagacaggg gtgggtccac     480
tttataagat ttgggtaggt agtggaaaat tacaatcaaa ggggggttgtt ctctggctgg    540
ccagggtggg ggtcacaagg tgctcagtgg gagagccttt gagccaggat gagccagaag    600
gaatttcaca aggtaatgtc atcagttaag gcagggactg gccattttca cttcttttgt    660
ggtggaatgt catcagttaa ggcaggaacc ggccattttc acttcttttg tgattcttca    720
cttgcttcag gccatctgga cgtataggtg caggtcacag tcacagggga taagatggca    780
atggcatagc ttgggctcag aggcctgaca cctctgagaa actaaagatt ataaaaatga    840
tggtcgcttc tattgcaaat ctgtgtttat tgtcaagagg cacttatttg tcaattaaga    900
acccagtggt agaatcgaat gtccgaatgt aaaacaaaat acaaaacctc tgtgtgtgtg    960
tgtgtgtgag tgtgtgtgta tgtgtgtgtg tgtgtattag agaggaaaag cctgtatttg   1020
gaggtgtgat tcttagattc taggttcttt cctgcccacc ccatatgcac ccaccccaca   1080
aaagaacaaa caacaaatcc caggacatct tagcgcaaca tttcagtttg catattttac   1140
atatttactt ttcttacata ttaaaaaact gaaaatttta tgaacacgct aagttagatt   1200
ttaaattaag tttgttttta cactgaaaat aatttaatat ttgtgaagaa tactaataca   1260
ttggtatatt tcattttctt aaaattctga accctcttc ccttatttcc ttttgacccg    1320
attggtgtat tggtcatgtg actcatggat ttgccttaag gcaggagg                1368
```

<210> SEQ ID NO 34
<211> LENGTH: 755
<212> TYPE: DNA
<213> ORGANISM: Artificial Sequence
<220> FEATURE:
<223> OTHER INFORMATION: sequence of STAR34

<400> SEQUENCE: 34

```
actgggcacc ctcctaggca ggggaatgtg agaactgccg ctgctctggg gctgggcgcc     60
atgtcacagc aggagggagg acggtgttac accacgtggg aaggactcag ggtggtcagc    120
cacaaagctg ctggtgatga ccaggggctt gtgtcttcac tctgcagccc taacacccag    180
gctgggttcg ctaggctcca tcctgggggt gcagaccctg agagtgatgc cagtgggagc    240
ctcccgcccc tccccttcct cgaaggccca gggtcaaac agtgtagact cagaggcctg     300
agggcacatg tttatttagc agacaaggtg gggctccatc agcggggtgg cctggggagc    360
```

-continued

| | |
|---|---|
| agctgcatgg gtggcactgt ggggagggtc tcccagctcc ctcaatggtg ttcgggctgg | 420 |
| tgcggcagct ggcggcaccc tggacagagg tggatatgag ggtgatgggt ggggaaatgg | 480 |
| gaggcacccg agatggggac agcagaataa agacagcagc agtgctgggg ggcaggggga | 540 |
| tgagcaaagg caggcccaag accccagcc cactgcaccc tggcctccca caagccccct | 600 |
| cgcagccgcc cagccacact cactgtgcac tcagccgtcg atacactggt ctgttaggga | 660 |
| gaaagtccgt cagaacaggc agctgtgtgt gtgtgtgcgt gtatgagtgt gtgtgtgtga | 720 |
| tccctgactg ccaggtcctc tgcactgccc ctggg | 755 |

<210> SEQ ID NO 35
<211> LENGTH: 1193
<212> TYPE: DNA
<213> ORGANISM: Artificial Sequence
<220> FEATURE:
<223> OTHER INFORMATION: sequence of STAR35
<220> FEATURE:
<221> NAME/KEY: misc_feature
<222> LOCATION: (355)..(1191)
<223> OTHER INFORMATION: "N" stands for any nucleotide on various positions
<220> FEATURE:
<221> NAME/KEY: misc_feature
<222> LOCATION: (312)..(1191)
<223> OTHER INFORMATION: "N" stands for any nucleotide on various positions

<400> SEQUENCE: 35

| | |
|---|---|
| cgacttggtg atgcgggctc ttttttggtt ccatatgaac tttaaagtag tcttttccaa | 60 |
| ttctgtgaag aaagtcattg gtaggttgat ggggatggca ttgaatctgt aaattacctt | 120 |
| gggcagtatg gccattttca caatgttgat tcttcctatc catgatgatg gaatgttctt | 180 |
| ccattagttt gtatcctctt ttatttcctt gagcagtggt ttgtagttct ccttgaagag | 240 |
| gtccttcaca tcccttgtaa gttggattcc taggtatttt attctctttg aagcaaattg | 300 |
| tgaatgggag tncactcacg atttggctct ctgtttgtct gctgggtgta taaanaatgt | 360 |
| ngtgatnttn gtacattgat ttngtatccn tgagacttng ctgaatttgc ttnatcngct | 420 |
| tnngggaacc ttttgggctg aaacnatggg attttctaaa tatacaatca tgtcgtctgc | 480 |
| aaacagggaa caatttgact tcctcttttc ctaattgaat acactttatc tccttctcct | 540 |
| gcctaattgc cctgggcaaa acttccaaca ctatgntngn aataggagnt ggtgagagag | 600 |
| ggcatccctg ttcttgttgc cagnttttca aagggaatgc ttccagtttt ggcccattca | 660 |
| gtatgatatg ggctgtgggt ngtgtcataa atagctctta tnatttgaa atgtgtccca | 720 |
| tcaataccta atttattgaa agttttagc atgaangcat ngttgaattt ggtcaaaggc | 780 |
| ttttctgca tctatggaaa taatcatgtg gttttgtct ttggctcntg tttatatgct | 840 |
| ggatnacatt tattgatttg tgtatatnga acccagcctn ncatcccagg gatgaagccc | 900 |
| acttgatcca agcttggcgc gcngnctagc tcgaggcagg caaaagtatg caaagcatgc | 960 |
| atctcaatta gtcagcaccc atagtccgcc cctacctccg cccatccgcc cctaactcng | 1020 |
| nccgttcgcc cattctcgcc catggctgac taatnttttt annatccaag cggngccgcc | 1080 |
| ctgcttganc attcagagtn nagagnnttg gaggccnagc cttgcaaaac tccggacngn | 1140 |
| ttctnnggat tgacccnnt taaatatttg gttttttgtn ttttcanngg nga | 1193 |

<210> SEQ ID NO 36
<211> LENGTH: 1712
<212> TYPE: DNA
<213> ORGANISM: Artificial Sequence
<220> FEATURE:
<223> OTHER INFORMATION: sequence of STAR36

<400> SEQUENCE: 36

```
gatcccatcc ttagcctcat cgatacctcc tgctcacctg tcagtgcctc tggagtgtgt    60
gtctagccca ggcccatccc ctggaactca ggggactcag gactagtggg catgtacact   120
tggcctcagg ggactcagga ttagtgagcc ccacatgtac acttggcctc agtggactca   180
ggactagtga gccccacatg tacacttggc ctcagggac tcaggattag tgagccccca   240
catgtacact tggcctcagg ggactcagga ttagtgagcc ccacatgtac acttggcctc   300
aggggactca ggactagtga gccccacatg tacacttggc ctcagggac tcagaactag   360
tgagccccac atgtacactt ggcttcaggg gactcaggat tagtgagccc cacatgtaca   420
cttggacacg tgaaccacat cgatgtgctg cagagctcag ccctctgcag atgaaatgtg   480
gtcatggcat tccttcacag tggcacccct cgttccctcc ccacctcatc tcccattctt   540
gtctgtcttc agcacctgcc atgtccagcc ggcagattcc accgcagcat cttctgcagc   600
accccgacc acacacctcc cagcgcctg cttggccctc cagcccagct cccgcctttc   660
ttccttggggaa agctccctg acagacacc ccctcctccc agccatggct ttttcctgct   720
ctgccccacg cgggaccctg ccctggatgt gctacaatag acacatcaga tacagtcctt   780
cctcagcagc cggcagaccc agggtggact gctcggggcc tgcctgtgag gtcacacagg   840
tgtcgttaac ttgccatctc agcaactagt gaatatgggc agatgctacc ttccttccgg   900
ttccctggtg agaggtactg gtggatgtcc tgtgttgccg ccaccttttt gtccctggat   960
gccatttatt ttttttccaca aatatttccc aggtctcttc tgtgtgcaag gtattagggc  1020
tgcagcgggg gccaggccac agatctctgt cctgagaaga cttggattct agtgcaggag  1080
actgaagtgt atcacaccaa tcagtgtaaa ttgttaactg ccacaaggag aaaggccagg  1140
aaggagtggg gcatggtggt gttctagtgt tacaagaaga agccagggag ggcttcctgg  1200
atgaagtggc atctgacctg ggatctggag gaggagaaaa atgtcccaaa agagcagaga  1260
gcccacccta ggctctgcac caggaggcaa cttgctgggc ttatggaatt cagagggcaa  1320
gtgataagca gaaagtcctt gggggccaca attaggattt ctgtcttcta aagggcctct  1380
gccctctgct gtgtgacctt gggcaagtta cttcacctct agtgctttgg ttgcctcatc  1440
tgtaaagtgg tgaggataat gctatcacac tggttgagaa ttgaagtaat tattgctgca  1500
aagggcttat aagggtgtct aatactagta ctagtaggta cttcatgtgt cttgacaatt  1560
ttaatcatta ttattttgtc atcaccgtca ctcttccagg ggactaatgt ccctgctgtt  1620
ctgtccaaat taaacattgt ttatccctgt gggcatctgg cgaggtggct aggaaagcct  1680
ggagctgttt cctgttgacg tgccagacta gt                                1712
```

<210> SEQ ID NO 37
<211> LENGTH: 1321
<212> TYPE: DNA
<213> ORGANISM: Artificial Sequence
<220> FEATURE:
<223> OTHER INFORMATION: sequence of STAR37

<400> SEQUENCE: 37

```
atctctctct gccaaagcaa cagcggtccc tgccccaacc agactacccc actcagtggg    60
gttacggatg ctgctccagc atcctaacac tgcccagctg gtgcctgcct gtgctcaccc   120
acaaccccca ggccggcctt ccctgcagcc tgggcttggc caccttggcc tgattgagca   180
```

-continued

```
ctgaggcctc ctgggcaccc agccccatca ctgcacctgc tgcttccagc cccaccccac      240
cggctcaggg gttcttccca gcggcgctga tcatgaagtc aacatgcacg caagtcgtct      300
caggaaactt tttaatgaaa gtgtcggcca cggtggtgtg taggtggctg agctcagatt      360
gcagctgcta agacaccagc cacttaccaa gagaaagcca ggctgcttca aacccagggc      420
cggaggcaaa aaagcatcac ttccagccgg ggagtctgga agccacgcct tgtgggaggt      480
cacactggca tctaggcctt cgcctgcact gcagaaggag agccgggtcc ccctcctgga      540
gaacgctgcg ttccccagcc ccacaccggc tttgccacca cacaggctgt tgaggcagga      600
ggcgggtaag acgtagctgt agacccaaag caaccaccag ccctgggacc ctgcgggaga      660
ggagcacttt tagaacatgg aaaaatgtgg tcatcccatc attagacagc acacatccta      720
cataaataaa aagtcgtatg gggaaggagg ttggggaggg aataaaaaat tggcacagac      780
attgatagac tggtttccag tttcaaggta acagatgcac atcatgagac cagaggaggc      840
agagacaagg gctgaatttg gcttttctaa gcaacatgtg ttcctgcgca gggctgaatg      900
gtcgctgaga cagagatgga agccaggaca agggagccca ccgggcccag ataggtacag      960
agagcagagg ctcctgttct gtcctcgcca cccatgaggg tgacactgct tgtaaatggt     1020
ggctgtgctc tcccagcaag aaaaaagcac aactaaatcc acactgcaca cagacgcaga     1080
cagaaagcct tcaagtggct ctgttttctg ctccctgcct tgccaggtcc acaagcagag     1140
aggagtgtca ggcacatggc cccgctgtca ggctccccag tgagctgtag gctcagcagg     1200
agctgcccac tgcacacag gggacaccca ctcctgccac cttgggagcg gttgccagac     1260
agagccgcac tgggtgctgg tgtcatccag ggaccccaca cacttcctta aatgtgatcc     1320
t                                                                    1321
```

<210> SEQ ID NO 38
<211> LENGTH: 1445
<212> TYPE: DNA
<213> ORGANISM: Artificial Sequence
<220> FEATURE:
<223> OTHER INFORMATION: sequence of STAR38
<220> FEATURE:
<221> NAME/KEY: misc_feature
<222> LOCATION: (348)..(949)
<223> OTHER INFORMATION: "N" stands for any nucleotide on various
      positions

<400> SEQUENCE: 38

```
gatctatggg agtagcttcc ttagtgagct ttcccttcaa atactttgca accaggtaga       60
gaattttgga gtgaaggttt tgttcttcgt ttcttcacaa tatggatatg catcttcttt      120
tgaaaatgtt aaagtaaatt acctctcttt tcagatactg tcttcatgcg aacttggtat      180 cctgttttcca tcccagcctt ctataaccca gtaacatctt ttttgaaacc agtgggtgag     240
aaagacacct ggtcaggaac gcggaccaca ggacaactca ggctcaccca cggcatcaga      300
ctaaaggcaa acaaggactc tgtataaagt accggtggca tgtgtatnag tggagatgca      360
gcctgtgctc tgcagacagg gagtcacaca gacacttttc tataatttct taagtgcttt      420
gaatgttcaa gtagaaagtc taacattaaa tttgattgaa caattgtata ttcatggaat      480
attttggaac ggaataccaa aaaatggcaa tagtggttct ttctggatgg aagacaaact      540
tttcttgttt aaaataaatt ttattttata tatttgaggt tgaccacatg accttaagga      600
tacatataga cagtaaactg gttactacag tgaagcaaat taacatatct accatcgtac      660
atagttacat ttttttgtgt gacaggaaca gctaaaatct acgtatttaa caaaaatcct      720
```

```
aaagacaata cattttattt aactatagcc ctcatgatgt acattagatc gtgtggttgt      780
ttcttccgtc cccgccacgc cttcctcctg ggatggggat tcattcccta gcaggtgtcg      840
gagaactggc gcccttgcag ggtaggtgcc ccggagcctg aggcgggnac tttaanatca      900
gacgcttggg ggccggctgg gaaaaactgg cggaaaatat tataactgna ctctcaatgc      960
cagctgttgt agaagctcct gggacaagcc gtggaagtcc cctcaggagg cttccgcgat     1020
gtcctaggtg gctgctccgc ccgccacggt catttccatt gactcacacg cgccgcctgg     1080
aggaggaggc tgcgctggac acgccggtgg cgcctttgcc tgggggagcg cagcctggag     1140
ctctggcgga agcgctggga gcggggcctc ggaggctggg cctggggacc caaggttggg     1200
cggggcgcag gaggtgggct cagggttctc cagagaatcc ccatgagctg acccgcaggg     1260
cggccgggcc agtaggcacc gggcccccgc ggtgacctgc ggacccgaag ctggagcagc     1320
cactgcaaat gctgcgctga ccccaaatgc tgtgtccttt aaatgtttta attaagaata     1380
attaataggt ccgggtgtgg aggctcaagc cttaatcccc agcacctggc gaggccgagg     1440
aggga                                                                 1445

<210> SEQ ID NO 39
<211> LENGTH: 2331
<212> TYPE: DNA
<213> ORGANISM: Artificial Sequence
<220> FEATURE:
<223> OTHER INFORMATION: sequence of STAR39

<400> SEQUENCE: 39
tcactgcaac ctccacctcc caggttcaag tgattctcct gcctcggcct cccgagtagc       60
tgggactaca ggtgcatgac accgcacctg gctagttttt gtattttag tagagacagg      120 gtttcactat gttggccagg ttggtctcga actcctgacc ttgtgatccg cccacctcgg      180
cctcccaaag tgctgggatt acagagtgag ccactgcgcc tggcctgcac cccttactat      240
tatatgcttt gcattttctt ttagatttga agaacctcat tataaactct agcactaatc      300
ttatgtcagt taaatgcata gcaaatatct cctgacgtgg gagaatatat atttgcaagt      360
cttcttgtga acatatgttt tcagttctag ggagccagac gcctatgagt gaaaagccta      420
gtcatcgtgg agaagtgcat tcaactttgt aagaaactgc caaacccttta ttcataatgg     480 ttgtataaat tttacattac caccaataat gtatgagagt tccagttgct tcacatcctc      540
accagcattt tgttttgtct gtcttttttc ctttggttat tctagtgggc ataagatata      600
atagtatccc ttgtggttta atgtaaattc cactgaagac taataacatt tgcatatttc      660
taattaataa gccttttttaa gtgacttttc aagtctttgc tcattttat tagatatttg      720 ccttcttatt attgatttga aagaattata tttatatgct tatattctgg ttataagccc      780
tttgtcatta ttttccaaaa caatatttgg ttgtttctgt actactttcc ttgctccttt      840
gaattgactt ggtgccttgg ccaaaaatca attgaccaca tacatgtggg tgcatctcca      900
gactaccaca ttccgtttat ctatttgtct ctccttgtgt caataacact ctgtcttgat      960
aatggtaagt tttgagatca ggttgtgtaa gtcctcctaa ttttttcctgg gttttcaata    1020 ttgctttgct ttttaaaaat tttgtatttt catttacatt ttaaaataaa cttgttagtg     1080
ggattttgat tggcattgca ctgaactcgt ggatcaattt ggggagattg gacattctta     1140
tatatggatc ccgtggtcat caactttaag aactctttct catccattag taactcaatc     1200
taggttcaga tgctactcgt tttctgctca gtctgtgtct gagcccctta tgctcttcat     1260
tttgtcatcc aattaaacctc agctttgcat caatactatt tcttgctttg gtgcctgtta    1320
```

-continued

| | |
|---|---|
| cctctcctct aatcaccaat ccacaactta cctccaaatt cagggcttgt ctcattcttc | 1380 |
| ccaggaggag tgctgctcag tctatctact tagtattata atttctctgg cttggtatca | 1440 |
| aggcactccc atttccggct tccatgagat gtctcagagg gcatgctgcc cggtgtagct | 1500 |
| gcatggtcaa gcttcttcat atctcttgcc tcatcactta aactcactat tttgtactcc | 1560 |
| tgcttcagct atagggagct actgttagtt tcttgaagac atatgctctc tctctctctc | 1620 |
| acatctggac ctgagcacat cctgttactg ctgcttgaaa caatgtgatc cccaggcaca | 1680 |
| caccattagc ttagaagcct cccctgattc ttcaaggctg gttgagtccc ttctctgtgc | 1740 |
| tctcatgaca acagttggca attcctcgtt gcagcaccta gcccatgatg ctctttggag | 1800 |
| gcagagactg agtctttctc actattgaat ttccagcatt catcacagag cctggcatat | 1860 |
| ataaagccct ccatcatatg tattaagtga atggataaat gaaaaaaagt tatatatatg | 1920 |
| tacatatatg tgtatatatg tatgtgtata tatgtgtata tatgtgtgta tatgtgtgtg | 1980 |
| tatatatgta catatatatg tatctatgta catatatgta tatatgtata tatgtgtgtg | 2040 |
| tgtatatgtg tgtgtgtatg tatatatatt acaatgaaat actattcagc cttaaaaagg | 2100 |
| cagggaatcc tgtcatttaa cacaatatgg ataaacctag aggactctaa aggcaaatac | 2160 |
| cacatgttct cactcacaaa atctaaacaa gttgaactcc tacaagtaga gagtaggatg | 2220 |
| atggttacca agggctgggg gacgggagag gatggggaaa gcatagctgt ccatcaaagg | 2280 |
| gtagaaagtt tcatttagac aagaggaatc agctttagtg atctatttca c | 2331 |

<210> SEQ ID NO 40
<211> LENGTH: 1071
<212> TYPE: DNA
<213> ORGANISM: Artificial Sequence
<220> FEATURE:
<223> OTHER INFORMATION: sequence of STAR40

<400> SEQUENCE: 40

| | |
|---|---|
| gctgtgattc aaactgtcag cgagataagg cagcagatca agaaagcact ccgggctcca | 60 |
| gaaggagcct tccaggccag cttgagcat aagctgctga tgagcagtga gtgtcttgag | 120 |
| tagtgttcag ggcagcatgt taccattcat gcttgacttc tagccagtgt gacgagaggc | 180 |
| tggagtcagg tctctagaga gttgagcagc tccagcctta gatctcccag tcttatgcgg | 240 |
| tgtgcccatt cgctttgtgt ctgcagtccc ctggccacac ccagtaacag ttctgggatc | 300 |
| tatgggagta gcttccttag tgagctttcc cttcaaatac tttgcaacca ggtagagaat | 360 |
| tttggagtga aggttttgtt cttcgtttct tcacaatatg gatatgcatc ttcttttgaa | 420 |
| aatgttaaag taaattacct ctcttttcag atactgtctt catgcgaact tggtatcctg | 480 |
| tttccatccc agccttctat aacccagtaa catcttttttt gaaaccagtg ggtgagaaag | 540 |
| acacctggtc aggaacgcgg accacaggac aactcaggct cacccacggc atcgactaa | 600 |
| aggcaaacaa ggactctgta taaagtaccg gtggcatgtg tattagtgga gatgcagcct | 660 |
| gtgctctgca gacagggagt cacacagaca cttttctata atttcttaag tgctttgaat | 720 |
| gttcaagtag aaagtctaac attaaatttg attgaacaat tgtatattca tggaatattt | 780 |
| tggaacggaa taccaaaaaa tggcaatagt ggttctttct ggatggaaga caaacttttc | 840 |
| ttgtttaaaa taaattttat tttatatatt tgaggttgac cacatgacct taaggataca | 900 |
| tatagacagt aaactggtta ctacagtgaa gcaaattaac atatctacca tcgtacatag | 960 |
| ttacattttt ttgtgtgaca ggaacagcta aaatctacgt atttaacaaa aatcctaaag | 1020 |

```
<210> SEQ ID NO 41
<211> LENGTH: 1135
<212> TYPE: DNA
<213> ORGANISM: Artificial Sequence
<220> FEATURE:
<223> OTHER INFORMATION: sequence of STAR41

<400> SEQUENCE: 41
tgctcttgtt gcccaggctg cagtgcaatg gcgctgtctc ggctcatcgc aacctccgcc      60
tcccagattc aagtgattct cctgcctcac cctcccaagt agctgggatt accagtatgc     120
agcaacacgc ccggctaatt ttgtatttgt aatagagacg gggtttcttc atgttggtca     180
ggctggtctc aaattcctgc cctcaggtga tctgcccacc ttggcctccc aaagtgctgg     240
gattacaggc atgagccact gtgcccggcc tgggctgggg cttttaaggg gactggaggg     300
tgagggctg gaaaattggg agagttgatt ggtggggcaa gggggatgta atcatcaggg      360
tgtacaaact gcactcttgg tttagtcagc tcctcgtggg gtccttcgga gcagctcagt     420
cagtagctcc atcagtatac aggacccaaa ggaatatctc aaagggaaaa cagcatttcc     480
taaggttcaa gttgtgatct acggagcagt taggggaact acaatcttgt gacagggtct     540
acatgcttct gaggcaatga gacaccaagc agctacgagg aagcagtcag agagcacgcc     600
gacctagtga ctgatgctga tgtgctgcga gctgggttca ttttcatttc tcccctcccc     660
ctgccctcat taattttgta aagtttatag ggaacatttc acccactctg ctgtggatcc     720
ctgtcactta cggagtctgt catcttggct gtatgggctg tggcctctgc ggtgcccatt     780
ctcaggaggt gtgagaccca tgaggaccgg aggtggacaa ggctagagac cacacccccc     840
cgctccatcc aatcatgttt tcctgggtgc ttggtttcta tgcaggctgc atgtccttag     900
tccctgcatg ggaacagctc ctgtggtgag caggcccctg aggaaggcct tgagcgggaa     960
tggagcctag gcttaggctg cctggtaaga gctggaggga accagccgag gcttgtgcta    1020
cttttttttc cagaatgaaa tacgtgactg atgttggtgt cctgcagcgc acgtttccc     1080
gccacaacca ccggaacgag gatgaggaga acacactctc cgtggactgc acacg         1135

<210> SEQ ID NO 42
<211> LENGTH: 735
<212> TYPE: DNA
<213> ORGANISM: Artificial Sequence
<220> FEATURE:
<223> OTHER INFORMATION: sequence of STAR42

<400> SEQUENCE: 42
aagggtgaga tcactaggga gggaggaagg agctataaaa gaaagaggtc actcatcaca      60
tcttacacac tttttaaaac cttggttttt taatgtccgt gttcctcatt agcagtaagc     120
cctgtggaag caggagtctt tctcattgac caccatgaca agaccctatt tatgaaacat     180
aatagacaca caaatgttta tcggatattt attgaaatat aggaattttt cccctcacac     240
ctcatgacca cattctggta cattgtatga atgaatatac cataattta cctatggctg      300
tatatttagg tcttttcgtg caggctataa aaatatgtat gggccggtca cagtgactta     360
cgcccgtagt cccagaactt tgggaggccg aggcgggtgg atcacctgag gtcgggagtt     420
caaaaccagc ctgaccaaca tggagaaacc ccgtctctgc taaaaataca aaattaact      480
ggacacggtg gcgtatgcct gtaatcccag ctactcggga agctgaggca ggagaactgc     540
ttgaacccag gaggcggagg ttgtggtgag tcgagattgc gccattgcac tccagcctgg     600
```

```
gcaacaagag cgaaattcca tctcaaaaaa aagaaaaaag tatgactgta tttagagtag      660
tatgtggatt tgaaaaatta ataagtgttg ccaacttacc ttagggttta taccatttat      720
gagggtgtcg gtttc                                                       735
```

<210> SEQ ID NO 43
<211> LENGTH: 1227
<212> TYPE: DNA
<213> ORGANISM: Artificial Sequence
<220> FEATURE:
<223> OTHER INFORMATION: sequence of STAR43

<400> SEQUENCE: 43

```
caaatagatc tacacaaaac aagataatgt ctgcccattt ttccaaagat aatgtggtga       60
agtgggtaga gagaaatgca tccattctcc ccacccaacc tctgctaaat tgtccatgtc      120
acagtactga gaccaggggg cttattccca gcgggcagaa tgtgcaccaa gcacctcttg      180
tctcaatttg cagtctaggc cctgctattt gatggtgtga aggcttgcac ctggcatgga      240
aggtccgttt tgtacttctt gctttagcag ttcaaagagc agggagagct gcgagggcct      300
ctgcagcttc agatggatgt ggtcagcttg ttggaggcgc cttctgtggt ccattatctc      360 cagccccct gcggtgttgc tgtttgcttg gcttgtctgg ctctccatgc cttgttggct      420
ccaaaatgtc atcatgctgc accccaggaa gaatgtgcag gcccatctct tttatgtgct      480
ttgggctatt ttgattcccc gttgggtata ttccctaggt aagacccaga agacacagga      540
ggtagttgct ttgggagagt ttggacctat gggtatgagg taatagacac agtatcttct      600 cttcatttg gtgagactgt tagctctggc cgcggactga attccacaca gctcacttgg      660 gaaaactta ttccaaaaca tagtcacatt gaacattgtg gagaatgagg acagagaag       720 aggccctaga tttgtacatc tgggtgttat gtctataaat agaatgcttt ggtggtcaac      780
tagacttgtt catgttgaca tttagtcttg cctttcggt ggtgatttaa aaattatgta       840
tatcttgttt ggaatatagt ggagctatgg tgtggcattt tcatctggct ttttgtttag      900
ctcagcccgt cctgttatgg gcagccttga agctcagtag ctaatgaaga ggtatcctca      960
ctccctccag agagcggtcc cctcacggct cattgagagt ttgtcagcac cttgaaatga     1020
gtttaaactt gtttattttt aaaacattct tggttatgaa tgtgcctata ttgaattact     1080
gaacaaccct atggttgtga agaattgatt tggtgctaag gtgtataaat ttcaggacca     1140
gtgtctctga agagttcatt tagcatgaag tcagcctgtg gcaggttggg tggagccagg     1200
gaacaatgga gaagctttca tgggtgg                                        1227
```

<210> SEQ ID NO 44
<211> LENGTH: 1586
<212> TYPE: DNA
<213> ORGANISM: Artificial Sequence
<220> FEATURE:
<223> OTHER INFORMATION: sequence of STAR44

<400> SEQUENCE: 44

```
tgagttgggg tcctaagcca gaagttaact atgctttcat atattcttgc aagtagaagt       60
acagtgttgg tgtaaattcc ccttagatgg atagctaagc ccagaggaaa taatggtaat      120
tggaaccata tgaccgtatg caattcatgt gcatatttat atcaagaaaa gaacattata      180
ggtcgggtga gaccctattt tgttctgaca atgtcatctg tatttacatg tctgtttcgg      240
gagtttggat gtcaagggat tctgtgctgg attgtaaagc atgtgcttct gcttgatgta      300
```

| | |
|---|---|
| gctactcaat tttgtattct tgactaataa agtcataaac ataattcaac ctctgtgtgc | 360 |
| gtgctctcct tccattaatt tatactttag caaaaagtat tgaatgtgtg tgttatgtaa | 420 |
| caatttccta taaattatat taaatgattt attagcttta ttcaataaag tttttaagtgt | 480 |
| tttcttctat gactacatta tttgttaaca agaaatttct ttaactgaaa acttcaagga | 540 |
| agactatctg ggtaactctt tcaaaaagaa ttgtccctgt attttgggat tgaatatatt | 600 |
| aatttcttgt actgttttaa cagcacataa ttttacaaga caagccactt tttcaaagcc | 660 |
| tgcttctcct cccatttttcc ctatctctgt gattgacacc tccaacccct gtagcctgcc | 720 |
| tctgctctct cttaaccagt cctactgata ctacttccta agtattttttc agccctgtcc | 780 |
| ttcctctcca tcatgatgga ttcacttcca gttgaaatcc ttatggtacc ctccctggat | 840 |
| tatggcagta atcagagagc tggtctcctt aactcaggat tcacttcttc tcatctgttg | 900 |
| ttcacagtga catcagaaag atattttaaa atgatgaact agaattaatt atataaaaca | 960 |
| cacatacaca cataaataat acttaaattt ttcaatgatg ttccaattat gtaaaatata | 1020 |
| atataggagg cactttatgt tctggcctca atctttcaat tcaaacttat ctcctgccac | 1080 |
| tatctccttt gaacattgta ttccagctac tttagaataa taataataca taatattcat | 1140 |
| agagcccttc ctgggttcct atcaccgtac aaaatacttc acatataaca tttaatcttt | 1200 |
| gacaacttta ttaggcatgc acaattatta tctatctata tatctatatc tatatatata | 1260 |
| aaatctatat tttatagata agaaaataga gggtaaaaac ttgccaaaat tacaaagctt | 1320 |
| agaagtgtag cagttgggat ttgaatctag gcatcctgcc tctatagtct acagtggctt | 1380 |
| tcttgtgcca aaagccttgc agttccctag acttaacatt tctcaaaatc tgtgtctttc | 1440 |
| acatgctctt ccaattgtct ggaaaatctt tcccaacctc agtctaactg tggtactcat | 1500 |
| gttcaccca caagaattga ctccatctgt cccctctcca tgaaaatttc tttgaatctc | 1560 |
| agcactttgg gaggctgagg caggtg | 1586 |

<210> SEQ ID NO 45
<211> LENGTH: 1981
<212> TYPE: DNA
<213> ORGANISM: Artificial Sequence
<220> FEATURE:
<223> OTHER INFORMATION: sequence of STAR45

<400> SEQUENCE: 45

| | |
|---|---|
| cacgccccag cgtgccctgg actactgctc cgcaggactc ctgttctgct gcaccctgga | 60 |
| ctacggcacc agaggaccca gctccgccg gcctgagcta tggcaccaga ggacccagct | 120 |
| cccggcagcc tggactatgg caccagagga cccagccccc cgcttcctgg gctaaggcac | 180 |
| agtaggaccc tgcctcatcg tgtactcctg ctcaggagga ccctcgcagg gcggcgcact | 240 |
| ggactaagct actgaaggag ccccaccccct gcctaaccct ggactaaggc actggagaac | 300 |
| tcttgctccg cagagccacg gactcttgca caagagaacc tcagcccagc cgtgccctgg | 360 |
| actgtggcac agtagggccc acaccacgcc atggactcct gtattggagg aagagtagtg | 420 |
| ataaatgtcc aggtttacaa cttgaaaagt agcaatcaat gtgccacaat agatggatgt | 480 |
| gatgtaaaat tataaatgat gaaaacatta tgtgtaattg cctagccaga acagttacac | 540 |
| aagacaaaga cgtaaaagaa atccacatag ggaaggaaga ggtaagattg tttctgtttt | 600 |
| ttgaaaatat aatcttaaga tagagaaaat cttaaagatt ccaccaaaat aaatggttat | 660 |
| agctgatgaa gaaattcaat aaagttaata gttacaaaat caacatacaa atatcattat | 720 |
| tgtttctatt aactaatgac aaactattac ctgaaaaata aaggcaattc aatttataat | 780 |

| | | | | |
|---|---|---|---|---|
| agaatcaaaa | cagatatata | aatatataaa | agacaggagt | aaatttaatc | aaaaccataa | 840 |
| aagatttaca | tactgaaaac | tatagcacat | tgatgaaaaa | aattaaaatg | gcataaataa | 900 |
| atggagaaac | atccttcatt | gatggattca | aaaattagta | ttgtaaaagt | gtcaatgcta | 960 |
| cccaaagcaa | tctacagatt | aaatgcaacc | actatcaaat | tccaatgtca | ttcttcacag | 1020 |
| aaatagaaaa | attactgcta | aaatttgtat | ggaaccacaa | aagacctgga | ccaaccaaag | 1080 |
| caatcttgaa | caaaaagaac | aaagctggag | gcatcagact | acctgactcc | aaactctatt | 1140 |
| acaaagctat | aggaattaaa | acagcatagc | aatggcataa | aaacagacat | gtaaaacagt | 1200 |
| acaaagggat | atagaacctg | taaataaatc | cgtgtgtctg | tggtcaattg | attttttgat | 1260 |
| aaaataacta | aaaatacaca | gtgaagaaag | aaaattattt | tcaataaatg | gtgtagacaa | 1320 |
| aactgactat | ccacatacag | aagaataaaa | tttgactttt | attttgctct | ttatacaagc | 1380 |
| atcaaatcaa | aattaaagtt | taatgtaaa | actactacaa | ggaaatatag | aaggagactg | 1440 |
| tatgacattg | gcctgagcta | tgattttctg | tagattattc | caaaaggcaa | caaaagcaaa | 1500 |
| acacacaaat | gagactgcat | aaaacttaaa | acttttccac | aggaaaagaa | gcaatgatag | 1560 |
| aattaagaga | acccacaaat | gggataatat | ttttaaacca | tacatcaggt | aagggggctca | 1620 |
| tataataata | tataagcaac | tcaacctact | caaaaataag | aaaaaaacta | tgcttattaa | 1680 |
| aaaataagca | aagaatcaga | atagacattt | cctacatcat | acaaaaggcc | aaccaggtac | 1740 |
| atgaaaaaat | cataaacatt | cctaattatc | agagaagtgc | aaatcaatgc | cacaatgaga | 1800 |
| tatcacctca | cacattttac | tagggctatt | ataaaaaaag | atggaagata | agtgttggtg | 1860 |
| aggatgtgga | gaaaagaaa | ccctgtacac | tgttggtagg | aatggaaatt | agtacagcca | 1920 |
| tcttggaaaa | cagtacgaag | ctttctcaag | aaattataaa | tttatttacc | ctatgatcca | 1980 |
| t | | | | | | 1981 |

<210> SEQ ID NO 46
<211> LENGTH: 1859
<212> TYPE: DNA
<213> ORGANISM: Artificial Sequence
<220> FEATURE:
<223> OTHER INFORMATION: sequence of STAR46

<400> SEQUENCE: 46

| | | | | |
|---|---|---|---|---|
| attgtttttc | tcgcccttct | gcattttctg | caaattctgt | tgaatcattg | cagttactta | 60 |
| ggtttgcttc | gtctccccca | ttacaaacta | cttactgggt | ttttcaaccc | tagttccctc | 120 |
| attttatga | tttatgctca | tttctttgta | cacttcgtct | tgctccatct | cccaactcat | 180 |
| ggcccctggc | tttggattat | tgttttggtc | tttttatttt | tgtcttcttc | tacctcaaca | 240 |
| cttatcttcc | tctcccagtc | tccggtaccc | tatcaccaag | gttgtcatta | acctttcata | 300 |
| ttattcctca | ttatccatgt | attcatttgc | aaataagcgt | atattaacaa | atcacaggt | 360 |
| ttatggagat | ataattcaca | taccttaaaa | ttcaggcttt | taaagtgtac | ctttcatgtg | 420 |
| gttttggta | tattcacaaa | gttatgcatt | gatcaccacc | atctgattcc | ataacatgtt | 480 |
| caatacctca | aaaagaagtc | tgtactcatt | agtagtcatt | tcacattcac | cactccctct | 540 |
| ggctctgggc | agtcactgat | ctttgtgtct | ctatggattt | gcctagtcta | ggtattttta | 600 |
| tgtaaatggc | atcatacaac | atgtgacctt | tgtttggct | ttttttcattt | agcaaaatgt | 660 |
| tatcaaggtc | tgtccctgtt | gtagcatgta | ttagcacttc | atttcttata | tgctgaatga | 720 |
| tatactttat | ttgtccatca | gttgttcatg | ctttatttgt | ccatcagttg | atgaacattt | 780 |

| | |
|---|---:|
| gcgttttttgc cactttgggc tattaagaat aatgctactg tgaacaagtg tgtacaagtt | 840 |
| cctctacaaa ttttttgtgtg dacatatcct ttcagttctc tcaggtgtat atctgggaat | 900 |
| tgaattgctg ggtcgtgtag tagctatgtt aaacactttg agaaactgct ataatgttct | 960 |
| ccagagctgt accattttaa attctgtgta tgaggattcc acgttctcca cttcctcacc | 1020 |
| agtgtatgga tttgggggta tacttttttaa aaagtgggat taggctgggc acagtggctc | 1080 |
| acacctgtaa tcccaacact tcaggaagct gaggtgggag gatcacttga gcctagtagt | 1140 |
| ttgagaccag cctgggcaac atagggagac cctgtctcta caaaaaataa tttaaaataa | 1200 |
| attagctggg cgttgtggca cacacctgta gtcccagcta catgggaggc tgaggtggaa | 1260 |
| ggattccctg agcccagaag tttgaggttg cagtgagcca tgatggcagc actatactgt | 1320 |
| agcctgggtg tcagagcaag actccgtttc agggaagaaa aaaaaaagtg ggatgatatt | 1380 |
| tttgacactt ttcttcttgt tttcttaatt tcatacttct ggaaattcca ttaaattagc | 1440 |
| tggtaccact ctaactcatt gtgtttcatg gctgcatagt aatattgcat aatataaata | 1500 |
| taccattcat tcatcaaagt tagcagatat tgactgttag gtgccaggca ctgctctaag | 1560 |
| cgttaaagaa aaacacacaa aaacttttgc attcttagag tttattttcc aatggagggg | 1620 |
| gtggagggag gtaagaattt aggaaataaa ttaattacat atatagcata gggtttcacc | 1680 |
| agtgagtgca gcttgaatcg ttggcagctt tcttagtagt ataaatacag tactaaagat | 1740 |
| gaaattactc taaatggtgt tacttaaatt actggaatag gtattactat tagtcacttt | 1800 |
| gcaggtgaaa gtggaaacac catcgtaaaa tgtaaaatag gaaacagctg gttaatgtt | 1859 |

<210> SEQ ID NO 47
<211> LENGTH: 1082
<212> TYPE: DNA
<213> ORGANISM: Artificial Sequence
<220> FEATURE:
<223> OTHER INFORMATION: sequence of STAR47

<400> SEQUENCE: 47

| | |
|---|---:|
| atcattagtc attagggaaa tgcaaatgaa aaacacaagc agccaccaat atacacctac | 60 |
| taggatgatt taaaggaaaa taagtgtgaa gaaggacgta aagaaattgt aaccctgata | 120 |
| cattgatggt agaaatggat aaagttgcag ccactgtgaa aaacagtctg cagtggctca | 180 |
| gaaggttaaa tatagaaccc ctgttggacc caggaactct actcttaggc accccaaaga | 240 |
| atagagaaca gaaatcaaac agatgtttgt atactaatgt ttgtagcatc acttttcaca | 300 |
| ggagccaaaa ggtggaaata atccaaccat cagtgaacaa atgaatgtaa taaaagcaag | 360 |
| gtggtctgca tgcaatgcta catcatccat ctgtaaaaaa cgaacatcat tttgatagat | 420 |
| gatacaacat gggtggacat tgagaacatt atgcttagta aaataagcca gacacaaaag | 480 |
| gaatatattg tataattgta attacatgaa gtgcctagaa tagtcaaatt catacaagag | 540 |
| aaagtgggat aggaatcacc atgggctgga ataggggga aggtgctata ctgcttattg | 600 |
| tggacaaggt ttcgtaagaa atcatcaaaa ttgtgggtgt agatagtggt gttggttatg | 660 |
| caaccctgtg aatatattga atgccatgga gtgcacactt tggttaaaag gttcaaatga | 720 |
| taaatattgt gttatatata tttccccacg atagaaaaca cgcacagcca agcccacatg | 780 |
| ccagtcttgt tagctgcctt cctttacctt caagagtggg ctgaagcttg tccaatcttt | 840 |
| caaggttgct gaagactgta tgatggaagt catctgcatt gggaaagaaa ttaatggaga | 900 |
| gaggagaaaa cttgagaatc cacactactc accctgcagg gccaagaact ctgtctccca | 960 |
| tgctttgctg tcctgtctca gtatttcctg tgaccacctc cttttcaac tgaagacttt | 1020 |

```
gtacctgaag gggttcccag gttttcacc tcggcccttg tcaggactga tcctctcaac    1080
ta                                                                  1082
```

<210> SEQ ID NO 48
<211> LENGTH: 1242
<212> TYPE: DNA
<213> ORGANISM: Artificial Sequence
<220> FEATURE:
<223> OTHER INFORMATION: sequence of STAR48

<400> SEQUENCE: 48

```
atcatgtatt tgttttctga attaattctt agatacatta atgttttatg ttaccatgaa     60
tgtgatatta taatataata tttttaattg gttgctactg tttataagaa tttcattttc    120
tgtttacttt gccttcatat ctgaaaacct tgctgatttg attagtgcat ccacaaattt    180
tcttggattt tctatgggta attacaaatc tccacacaat gaggttgcag tgagccaaga    240
tcacaccact gtactccagc ctgggcgaca gagtgagaca ccatctcaca aaacacata    300
aacaaacaaa cagaaactcc acacaatgac aacgtatgtg ctttcttttt ttcttcctct    360
ttctataata tttctttgtc ctatcttaac tgaactggcc agaaacccca ggacaatgat    420
aaatacgagc agtgtcaaca gacatctcat tcccttccct agctttata aaaataacga    480
ttatgcttca acattacata tggtggtgtc gatggttttg ttatagataa gcttatcagg    540
ttaagaaatt tgtctgcgtt tcctagtttg gtataaagat tttaatataa atgaatgttg    600
tattttatca tcttattttt ttcctacatc tgctaaggta atcctgtgtt ttcccctttt    660
caatctccta atgtggtgaa tgacattaaa ataccttcta ttgttaaaat attcttgcaa    720
cgctgtatag aaccaatgcc tttattctgt attgctgatg gattttgaa aaatatgtag    780
gtggacttag ttttctaagg ggaatagaat ttctaatata tttaaaatat tttgcatgta    840
tgttctgaag gacattggtg tgtcatttct ataccatctg gctactagag gagccgactg    900
aaagtcacac tgccggagga ggggagaggt gctcttccgt ttctggtgtc tgtagccatc    960
tccagtggta gctgcagtga taataatgct gcagtgccga cagttctgga aggagcaaca   1020
acagtgattt cagcagcagc agtattgcgg gatccccacg atggagcaag ggaaataatt   1080
ctggaagcaa tgcaatatc agctgtggct atagcagctg agatgtgagt tctcacggtg   1140
gcagcttcaa ggacagtagt gatggtccaa tggcgcccag acctagaaat gcacatttcc   1200
tcagcaccgg ctccagatgc tgagcttgga cagctgacgc ct                     1242
```

<210> SEQ ID NO 49
<211> LENGTH: 1015
<212> TYPE: DNA
<213> ORGANISM: Artificial Sequence
<220> FEATURE:
<223> OTHER INFORMATION: sequence of STAR49

<400> SEQUENCE: 49

```
aaaccagaaa cccaaaacaa tgggagtgac atgctaaaac cagaacccca aaacaatggg     60
agggtcctgc taaccagaa acccaaaaca atgggagtga agtgctaaaa ccagaaaccc    120
aaaacaatgg gagtgtcctg ctacaccaga acccaaaac gatgggagtg acgtgataaa    180
accagacacc caaaacaatg ggagtgacgt gctaaaccag aaacccaaaa caatgggagt    240
gacgtgctaa aacctggaaa cctaaaacaa tgcgagtgag gtgctaacac cagaatccat    300
aacaatgtga gtgacgtgct aaaccagaac ccaaaacaat gggagtgacg tgctaaaaca    360
```

| | |
|---|---|
| ggaacccaaa acaatgagag tgacgtgcta aaccagaaac ccaaaacaat gggaatgacg | 420 |
| tgctaaaacc ggaacccaaa acaatgggag tgatgtgcta aaccagaaac ccaaaacaat | 480 |
| gggaatgaca tgctaaaact ggaacccaaa acaatggtaa ctaagagtga tgctaaggcc | 540 |
| ctacatttg gtcacactct caactaagtg agaacttgac tgaaaggag gattttttt | 600 |
| tctaagacag agttttggtc tgtccccag agtggagtgc agtggcatga tctcggctca | 660 |
| ctgcaagctc tgcctcccgg gttcaggcca ttctcctgcc tcagcctcct gagtagctgg | 720 |
| gaatacaggc acccgccacc acacttggct aatttttgt atttttagta gagatggggt | 780 |
| ttcaccatat tagcaaggat ggtctcaatc tcctgacctc gtgatctgcc cacctcaggc | 840 |
| tcccaaagtg ctgggattac aggtgtgagc caccacaccc agcaaaaagg aggaattttt | 900 |
| aaagcaaaat tatgggaggc cattgttttg aactaagctc atgcaatagg tcccaacaga | 960 |
| ccaaaccaaa ccaaaccaaa atggagtcac tcatgctaaa tgtagcataa tcaaa | 1015 |

<210> SEQ ID NO 50
<211> LENGTH: 2355
<212> TYPE: DNA
<213> ORGANISM: Artificial Sequence
<220> FEATURE:
<223> OTHER INFORMATION: sequence of STAR50

<400> SEQUENCE: 50

| | |
|---|---|
| caaccatcgt tccgcaagag cggcttgttt attaaacatg aaatgaggga aaagcctagt | 60 |
| agctccattg gattgggaag aatggcaaag agagacaggc gtcattttct agaaagcaat | 120 |
| cttcacacct gttggtcctc acccattgaa tgtcctcacc caatctccaa cacagaaatg | 180 |
| agtgactgtg tgtgcacatg cgtgtgcatg tgtgaaagta tgagtgtgaa tgtgtctata | 240 |
| tgggaacata tatgtgattg tatgtgtgta actatgtgtg actggcagcg tggggagtgc | 300 |
| tggttggagt gtggtgtgat gtgagtatgc atgagtggct gtgtgtatga ctgtggcggg | 360 |
| aggcggaagg ggagaagcag caggctcagg tgtcgccaga gaggctggga ggaaactata | 420 |
| aacctgggca atttcctcct catcagcgag cctttcttgg gcaataggg cagagctcaa | 480 |
| agttcacaga gatagtgcct gggaggcatg aggcaaggcg gaagtactgc gaggaggggc | 540 |
| agagggtctg acacttgagg ggttctaatg ggaaaggaaa gacccacact gaattccact | 600 |
| tagccccaga ccctgggccc agcggtgccg gcttccaacc ataccaacca tttccaagtg | 660 |
| ttgccggcag aagttaacct ctcttagcct cagtttcccc acctgtaaaa tggcagaagt | 720 |
| aaccaagctt accttcccgg cagtgtgtga ggatgaaaag agctatgtac gtgatgcact | 780 |
| tagaagaagg tctagggtgt gagtggtact cgtctggtgg gtgtggagaa gacattctag | 840 |
| gcaatgagga ctggggagag cctggcccat ggcttccact cagcaaggtc agtctcttgt | 900 |
| cctctgcact cccagccttc cagagaggac cttcccaacc agcactcccc acgctgccag | 960 |
| tcacacatag ttacacacat acaatcacat atatgttccc atatagacac attcacactc | 1020 |
| ataccttcac acatgcacac gcatgtgcac acacagtcac tcatttctgt gttggagatt | 1080 |
| gggtgaggac attcaatggg tgaggaccaa caggtgtgaa gattgctttc tagaaaatga | 1140 |
| ctcctgtctc tctttgccat tcttcccaat ccgatggagc tactaggctt ttccctcatt | 1200 |
| tcatgtttaa taaaccttcc caatggcgaa atgggctttc tcaagaagtg gtgagtgtcc | 1260 |
| catccctgcg gtggggacag gggtggcagc ggacaagcct gcctggaggg aactgtcagg | 1320 |
| ctgattccca gtccaactcc agcttccaac acctcatcct ccaggcagtc ttcattcttg | 1380 |
| gctctaattt cgctcttgtt ttcttttta tttttatcga gaactgggtg gagagctttt | 1440 |

```
ggtgtcattg gggattgctt tgaaaccctt ctctgcctca cactgggagc tggcttgagt    1500
caactggtct ccatggaatt tcttttttta gtgtgtaaac agctaagttt taggcagctg    1560
ttgtgccgtc cagggtggaa agcagcctgt tgatgtggaa ctgcttggct cagatttctt    1620
gggcaaacag atgccgtgtc tctcaactca ccaattaaga agcccagaaa atgtggcttg    1680
gagaccacat gtctggttat gtctagtaat tcagatggct tcacctggga agccctttct    1740
gaatgtcaaa gccatgagat aaaggacata tatatagtag ctagggtggt ccacttctta    1800
ggggccatct ccggaggtgg tgagcactaa gtgccaggaa gagaggaaac tctgttttgg    1860
agccaaagca taaaaaaacc ttagccacaa accactgaac atttgttttg tgcaggttct    1920
gagtccaggg agggcttctg aggagagggg cagctggagc tggtaggagt tatgtgagat    1980
ggagcaaggg ccctttaaga ggtgggagca gcatgagcaa aggcagagag gtggtaatgt    2040
ataaggtatg tcatgggaaa gagtttggct ggaacagagt ttacagaata gaaaaattca    2100
acactattaa ttgagcctct actacgtgct cgacattgtt ctagtcactg agataggttt    2160
ggtatacaaa acaaaatcca tcctctatgg acattttagt gactaacaac aatataaata    2220
ataaaagtga acaaaagctc aaaacatgcc aggcactatt atttatttat ttatttattt    2280
atttatttat tttttgaaac agagtctcgc tctgttgccc aggctggagt gtagtggtgc    2340
gatctcggct cactg                                                     2355
```

<210> SEQ ID NO 51
<211> LENGTH: 2289
<212> TYPE: DNA
<213> ORGANISM: Artificial Sequence
<220> FEATURE:
<223> OTHER INFORMATION: sequence of STAR51

<400> SEQUENCE: 51

```
tcacaggtga caccaatccc ctgaccacgc tttgagaagc actgtactag attgactttc      60
taatgtcagt cttcattttc tagctctgtt acagccatgg tctccatatt atctagtaca     120
acacacatac aaatatgtgt gatacagtat gaatataata taaaaatatg tgttataata     180
taaatataat attaaaatat gtctttatac tagataataa tacttaataa cgttgagtgt     240
ttaactgctc taagcacttt acctgcagga aacagttttt tttttatttt ggtgaaatac     300
aactaacata aatttattta caatttталад catttталад tgtatagttt agtggagtta     360
atatattcaa aatgttgtgc agccgtcacc atcatcagtc ttcataactc ttttcatatt     420
gtaaaattaa aagtttatgc tcatttaaaa atgactccca atttcccccc tcctcaacct     480
ctggaaacta ccattctatt ttctgcctcc gtagttttgc ccactctaag tacctcacat     540
aagtggaatt tgtcttattt gcctgtttgt gaccggctga tttcatttag tataatgtcc     600
tcaagtttta ttcacgttat atagcatatg tcataatttt cttcactttt aagcttgagt     660
aatatttcat cgtatgtatc tcacattttg cttatccatt catctctcag tggacacttg     720
agttgcttct acattttagc tgttgtgaat actgctgcta tgaacatggg tgtataaata     780
tctcaagacc ttttttatcag ttttttaaaa tatatactca gtagtagttt agctggatta     840
tatggtaatt ttattttttaa ttttttgagga actgtcctac ccttttattc aatagtagct     900
ataccaattg acaattggca ttcctaccaa cagggcataa gggttctcaa ttctccacat     960
attccctgat acttgttatt ttcaggtgtt ttttttttttt tttttttttt atgggagcca    1020
tgttaatggg tgtaaggtga tatttcatta tagttttgat ttgcatttcc ctaatgatta    1080
```

```
gtgatgttaa gcatctcttc atgtgcctat tggccatttg tatatcttct ttaaaaatat   1140
atatatactc attcctttgc ccatttttga attatgttta ttttttgtta ttgagtttca   1200
atacttttct ataaaccta ggtattaatc ctttatcaga cttaagattt gcaaatattc    1260
tctttcattc cacaggttgc taattctctc tgttggtaat atcttttgat gctgttgtgt   1320
ccagaattga ttcattcctg tgggttcttg gtctcactga cttcaagaat aaagctgcgg   1380
accctagtgg tgagtgttac acttcttata gatggtgttt ccggagtttg ttccttcaga   1440
tgtgtccaga gtttcttcct tccaatgggt tcatggtctt gctgacttca ggaatgaagc   1500
cgcagacctt cgcagtgagg tttacagctc ttaaaggtgg cgtgtccaga gttgtttgtt   1560 cccctggtg ggttcgtggt cttgctgact tcaggaatga agccgcagac cctcgcagtg    1620
agtgttacag ctcataaagg tagtgcggac acagagtgag ctgcagcaag atttactgtg   1680
aagagcaaaa gaacaaagct tccacagcat agaaggacac cccagcgggt tcctgctgct   1740
ggctcaggtg gccagttatt attcccttat ttgccctgcc cacatcctgc tgattggtcc   1800
attttacaga gtactgattg gtccatttta cagagtgctg attggtgcat ttacaatcct   1860
ttagctagac acagagtgct gattgctgca ttcttacaga gtgctgattg gtgcatttac   1920
agtcctttag ctagatacag aacgctgatt gctgcgtttt ttacagagtg ctgattggtg   1980
catttacaat cctttagcta gacacagtgc tgattggtgg gtttttacag agtgctgatt   2040
ggtgcgtctt tacagagtgc tgattggtgc atttacaatc ctttagctag acacagagtg   2100
ctgattggtg cgtttataat cctctagcta gacagaaaag ttttccaagt ccccacctga   2160
ccgagaagcc ccactggctt cacctctcac tgttatactt tggacatttg tcccccaaa    2220 atctcatgtt gaaatgtaac ccctaatgtt ggaactgagg ccagactgga tgtggctggg   2280
ccatgggga                                                            2289

<210> SEQ ID NO 52
<211> LENGTH: 1184
<212> TYPE: DNA
<213> ORGANISM: Artificial Sequence
<220> FEATURE:
<223> OTHER INFORMATION: sequence of STAR52

<400> SEQUENCE: 52
cttatgccat ctggcggtgc catgtggaac ttcgctgaag aagctaaatt tactgaccat     60
ctgtgcctag agcgggtttc tccaaggaaa ggctctgtaa atctcgtcct tttgaaatct    120
aggggaaaac agcctccttc actgaggatt aatttaaaga aaggggggaaa taggaaaatt   180 ccatgcgttg gaagtccatt tagatttcta catgaaccat catatatgtg cactacataa    240 ttcttattt ttattttta aaaagggat aatttatatt ccagtgacaa gtttgggaaa       300
ggccaaggca agcaattgag ttgaacatta tgtagcgttt atatagacct tgcagacgtc    360
tgtgcaatat ccaccactga acacgtgagg tcgtactcaa gtctctctgg cccctggtaa    420
tgtgactccc ttcctttatt tgcatgaatc gcctggattg ggtgtcaggt ttttaaaacg    480
tcaaggttta cgcctattgt tgtcaaccaa tcagcatcct actttgacgt gattggcttc    540
tactgtaggt gtcaatcatc caaaatttgc atactactcc tcaggccgcc gggagcctgt    600
cagtcggctg tggcagctgg aagagaagga atcggacgga gaagaatgaa aaatcacttt    660
gctttcgcaa agcgaaagaa agtattcttt tcctcatta tttttaaata aatttgattg     720
tatatttacc taataaaata aacattcaat taaacaaaaa taagcaacta tcaaagattt    780
gtttactaat tttcgtaatg tttactgttt caataagtag ccaaaggaat attaaaacac    840
```

```
aaaaatatga atgctgataa ttttatgtca taaagaccat tttaaaacta aaagtgaaca    900
tggggtttct aaataaaatt accgtggtag cgtaaaaaca ctgctttcaa tacttgggca    960
tgctgaaagt gctgcatcct aagataaaaa atacaccaag gggggatttt caaagaacat   1020
tattttgctt ttaataatcc tgtatttctg tcactttgcc cttttattt atttaccgtg   1080 aactcacaga cagaatatta cttggagttt ctgaaatact tgtgtttgta catttctcat   1140
cttacacgta cccacacacc ccaaaataaa aaacaaaga agag                    1184
```

<210> SEQ ID NO 53
<211> LENGTH: 1431
<212> TYPE: DNA
<213> ORGANISM: Artificial Sequence
<220> FEATURE:
<223> OTHER INFORMATION: sequence of STAR53

<400> SEQUENCE: 53

```
ccctgaggaa gatgacgagt aactccgtaa gagaaccttc cactcatccc ccacatccct     60
gcagacgtgc tattctgtta tgatactggt atcccatctg tcacttgctc cccaaatcat    120
tcccttctta caattttcta ctgtacagca ttgaggctga acgatgagag atttcccatg    180
ctctttctac tccctgccct gtatatatcc ggggatcctc cctacccagg atgctgtggg    240
gtcccaaacc ccaagtaagc cctgatatgc gggccacacc tttctctagc ctaggaattg    300
ataacccagg cgaggaagtc actgtggcat gaacagatgg ttcacttcga ggaaccgtgg    360
aaggcgtgtg caggtcctga gatagggcag aatcggagtg tgcagggtct gcaggtcagg    420
aggagttgag attgcgttgc cacgtggtgg gaactcactg ccacttattt ccttctctct    480
tcttgcctca gcctcaggga tacgacacat gcccatgatg agaagcagaa cgtggtgacc    540
tttcacgaac atgggcatgg ctgcggaccc ctcgtcatca ggtgcatagc aagtgaaagc    600
aagtgttcac aacagtgaaa agttgagcgt cattttcctt agtgtgccaa gagttcgatg    660
ttagcgttta cgttgtattt tcttacactg tgtcattctg ttagatacta acattttcat    720
tgatgagcaa gacatactta atgcatattt tggtttgtgt atccatgcac ctaccttaga    780
aaacaagtat tgtcggttac ctctgcatgg aacagcatta ccctcctctc tccccagatg    840
tgactactga gggcagttct gagtgtttaa tttcagattt tttcctctgc atttacacac    900
acacgcacac aaaccacacc acacacacac acacacacac acacacacac acacacacac    960
acacaccaag taccagtata agcatctgcc atctgctttt cccattgcca tgcgtcctgg   1020
tcaagctccc ctcactctgt ttcctggtca gcatgtactc ccctcatccg attcccctgt   1080
agcagtcact gacagttaat aaacctttgc aaacgttccc cagttgtttg ctcgtgccat   1140
tattgtgcac acagctctgt gcacgtgtgt gcatatttct ttaggaaaga ttcttagaag   1200
tggaattgct gtgtcaaagg agtcatttat tcaacaaaac actaatgagt gcgtcctcgt   1260
gctgagcgct gttctaggtg ctggagcgac gtcagggaac aaggcagaca ggagttcctg   1320 accccgttc tagaggagga tgtttccagt tgttgggttt tgtttgtttg tttcttctag   1380
agatggtggt cttgctctgt ccaggctaga gtgcagtggc atgatcatag c            1431
```

<210> SEQ ID NO 54
<211> LENGTH: 975
<212> TYPE: DNA
<213> ORGANISM: Artificial Sequence
<220> FEATURE:
<223> OTHER INFORMATION: sequence of STAR54

```
<400> SEQUENCE: 54
ccataaaagt gtttctaaac tgcagaaaaa tcccccctaca gtcttacagt tcaagaattt      60
tcagcatgaa atgcctggta gattacctga cttttttgc caaaaataag gcacagcagc       120
tctctcctga ctctgacttt ctatagtcct tactgaatta tagtccttac tgaattcatt     180
cttcagtgtt gcagtctgaa ggacacccac attttctctt tgtctttgtc aattctttgt     240
gttgtaaggg caggatgttt aaaagttgaa gtcattgact tgcaaaatga gaaatttcag     300
agggcatttt gttctctaga ccatgtagct tagagcagtg ttcacactga ggttgctgct     360
aatgtttctg cagttcttac caatagtatc atttacccag caacaggata tgatagagga     420
cttcgaaaac cccagaaaat gttttgccat atatccaaag ccctttggga atggaaagg      480 aattgcgggc tcccattttt atatatggat agatagagac caagaaagac caaggcaact     540
ccatgtgctt tacattaata aagtacaaaa tgttaacatg taggaagtct aggcgaagtt     600
tatgtgagaa ttcttttacac taattttgca acatttttaat gcaagtctga aattatgtca     660
aaataagtaa aaatttttac aagttaagca gagaataaca atgattagtc agagaaataa     720
gtagcaaaat cttcttctca gtattgactt ggttgctttt caatctctga ggacacagca     780
gtcttcgctt ccaaatccac aagtcacatc agtgaggaga ctcagctgag actttggcta     840
atgttggggg gtccctcctg tgtctcccca ggcgcagtga gcctgcaggc cgacctcact     900
cgtggcacac aactaaatct ggggagaagc aacccgatgc cagcatgatg cagatatctc     960
agggtatgat cggcc                                                       975

<210> SEQ ID NO 55
<211> LENGTH: 501
<212> TYPE: DNA
<213> ORGANISM: Artificial Sequence
<220> FEATURE:
<223> OTHER INFORMATION: sequence of STAR55

<400> SEQUENCE: 55
cctgaactca tgatccgccc acctcagcct cctgaagtgc tgggattaca ggtgtgagcc      60
accacaccca gccgcaacac actcttgagc aaccaatgtg tcataaaaga aataaaatgg     120
aaatcagaaa gtatcttgag acagacaaaa atggaaacac aacataccaa aatttatggg     180
acacagcaaa agcagtttta ggagggaagt ttatagtgat gaataccttac ctcaaaatca     240 ttagcctgat tggatgacac tacagtgtat aaatgaattg aaaaccacat tgtgccccat     300
acatatatac aatttttatt tgttaattaa aaataaaata aaactttaaa aagaagaaa      360 gagctcaaat aaacaaccta actttatacc tcaaggaaat agaagagcca gctaagccca     420
aagttgacag aaggaaaaaa atattggcag aaagaaatga aacagagact agaaagacaa     480
ttgaagagat cagcaaaact a                                                501

<210> SEQ ID NO 56
<211> LENGTH: 741
<212> TYPE: DNA
<213> ORGANISM: Artificial Sequence
<220> FEATURE:
<223> OTHER INFORMATION: sequence of STAR56

<400> SEQUENCE: 56
acacaggaaa agatcgcaat tgttcagcag agctttgaac cggggatgac ggtctccctc      60 gttgccggc aacatggtgt agcagccagc cagttatttc tctggcgtaa gcaataccag      120
gaaggaagtc ttactgctgt cgccgccgga gaacaggttg ttcctgcctc tgaacttgct     180
```

-continued

```
gccgccatga agcagattaa agaactccag cgcctgctcg gcaagaaaac gatggaaaat      240
gaactcctca agaagccgt tgaatatgga cgggcaaaaa agtggatagc gcacgcgccc       300
ttattgcccg gggatgggga gtaagcttag tcagccgttg tctccgggtg tcgcgtgcgc      360
agttgcacgt cattctcaga cgaaccgatg actggatgga tggccgccgc agtcgtcaca      420
ctgatgatac ggatgtgctt ctccgtatac accatgttat cggagagctg ccaacgtatg      480
gttatcgtcg ggtatgggcg ctgcttcgca gacaggcaga acttgatggt atgcctgcga      540
tcaatgccaa acgtgtttac cggatcatgc gccagaatgc gctgttgctt gagcgaaaac      600
ctgctgtacc gccatcgaaa cgggcacata caggcagagt ggccgtgaaa gaaagcaatc      660
agcgatggtg ctctgacggg ttcgagttct gctgtgataa cggagagaga ctgcgtgtca      720
cgttcgcgct ggactgctgt g                                                741
```

<210> SEQ ID NO 57
<211> LENGTH: 1365
<212> TYPE: DNA
<213> ORGANISM: Artificial Sequence
<220> FEATURE:
<223> OTHER INFORMATION: sequence of STAR57

<400> SEQUENCE: 57

```
tccttctgta aataggcaaa atgtatttta gtttccacca cacatgttct tttctgtagg       60
gcttgtatgt tggaaatttt atccaattat tcaattaaca ctataccaac aatctgctaa      120
ttctggagat gtggcagtga ataaaaagt tatagtttct gattttgtgg agcttggact       180
ttaatgatgg acaaaacaac acattcttaa atatatattt catcaaaatt atagtgggtg      240
aattatttat atgtgcattt acatgtgtat gtatacataa atgggcggtt actggctgca      300
ctgagaatgt acacgtggcg cgaacgaggc tgggcggtca gagaaggcct cccaaggagg      360
tggctttgaa gctgagtggt gcttccacgt gaaaaggctg gaaagggcat tccaagaaaa      420
ggctgaggcc agcgggaaag aggttccagt gcgctctggg aacggaaagc gcacctgcct      480
gaaacgaaaa tgagtgtgct gaaataggac gctagaaagg gaggcagagg ctggcaaaag      540
cgaccgagga ggagctcaaa ggagcgagcg gggaaggccg ctgtggagcc tggaggaagc      600
acttcggaag cgcttctgag cgggtaaggc cgctgggagc atgaactgct gagcaggtgt      660
gtccagaatt cgtgggttct tggtctcact gacttcaaga atgaagaggg accgcggacc      720
ctcgcggtga gtgttacagc tcttaaggtg gcgcgtctgg agtttgttcc ttctgatgtt      780
cggatgtgtt cagagtttct tccttctggt gggttcgtgg tctcgctggc tcaggagtga      840
agctgcagac cttcgcggtg agtgttacag ctcataaaag cagggtggac tcaaagagtg      900
agcagcagca agatttattg caaagaatga agaacaaag cttccacact gtggaagggg      960
accccagcgg gttgccactg ctggctccgc agcctgcttt tattctctta tctgccccca     1020
cccacatcct gctgattggt agagccgaat ggtctgtttt gacggcgctg attggtgcgt     1080
ttacaatccc tgcgctagat acaaaggttc tccacgtccc caccagatta gctagataga     1140
gtctccacac aaaggttctc caaggcccca ccagagtagc tagatacaga gtgttgattg     1200
gtgcattcac aaaccctgag ctagacacag ggtgatgact ggtgtgttta caaaccttgc     1260
ggtagataca gagtatcaat tggcgtattt acaatcactg agctaggcat aaaggttctc     1320
caggtcccca ccagactcag gagcccagct ggcttcaccc agtgg                     1365
```

<210> SEQ ID NO 58

<210> SEQ ID NO 58
<211> LENGTH: 1401
<212> TYPE: DNA
<213> ORGANISM: Artificial Sequence
<220> FEATURE:
<223> OTHER INFORMATION: sequence of STAR58

<400> SEQUENCE: 58

| | | | | | |
|---|---|---|---|---|---|
| aagtttacct | tagccctaaa | ttatttcatt | gtgattggca | ttttaggaaa | tatgtattaa | 60 |
| ggaatgtctc | ttaggagata | aggataacat | atgtctaaga | aaattatatt | gaaatattat | 120 |
| tacatgaact | aaaatgttag | aactgaaaaa | aaattattgt | aactccttcc | agcgtaggca | 180 |
| ggagtatcta | gataccaact | ttaacaactc | aactttaaca | acttcgaacc | aaccagatgg | 240 |
| ctaggagatt | cacctattta | gcatgatatc | ttttattgat | aaaaaaatat | aaaacttcca | 300 |
| ttaaatttt | aagctactac | aatcctatta | aattttaact | taccagtgtt | ctcaatgcta | 360 |
| cataatttaa | aatcattgaa | atcttctgat | tttaactcct | cagtcttgaa | atctacttat | 420 |
| ttttagttac | atatatatcc | aatctactgc | cgctagtaga | agaagcttgg | aatttgagaa | 480 |
| aaaaatcaga | cgttttgtat | attctcatat | tcactaattt | atttttaaa | tgagtttctg | 540 |
| caatgcatca | agcagtggca | aaacaggaga | aaaattaaaa | ttggttgaaa | agatatgtgt | 600 |
| gccaaacaat | cccttgaaat | tgatgaagt | gactaatcct | gagttattgt | ttcaaatgtg | 660 |
| tacctgttta | tacaagggta | tcacctttga | aatctcaaca | ttaaatgaaa | ttttataagc | 720 |
| aatttgttgt | aacatgatta | ttataaaatt | ctgatataac | atttttatt | acctgtttag | 780 |
| agtttaaaga | gagaaaagga | gttaagaata | attcactttt | cattagcatt | gtccgggtgc | 840 |
| aaaaacttct | aacactatct | tcaaatcttt | ttctccattg | ccttctgaac | atacccactt | 900 |
| gggtatctca | ttagcactgc | aaattcaaca | ttttcgattg | ctaattttc | tccctaaata | 960 |
| tttatttgtt | ttctcagctt | tagccaatgt | ttcactattg | accatttgct | caagtatagt | 1020 |
| gacgcttcaa | tgaccttcag | agagctgttt | cagtccttcc | tggactactt | gcatgcttcc | 1080 |
| aacaaaatga | agcactcttg | atgtcagtca | ctcaaataaa | tggaaatggg | cccatttact | 1140 |
| aggaatgtta | acagaataaa | aagatagacg | tgacaccagt | tgcttcagtc | catctccatt | 1200 |
| tacttgctta | aggcctggcc | atatttctca | cagttgatat | ggcgcagggc | acatgtttaa | 1260 |
| atggctgttc | ttgtaggatg | gtttgactgt | tggattcctc | atcttccctc | tccttaggaa | 1320 |
| ggaaggttac | agtagtactg | ttggctcctg | gaatatagat | tcataaagaa | ctaatggagt | 1380 |
| atcatctccc | actgctcttg | t | | | | 1401 |

<210> SEQ ID NO 59
<211> LENGTH: 866
<212> TYPE: DNA
<213> ORGANISM: Artificial Sequence
<220> FEATURE:
<223> OTHER INFORMATION: sequence of STAR59

<400> SEQUENCE: 59

| | | | | | |
|---|---|---|---|---|---|
| gagatcacgc | cactgcactc | cagcctgggg | gacagagcaa | gactccatct | cagaaacaaa | 60 |
| caaacacaca | aagccagtca | aggtgtttaa | ttcgacggtg | tcaggctcag | gtctcttgac | 120 |
| aggatacatc | cagcacccgg | gggaaacgtc | gatgggtggg | gtggaatcta | ttttgtggcc | 180 |
| tcaagggagg | gtttgagagg | tagtcccgca | agcggtgatg | gcctaaggaa | gcccctccgc | 240 |
| ccaagaagcg | atattcattt | ctagcctgta | gccacccaag | agggagaatc | gggctcgcca | 300 |
| cagaccccac | aaccccaac | ccaccccacc | ccaccccctc | ccacctcgtg | aaatgggctc | 360 |
| tcgctccgtc | aggctctagt | cacaccgtgt | ggttttggaa | cctccagcgt | gtgtgcgtgg | 420 |

| | |
|---|---|
| gttgcgtggt gggtggggc cggctgtgga cagaggaggg gataaagcgg cggtgtcccg | 480 |
| cgggtgcccg ggacgtgggg cgtggggcgt gggtggggtg gccagagcct tgggaactcg | 540 |
| tcgcctgtcg ggacgtctcc cctcctggtc ccctctctga cctacgctcc acatcttcgc | 600 |
| cgttcagtgg ggaccttgtg ggtggaagtc accatccctt tggactttag ccgacgaagg | 660 |
| ccgggctccc aagagtctcc ccggaggcgg ggccttgggc aggctcacaa ggatgctgac | 720 |
| ggtgacggtt ggtgacggtg atgtacttcg gaggcctcgg gccaatgcag aggtatccat | 780 |
| ttgacctcgg tgggacaggt cagctttgcg gagtcccgtg cgtccttcca gagactcatc | 840 |
| cagcgctagc aagcatggtc ccgagg | 866 |

<210> SEQ ID NO 60
<211> LENGTH: 2067
<212> TYPE: DNA
<213> ORGANISM: Artificial Sequence
<220> FEATURE:
<223> OTHER INFORMATION: sequence of STAR60
<220> FEATURE:
<221> NAME/KEY: misc_feature
<222> LOCATION: (92)..(1777)
<223> OTHER INFORMATION: All "N" on various positions stand for any
    nucleotide

<400> SEQUENCE: 60

| | |
|---|---|
| agcagtgcag aactggggaa gaagaagagt ccctacacca cttaatactc aaaagtactc | 60 |
| gcaaaaaata acacccctca ccaggtggca tnattactct ccttcattga gaaaattagg | 120 |
| aaactggact tcgtagaagc taattgcttt atccagagcc acctgcatac aaacctgcag | 180 |
| cgccacctgc atacaaacct gtcagccgac cccaaagccc tcagtcgcac caagcctctg | 240 |
| ctgcacaccc tcgtgccttc acactggccg ttccccaagc ctggggcata ctnccccagct | 300 |
| ctgagaaatg tattcatcct tcaaagccct gctcatgtgt cctnntcaac aggaaaatct | 360 |
| cccatgagat gctctgctat ccccatctct cctgccccat agcttaggca nacttctgtg | 420 |
| gtggtgagtc ctgggctgtg ctgtgatgtg ttcgcctgcn atgtntgttc ttccccacaa | 480 |
| tgatgggccc ctgaattctc tatctctagc acctgtgctc agtaaaggct tgggaaacca | 540 |
| ggctcaaagc ctggcccaga tgccaccttt tccagggtgc ttccggggc caccaaccag | 600 |
| agtgcagcct tctcctccac caggaactct tgcagcccca ccctgagca cctgcaccc | 660 |
| attacccatc tttgtttctc cgtgtgatcg tattattaca gaattatata ctgtattctt | 720 |
| aatacagtat ataattgtat aattattctt aatacagtat ataattatac aaatacaaaa | 780 |
| tatgtgttaa tggaccgttt atgttactgg taaagcttta agtcaacagt gggacattag | 840 |
| ttaggttttt ggcgaagtca aaagttatat gtgcattttc aacttcttga ggggtcggta | 900 |
| cntctnaccc ccatgttgtt caanggtcaa ctgtctacac atatcatagc taattcacta | 960 |
| cagaaatgtt agcttgtgtc actagtatct ccccttctca taagcttaat acacatacct | 1020 |
| tgagagagct cttggccatc tctactaatg actgaagttt ttatttatta tagatgtcat | 1080 |
| aataggcata aaactacatt acatcattcg agtgccaatt ttgccacctt gaccctcttt | 1140 |
| tgcaaaacac caacgtcagt acacatatga agaggaaact gcccgagaac tgaagttcct | 1200 |
| gagaccagga gctgcaggcg ttagataaa tatggtgacg agagttacga ggatgacgag | 1260 |
| agtaaatact tcatactcag tacgtgccaa gcactgctat aagcgctctg tatgtgtgaa | 1320 |
| gtcatttaat cctcacagca tcccacggtg taattatttt cattatcccc atgagggaac | 1380 |
| agaaactcag aacggttcaa cacatatgcg agaagtcgca gccggtcagt gagagagcag | 1440 |

-continued

```
gttcccgtcc aagcagtcag accccgagtg cacactctcg accctgtcc agcagactca       1500 ctcgtcataa ggcggggagt gntctgtttc agccagatgc tttatgcatc tcagagtacc       1560
caaaccatga agaatgagg cagtattcan gagcagatgg ngctgggcag taaggctggg       1620
cttcagaata gctggaaagc tcaagtnatg ggacctgcaa gaaaaatcca ttgtttngat       1680
aaatagccaa agtccctagg ctgtaagggg aaggtgtgcc aggtgcaagt ggagctctaa       1740
tgtaaaatcg cacctgagtc tcctggtctt atgagtnctg ggtgtacccc agtgaaaggt       1800
cctgctgcca ccaagtgggc catggttcag ctgtgtaagt gctgagcggc agccggaccg       1860
cttcctctaa cttcacctcc aaaggcacag tgcacctggt tcctccagca ctcagctgcg       1920
aggcccctag ccagggtccc ggccccggc cccggcagc tgctccagct tccttcccca       1980
cagcattcag gatggtctgc gttcatgtag acctttgttt tcagtctgtg ctccgaggtc       2040
actggcagca ctagccccgg ctcctgt                                           2067
```

<210> SEQ ID NO 61
<211> LENGTH: 1470
<212> TYPE: DNA
<213> ORGANISM: Artificial Sequence
<220> FEATURE:
<223> OTHER INFORMATION: sequence of STAR61
<220> FEATURE:
<221> NAME/KEY: misc_feature
<222> LOCATION: (130)..(976)
<223> OTHER INFORMATION: "N" stands for any nucleotide on various positions

<400> SEQUENCE: 61

```
cagcccccac atgcccagcc ctgtgctcag ctctgcagcg gggcatggtg ggcagagaca         60
cagaggccaa ggccctgctt cggggacggt gggcctggga tgagcatggc cttggccttc        120
gccgagagtn ctcttgtgaa ggaggggtca ggaggggctg ctgcagctgg ggaggagggc        180
gatggcactg tggcangaag tgaantagtg tgggtgcctn gcaccccagg cacggccagc        240
ctggggtatg gacccggggc cntctgttct agagcaggaa ggtatggtga ggacctcaaa        300
aggacagcca ctggagagct ccaggcagag gnacttgaga ggccctgggg ccatcctgtc        360
tcttttctgg gtctgtgtgc tctgggcctg ggcccttcct ctgctccccc gggcttggag        420
agggctggcc ttgcctcgtg caaaggacca ctctagactg gtaccaagtc tggcccatgg        480
cctcctgtgg gtgcaggcct gtgcgggtga cctgagagcc agggctggca ggtcagagtc        540
aggagaggga tggcagtgga tgccctgtgc aggatctgcc taatcatggt gaggctggag        600
gaatccaaag tggcatgca ctctgcactc atttctttat tcatgtgtgc ccatcccaac        660
aagcagggag cctggccagg agggcccctg ggagaaggca ctgatgggct gtgttccatt        720
taggaaggat ggacggttgt gagacgggta agtcagaacg ggctgcccac ctcggccgag        780
agggccccgt ggtgggttgg caccatctgg gcctggagag ctgctcagga ggctctctag        840
ggctgggtga ccaggnctgg ggtacagtag ccatgggagc aggtgcttac ctggggctgt        900
ccctgagcag gggctgcatt gggtgctctg tgagcacaca cttctctatt cacctgagtc        960
ccnctgagtg atgagnacac ccttgttttg cagatgaatc tgagcatgga gatgttaagt       1020
ggcttgcctg agccacacag cagatggatg tgtagctgg gacctgaggg caggcagtcc       1080
cagcccgagg acttcccaag gttgtggcaa actctgacag catgacccca gggaacaccc       1140
atctcagctc tggtcagaca ctgcggagtt gtgttgtaac ccacacagct ggagacagcc       1200
accctagccc cacccttatc ctctcccaaa ggaacctgcc cttccccttc attttcctct       1260
```

-continued

| | |
|---|---|
| tactgcattg agggaccaca cagtgtggca gaaggaacat gggttcagga cccagatgga | 1320 |
| cttgcttcac agtgcagccc tcctgtcctc ttgcagagtg cgtcttccac tgtgaagttg | 1380 |
| ggacagtcac accaactcaa tactgctggg cccgtcacac ggtgggcagg caacggatgg | 1440 |
| cagtcactgg ctgtgggtct gcagaggtgg | 1470 |

<210> SEQ ID NO 62
<211> LENGTH: 1011
<212> TYPE: DNA
<213> ORGANISM: Artificial Sequence
<220> FEATURE:
<223> OTHER INFORMATION: sequence of STAR62

<400> SEQUENCE: 62

| | |
|---|---|
| agtgtcaaat agatctacac aaaacaagat aatgtctgcc cattttttcca aagataatgt | 60 |
| ggtgaagtgg gtagagagaa atgcatccat tctccccacc caacctctgc taaattgtcc | 120 |
| atgtcacagt actgagacca gggggcttat tcccagcggg cagaatgtgc accaagcacc | 180 |
| tcttgtctca atttgcagtc taggccctgc tatttgatgg tgtgaaggct tgcacctggc | 240 |
| atggaaggtc cgttttgtac ttcttgcttt agcagttcaa agagcaggga gagctgcgag | 300 |
| ggcctctgca gcttcagatg gatgtggtca gcttgttgga ggcgccttct gtggtccatt | 360 |
| atctccagcc cccctgcggt gttgctgttt gcttggcttg tctggctctc catgccttgt | 420 |
| tggctccaaa atgtcatcat gctgcacccc aggaagaatg tgcaggccca tctcttttat | 480 |
| gtgctttggg ctattttgat tccccgttgg gtatattccc taggtaagac ccagaagaca | 540 |
| caggaggtag ttgctttggg agagtttgga cctatgggta tgaggtaata gacacagtat | 600 |
| cttctctttc atttggtgag actgttagct ctggccgcgg actgaattcc acacagctca | 660 |
| cttgggaaaa ctttattcca aaacatagtc acattgaaca ttgtggagaa tgagggacag | 720 |
| agaagaggcc ctagatttgt acatctgggt gttatgtcta taaatagaat gctttggtgg | 780 |
| tcaactagac ttgttcatgt tgacatttag tcttgccttt tcggtggtga tttaaaaatt | 840 |
| atgtatatct tgtttggaat atagtggagc tatggtgtgg cattttcatc tggcttttg | 900 |
| tttagctcag cccgtcctgt tatgggcagc cttgaagctc agtagctaat gaagaggtat | 960 |
| cctcactccc tccagagagc ggtcccctca cggctcattg agagtttgtc a | 1011 |

<210> SEQ ID NO 63
<211> LENGTH: 1410
<212> TYPE: DNA
<213> ORGANISM: Artificial Sequence
<220> FEATURE:
<223> OTHER INFORMATION: sequence of STAR63

<400> SEQUENCE: 63

| | |
|---|---|
| gcgtctgagc cgctgggaac ccatgagccc cgtccatgga gttgaggaag ggggttcgcc | 60 |
| ccacggggtg ggcgccctct acacagcgcg cttcctcttc tctcgttagc gccgcgggac | 120 |
| cagcctctgg ttctgcacct cgcgctctgg gagcagcgcc cggctttggc gagcgcttcc | 180 |
| ccggggctgc ccagcctctg ctccgctcgc cccgccaggc ccggctccgc gaagccccca | 240 |
| gggtccagtc caaggccccg attccccaag gccagggccc cggggcagca ttggaacagg | 300 |
| gcgcggacgc cagtcctccg agcatggagt aactgcagct tttgagaaaa gaaagcggac | 360 |
| cccaccccat cgagaacgcg gcgccttgtt tagggacgtt cctgggccgt cacggagtgt | 420 |
| cgccggctcc tcggcccctc cctcctccaa gcccccaccc ccgacagcgg cctccctggg | 480 |

```
gacctcccct cgggctgcgc tttcagccca aacacaggga ggtcttccag gagcctgccc      540
agtccccaca gcagcccaga gacccccact cccacctgta cctgccaagc cttcagagag      600
ggcggcctgg acatgccccg cacgggagga gccccgcctc agcacccctg caagtggcag      660
caacccagaa cacccgtgag aggcctctga gcagcccagg aagtggctgg aagacgcata      720
ggcagctcac tcctctgtaa gagcaaggac cggagaacac atgctgaccc ctgcttttgc      780
agaggggcga tgcttcagga caggcgcgct cagcaggtgt ccatcttatt tcacacccttt    840 gtgtttatat catcttattt tgcattttat gtctaattaa caatatgcag ctggccaggc      900
gcagtggctc aagcctctaa tcccagcact ttgggaggcc gaggcaggtg tatcacttga      960
gggcaggagt tcgggaccgg cctgggcaac atagcaaaac cccattgcta ataaaaatac     1020
aaaaattagc cagccatggt ggcgggcacc tgcagtccca gctactccgg aagctgaagc     1080
aggagaatca cttgaaccca ggaggcggag gtggcagtga gctatcaagc cattacactc     1140
cagcctgggc aacagagaaa gactgtctca aaaaaaaatt aatacgcagc agaatattat     1200
gtggtcagcc caagcagtcc cccccactca gccctctgtc cctacagctc caggcactcc     1260
cccagcccct ccctggaca agaggtaatg cccagagggt gaaaatccac caaggttaag      1320
ccagaaacaa aaagctcaaa gcttcggcat ctccctccgc tcagacccctt agagcagatt    1380 cctctcatcg acagcacgat caggctgtgg                                       1410

<210> SEQ ID NO 64
<211> LENGTH: 1414
<212> TYPE: DNA
<213> ORGANISM: Artificial Sequence
<220> FEATURE:
<223> OTHER INFORMATION: sequence of STAR64

<400> SEQUENCE: 64
agagatcttt taagggctca aaagaccctg cggctcccct gccaatagct ctgccatcgt       60
ccccagagct ttcgaggacc ctccaccatc ggcgccaacc ccagctgagc tgggtgctcg      120
tctgcaggcc tctgctccat ctcagcctga gcatgaggcc ctgctgtgct gcttccagca      180
gcagggacag ggctgatgag cctggccctt gcaagcatct tcctgtgccg aatacaattc      240
cacagacaga ggatttaaaa tccaagtgga ggtgacagga agaaaggaa acctccagg        300 tatcagaaga aggaggggg tgtgaagaca gtatgggagg aaggtcaggc tggggctcag      360
ctctgggaag tgccagcctg aacaggagtc acgcccgggt ccacatgcaa gggaatgagg     420
accgaggccc tgcatgtggc agggccttcc gcaggctgcc ccgtctgtga acaggacacc     480
agaagaagtc tgccttccag cctggcaaag tggcaaggaa cctctgggtg gaaaacaaa      540 tcaacaaaca aattgtcagt aaaaaacaga aactcacac tttcctttct cttgacctct      600 tgaaaaagc aaatccactg cagctcacca aaggcaaaga gaaacctta gaatacccca      660 gagagaaaag acacgttact tgcaaaagaa catctaatgc agggagataa tgaaaataca      720
gactcttcaa agggctgaag gaaaaaaacc gtccacctag aattctatcc ccaaactgtc     780
atctgagagc aagggcaaaa caaacgcttt tcagacagg ctggacgagg tcgctcacgc      840
ctgtaatcct agcactttgg gaggccaagg tgggaggacc gctttaagcc agaagtttga      900
gaccagtgtg ggtaacataa tgagaccccca tctctaagaa aaagaaatta aataagacaa     960 gacttttttca gacaacaagt gctctgagag ctggcctatc ttggctgtct tgtaaagaat    1020
tgctgcgaga cacctcatta ggaaagagac tgaatctaga aggaaagagc agagcatgag    1080
gtacaatgag gagcaaataa acaggtcacc atataagcaa acccaaatac acattcacta    1140
```

```
tacgaaacaa taaaaatgac tcatttgggg ggttaaaaca ctgttgaact aaaatcctgg      1200
ataacagcag catgaaaggt ggggtggtgg tcccaggaaa gcattcaaag gtccatgtct      1260
catttgggag gagggtaggg agactcatga acttgaggct cccttcaggc aagcacagtg      1320
caaaaaaatt ataataatgg gaaacagata cagtagactg tgatgtacaa ctctcagagc      1380
agtagaaggg agggtataaa acaaatctga tcca                                 1414

<210> SEQ ID NO 65
<211> LENGTH: 1310
<212> TYPE: DNA
<213> ORGANISM: Artificial Sequence
<220> FEATURE:
<223> OTHER INFORMATION: sequence of STAR65

<400> SEQUENCE: 65
tcgagaccag cctggccaac atggtgaaac attgtctcta ttacaaatac aaaaattagc       60
caggtgtagt ggtgcatgcc tgcagtccca gccatttggg aggctgaagt tggagaatcg      120
cttaaacctg ggaggtggag gttgcattga gccgagaagc actccagcct ggatgacgga      180
gcaagactgt ctcaaaaaga aaaaaaaaag aagcagcagc aaatatccct gtcctgatgg      240
aggctatata acaaccaaac aagtgaatgc ataagacaat ttcaaggtta tggtagatac      300
cataagtggg agatgaacaa tgagaacaca tggacacagg gaggagaaca tcacacactg      360
gggcctctcg gggggtgggg aaatagggggg tgatagcatt aggagaaata cctaatgtcg      420
ataacaggtt agtgggtgca gcaaaccacc atggcacgtg tatatctatg taacacacct      480
gcacgttctg cacatgtatc ccagaactta agtataata aaaaaagaca ttaaaaaatt      540
atgatataaa atcccaattc aagttgtttt aaaaagagaa aacaattatc tttatataat      600
agcggaaaat atagatggcg gaattaaagc ctcgtcatat tttctaacag aactttctga      660
taaacttgat taaataaaaa ttttaaatat cactaaacac atagaagaaa taaatttaaa      720
ccttcacaaa aaataaagta caatgaatga agacaaggtg tacttgaaaa aagaactgaa      780
taaatattct acatataaaa aaaatctgat gatattgtgg tgattcttta ctttgctact      840
agtttctctt ttttcttct gaaaaatttc ttgggatgta tttggtttca ttagtaaaat      900
tctaagtttc tttgcaatct gaacattgga gcttcatcca tagccagtat gccctaacat      960
tatctttgga caactgtaaa attagaacac tgccagacat atttaatgta tgatgtatat     1020
caacactggg acacatttta tactatcttt attccaaaat caaatgattc actgtggttt     1080
ataaatgtac atggatatat ctctacctaa gcagatagtt aggagagtta gtaaaaatga     1140
ggtggaaaat aggagtcact gtcccttcac agggagagaa ttctgctttt ctcctaatat     1200 acccttgct tgaacagact ccaacccctc atcttttgtc ctttaaatga ccacatttat     1260
tttaactttg ataaacaaca cagaaagata tttgatccat caacattcac               1310

<210> SEQ ID NO 66
<211> LENGTH: 2500
<212> TYPE: DNA
<213> ORGANISM: Artificial Sequence
<220> FEATURE:
<223> OTHER INFORMATION: sequence of T2F (STAR66F)

<400> SEQUENCE: 66
gcaggttgga tggtgctgac ccctcctcgg gttggcttcc tgtctccagg tggacgtcct       60
gtactccagg gtctgcaagc ctaaaaggag ggacccagga cccaccacag acccgctgga      120
```

-continued

```
ccccaagggc cagggagcga ttctggccct ggcgggtgac ctggcctacc agaccctccc    180
gctcagggcc ctggatgtgg acagcggccc cctggaaaac gtgtatgaga gcatccggga    240
gctgggggac cctgctggca ggagcagcac gtgcggggct gggacgcccc ctgcttccag    300
ctgccccagc ctagggaggg gctggagacc cctccctgcc tccctgccct gaacactcaa    360
ggacctgtgc tccttcctcc agagtgaggc ccgtccccg ccccgcccg cctcacagct      420
gacagcgcca gtcccaggtc cccgggctgc cagcccgtga ggtccgtgag gtcctggccg    480
ctctgacagc cgcggcctcc ccgggctcca gagaaggccc gcgtctaaat aaagcgccag    540
cgcaggatga aagcggccag cctcgcagcc tgctcttctt gaaagctggg cgggttgggg    600
cggggggctt ctctggaagg cttggagctg tccctctgg ccttggggga ctggctgccc    660
ccggggcgcc cggcctagc cgaggcggtg ctcctgccgg ccagactctc ggtcagtgcg     720
ggcacggggt cccagccact cctagggggc agcgcagccg caggctggc cgccccgggg    780
tgggacttgg accctggact ccacgggagg gctccgccac ccagcctggt gttacataag    840
gggtggtgga ggtgggcagt cgagcgttaa agagtaacct gctgccggga agcccgccaa    900
gcaatcgcgg ccccttcccc ggctctggca gtctgcgag cgcgcccgtg gggaacgggc     960
cctccccggc ggggcgcgcg ggcgcgcgag gtgggcggag gcctcggagc tgtgccgggc   1020
cgggcctccc tccctaggcc agcgcgggag cgacccggag ggggcgggcc cggggcgggg   1080
cctcgaagcg ctggccggcg ggagcgcggc cggccgggcc cgcccgcctg cggtgtggac   1140
gccgcgcggc caatgcgcgc gccgggacgg gacgggacgg ggcggggcgg ggcgggacga   1200
gacggggcgg ggcggggcgg gccgggcagc ctccgggcgg cgcggcgcgg gcggcggccg   1260
gatccagggc ggggtcggc ggcccggcca gccggccg gccgggcc gcgtcctgag        1320
agtcagccct cgccgctgca gcctcggcgc ccggccggcc ggccatggag cgccccccgc   1380
cccgcgccgc cggccgggac cccagtgcgc tgcgggccga ggcgccgtgg ctgcgcgcgg   1440
agggtccggg gccgcgcgcc gcgcccgtga cggtgcccac gccgccgcag gtaccgggcg   1500
ccggtgggcg gggcgccga ccaagtttct ctcgctgcaa agatggcgtc agtgctgccc    1560
aaacttcggg ccccggggg cggggcagcg gggagggcgg ccgcgtcggt ccgcgcgtgt    1620
ccgtgggtcc cgccggggct gcgccgggcg gccgggagc ccttcccgcc gcgccgggct    1680
ggggggcgggg ccggggcgg ggccgcgccg tccacaccgg ccgcagccgg ttttcgaggc   1740
gggcgccgag cggatccgcg gcggaggttg agggaccccc ctcccccggc caccgcctcc   1800
gctgagtctg cccctcccc atccgcaggg ctcttccgtg ggcggcggct tcgcgggctt    1860
ggagttcgcg cggccgcagg agtcggagcc gcgggcctcg gacctggggg ccccccggac   1920
gtggacgggg gcggcggcgg ggccccggac tccgtcggcg cacatccccg tcccagcgca   1980
gaggtgagcg ggaggcccgg tgcctcggga ctcggtgtgc gcaggggcgg tgggtggggt   2040
gcggagacac cggcccgac ggaggccagg tcagggcccc aggtttgtaa ttaccagcca    2100
ccccaagct cttcagccct ggaggagctg agcagaaatg atcgatgact gggagtccct    2160
acacctccct ccaccgcagt tcctcggggc tagagctcag aacccggagc gggtggctgt   2220
gcgtctctgt gcagaagagg ctgcgcggtc ggcatggggc gactgtccag gaatccctgg   2280
ggctcctgac cgccacctcc caaccctgc caggccggac acctcggtct ggctgccagg    2340
gcaggggcgg gccctggcct ggctcgctgg ggcctgggga gctgccgtg cttccagccc    2400
agtctccccc tggctgctgc cggctgctgg ccactcccac ctcccaggcc tggcgtgagg   2460
cccacagctg ctgttgcaca accctggtta atgtgtgatg                         2500
```

<210> SEQ ID NO 67
<211> LENGTH: 2500
<212> TYPE: DNA
<213> ORGANISM: Artificial Sequence
<220> FEATURE:
<223> OTHER INFORMATION: sequence of T2R (STAR66R)

<400> SEQUENCE: 67

```
gtttggggta gagagaacat actgattatg ggactttgct ttgcagctta gtgctgtcct      60
gtcagtggga agcaacaggg ggcagaactc agcttgtgcc catagaggga atgtttatac     120
taggcctgtc cagaggcaaa tcatccatcc tagcaattgg aacctgactt ttggcaagtc     180
ctgccaccat gggctaaagt gttctggggt tctaaataaa catgaaaggc aacctagacc     240
acaaggactg caattcctgc acaagtcctg gtgctgtgtt gggcttggag ccagggaact     300
tggagtgcat ggaacctagt gagataccag ctgagacaac caaggaagtg cttgtgtcac     360
ccctccacca accccaggca gtacagattg tacctccaag acccccttcca tctgcttgag     420
gaaggtggag gggaagagga cttttgttttg caacttggat tccagcccat ccacagtaga     480
ataaggcaac gggcagactc ctaaggcccc catcccagac cctagctcct ggatgacatt     540
tctaaacaca ccatgggcca aagggaacc cattgccttg aagggaaggg cccagtcctg     600
gcagaattta tcatgtgctg aataaacagc ccttgggccc tgaataatta gtattggtag     660
ccaggcagta tttaccacag gccttgggtg agacccagag ccatgttggc ttcaggtgtg     720
acccagcaca ttcccagctg tggtaacttt ggggagagac cacttctgct tgagaaaagg     780
agacagaaga gtaaaggggt ctttatcttg cagcctggta ccagcttggc cgcagtgggg     840
tagagcacca agagagcacc tgggataaac aaaatcaaaa aacctttagc tagactaaga     900
gtaaagagag aagacccaag taaatataat caaagacaaa aaggagaga cattacaacc     960
aatacctcag aaattcaaag tatcattagc agctactttg aacaactata tgccagtaaa    1020
ttggaaaacc tagaagaatt atataaattc ctaacatata caacctacca agattgaacc    1080
atgaagaaat ttaaagcctg aataggccaa taacaagcaa tgagattgga gccctaatac    1140
aaagtttaca atgagaaaca ttgctcaaac aaatcataga tgacacaaac aaatggaaaa    1200
catccaatgc tcatggacag gaaaaaatat ttaaatttct atactgccca aagcagttta    1260
tacattcaat gctattcctg tcaaaatacc aatcttattc ttcacaaaaa aaaaattaaa    1320
aattacacag aaccaaaaaa gagcccaaat acccaaggca atttaagca aaaagaacaa    1380
agctggaggc atcacgttac ctgtgatcca cactataggg ctacagtaaa tgaaacagca    1440
aggtgctggt atacaaacag acacataaac caatggaata gaataaagag cttagaaata    1500
atgctccaca cctccagcca tccgatgttt gagaaagtag acataaacaa gcaatgagga    1560
gaggactccc tattcattaa atcaactcaa gacggaccaa aaacctaaat gtaaacaaaa    1620
caaacaaaaa aaataactgc taaaaccctg ggagatgacc taggaaatac cattctggac    1680
agtacctggt gaaaatttca tgctgaagac accaaaaaca attgcagcaa aagaaaaaat    1740
tgacatatgg gatcaaatta aactttagag cttttgcaca gcaaaataaa ctatcaacag    1800
agtaaatagg caccctacag gaagggagaa aatattttca atctgtgctc tgacaaagtc    1860
ctaatatcca gagcctataa ggaacttaaa caaatttaca aacaaaaaac aaacaacact    1920
attacgagtt ggaaaaggac atgaatcgac acttttcaaa agaagacata catgtggcta    1980
acaagcatat gaaaaaatg ctcaacatta ctaatcatta gagaaatgca aatcaaaacc    2040
```

```
acaatgagat accatctcaa ccagtctgaa tggctgttat taaaaaaatc agaaaaaaac   2100
agatgctggc aaggttgtgg agaaaaggaa acacttatac attgttgggg ggagtgtaaa   2160
ttaattcagc cattgtggaa agtattgtgg tgattttcta aagaactaaa aaggaattac   2220
tattttacct ggaaatttca ttattgggta tatacccaaa gaaatatgaa ttattttact   2280
ataaagacag atgcatgcat gtgttcattg tagcactatt cacagtagca aagacatgtt   2340
atcaacctaa atgcccatta acagtaaact ggataaggaa aatatggtac atatacactg   2400
tggaatacta tgcagtcata aaaagaatga gataatgttc attgcagcaa catggatgga   2460
actggagacc attatccttg ggaaactaac aaagcaacag                        2500
```

<210> SEQ ID NO 68
<211> LENGTH: 2501
<212> TYPE: DNA
<213> ORGANISM: Artificial Sequence
<220> FEATURE:
<223> OTHER INFORMATION: sequence of T3F

<400> SEQUENCE: 68

```
agatttgccc tcaagattac aactgctggg gctaaagtgg tacagagcct gagttcagta     60
ggcttccata gtctcactca agaatgcaag tttacctctc aatctttcaa tcatcacaat    120
tataacaact ttaaaagag ccaacatgat atttgcttat cacttttcta ctcacattcc     180
agtattaact caaagtgtc aacacaacct tcgtgataaa tactattaac gtcatcattc     240
ctactgtaca gatgatgata gtgacacata ggttaagttg cccaaggtct tattattaag    300
ggtcatagcc aggatttgat ctcttcagta aagttctagt caatgctctt aaccattaag    360
ccatgcaaca cacccagagc caactgggtt gtgttgatga ttataatatt tgttttaaca    420
aacaataatt tttcctaaat ataatataga ttttccataa ataccataaa ttcttgatta    480
tttatttcac tttattccaa aaggaagttg aattctgaga tttaaatgaa tagcaaacaa    540
cagttgctta atttcactac ttttgtcact tgtagccagt acttaaaaag agatacataa    600 tttattttg ttgatttgca tttcacatat aattgtaaga tcctggagaa taaagactat    660
atgtgttata ccattttact ctctcacaca gtgtgtaggc ctaggctttg tgcatagcaa    720
gtgttaaaaa gtaatgtgac tcgtgatagt tattagattt attgaaattc agaaatttag    780
ggaaatgcac aataaaatgt acattttgtg attccggtca aattacttaa aaattatatt    840
tttcctatga ataattttta tttcacttaa attatgtata acaaaataac atgcataatt    900
aaacatttac cacaaagaaa atatttgtac tattgttatc acaataaaga acttgctaca    960
taaattcaat tacacttttg tggaaagtat cttcattata taaaaacaat ctacatttag   1020
aataggaaaa ttgtacaaaa catgaaaata taaacaaatt aagcgagaat tatctaaaaa   1080
gcaactcttc agaatttaga agaattgtct agaataaaaa gaatttagaa gaattatcta   1140
agaaacaacc ataaatattc tgatgtattt aagactcata ttctagaatc ctgactatta   1200
ttttttatac ttctatggct aatctcaagt ttagctttat ttttctaaag caatgaggcc   1260
tgtagaatat ttttttcagaa ttctctgagg tttttttcttt tttgtctttc ctgtcatagt   1320
atgccaatta ttcatgggtt tatagaatat gtatgcactg ctaagagcag caaaacaaaa   1380
gatatatgtg ctatttatta attcatgttg ctttatttaa attacttgaa aatgataaag   1440
aaaaaactat tgtatttaca acagcaacca aatatagact acctgtaact acatctaaca   1500
gaataaataa aatataacat acaatatgta gtaaatatat ttataatata tatgttcact   1560
aaatagttaa cctgtaactt acttacagta aatatatata atatctactg agatagtacc   1620
```

-continued

| | |
|---|---|
| acatttatt aaggattaaa cttttaataa ttcagaagaa taaatataat aaatttcatt | 1680 |
| tgttctcaaa ctaatttgtt tttatttgtt tgttttttgt attttaattt gacagtagtt | 1740 |
| ccaagatatt tgggtata taatgagtg ataattgcaa agaaaattct gaaaggaaa | 1800 |
| agactaagcg tgaattgaaa gtaaaattcg ttaaaggta taataaactg tgatactgta | 1860 |
| acaataattg aaaatagata aagaaaaagg taacatcaat aaatagtcta ttatatatgt | 1920 |
| gaattatgtt aataaaagtg acattttatt ttcaatccac aatttctgaa atatatatgg | 1980 |
| caatatttt ctgttttat ttttcaacct ctgattactt tattcatttt ttttcttttt | 2040 |
| ctagaattta cttgtatttt ctctgtgtct aatatatgat tattctgaa ctagcatcat | 2100 |
| tggtcctgga accagactat attattccca aggtagagca tcaaatata acaattaaat | 2160 |
| aaatactttt agttacttta caacctttt gtctttcatt ataattttgg aattatagtt | 2220 |
| tagtacaata cagatagttt taatatctgt tagagtgaag atatatatat atgtgtgtgt | 2280 |
| gttttgaga tggagtctca ctctgttgcc caggctggag tacagtggtg ccatctcggc | 2340 |
| tcacggcaac ctctgcgtcc caggttcaag caattctcct gcctcagcct cccgggtagc | 2400 |
| tgggactaca ggcgagtgtc accacgcctg gctaatttt tgtatttta gtagagacag | 2460 |
| ggtttcacca tattagccag gatggtctcg gtctcctgac t | 2501 |

<210> SEQ ID NO 69
<211> LENGTH: 2511
<212> TYPE: DNA
<213> ORGANISM: Artificial Sequence
<220> FEATURE:
<223> OTHER INFORMATION: sequence of T3R

<400> SEQUENCE: 69

| | |
|---|---|
| cttttggtgc cctgtccctt ataatttcct cgtgtgtcct ttcccatttg cttatccgat | 60 |
| gacttgcttc tctcacccat tggattgtga gcctcttgtg gtcaggggca gtgctctgta | 120 |
| agctgctgtg tccccagaat ctggcccagt gtaggcactc agcagctata gactgatgtt | 180 |
| aagagaaaat gcacatttca tctcagcctc agagcagttc tgggaaacag ataggaaacc | 240 |
| aaagctctgc aagaacgtgg gactctctca gggccatcac aacactgttg ttggtctcat | 300 |
| gtttggtgac tgggtctcct attcctggtc tctttcctag gcataatgct tttatataaa | 360 |
| gtcccttcca ttgttttttt gtttgttttc ttttttcagc ctaaataact tagtttctct | 420 |
| aaactttct cccagggact cttttttaac cctttgaatt attgctgatt attatcttaa | 480 |
| taacttttat ttttttttcca ttttgcatgt catattttag caaagcatta aaggaacac | 540 |
| ggcacaaagc acacccatat ttttggatgc tgtggatttc atcatgctgc ttattccatt | 600 |
| atatctagtc agtacctcca aggcattaat gctgccttac ctccttcatt cgaagacttc | 660 |
| cctgtgcaag gtggaatata cgtaaggagg caaacagact gggttatatg cctgctctgc | 720 |
| tttacagagg cctcttccag gagtgtaata cggggggttgc tcatactctg aagaagatag | 780 |
| tggcaggcta ttactgtcat gagagccaga acgtggctgg cttcttacag acatggcttc | 840 |
| ataggggcat gccacgtgat tcctgagtaa gccttctggt gtgaattccc tgctcactgg | 900 |
| ggtgattctt cacttcccac agttcaacct gctgtattat cctcttacct atgcttttct | 960 |
| gtgatccata gaggtaattt aattttcagt ccatgtacct accctgccta cttagttttct | 1020 |
| tctcagtgcc acacttaatt ccttcacatt tactgattaa ttaaatgaga agactatgcc | 1080 |
| aggtgaaggt tcagcatctt cagaactcta catgatgcat tccctgaggc tgccttttcaa | 1140 |

-continued

```
taactgaggt gatattcttt gagcagtgtg acctgttaga ggtgcccagt caggtccgat     1200
gaaaagccct ctgatttgtt gaaatagtgc attagtaaag tattatagtt tattttcaca     1260
aagctagatt agttgttaca tgttggtttt tgttttgcct agccctaaca agtatggagg     1320
tgaccttgat gtgtctatag aatatcagga atatctggct gggtgggtgg ctcacacctg     1380
taatcccaac aatttgggag gccgaggtgg gcggatcacc tgaggtcagg agtttgagag     1440
aggcctggcc aacatggtga accccgtctc tactaaaaa tacaaaaatt agccaggtgt     1500
ggtggcaggt gcctgcaatc tcagctactc cggaggctga tgcagggaa tcacttgaac     1560 ccgggaggta gaggttgcag tgagccaaga ttgtgccact gcactccagc ctgggcaaca     1620
gagcgagatt ctgcctcaaa aaaaaaaaa aaaaaaaa aaaaaaaga atatcaggaa     1680 tatccatttt atgtctcaac tcacatacct cacagttttc tggtccaatt tttaggcact     1740
ttatcaggcc ctcatatgtt ttcaaaaata attgctaatg actttgatga agctaggcaa     1800
gatatttttt ggtttaggg cagtttgggc tatagtttgc agccttccta ctttaataga     1860
agaattttta aactagattc tcccccttct cagggtggct ttctgccttt ccattctagt     1920
gcttcacaca gaaatgacaa gctcacaggg gacttatcta gaaaggccg agataaaaat     1980 aagtacaatg ttaaaaaaat ctatcttata gtatcattta tttagagctt cctctccttt     2040
tctaatgaaa ggctgctgta gtttcctttt gtgctttttt tgctgaaggc ttttcagtaa     2100
tattcccgtg tgtcccctgt gatgctaaaa gcatgagctt gggggcaggt tgactggcat     2160
tcaggtcttt gctcagcctc cagccgcaag acaaggcgaa taatattgat ctcatggagc     2220
tgaaatgaaa attaactttt ctaatctgtg aaaatgcttt gttataatcc ttaaatacat     2280
gaatacatag gttgaaatag caagtaccaa gtgctgacat tatgtccaca attgccacat     2340
gccatgtcct tatgattttt gccagatgtt taataagatt ataaatgaat aggttattaa     2400
atgggcatct cctactctct aggtgttct gtttctgctt ctctgttttc tgtttgtatc     2460
tccatttatt ttaatgccta ccattatgtg aagtctgcca ccttcctata c     2511
```

<210> SEQ ID NO 70
<211> LENGTH: 1500
<212> TYPE: DNA
<213> ORGANISM: Artificial Sequence
<220> FEATURE:
<223> OTHER INFORMATION: sequence of T5F

<400> SEQUENCE: 70

```
gaactcaata ggggtcttgt acggagcagg ggcttggtcc ctcgtacctc tggccatacc       60
tatggagccc aggggatgct tggcagcacc tgggaggtgc caaccccggg tggcaaggga      120
gggccggtcc cacgctcaca ttgtcttctg ttctctctct ctctttatct gtgtcgatgt      180
ctctctctct tccccgtgc ccgtgccatc ctctccaccc ctggattcct gtctctgctt      240
ggctttcacc cacttctcct ccccacccac ggctgctcct cctcctgtcc ccacctcctc      300
cccgggtgca ggacgggcct cttcacacct gacctcgctt tgaagccac agtgaaaaag      360 caggtgcaga agctcaaaga gcccagtatc aagtgtgtgg atatggtagt cagtgagctc      420
acagccacca tcagaaagtg tagcgaaaag gtatgacggc cgcctgggcg gggctgggcc      480
tggccgtcca ttccttgtgg ccacagcctc ccgtgggcag aaggatctgc tgagccggcc      540
tcacggctac ccgcagggac ccagccctag tgtttcctgc cagtttctaa ccctgggtac      600
ttgcactcat gaccccctcca ggcccccatc ccagaagact tgactccaac ccaagcctcc      660
ttggtggcac ctatgctagt gatgaagatg atgttaagga gatggcagct gtttactgag      720
```

-continued

| | |
|---|---|
| cacctactat gtgccaagca cacgctaagt gcttgcccct actatctgac tcagtcctct | 780 |
| caaccaccct aagacgtggg tagtgttgtt attcccattt tgcagatggc aaaacagagt | 840 |
| ctcagaaaag agaagcagag tgtgattcag ttttaggaag gacagaggaa ggggtctgag | 900 |
| gtcagggcct cctgggcagg gggagctgtc ctagttcctc aaaaccaatt tgcctgaaag | 960 |
| catattggat tactcacttt acagtaatcc gtgcgtgaga gacaggggcg gtctcttttg | 1020 |
| agttgtctgt gacttttag atgccttttt cctatttgtc tgcttttggg cattttgagg | 1080 |
| atttttagcc aggttgtcta aagcagttct tcccagggga gtgcgagaga atcagttgcc | 1140 |
| tgcaggagct tctccagcag gctaaatcag aggtgccagg ggtgagccca gcctcaccta | 1200 |
| tatctgaagg acttccctat gctggtgggt ggaggcacat ccaccttagc attgagtttc | 1260 |
| aaataagcat caatcatctc cattcctttt tttttttttt tttttttttg agatggaatc | 1320 |
| ttgctctgtc gcccaggctg gagtgcagtg gcaccatctt ggctcactgc aacctctgcc | 1380 |
| tcctgggttc aagtattctc ctgcctcagc ctcccgggtg gctgggatta ctagcatgta | 1440 |
| ccaccacacc tggctaattt ttgtattttt agtagagatg gggttttgcc acgttggcca | 1500 |

<210> SEQ ID NO 71
<211> LENGTH: 1500
<212> TYPE: DNA
<213> ORGANISM: Artificial Sequence
<220> FEATURE:
<223> OTHER INFORMATION: sequence of T5R

<400> SEQUENCE: 71

| | |
|---|---|
| gattacaggc gtgagccacc acacctggcc cagtggggtc cttctaaaat gcaaagctga | 60 |
| tcatgtctct tcttccaggc ttaaagcccc cccatggctt cctgcagccc tggtgcacgc | 120 |
| cttacgccaa gcctgaaaac actctgcaca cccaccccctt ccctgcacaa acgggcctct | 180 |
| gcacactacc tgccccggcc atgccccgc aaccagccct ctctgcttat ctaccttggc | 240 |
| cttctctctg gtcaagcccc aggcccgtcc ctgcccctag gccttcactt agagcctcag | 300 |
| aagcacttct tgcaggaagc cctccagact ccagaatggg tccagaacct acttcctttt | 360 |
| cgtggcattt ctgtattctt ttttttttc ttccatagag ccagggtctc actgtgtttc | 420 |
| ctaggctagt ctcgaactcc tgggctcaac tgatcctcct gccttggcct tccatagtgc | 480 |
| tgggattaca ggcatgagtc attgcacccg gcctccacag tcttaattaa ttggttggag | 540 |
| cattatttgc attaatatct ctcaccaccc tccccattcc tgtccaagac tcagggagg | 600 |
| gccaggccag atgtatcatc tgcaccaggg agtcccctgc aggggcttcc agatgtctgc | 660 |
| taaatgaaca cacagctctc tctggccagt ccaaggcacc ccaggaggcc accagaagcc | 720 |
| tgcagcctcc ctccctccct cctgctaagc ccaaggaatg agcactgagc agggaatggt | 780 |
| aatctggaca catccatact ctgcccttca gaaactacct agctgtcacc ctgcacgaaa | 840 |
| caggcaccag cctgagagtc aggaggcctg ggctctgggt ccacctagac agctgtgggg | 900 |
| cgcaggacca accgcacccc aatctctaag cctgggtttt tccatacgta aaaaaatgag | 960 |
| ggcagggcgg gttagacact agaccagatc tgtgatgaca ggcccgttgg aaggctggag | 1020 |
| gcggggcccc tcgctgaagg aaaatgcctt acctccagaa gtggcccgcc ctggagtggc | 1080 |
| cagcaaaggg ggcattgccc ctgcgctgga atacacccag aagcagggtg tgagcaggag | 1140 |
| ctgcggagac cttcagggac aggacagtct agggaggggg tgagcccttt gcagatctcc | 1200 |
| tgcttatgcc aggagaaagg taaacacctc tcaaacacac aaggagccag ggggctgtgg | 1260 |

```
gctggaacct atagccggca acagcgtata gcttaggatt ttatagcatt gttctaccct   1320
agttatgttt cctatacttt tgtttgtttg tttgtttgtt tgtttgtttg tttgaaatgg   1380
agtctcactc tgtcgcccag gctggagtgc aatggcacga tcttggctca ctgcagcctc   1440
tgtcttccag gttcaagtga ttctcctact tcagccttcc tgagtagctg gaattacagg   1500
```

<210> SEQ ID NO 72
<211> LENGTH: 1199
<212> TYPE: DNA
<213> ORGANISM: Artificial Sequence
<220> FEATURE:
<223> OTHER INFORMATION: sequence of T7

<400> SEQUENCE: 72

```
ccatcttata aatatatcat aatttactga aaaatatttc agtaatgttg aaaggcctct     60
gtgccatttc cagcttgagg ctattcctaa aaatccttgc acatgtcttt cagtgcacac    120
atgtatacat ttcggttggg tatgcctagg agtggaatga ctggttatag ggtacactta    180
cgttgagctt tggtagatac taccaactgc cagttttcca aagttgtacc aatttacatt    240
cctaccacca gtacatgagg gttccagatg ctgaacgtcc tcactaatgc ttggtaatgt    300 ctgcctttt catttagtc attctggagg tagtgtgata atatctcatc gtggttattt    360
gctttagcct gatgattaac gatcctgacc attttttgga acatttggag atcatctttt    420
gtgaagtaac tactcaaata ttttgcccat tttgctactg ggttgttcaa aagattcatt    480
aaaagaactt cttttatata tgggtttgta gttgttatt agatattcta gagactagcc    540
agatccctat actacaaata cttctctccta ctttgtagtt tgccttttta ctttctttta    600
tatacatata atttttcccc ctccaaaaga cagggtcttg ctctgttgcc caggctggag    660
tgtagtggtg caatcatagc tcactgcagc cttgaactcc taagctcaag caatcctcct    720
tcctcagact ctggagtagt tggaacaata ggcacatggc attatgcgca gtcaacttta    780
aaaaaaaaaa aaattgtaga gatgaggtct tactatgttg ttgcccaggc tgatctttaa    840
ctcctggtct aaagcaatcc tcctgcctca gcctccctcc caagtagcta agaatacagg    900
tgtgcaccac cacatctagc tttactttct taatggcgtc ttttaatgaa cagataattc    960
ctaagtttga tgtagtcaaa tcatcatttt ttcctttata gtcagcattt atatccagtt   1020
caagtaaaga atatcatgaa aacattcttc tttgttttct tttagaaact ttcataaagt   1080
agcatttaaa atgtgaattt tcctataatc ctagcacttc aggaggctgt gccaccgcac   1140
tctagcctgg gcaacagagc gagaccttgt ctcaaaataa aaattaaaaa aaaaaaat    1199
```

<210> SEQ ID NO 73
<211> LENGTH: 1602
<212> TYPE: DNA
<213> ORGANISM: Artificial Sequence
<220> FEATURE:
<223> OTHER INFORMATION: sequence of T9F

<400> SEQUENCE: 73

```
tgagcatctc tgaactattg cgccatgtat ttccaatttt catattgtgt atttgtatat     60
tttatatgta atagtatagg tgtaatatgt aaatatattt tatatgtatt taaaatcttt    120
atattttgaa gggttttgtt tcaactatta cttgttaatt tcacagtccc tttctttgat    180
gttagcaaat agtaccttca tgaacctcag aggacttgga tctgaatgtg caatgccctc    240
tagtatttca aataatagtt cagttggtat agtatttttt taatctgcaa aaacaatac    300 ttgctaatat agctatgtta gagtaaacaa taaatcgaga ataaatttat agcctttgaa    360
```

-continued

| | |
|---|---|
| acaaaacaaa ccaaaaattt tactcctttt tggctttcat ccctgcactg gtatcttaac | 420 |
| ttctgtttgt ataaaagaat accattttt cacagaagac aaagaacaat cagccaatct | 480 |
| aataattatt ttatggccat gctctgaaat acaattaaaa ttatgattgt ggacaatatg | 540 |
| cctttcggg acctggctga tggtatttct ggtgtgaccc caactttcca gtcagttcag | 600 |
| ggcaataaac attggataca ggacagcttt ggggatgaaa tagaattaaa tttagtgtag | 660 |
| tttttgccac ttttagctgg atgcctggcg aggggttttg tgccctctga gagcctccgt | 720 |
| cttctcaact gaggggtggt tgtgagtttt gggtcaaatg cttggtgttt agtagatgct | 780 |
| tggagcttcc atgaaacatg caaccacggc gttgctgcta tttgttcaga tgcgagagga | 840 |
| acatgacttt tggctgcctg agtgttctca tagcatctgg gccttccttg tgagatcgtc | 900 |
| agaaagtgtt tcctgcacaa agcctgtact gcggccctgg cgtgggctg attgtcccgc | 960 |
| tactctgctg tgatggctga attcaaagag tggccgatag gagcacgtat ggtgggtgcc | 1020 |
| ttgttaacag ctcatagcag aaacgtgaca agcgggagag ggctttgggt tgtcctgaac | 1080 |
| ttcaaacacc tgtaactgct gcgggaagag cggcacgtgg atgaaacgga cacagagggg | 1140 |
| gaataggcag gaaaggacgc gggctctttt cgaagcagca ggtctcaagg cggccagcca | 1200 |
| ctggcgcagc tgcagctgaa gccacggcag agtctccatc cttcccacta tctgctgaat | 1260 |
| cagagaaagt ggcaggcaac attttagtg ccttaaattt agaacgcttg ctcaaaatca | 1320 |
| gaccctactt aaaataagga gcgatacccct catttcttaa atagtaaaaa tgccctcagc | 1380 |
| agaattaacg ggagtatctt ccaacttcat atcctgaatg gaaagtctg tccaccatcc | 1440 |
| cgaggacgtg tttgaagcgc agtgtgaaaa tccagcacgt cgtggaccgg ccagacccct | 1500 |
| gtgccgtgag aggcggggcg gcggggccgt ggggcgctcg cactcccgag ctcatcgtgg | 1560 |
| catgcgctga gccgaaaacc acgaggtaga gggaatgaga tc | 1602 |

<210> SEQ ID NO 74
<211> LENGTH: 1602
<212> TYPE: DNA
<213> ORGANISM: Artificial Sequence
<220> FEATURE:
<223> OTHER INFORMATION: sequence of T9R

<400> SEQUENCE: 74

| | |
|---|---|
| gagcttgatt gtctggccgc gaaaacaggg caggcccgtg tccaacatga tagtgaccag | 60 |
| ggagacgacc acatccatgt agggcctggg gagagacagg agggagcggt gggctgaggc | 120 |
| cagcctaggt ggtggccctg cctgtagtcc tgtggactgg ctgatgccaa cagcctcagg | 180 |
| tgtgggctcc tgccacccac ctcgcctgcc acatcttgca catccccgag gcaactttcg | 240 |
| atctgctgca ctcggtcacc cgtactgccc aggcaagggc tgcccatacg cactctggac | 300 |
| aggctgagtg tcctgccctg tcccccacat aaggctgccg gccatggctt ctgcacctgg | 360 |
| gtgggatgca gacacgctga cctgcctttc tctgcggggc agtggggatg aacccaggtt | 420 |
| ggactgtggc cttggccaag tgacctgtat atgaaactgg gacaaagccc atctttggca | 480 |
| cgtagcctgt ggggtggcag gtgctcaggc tttggtgaca aggtggatgg gatgcccaga | 540 |
| aagggagagc ccatggctga aggcgtgggc aggattgtgg ggaaggtggt tggaattaga | 600 |
| tgcccagagc aagaatttat tggcacaggt gggcagacag aggtgaccaa aggacaggtg | 660 |
| taggtcagca ggtggctgct agcacctacc tcactctctg gaaccgatt cccttcatcc | 720 |
| taaaggggat ctcagaacgt tccacacacc ccctccgcct ccaccctggc cctcacccag | 780 |

-continued

```
gctcaccgca cagccaggta gcctggacac acatctccat gaaccacttg aagggtgtgg      840
cctccatctt gccccccatg atcatcacca tctcatccgt cagcttgatg tcgggttccc      900
agccgagatt gccgcccggc gagctttcaa acatgaagcc aaagtctgca aaaccccaaa      960
gagctgcctg tgactgggta ggagccaggg cgggcaagga cgagtggtct gttttgagga     1020
gtggaaaagg actcttcaac aggagcaccc cctccacccc caaaaggcag gttgtgtttt     1080
cttggagaca gtgatggggt gggtggtggg gcagcaggca gagaaagaga agggaggaag     1140
tggaggaagg agccaagctg gggcactgaa cctggaccag ccccactccg cccagctcca     1200
gcttctgact cagagcaatg gcggctctcg ccccagctcc ctggggccgg ggccaggcac     1260
cctctacagc agaacagctt ggtggccgac agttcggacc tcagagctgg accctgacac     1320
tcctggcagg gtggtcctgg gcattctcct ctctgtgggg tggggatccc tatccacccc     1380
tgggtgccgg ggtgaaggga gaggagggtg gcgctgtggc tggctgaccg atgtggatga     1440
tatgcccctt cttgtccagc ataatgttgc cgttgtgtct gtccttgatc tgcagcagga     1500
acagcaggag gctgtaggcg ccatgcttc ggatgaagtt gtagcgggcc tgtgcagaga     1560
gcgccctggg ctcaaaaagg ccctggggcc tgtgggcatt ct                       1602
```

<210> SEQ ID NO 75
<211> LENGTH: 1301
<212> TYPE: DNA
<213> ORGANISM: Artificial Sequence
<220> FEATURE:
<223> OTHER INFORMATION: sequence of T10F

<400> SEQUENCE: 75

```
aatcaaactg gacccttatc ttccaccata tacaaaaatt aatgcaaggt ggattaaaga       60
tttaattgta aggcctcaaa ctataaaatc ttaaaggaa acctaggaaa taccatctgg      120
acatcagcct tgggacataa tttataacta agtcctcaaa agcaattgca acaaaaaaca      180
aaaactgaca agtgagacct aattaaacta aagaacttt gcacagcaaa agaaactatc      240
aacagaataa acagcaacc tacagaatgg gagaaaatac ttgcaaacta tgcatccaac      300
aaaggtttaa tatccagaat ccataaggca cttaaacaac tcaacaaaca aaaaacaaat      360
aacttcattt aaaaaagac atgaacagac acttctcaaa agaagacata caagtagaca      420
aaaaacatag gaaaaaata cttaccatca ctaatcatca gaaaaatgca aatctaaacc      480
ataatgagat atcatctcac accagtccaa atggccatta taaaaagac aaaaaacaac      540 agaagctggc aaggctgtgg agaaaaagga acacttatac acttttggtg ggaaagtaaa      600
ttagttcagc cactgtggaa agcagtttgg agatttctca aagaactaaa aatagaacta      660
ccatatgacc caacaattcc attactggtt agatacccag aggaaaataa attgttctac      720
aaaaaagaca tgtgcacttg tatgttcatt gcagcactat tcacaatagc aaagacatga      780
aatcaaccta ggtgcctgtc agcagtgaat tggataaaga aatgtggta catatacacc      840 atggaatact acacagccat aatagaagaa tgaaatcatg ttctttgcag caacatggat      900
ccagctggag gccatcatcc taagcgaatt aacagaggaa caaaaaacca ataccacat      960 gtcctcactt gcaaatgaga ggtatatata gacataaaca tgggaacaat ggacactggg     1020
gactcctgga ggagggaaag aagtggcagg caaaggttg aaaaactact tattgggtac     1080
tatactcact acctgggtaa tccgctagta gggatcattt gttccccaaa cctcagtatc     1140
acataatata cccatgtaac aaacctgcac atgtaccccc gaatctaaaa taaaagttgc     1200
aattattaaa ataaaataaa aataaagcta gcaatgagcc ctatacatga aaatcaataa     1260
```

<210> SEQ ID NO 76
<211> LENGTH: 1300
<212> TYPE: DNA
<213> ORGANISM: Artificial Sequence
<220> FEATURE:
<223> OTHER INFORMATION: sequence of T10R

<400> SEQUENCE: 76

```
aacataatca tggctgtata gaggggcttg tcatttatag c                 1301
```

<210> SEQ ID NO 76
<211> LENGTH: 1300
<212> TYPE: DNA
<213> ORGANISM: Artificial Sequence
<220> FEATURE:
<223> OTHER INFORMATION: sequence of T10R

<400> SEQUENCE: 76

```
aattttacac acacacacac acacacacac acacacacac acaatatcgc tcagccttaa    60
aaacatgcta ctaatcggct ttaagaaaag aagaaaattc tgtcatttct gacaccatgg   120
aagaacttca acattacgtt aggtgaacta attcaggtac agaagaatac tacagtatct   180
cacttatata tggaatgtaa aaatgttgaa ctcaaaagta gagaatggaa tggtggttac   240
caggccttga gagagagggg taaaggttgg tcaaaagatg caaaatttca gttaagagga   300
aggagtacaa gagatttatt gtacatcatg gtgactataa ttgataacaa tgtgcttttt   360
tcttgacaat tgctaagagt agaatttgtt tatgggcacc aagcttgatt ccaagtcttt   420
gctattgtga atagtgctgc catgaacatg caaatgcgtg tgtcttttgg gtagaatgat   480
ttgttttctt ttggatatat acccactaat gggattgctg ggtcaaatgg tagttctaag   540
ttctttgaga atctacaaa ctgctttctg tggtggccaa actaatttac actcccatta    600
actgtgtcta agtgttccct tttctccatg tcctcaccag catctgttgt tttttttgact  660
ttttaataat agccattctg actggtgtaa ggaggtatgc cattgtggtt tgatttgcat   720
ttctctgatt agtaaaatga agcatttttt gtatgtttgt cagccatgta tatgtcttct   780
tttgagaaat atctgttcat ttattttgcc cacttttaaa tgaggttatt tggttttgct   840
tgttcaattg tttaaattct ttatcgatgc tgtatattag acctttgttg aatgtgtagt   900
tttgagaata ttttctctcc ttctgtaggt tgtctgttta ctcttttgat agtttatttt   960
gctgtgcaga aactctttag tttaattggg cctcatttgt caattttttgc tttcgttgta  1020
cttgcttttg gtgacattgt cacaaattct ttcctaaggt caatgttcaa aatggtgttt  1080
cctaggtctt cttctaaaag tcttatagtt tgagggttta catttaaatc tttaatctat  1140
cttaagttaa tatttgtata tggtgagaga aaggggtcca gtttaattct tttgcatatg  1200
actagccagc tatcccagca ctatttatta aatagggagt actttcctca ttgcttattt  1260
ttgtcgactt tgttcaagat cagatggctg taggtgtgtg                        1300
```

<210> SEQ ID NO 77
<211> LENGTH: 2001
<212> TYPE: DNA
<213> ORGANISM: Artificial Sequence
<220> FEATURE:
<223> OTHER INFORMATION: sequence of T11F

<400> SEQUENCE: 77

```
tctttggggt atgattatat gtctaggtaa aactcttta agaagatgaa gcagagagga     60
ttgaattgac aaagacagct ctttaaaaat taaggttatt tcaagactaa gaacataact   120
gcttaattgc aggtaataac agaaaaaact tggaaataaa catcccatta tttgacctcc   180
aaggcagaag actggcacca aggaaatggc agcttcgtcc ctttcctgtc ttgggcattg   240
gtaaaaggag ttgtctagac atgtttgatt tctgtttcag cccttattag tagttatgcc   300
atggcaaatt attcaatttc tctgactcag tttccttatt cagaaaatgg aagcataatt   360
```

```
cttgcctcat agggccatga agattaaatg aggggtgtct tgaagtgtct gggacataaa    420
tcttcaataa aagctaattc cttttttta cagttatctc aaaccttta gtgaattggt     480 gcttatcagt gagctttta ggtgatgcaa agaccctgct ttgctcattt taaggaacag    540 ttattttct ttctccattt tgaagtttct tgtttgctgc ctggttgata tggtttggct    600
gtgtccccac ccatatctca tcttgaattg tagttcccat aatccccaca tgtcatggga   660
gggacctggt gggaggtaat tgaaccatgg gggtggttac cctcatgctg ttcttgtgat   720
agtgagtgag ttctcacaag agctgatggt tttataaggg gcttccccct tcgcttggca   780
ctcattctct ctcctgttac cctgtgaaga ggtgtctcct gccgtgattg taagtttccc   840
gaggcctccc ggccatgtga aactgtgagt caattaaacc tctttctttt ataaattacc   900
aagtcttggg tattccttca aagcagcatg agaacagact aatacattgg tttaaattag   960
aatgccaaaa tttaaataat tttatcttg aatagtagat ggaattaact ttctcttgaa   1020
agatatattt taaaaaattg aacttacaca gacagttttg aaatggtctt attttagttt   1080
tatttattta tttatttga acagagtct cacagtgtcg cccaggctgg agtgcaatgg    1140
cacaatctcg gctcactgca acctccacct ccagggtcaa gcgattctct tgcctcagct   1200
tcctgagtag ctgggattat aggcgcccac caccatgccc agctaatttt tgtgttttta   1260
gtagagacgg ggtttcacca tgttggccag gctggtctcg aactcctgac atcgtgattc   1320
tcccacctcg gcctcccaaa gtctcaggat tacaggcatg aaccaccgcg cctggctgaa   1380
attgttttta ttatagatgt tgcttgtgca gttttgttag aagttcgtga cttttaacag   1440
tgatgaaaat acttcgtcat tcaacaggtt attttctgc tggttgtagg ttatttgtaa    1500
ggaactgtta gtctcctatc tgggtggaca tgtaatagta tcagttactg aaccagaact   1560
ttaaacacct ttctgatact cacactggga ggtcaccaag tatctcagaa taaaatgtcc   1620
caaactgaac ctaccatgtt cccagaaacc cagcccttct caaattccca gacttggtga   1680
atgggagcct gtccttgcag tcttgtagcc caaaacctag ggcttaagaa caccttcttc   1740
cttactccca tatgcaaccc atcaagttcc atgcatttca tctcctaatc tcaaatccct   1800
tcacccatct ccacagccac cccgctagtc cgggctgcca ttgtctctca cttaaaatgt   1860
tgttattgtc taactgacct tcctgaaccc tttcttgcct ctttccagtt tattttccac   1920
actacagcca gaaaaagctt ttcaaaatac gcatctggtc acctgcatac ctgtctccag   1980
accacataca ataagccttc a                                            2001

<210> SEQ ID NO 78
<211> LENGTH: 2001
<212> TYPE: DNA
<213> ORGANISM: Artificial Sequence
<220> FEATURE:
<223> OTHER INFORMATION: sequence of T11R

<400> SEQUENCE: 78
tctgccagcg gctcccgcgc caggtcctcg aagcgcacca ggcggtagcg gccgcgcagg     60
aagggtggcg gcttgagtgt ggcggcctcg gcgatgcgca cgtggctgcg gcacacctcg    120
cgaatcaggc gcaggtgagg gtcggcctcc acccacttgc cgttggtgcc cagcacgatg    180
ccgttgtcgc gtgccagtat cgggcccgcc gcctcccggg agcgcagcac ggcccgcggg    240
tcgcgcacca ggtgcacgat gcgcaggttg agcgcggggt cgctgagcag cgggtagagc    300
acctgcaggt tgaagaagcg cacctccttg agcaccacgt ggctgtagga gcggcaggcc    360
tcccgggcca ggctgaatgg ctgccgcgtg cacagtgtct tgcatacgtc ctgcttgctg    420
```

```
atggtgcctc ggggaaaggc gctgcaggcg ggcggcgagc acagcgcgcg gctcgttgcc      480
cagttgaaaa aggcggacag gtttcggctc tgtggcatgt aggcatcaaa cacgtccatg      540
tcgcacaaaa agatagagcg catcaggtcg cgcacggcca tgtgcagcgt tgccgcgctg      600
ccctgcgaca gggtggtcca cacatgccac gcgggctcca tcaggtagaa gacgtcgggg      660
tgctggctga agagctggcc caagaaggat gagcccgagc gccacgagga cagcaccagc      720
acgtgcacac gatcctcgcc gccggctggg gatgagggcc ctggccggga gatgatgaag      780
agcaggaggc aggtggtctg tgccaggagg agcactgtca ctgtcttgct ggagaaccgt      840
ggcagccaca tgcgggcggc tgggggcctt cgggtggagt gggcaacttt agggacccgg      900
gccctcatgc ccatcccatg ccccaattac tgcccagtgc cctcagggat cagccctcag      960
attcggctac cctacccatt ggacttccca agactcccaa ggtctcagtc gagcactttc     1020
ccaggaatac ggagtcaaga cataggccag aatatagtct gtgctcacag cagaagtcca     1080
gttgcagaat aatgtgggat atcatcaaac tgtctaccta cccacccacc cacctactta     1140
catacctaca ggctatctat ctgtagagag aaatactatg tttcaaagag aactcctgtc     1200
ttttgcttca ggatacctct tagagagacc cttttaggtt gtggagctaa aagggcttga     1260
tgggggcttc ggtggatgtc agagcaccac caggctcgcc gaggttgaat cctggctctg     1320
ccacttccta gcctatgatc ttgcttatga agatcactta aatctctctg tgacggatca     1380
ctttacccgt gtgtgaaaga gggataattc cggtacctgg ctcacaggat ctgggggat      1440 tggggggtta ttataatgaa gatgggggaa gggaacacgc agtcatgccc ataactgagg     1500
attgcacctt ttacaaggtg tgcttctgta ttatataatt ttttttaacag gcaggtataa     1560 aactttgtc agccaggcgc ggtggctcac gcctgtaatc ccagcattat gggaggccga     1620
ggcgggcgga tcacgaggtc aggagatcga gaccatcctg gctaacacag tgagaccca      1680 tctctactaa aaatacaaaa aattagccag gcgtgatggt gggcgcctgt agtcccagct     1740
actcgggagg ctgaggcagg agaatggcgt gaacctggga ggcagaggtg gcagtgagct     1800
gagattgcgc cactgcactg cagcctgagt gaagagtgag actccgtttc aaaaaaaaa     1860 aaaaaaacaa caaaaaaaaa acttttgtca ttaaagataa acaagtaaat aaagtggaca     1920
aagaacagca actgttgtca tcactggtgg ggagtgaagt gctgtaggca gcatgggctc     1980
cagaaggagg gtgtcctgga g                                                2001
```

<210> SEQ ID NO 79
<211> LENGTH: 2100
<212> TYPE: DNA
<213> ORGANISM: Artificial Sequence
<220> FEATURE:
<223> OTHER INFORMATION: sequence of T12

<400> SEQUENCE: 79

```
tggcatccag catggagccc acagcttccc tttgtagaat tgcccagttg ttgcagagtg       60
ctttggtctc aatgggtcta aagctcttga tgatataaga gcttcaactt ccttttccct      120
ctcctccccg caggctgcac aatgtcctgg tgaatcacct gggacttcag agctctgcca      180
ccctgggtgt gaagctcagg tctgctcttg gtagcttggt cagtgtgaag tacaccgtga      240
ttttgggcaa gctgcttaac ctccctggcc ctccgttttcc tcatctgtag aatggggata     300
ttcacagaac ctacttgtag ggccatggtg aggattaaat gatgaacagt gctggcaaac      360
aggaaatgct atataagtgt ccctagcaat atacacaccg cacatcctca gtcaccacgt      420
```

```
gtgttcactg aggtatgggc catgtgtggg tggaattgtg ttccctaaaa agatatgttg      480
atgtgctaac ttgaggtccc tgtgaatgca ggaaaccaaa atatttcttc tcaaaatagt      540
gaggattgtt aagttaaaga cactgaaaat gcagggaac actgccttgg cctctacttg       600
cctgatgaca ggcacgaatc cttccttact taagacacat cacttgctta tcagcccaga     660
gaaagcacct gcaggcacca ggaaaatcta ggaacagatt ttactctctt cccacatttt     720
cccacttttt caaacactga aactgctctc tcctttgtct tgtcactaga taggatttat     780
ggctctttgt taaaatattg tttaagcaag gcttctacgc cactagcttg agagagaaat     840
acttttgaac tgaggcctct tccgcatgat aggcagagca tgcattaata catttctgct     900
tgtttctctt ttgttaatct gacttttgtt ttccagagtg tctcaaataa gaacataaaa     960
gggaggggag aaattatagt ttctccccta catgaactta ttcggatata gggtctttgc    1020
agatgtaatc aagttaagat gaagtcatat ttgattagga taggccctaa ttaaatatgg    1080
ttgctgtctt tataaaatga gaagaagaga ccaggtgtgg tggctcacac ctataatccc    1140
agaactttgg gatgccaagg caggaggatt gcttgaggcc aggagtttga gactagcctg    1200
ggcaacacag caagactcca tctccaaaaa aattaaaaat tagctgggca tggtggcatg    1260
cacctgtagc cccagctact tggtgggctg aggcaggagg atcaattgat cccaagagtt    1320
caaagctgca gtgagctatg atggcaccac ggcaacctgg gtgacagagc gagaccctgt    1380
ctcttaaaga agaaaaaaag aggagaaaaa aacagagaca cagaaaaaag tccttgggat    1440
gataaatgca gaaattggag ccatatatcc acaagacaag gaaccaccag gattcttggg    1500
aactccagaa gctaagaaga gggcatggaa caggttctac cctagggcct tcagagggag    1560
cgcagccctg cagacaccct gagttcagac ttctggcctc cagaactgcg aaagaataac    1620
tttctgttgt tacagcagcc ctaaggcact agtacaggtg acatgtattg ctcttctgaa    1680
gagcagggtg tctacagcgg cagaggtctg ggtcctggca cgtgcccttt aggattccaa    1740
tatccttagg ggcctgctgg tgctgacagt tccagaacca taagacagaa ttcctgcggg    1800
ccagtttgga agcagagaca ggaaactgga agagccctta gcctgtgctt gggcttaaag    1860
ccctttagct tgtggcttta actctgaaac ttctagaggg catcttgcag gtcagtgtga    1920
ggtacagaag ttgtcacaag cttcctggct caaagaaagt gagacttcac gaacttttct    1980
ggacatcaca ccagcactta tgaagttatc ttgttaagca cagatgaaat cagaaataca    2040
ggcattcacc atcacttaaa caaagctcag attgtagagt gcgaggaaga atcggtggga    2100
```

<210> SEQ ID NO 80
<211> LENGTH: 1700
<212> TYPE: DNA
<213> ORGANISM: Artificial Sequence
<220> FEATURE:
<223> OTHER INFORMATION: sequence of T13F

<400> SEQUENCE: 80

```
cagatctcta aagtattggg tgtggactag agctctggac ggcctaaagg aaaggaatgt       60
gccggttcac agggacccgc ggctaagctc aagggtaaaa tacagcttta caaagcatct     120
ttaggctgtt ccttcccaaa cgtgcttaga agggaacagg gaaaggcggg tgtgttttct     180
cactgaggtt cttctagtgg ctggaatctg atagagtacc aagttgtagg gatatggata     240 tatttttccct ttggcactcc ataaagctaa atgttgggct gaaaaaagga tgcagcctat     300
aaacaagtat ttttcctgaa accaactgca tgaggaaacg ctgcgctccc cctcagggag    360
cagtttctga agccagctga gcacagctgg cactggccag agggagccct ccacccctccc   420
```

```
accacgtatg cccacctgca aacctgggtt ctgagtcccc atgcagggga cagacctgaa      480
aattccagtt tgtgtccttt caggtcatcg acaggaatga cagcctggca agctgcagtg      540
actgcacaca gctaccctgt gagctccact tgtgtgggtg caggtgggcg acaggagtgt      600
gtgacacaga caggcactcc accaggagga aacccacagc agacgtcaac catcgcttta      660
ttaaggctgc gagtcggggg gctgagtcat gcactccaca gacacccca ctgctcccaa       720 ggtccacttt tggatgaccc tgaaggcaga gactcctgag atctgggcca caatctaggg      780
tgagccaccc acagtgccct gctggacagg ggggtatgcg gactgcacgg ggggccctc       840 agcagggtc ttcctgccta gggtggggct ggctccagtg ggtcctgggc tcaggcaggg      900
ggggtggcag ggaggcaggg acatccccc gccctctggc ctatggcttt gttgccctat       960
tgccaccagc gcagaagcaa tgtgctatac cgtgaggtga tgaagaagag ccccggggagg     1020 gagcaggcag ctctgtgcct ggggcctggc cagacctcag gggtgctgtg ccctgctcc       1080 tgttcccct cagctcctcc cagcaatggg tctcctccag tggaggtcag tcactcagaa       1140
gtggacccgc agcacgtctt ggctagcaac cggccgctgg caggctgtgc acgtcatggg      1200
cagggagcgt tgcttctcac ccaggcaggg tcggcacagg aggtggccgc agggcagctg      1260
gtacaccggc tccttttga agtagggaga aaatactctt ttgcaggagg cacattcggg       1320
gcccaggatg ctcccaggct gctctggtaa atcaggaagg aaaacaggcc agggttagga      1380
aagctgctcc atggtccagg ctgctctgag gggcagagcc ttcccaccgt gctgctgcag      1440
catctggctt catccctccc gagtccatcc cagtctgatc aggtagggga gtggaagcgg      1500
gagagggagc ctgggaaccc gggaggcctc ttctctatca tctttgacca aatctcagtg      1560
cctctacgaa tgcttgagaa gagctggctt ctgagggcag caggcaggac tgggcccttc      1620
ctcctggtct cccagcaagg tttactttcc cctgcgatag gtggccaagg ctggagcaag      1680
gcacagctca ctctgacaag                                                  1700
```

<210> SEQ ID NO 81
<211> LENGTH: 1701
<212> TYPE: DNA
<213> ORGANISM: Artificial Sequence
<220> FEATURE:
<223> OTHER INFORMATION: sequence of T13R

<400> SEQUENCE: 81

```
gaatctgacc actcagtccc acatcccagg attcagagaa aaagaattcc agtgagggct      60
ctggacccca cacagctaag gcttccaggg tttaggcaag ccctgaggga cacccatcat      120
aattacccag acgggggccc agcatcccgc cccagcattc tgccttgcaa ggagctccct      180
caccagggct cagggaaggg acagcctgca gttccagcaa gggaggcctg cagagtcagc      240
cacaggtggc cactatcggt tgcttggtgc caacttagtg tgaggggggca gggcccagac     300 tcgagggtgc cattaccgtc ccccatcgtg tacttctttt cctcgtagct tgagtctgtg      360
tattccagga gcaggcggat ggaatgggcc agctgggaga gatggcccac agctcgggtc      420
agagatggag ggtccctgac tttgtgacga ctctgcacaa ggggagcccc atctcctcct      480
ctcgttcctg cctcacccgc cccaccccg cacgccagc cacacgcaca gacagcggca      540
agcacagacc ccgctgtcag ggacagccct gaagaggaac cgtccctaga gcccgtcctg      600
cagctgctcc acacttcccc gccccacgc accccgtcc caccgccag cggaccctgg       660 ctcacccgc ggatgttcca gtaccccagt gtcatgggca tggtgctggt tgctgtggat       720
```

| | |
|---|---|
| tctgcagaca ggcctcagcg gggcggggct cagcgtttgt gagaggccca gagagggtag | 780 |
| aggggaagcc ttgctgcgac cccgccccac ggcccgccct gcccccgaaa cgggccaatc | 840 |
| tggaggcctg gagcgcgctc atggggctag gagtaggatc tcctcccacc tcccagcccc | 900 |
| gtgggtttca ggagagagat caggacgccc agaagcccag ggcgggggag aactggttga | 960 |
| gtccaggggt tcaagactga actgagctat gatcgcgccg ctgcactcta ggttaggcaa | 1020 |
| gaaagaaagg ctctctctaa aacagagaga ttctgaataa agtaataata gcctaataaa | 1080 |
| gaaaaataac acaaaagaac atttggtgct cagggattca ctggataagt tttcaaaact | 1140 |
| tttcaatgta tgatagagat tgttataaac tgcggacata cgtggcatga cagacctaac | 1200 |
| gtgggaagga caacacaggc aaggatgatt ataactcact gtcacttatc agcctaaatc | 1260 |
| caaacgtcag gaataccgcc tcagagaaaa gaaaatgatg tttttgtcat aagtggtgct | 1320 |
| gtgctcctag ggagcttgct gggtgggaag agagacagaa aggtggggag caggggctgg | 1380 |
| tggacttggg gagggaggag aaagcccatg tggaaacgtt agaatctggg gtaatcagag | 1440 |
| gtctttgtat tcattcgttt tgtaaatttc tcaaactctc atgttaaatc aaaataaaaa | 1500 |
| gttaaaaaaa aaaaactacc aggacagaca tacacaaata ttattaactg aaataaatgt | 1560 |
| tccatcaaaa aggacttacc ttaactacat gagttatatt atgatttcta ttattattat | 1620 |
| tattattatt ttaatattag tatccatcca gcacaccact ggtcttcaag tggaggtaac | 1680 |
| tttgccccctc aggggacatg t | 1701 |

<210> SEQ ID NO 82
<211> LENGTH: 1482
<212> TYPE: DNA
<213> ORGANISM: Artificial Sequence
<220> FEATURE:
<223> OTHER INFORMATION: sequence of T14
<220> FEATURE:
<221> NAME/KEY: misc_feature
<222> LOCATION: (132)..(978)
<223> OTHER INFORMATION: "N" stands for any nucleotide on various positions

<400> SEQUENCE: 82

| | |
|---|---|
| atcagccccc acatgcccag ccctgtgctc agctctgcag cggggcatgg tgggcagaga | 60 |
| cacagaggcc aaggccctgc ttcggggacg gtgggcctgg gatgagcatg gccttggcct | 120 |
| tcgccgagag tnctcttgtg aaggaggggt caggaggggc tgctgcagct ggggaggagg | 180 |
| gcgatggcac tgtggcanga agtgaantag tgtgggtgcc tngcaccca ggcacggcca | 240 |
| gcctggggta tggacccggg gccntctgtt ctagagcagg aaggtatggt gaggacctca | 300 |
| aaaggacagc cactggagag ctccaggcag aggnacttga gaggccctgg ggccatcctg | 360 |
| tctctttttct gggtctgtgt gctctgggcc tgggcccttc ctctgctccc ccgggcttgg | 420 |
| agagggctgg ccttgcctcg tgcaaaggac cactctagac tggtaccaag tctgccccat | 480 |
| ggcctcctgt gggtgcaggc ctgtgcgggt gacctgagag ccagggctgg caggtcagag | 540 |
| tcaggagagg gatggcagtg gatgccctgt gcaggatctg cctaatcatg gtgaggctgg | 600 |
| aggaatccaa agtgggcatg cactctgcac tcatttctttt attcatgtgt gcccatccca | 660 |
| acaagcaggg agcctggcca ggagggcccc tgggagaagg cactgatggg ctgtgttcca | 720 |
| tttaggaagg atggacggtt gtgagacggg taagtcagaa cgggctgccc acctcggccg | 780 |
| agagggcccc gtggtggtt ggcaccatct gggcctggag agctgctcag gaggctctct | 840 |
| agggctgggt gaccaggnct ggggtacagt agccatggga gcaggtgctt acctgggggct | 900 |

| | |
|---|---|
| gtccctgagc aggggctgca ttgggtgctc tgtgagcaca cacttctcta ttcacctgag | 960 |
| tcccnctgag tgatgagnac acccttgttt tgcagatgaa tctgagcatg gagatgttaa | 1020 |
| gtggcttgcc tgagccacac agcagatgga tggtgtagct gggacctgag ggcaggcagt | 1080 |
| cccagcccga ggacttccca aggttgtggc aaactctgac agcatgaccc cagggaacac | 1140 |
| ccatctcagc tctggtcaga cactgcggag ttgtgttgta acccacacag ctggagacag | 1200 |
| ccaccctagc cccacccttta tcctctccca aggaacctg cccttttccct tcattttcct | 1260 |
| cttactgcat tgagggacca cacagtgtgg cagaaggaac atgggttcag gacccagatg | 1320 |
| gacttgcttc acagtgcagc cctcctgtcc tcttgcagag tgcgtcttcc actgtgaagt | 1380 |
| tgggacagtc acaccaactc aatactgctg ggcccgtcac acggtgggca ggcaacggat | 1440 |
| ggcagtcact ggctgtgggt ctgcagaggt gggatccaag ct | 1482 |

<210> SEQ ID NO 83
<211> LENGTH: 1680
<212> TYPE: DNA
<213> ORGANISM: Artificial Sequence
<220> FEATURE:
<223> OTHER INFORMATION: sequence of T17

<400> SEQUENCE: 83

| | |
|---|---|
| ggcgccacta cgggattaag cctgaaaccc gagcggcccc ggccccccgcc acggccgcct | 60 |
| ccaccacctc ctcctcctcc acttccttat cctcctcctc caaacggact gagtgctccg | 120 |
| tggcccggga gtcccagggg agcagcggcc ccgagttctc gtgcaactcg ttcctgcagg | 180 |
| agaaggcggc agcggcgacg gggggaaccg ggcctggggc agggatcggg gccgcgactg | 240 |
| ggacgggcgg ctcgtcggag ccctcagctt gcagcgacca cccgatccca ggctgttcgc | 300 |
| tgaaggagga ggagaagcag cattcgcagc cgcagcagca gcaacttgac ccaagtaagt | 360 |
| gcaaaagaaa ttgcccccctg atttattgct gaaacctgta aggctcgaat gtgcaaaact | 420 |
| gatagtttta ctaacctata aaaacgtcta gacgcctacc caagcctagg cgaacaacat | 480 |
| gcatccataa aaagagcttc ccataaccac ctaccctggg cgctcagtta gtacggtaaa | 540 |
| cagagcgcga gcattaaggc tttttatgat aattccccac aagttgtgaa aagcgaccat | 600 |
| ccttggtgaa attaatttaa cgacctctct tccccaccct gtggtctctc cctgcctccc | 660 |
| ctcctctcct ctctccccgt ctccaaacct ccctctttgt agacaacccc gccgcgaact | 720 |
| ggatccacgc tcgctccacc cggaaaaagc gctgtcccta caccaaatac cagacgcttg | 780 |
| agctggagaa agaattcctc ttcaacatgt acctcacccg ggaccggcgc tacgaggtgg | 840 |
| ccaggattct caacctaaca gagagacagg tcaaaatctg gtttcagaac cgtaggatga | 900 |
| aaatgaaaaa gatgagcaag gagaaatgcc caaaggaga ctgacccggc gcggtgctgg | 960 |
| cgggagcgct caagggcagc ggatttgttg ttgttgctgt tttcctttgt gggtgtttgg | 1020 |
| tgcttgattt ccagaaactc tccagcgact tggacttctt cttcttttttt tttttctttt | 1080 |
| tagatagaag tgactgtgtg gttggtctct gaggtatttg ggggactctg tatttgctcg | 1140 |
| tttacgtgtt ggaaaaacca agtggctttg gggtttcgcc ctatcccact ccctctcttt | 1200 |
| cctgctccat tggttcctta agaaatgcta tattttgtga gtgcaagctg gcttggggag | 1260 |
| ccctctcttg tgtaaatgtc cccatgtttt ctgaaaagtg ctgtagttta gtcccctcac | 1320 |
| ccccagcact gcccaaacag gggccaagtg cgccccaatt ccaagaatga aggcagagcg | 1380 |
| acaacagtgc ggacacccccg gctgctagcc cacggtgaag cccggcgggg ttgcccacca | 1440 |
| gttgcgaaag ccccctttcc tcagggagca cgcgggacct cggtggagat ctccagtgag | 1500 |

```
gcttagagga gcccagggcc tcgggcgggt tggggtttgt cctcagtgca ttggacgcgc   1560
tgctctctcc cctgaaggct gggctcgcgt gggcggccgc gggtggtggc cctcccggtt   1620
cctgcccgag gaccagttgt aaatgttact gcttcctact aataaatgct gacctgatca   1680

<210> SEQ ID NO 84
<211> LENGTH: 919
<212> TYPE: DNA
<213> ORGANISM: Artificial Sequence
<220> FEATURE:
<223> OTHER INFORMATION: sequence of T18

<400> SEQUENCE: 84
gatcatctac taggttgaaa ggagagaata tgacttccag aacagcactg atgcttaaaa     60
aggatgcctc tggaagaaaa ggaggaagag gagcaagtga tgggagaata cagtgggact    120
ttgggcacca tagggtcatc ctgagttttt caccaaaatc aggaacagcg gcaaaactgg    180
tttcactgaa gaagacacac gtttggagac atgtgtagtc tccaaggatt ctcacttaac    240
aaagcctatt tctgttgtta aaaccccctg cataatgcac ccacacacaa acacaaggct    300
tggtctgtgt tcctggccac ctaaagaaac tgattcccag taagtttaaa cctgaatgaa    360
atgtttctgc aaattcagcc tcaaaattcc tcctctacct ggcatccctg gcttgtaaac    420
tatgtgtctc attagttcat aaacaaagca gccctgactt tgccttgtac tcaaccacag    480
ccctaggagc cagtagaatt tgtccagagg tgctgggctt tggagcccaa gtggacaaag    540
tcagaccccc tttcctcagg gcaaagccct cccacagggc tgggacccca aaggctatgc    600
tggaagcagg ttcagcagca ggatatcaag gggcaaagct cctaattcaa aatcttcctg    660
gcttctgaac aaccattagg atggacagag aaaactttttg ccctgctctg agagggtccc    720
acagggcttt tggaagcaga gccaccattg agaaatccct ttcaacctga gtagtaattc    780
agatttttct cccactcctg cacaacttaa tttgctgaat ggaaaattca gccagaagtg    840
atgggctgct tgaaatcaac aaaacttgac acattcttcc catttttcatt ttactttatt    900 gttaaacaca taattgatc                                                 919

<210> SEQ ID NO 85
<211> LENGTH: 1174
<212> TYPE: DNA
<213> ORGANISM: Artificial Sequence
<220> FEATURE:
<223> OTHER INFORMATION: sequence of STAR A1

<400> SEQUENCE: 85
gatcaataga agaatggagt ttgtgtttgc tagccatagt tttgacgtgt gggagagttg     60
gagtctagaa ggttctctgg acgaatgtcg gcttgttaac tgcaggaatt cctctgtaag    120
tctctgtcct tacagaaaat ggcccgaaat tgaaaaaccc tacttcttgg aaaacagaaa    180
taatttgtgt aatgaatgtt gcaggcggtg ttggacgttc gtgtggagat attggcaatg    240
gtaggagacg atggtatcac acgttggatc gattaaaaag aaaaacagag tctctccatt    300
tgtgagtttc tctctttttaa ttacttttgt tactttaaca tccttaggat tcacagacga    360
aaaacagaga cacccaattt ttgtgtttcg agactgtgtc gtgtgttgtg tagttggtat    420
caaccaactt atatctgtaa tcattgtttc ttttttattta ttctcggttt gcagaaacat    480
ccgatgagct tgtcttagag ggacgttgt tgttgttttc tgggtctggt cgtgatgaac    540
tcgaaagcat tgtgtgtttg gttagtagtt tgaaataggt gtgtgtattg tatttgtata    600
```

-continued

```
tgctgcgttt gtgttttaga gatcatcgta cataaaacac atcatcgtac ataactaaaa      660
tttgagctaa actacaaaag aaagtaacct tcattttag tcgaaccagg ccccagctag       720
gcagctatct cgtaaataag attgctggct tacgatcgta ttccacgtgg caatttatgt      780
gccgtggatt taaatttgta cgtggcatga gtgttaggag aatgtccaca tggcttgtag      840
ttgttagtcc cacgctctga accagagcaa ccggctcctt acacgtgttc ggcttaaatc      900
catttttcga atgagattac acttctaacc ttgtctccct ctcccgctta taccaccacc     960
actctcacac aagtctctca agtcacaaac tctgtttcaa accaaagggg aactttgtgt    1020
gtgttgtcga gttttatggt gactgtaaac cctagccaag ctcattgttt gcctatgaaa   1080
atgagtctac cgggtttcaa tactcttccc cacacggcaa caacgatacc ggtttccata   1140
cggagcaata ggacgatgtc gtttttgag gatc                                  1174

<210> SEQ ID NO 86
<211> LENGTH: 910
<212> TYPE: DNA
<213> ORGANISM: Artificial Sequence
<220> FEATURE:
<223> OTHER INFORMATION: sequence of STAR A2

<400> SEQUENCE: 86
gatcaaaatt ttggtttctt cgctttgatt ttcttcttct tcttcttctt cttccctcaa      60
gttccttaga atatctttct catccatttt ttttggttct tgttttgtta agtgaacatt     120
ttagttgatt ttaaagtgct aaacttaaat gcagcatttt actaatataa aattacgctc    180
cattattgac cttatataca tagaacaaaa taatgttata atcttcgact tttttctaac    240
aaatattaac caatcatgtc actaagaaat taaaaaatac tagtatatag gaatctagtc    300
cattgtatat atcgtaaaca tggacacttc accaacgaac atgcatgggg tcttttttata    360 aggttcttta taccgaaacc attgttttgg tttttatgat aattgagtta gttttgtggc    420
ttttccgttc aactaaaagt ctcattatgt caactgctat taaaccggcg cacatggcat    480
gttttatgaa attaaggtca attggactcc aacttttcaa ttattaaaaa aaaagaaaaa    540
tgattgttgt atgccttggc gaagaagaaa agccgctagc tttattcatt atcaaacgaa    600
acaaaaacaa caacacatca ctaagaatct taaactctta accttacatc aaagtaactt    660
ttattacatt gcatacaaga aaagaacaaa ccagcattat taggtttgag attaaacctg   720
ttcccacaca tatacataga gatatgaact ctacaatttc aaaccagagc cttgaagttt    780
ctcctcaaca atcatgtcga ttttgttttc catttcagga gtcatataac tcttccaatc   840
accaacttcc cctttacgga aaaaactctt gaaacttact ccttccgaca agcttcctgt    900
tttgttgatc                                                            910

<210> SEQ ID NO 87
<211> LENGTH: 906
<212> TYPE: DNA
<213> ORGANISM: Artificial Sequence
<220> FEATURE:
<223> OTHER INFORMATION: sequence of STAR A3

<400> SEQUENCE: 87
gatcattaat cgcagatttt tacaagacag cagcttggag agcaacttac aagtgtgtta      60
taaactctga actcaacttg gaagatgttg acgttccaaa tgaaattgga agacaaacta    120
tcttcccacc aaggacaaga aggccgtctg ggaggccaaa aaggctacgt atcaaatcca    180
ttggcgaata tccggttcgt atttgtagga gtcccatttt ttcgacttta tctttattcc    240
```

```
gtatttaatt ttcaatttta tgtggtttaa cagaaatcaa agagcgtgaa ggtgaagatt      300
aacaggtgtg gcagatgcaa aaagactgga cacaacagga caagctgtag taatccaatc      360
tgaagatgtt ttaaaatcgg ctatattgat agaacgatga ccattttatt attgttttg       420 tgtttggaaa tggttatttt tggataaaat atgttgcatt ctatttata atttagttt        480 cgacttatta catataaatc tagtaaggta atatattagc aaattacaga taatgatgaa      540
aaacatggac aggtataggt ggataagata taaataaggt aggactgaat tgttacccgt      600
taataatgaa agaatatacg aaatactaaa cattaaataa ggaagttact aattattgga      660
caacaaaaag tttaattcct ttaaaagaa attggaatac agacagtttc attgacctaa       720
ttaagtactt ctttgaaaaa aatcaaacta ggagaataga agttgtaaat aattgaaggg      780
aaacgtcgat tcggtgaaaa ggttttttaa ttagtattta aagggaaata tcttctctta      840
tacagaatat cttgccccag aacaaatcgc ctcaaatact aaaagtgtgt acatcttctc      900
ttgatc                                                                 906

<210> SEQ ID NO 88
<211> LENGTH: 782
<212> TYPE: DNA
<213> ORGANISM: Artificial Sequence
<220> FEATURE:
<223> OTHER INFORMATION: sequence of STAR A4

<400> SEQUENCE: 88
gatcaaattc atatgcttat ttgtgattat actttgcttt gattcaggaa atcaaagaag       60
atagctccac cttacagggt gatactacac aatgacaact tcaacaagag ggaatatgtg      120
gttcaggtgt tgatgaaggt aatacccggc atgactgtag acaacgcggt taacattatg      180
caagaagctc atatcaacgg tttggcagtt gtgattgttt gtgctcaggc tgatgcagag      240
caacactgta tgcagctgcg cggtaacggc cttctcagtt ctgttgaacc tgatggtgga      300
ggctgctgaa actaattaaa ctcagtatag attttcccac cttccaggac tctctattta      360
gtcaaaaaca tttgttgttt taatgtatat aatatcagaa atttggtaca agactgttac      420
tatatgcaat gaaccttgcc cctacataga tctgttgtga gttttaagtg ttttcatttg      480
gaacttcaga atgcaaataa acaaaacttt attgaagtca aatggtgtta cagatgaatc      540
tttctgattc tgtaatcact aatgtaaatg tatctaagca attgtaaggg agtgacgtgt      600
ttcggtttca tctcgcccaa aaaagcattc aaacccaaga aacctgcagt ttcaagacat      660
tgatgggata ccatatagat gtatcaagca tcaaccggag taagaagcga ctgaatgccg      720
aagataatga aaagcattcc accggaaaga gccacctgca acaacataag agctatttga      780
tc                                                                     782

<210> SEQ ID NO 89
<211> LENGTH: 1356
<212> TYPE: DNA
<213> ORGANISM: Artificial Sequence
<220> FEATURE:
<223> OTHER INFORMATION: sequence of STAR A5

<400> SEQUENCE: 89
gatcctgtaa aacataaagt tagagataat tgtccgattt gtttgcccttt ttaatttgga     60 gagatatgaa ccaaaaacat atttcggaat gggtcccttt ttcatcgtgt gtaacagttt     120
taccaaacag taatactttg tgaaagtttt gattaattaa tgcaaaaaga ttagaaaaaa     180
```

```
gcgaaactaa ttttggatt acactagaaa aaggttaaaa tcaataacca aaaaagaaa      240 aaggttaaag ttacaaaaca caccggttta tagagtgaaa tgattattgt tctgttgaat    300
tgacgtgcca gcttagcatc accttactat tatcagtcac ctatatatca caattcacag   360
gcttcttgct ttctctcatt ggctcgtctt cttcccttc ttctccaatc accttagctt   420
gctgatcagg taaactagat tggtgtttcg tgttgtttc ttctcaactt aggtgtttga    480
tttgagaagt ttttctatgt atgttggcat gttgcgttcg tagcattgca tatcaacgga   540
taggtttgaa taggtagaat taatttgatt gatatatgaa agaatgtttg tatatatact   600
ctaggtctag gttattgaat attgagaaat ttattttgtt aggtttagat gaattattct   660
tcgatgagtg gttcaaagtt caattggcaa gtcttttcaa tgattgtagt attttggtga   720
tgataagtaa gttgttaatg actctcaagt ctgaattcat gttttggttt tgtttccttg   780
taaaaatgtg aacgttttc ttacagaagc tttcacaaac aaagtatggt taattgagtg    840
actaatccac taattctctt tgttgtttt atatcgttta ttaggtaatg ttttttttt    900 ttgggtgtgt aaaatatgat actgactcaa gatttatca tatttctgaa tccataagct    960
aaagtacatt tgagagaagc aagagagata gaatggggcg tggagttagt gcaggtggag  1020
gacaaagttc tttgggatat cttttggga gcggagaggc tccaaagcta gcagccgtta   1080
acaaaactcc agctgaaact gagtcttctg ctcatgctcc acctactcaa gctgctgctg  1140
caaacgctgt tgatagcatc aaacaagttc ctgctggtct caatagcaac tctgcaaaca  1200
attacatgcg tgcagaagga caaaacacag gcaatttcat cacggtatgt ctttaattct  1260
ttcgctgaat cgagtcctgt gtgctggtta tcggatagca aaaacatctg tatctttact  1320
tttcttagat tagttgtctg aaaatgaaag aagatc                            1356

<210> SEQ ID NO 90
<211> LENGTH: 1452
<212> TYPE: DNA
<213> ORGANISM: Artificial Sequence
<220> FEATURE:
<223> OTHER INFORMATION: sequence of STAR A6

<400> SEQUENCE: 90
gatcgactgg tacaatgcta gaagccctag aggttgtagg tgatagccac gatacatcct     60
taggtgatgt aagtcaactg aatataaatg gccatttacg tagacttcat gtcctagatg    120
atccctccta ttataacgtg aatctcggtt tcttggtgtg gaaaacgaaa tgattgatat    180 gttttgtca gggatttgag gtggtgaaca gtcgttatat gactagttat gatgatgaag    240
atacaccgcc aggaagtgga ttcaggacaa aactaagaga gttccataag aggtaaatga   300
cgcattaact catgcctctc aacattttgt cggcattcaa acagatgcat tcaagtctct    360
tttaataaac acaagaatcc catttgttta ttgttttgtt tgtatgcagt gcggcatcat    420
tcacagaact agataggaat tacctaacac cgttcttcac aagtaacaac ggagattatg    480
atgatgaggg taacatggag caacaccatg gtaacaacat aattctctga tctcttgttt    540
cactattatt tttgttgtta ttccgcaccc aaaaccatga aatttacaat tggggttatt    600
gcagaagaac gaatcccatt tactagaaga ggaaatctaa ataaccgcgg ctaagtttcc    660
gagatgagaa atctaatagt gtttttcag cggcatatat atgtacataa acaaactgg    720 atgtatggga ggaggtagtg acaaaggatt tgttctaagc taggtttctc tataatatgg    780
tactgtgttg ttggtgtaaa cctgaatgga tattgttagg ttgaaactaa ttacattcac    840
acaaagaaag aaaaaaactt gaagaaggcc atggctggtt tatactgaac cacgaatttt    900
```

```
gttagtttta aactcttagg gaaaatgcta taatgccttt tttgtcttgt agtcgtgttt      960
ggtttgaatt aaaaaaaaaa tagagaacgt cacggcacgc caaaagtgtg gaccttgttt     1020
attcgccgga agtaagtaac caaaaacgct tctaatcttt cgtttacaac aaatatctct     1080
ctctctctcg ctctctctcg ctctctcttt cttcttcttc atcttctttc atggctgtta     1140
ctggctgggc aatcacaatc tgaattcttt cttcctcctt gtctctctga ttttcgccga     1200
gttttggggg ctcttgttgt tacacgatga gtctggtggt tggtcagtct ctgggtttaa     1260
ctctagtcgg tgatggtctt tcgttacgca attccaaaat aaatgtcgga aaatcaaagt     1320
ttttctcggt aaatcggagg agattggcgc gtgcggccct ggtacaagct aggcctaagg     1380
aagacggagc ggcggcaagt ccttccccat cgtcgagacc ggcgtcagtt gtgcagtacc     1440
gacgagctga tc                                                        1452
```

<210> SEQ ID NO 91
<211> LENGTH: 1085
<212> TYPE: DNA
<213> ORGANISM: Artificial Sequence
<220> FEATURE:
<223> OTHER INFORMATION: sequence of STAR A7

<400> SEQUENCE: 91

```
gatctatctt atattgttag ttcatgtttg tttttaaaga ctgtttttat gtttcaatgg       60
tatattactg actggggcag taatattgtt gaagtctgta gattatggtc gcatggctga      120
aatactggtg cagagggctg cttctcctga tgaattcact cgattaacag ccatcacgtg      180
ggtaagcaga ataaccatg cttctgcttg gcgtcttcca gttatataga ttggtactat       240
tttgacttct cgggagattc atatactaag aatatctgct ttttattaaa tgttgtagat      300
aaacgagttc gtaaaacttg ggggagacca gctcgtgcgt tattatgctg acattcttgg      360
ggctatcttg ccttgcatat ctgacaaaga agagaaaatc agggtggtaa gtttgcttct      420
cctcctcagt gatggaaact gtaggttttg tatgcatctt tttactttct tgttttttg      480 attttatttt gcataaggtt gctcgtgaaa ccaatgaaga acttcgttca atccatgttg      540
aaccctcaga tggttttgat gttggcgcaa ttctctctgt tgcaaggagg ttagtttttc      600
tctattgttt ttttatatc cgtttgaata ttattaaatc gcgcctgttt atttgtgagt      660
ttttgcattg agcaggcagc tatcaagtga gtttgaggct actcggattg aagcattgaa      720
ttggatatca acacttttaa acaagcatcg tactgaggtg aagaaactgg tttttgcttg      780
ggcatcattc ttttctagtt agcctttttg tttatcgcgt tatagctaaa ttggtaatgc      840
tgcaacaggt cttgtgcttc ctgaatgaca tatttgacac ccttctaaaa gcactatctg      900
attcttctga tgacgtaagt tctatctccc tgactgttcg tttgattggt tggtgaactt      960
tataatataa aggtttggtt ttgtctagta ataaacttat ttgatatttg aactatctgg     1020
acttggaaat atactttagg tggtgctctt ggttctggag gttcatgctg gtgtagcaaa     1080
agatc                                                                1085
```

<210> SEQ ID NO 92
<211> LENGTH: 696
<212> TYPE: DNA
<213> ORGANISM: Artificial Sequence
<220> FEATURE:
<223> OTHER INFORMATION: sequence of STAR A8

<400> SEQUENCE: 92

```
gatcatcttt ttctaggtag ggaattgctt atctcggtaa gctaagaatg ttagaaacaa      60
agaactagga cagaacggga aatggagaag gaggttagaa tcaaagaaca gtaaatggag     120
aaggaggtta atgtgtattt cattctatct acattttaac taattgagtg tatccagtct     180
tatccattaa tgtaattaca agaagaatag taccaagcat gtaggttata gttttcactt     240
tactgggtga aggtttctgt agttcaagtg ggtcaaaagt ggtttgcgga aacatatctc     300
taataatttg attgagaggc tcctcgcact cacatggact taaacttttg tgtattatac     360
aaacatgatt cacatacaca tctcgtgtat attgcaatac atttggtaaa ttatctgaaa     420
ataataatga aggtttcttc aaagaggtc caggagctat ttccattaac actgttatac     480
tgaacagtat acaaaagaag actgcagtgc gagaatttat ggaggatgat aatgcatttg     540
agatattctt ctgaacactt tcatatcttt tatgtaaaac attttgatg agaaaatcac     600 cagtagtatc caaacacttt aatccagatg atgggaaaat gctttgttta aacctactac     660
gaagtatgct taatacttca ttattaccag ttgatc                               696

<210> SEQ ID NO 93
<211> LENGTH: 925
<212> TYPE: DNA
<213> ORGANISM: Artificial Sequence
<220> FEATURE:
<223> OTHER INFORMATION: sequence of STAR A9

<400> SEQUENCE: 93
gatctggttt cggtaattgt tgtttccggg aattgagtat agaaacacaa atacatattt      60
aaccctgatg aaagagggtg taaacttgtg cagatagatg cgaaaacaac gcacgacaaa     120
cttgtgaagt tggtgctcga tgataaagtt agacgaaatg ttgtatctct tattgttttg     180
cgacaaattt acatgtcacg gctgagttat atgcttaagg gaagatgaaa agttcagtca     240
atttacatgt caccactgag ttatacgttc caggaaagac gaaaggttcg atagaattac     300
attacggttg agttatatgc ttaagggaga acgaaacgtt cagtcaattt acatgtcacg     360
gctgagttat atgttccagg gaagacgaaa ggttcggtaa aattacatta cggatgagtt     420
atatgtttaa gggaagacat ctataaattt acatgtcacg gctgagttat atgttcaagg     480
gcaaacgaaa gatgagtgta aattatatgt tacggctgag ttatatgctt caaggaagac     540
gaaaggttcg gtaaattaca tgtcacggct gagttatcat tcagggaaga cgaaaggttg     600
tgtaaattat atgttacggc tgaggtacat cacgttaagg ctgagttata atacagatcg     660
gaaaacaaca tttttctggg gaagacaata tgaaatttat tggccaaaga acaacaatca     720
aattaagaaa cgtaagaata tgtttgaggg atacatagga ggaagacgaa actatatgaa     780
tcaaaacatt gatagaagta gaaatatctc taaatagatc gattgagagg aaaactaaac     840
gagagacata taaaatcaaa gtaaagagt agttattctt gattcaactc aaacctgtaa     900
caaatcatat aaaattctat agatc                                           925

<210> SEQ ID NO 94
<211> LENGTH: 1753
<212> TYPE: DNA
<213> ORGANISM: Artificial Sequence
<220> FEATURE:
<223> OTHER INFORMATION: sequence of STAR A10

<400> SEQUENCE: 94
gatctgaatg agatgtgttg gcgaacgcat atagttttttg tttcttgctg ttcataactt      60
tgcttatgga atttttattta tgtctttctc tataccctctt tggaccagtg ttccatttgc     120
```

-continued

```
aatagagagt cactcgtgaa aaaacaaat aatgtgtgtg tatcaattat tccctctcgg      180
ccttatattt tgtcttcttt ttgctaatta tatactattg atttagatat ttacttatat    240
tcatgacgtc ttcttcttat attcttattt aatttgaagt tagaaaatta acgttacaac    300
ttacaactat taaattattg ttaattggtt ttataataag tatcgctctt gtctccattc    360 acttgtctt tattgtcccc agtaccaaac taccaaatac aattcatatt cactaattaa     420
ttagtttgat gcaaaggatg atgcaatgtt aagaaaattg aaactctacc acattctaaa    480
atgaagcaac tctaccatat ttaatttctt tagacttgga atagtcacaa tatgaatgct    540
taggtagtta cggttagtta ggagtatcac acagaattga aaataccaaa ccacaatttt    600
aatcaggtga ttcggtacta attttttatta atgaataaaa acataaccga accaactcaa   660
agcagatatt aacctgaaaa tgaactcacc aaaacaataa tagaaagact caaatcgagc    720
cggaaaccag attgagcaac gaactcatgg gaatatcata tctatttatg tccagactat    780
taatatacat acctatgaca aatactatg catgcaatgc aagactgaag taaccatatt     840 ttttgggta aaccattgat aagctaaact tgaatatcca tagtacttca tcgtactatg     900
tatcaatagt atagtaagtt tgacacaatt acattcagtt tgatttttat catataaacc    960
tcccaacaat atttaaaacc gtatctatat ataaatttat ttgattaaat cagcctagaa    1020
gtttatagtt cagtgcagat aaattcaaat tttgatatat atcttaattg aattaaccgt    1080
cttttggtta aattattgtt acaagcttac aaaatccact atacaccaag ttggacttag    1140
atatcatata tgagattaac agccgattac acttgtacat tgacctgacc tatacaaacg    1200
actacaactt tatgtatata tatttctcta ttttggaaa ctcgtttgat ttgttttcac     1260
atgtcgtgaa atttacagct ttgtttccta ctctcaaaaa tagagcatag agctggctga    1320
tcacacttca aattaaaacc aacaacgtat ataaactata acccatgtga acacaaaaat    1380
ttagaccttt tttcaaaacc attccaattt ctaacaaaaa caaaattaga atcctaaaa     1440 tctgcaaggt gtatggaagg caaaaaggc taacaggatt aaaaacagtt tacattagtt     1500
attctcttta aaatagaaag aagattttcg ataaaaacgt cgtcgtatct tcgtcgacgt    1560
ctccgtcttt aatgggggag caaagggcaa gcggtgcttc ctcctccacc gactcatatt    1620
caactccttc gccgtctgcg tcaccgtctc catctccggc tccacgtcaa catgtcacgt    1680
tactcgaacc atctcatcaa cacaagaaga aaagcaaaaa agtcttccga gttttcgtt    1740 cggttttccg atc                                                      1753
```

<210> SEQ ID NO 95
<211> LENGTH: 1908
<212> TYPE: DNA
<213> ORGANISM: Artificial Sequence
<220> FEATURE:
<223> OTHER INFORMATION: sequence of STAR A11

<400> SEQUENCE: 95

```
gatctcactc aagctcatgc tcacgttcaa ggactttcca accgcaaggt tatcttcaac     60
ttgtactcat taaggcctct caatattcat gtgttatgtt catgtagatg tccggtccag    120
ttcaacaact gtttcattgc tttagttgtc acgagaaata tttgtatata ttattatggt    180
gtgcaaaaca tagtaaaatg ttgttcaatt ggcagatgat gatgatgaaa atggaaagtg    240
aatgggttgg agcaaatgga gaagcagaga aggcaaagac gaagggttta ggactacatg    300
aagagttaag gactgttcct tcgggacctg acccgttgca ccatcatgtg aacccaccaa    360
```

```
gacagccaag aaacaacttt cagctcccct gacctaatct cttgttgctt taaattattt      420
catattgtaa attactttct gctttatcgg ttttaccatt tcgggagtct tttttgtgtg      480
caatctgttt cgtttggtaa gcttgtagtt tcatgaaagt gaatgtaaga tatgcattac      540
gtttgttgct gaagtgaatg taagatacgc actattatat ctcatgattt tctaagaaaa      600
ccctcttaaa acgaagatgt ctatagcatt acgtttctat ttccatataa tacgttaaaa      660
tttatggttt ttacgtataa aatgcaaaat aaagacacaa gtatatctcc aaagcaatgt      720
accgttggga aaatttatta gtacgttttc aattgtcaat gcaaataatt aatggatgtg      780
atagtcacaa ttaaacatac aataataaaa atgatgatga tgattcgatg atgtggtggg      840
aaggataaat taaaccgact tggggcagt gacaggcagt gtcagtgtca aagacaacca      900
tttgtagtca ctatttctat cgaaggttgc aaattgaatg gtggaggagt atcaaaacga      960
cacacatact tgaaaagata ttttaataat ataaaaaaat tggtgatggc gtaataacaa     1020
acctagagct aattattatc cttaatgata ccaaatctat atgatacgat atttgtttta     1080
aaaagagtaa agactgacac ttgagatgtg acactggcga tttcgctcac gtcaccactt     1140
ttcccacctc aaataacgct tacggcttta tccattaatt ctaagtataa ttttaagtgt     1200
attttttctt gccaaattca aatatatctt actaaatgga tgaacattat aaaattgtta     1260
tcaaaaccat taaatgttct tataatttct ttcgttcctc caatgtcatc ccaagacttt     1320
ttgacctaat atatgataya tctaacttgc tttggaatcg tatgacatat atcttcaaat     1380
acatatttcg tatttttttt tcacgaaaac taatttagaa agtagaaaac cagctatttt     1440
aaagaaaata aagtgtgttt atatatattc taaaacaatg ctataagaac ataagaccaa     1500
gatatataca atgttatttt atatttatta ttaagcatta acattgaaat taaaaatatt     1560
aaacatgtat accaaagtaa tcaacattgt agttattact actctctctg ttcatttttg     1620
tttgattgtt tagaaaaaac acacatatta agaaaacata ttaaatattg attataaatg     1680 tattatttt aatgttttac agttttctat aactttaaac caatgataat taactatttt     1740
tttaaaaaat taccattcac ctatactaac caataaagat tacatagaaa actaaaaaaa     1800
ttaatctttt aaaaacaaat ttttttttcta aacaatcaaa caaaaaggaa cagaggggga     1860
atattttttt aatttaattt agattaccat tgtagttagt aattgatc                  1908
```

<210> SEQ ID NO 96
<211> LENGTH: 1403
<212> TYPE: DNA
<213> ORGANISM: Artificial Sequence
<220> FEATURE:
<223> OTHER INFORMATION: sequence of STAR A12

<400> SEQUENCE: 96

```
gatctattgc tgtttatggc aggctgtcat ttcagaaaag aatggtggtt tgggatgtaa       60
tgttggtgaa gatggtggtc ttgctccaga tatctcgagg tacatatatt tttcctctct      120
gatgctaatc tgcttgcatc tgtagattgt cgaaactgag aaaaccatgt tatggtttga      180
tggcttagtg cctaatatgt gtaattgcaa ctgtatgcag cctcaaggaa ggtttggagc      240
ttgtaaaaga agctatcaac cgaacagggt acaatgataa gataaagata gccattgata      300
ttgccgccac taatttttgt ttaggtaatt ttctgcttcc tggctaactg attttttgcg      360
gcttcttgta gtcatggata gtcttggttt ggttctcggc attgtcattc acaattggct      420
agtgagacga ataagatgtt aaatcatcaa atgtgtagcc tatcaatatc ttgctcttgc      480
aagtttcaac tatgttatac gttttttgtgt attatttctt accttgtgga actgttcttt      540
```

```
cctgaacagg taccaagtat gatttagata tcaagtctcc aaataaatct gggcaaaatt      600
tcaagtcagc ggaagatatg atagatatgt acaaagaaat ttgtaatggt atgtctggct      660
cgtctgaaca atattttttg tgtctatctt agtactcttg cagtattgta acgaccagat      720
tctctgtttg gtctccttgt gggtttagat tatccaattg tgtctataga agacccttttt     780
gacaaggagg actgggaaca caccaagtat ttttcgagtc ttggaatatg tcaggtccaa      840
ctcggttccc ctactattaa cggttcacat agattttgtg ttctttcaga tcacactgtc      900
ttctgattct tttctcagag tcaaatatct aaagagagag acccttaaat cttcttgtac      960
aatcattttc cttgtctaaa ttctcagtgt aaaactcttg taggtggtag gtgacgattt     1020
gttgatgtca aattcaaaac gagttgagcg tgccatacag gagtcttctt gtaatgctct     1080
tcttctcaag gtatttcgtc cgtcctattt tgtttattac tatgtattac ctgtgcacat     1140
attgtatgtt tactgcctaa gaacgacaaa gacataatgt gcatacggtg atacaggtga     1200
atcagattgg tacagtaaca gaagccattg aagtagtgaa aatggcaagg gatgcccagt     1260
ggggtgtggt gacatctcat agatgtggag aaacagagga ctctttcatc tctgacttat     1320
ctgtgggtct cgcaacaggt gtgattaaag ctggtgctcc ttgcagagga gaacgtacta     1380
tgaagtataa ccaggtctgg atc                                             1403

<210> SEQ ID NO 97
<211> LENGTH: 1140
<212> TYPE: DNA
<213> ORGANISM: Artificial Sequence
<220> FEATURE:
<223> OTHER INFORMATION: sequence of STAR A13

<400> SEQUENCE: 97
gatccatttc atatacatat taccaatttt ggcttttata ggtttgtatc cagaaggcct       60
tttcgtggct acgattaagg aaaatacgaa acaaaagtg aatttactca cttttgtagc       120
atggtttatt ctactttata tacctaagaa atatgagcaa caattacttc tgtaatgact      180
ttttactact tcgtagttgg tacaaactac aaaagattgt gttgttttta catgatactt      240
tataatatct atattaatat atttagtcgt gtttaatcaa aaaagcacca gtggtctagt      300
ggtagaatag taccctgcca cggtacagac ccgggttcga ttcccggctg gtgcattgag      360
ctatgatgat ataggcttca gcattggttg ggtccattgc attcttctga actatcagtt      420
gatgtatgcc acacctctga gctcttcttt ttttttcctc gtcaattaat tttttaaagt      480
tttgtctgcc taaaaacttt cttctttttg attaatcata ttaagcatct cggctataaa      540
aaccacggtc tactaactta acatgcattg gactagtttt agtggagagt gttcgagtta      600
aaatgagaag ctcacgattg cataacggaa catttgattc gctaggcatc tccatttgta      660
aaagtagcca ctccaataca aaatggtcga tgatggtgag tgggtgagac aaacccacca      720
ccacctcaag aagatatatt tctctggtta agaatttgaa tggttgacaa agaaacggtc      780
actctatata cttagaaaat atagtcatac atagacacca tcggtctagt tataataata      840
accactggat taatgcccag tgaaaataat tgagtagcca aaacatgaat ataacaatat      900
cccaatttac atacaacaac acaaaggagg ttttacacga ttctatagta caaactcata      960
acaacaaaaa atcacacttt tgtttaacag ttgcctttat ggctttacta cagtatcttg     1020
tccagggttt tcacacataa caatcacagt aaatcgtttc cttttctttg catcttccat     1080
tccttttgta cacgtaacat ctccggcttc ccgaccatca gctaagaacc agatgcgatc     1140
```

<210> SEQ ID NO 98
<211> LENGTH: 2125
<212> TYPE: DNA
<213> ORGANISM: Artificial Sequence
<220> FEATURE:
<223> OTHER INFORMATION: sequence of STAR A14

<400> SEQUENCE: 98

| | | | | | |
|---|---|---|---|---|---|
| gatccagcaa | ctaagtctta | tgctcaagtg | tttgctcccc | accatggatg | ggctatacgg | 60 |
| aaagctgttt | ctcttgggat | gtatgctctt | cccacaaggg | ctcacctact | taatatgctc | 120 |
| aaagaggatg | gtgagttcat | caactagtta | atatgctcaa | agtggatggt | gtgtttgata | 180 |
| aactagtagt | ttaagtagtc | agattagttt | caaggtcttc | acaggattag | gtagatatca | 240 |
| cggcaatatt | tggcctgtat | aagtcctggt | atcataagag | agaactcttt | gagattcaca | 300 |
| ttggttttaa | gttcatttgg | cagtaggata | ttagattttg | aattttccaa | tactatctct | 360 |
| gtttgagatt | tcataaatcg | agtttcttct | tcattatgtt | cgctgacgat | attgtttttt | 420 |
| tcatttattt | atgaatgttg | ttacagaggc | ggcggctaag | atacatatgc | aaagctatgt | 480 |
| caattcatcg | gcaccattaa | tcacgtatct | tgataatcta | ttcctctcca | agcaactcgg | 540 |
| tattgattgg | tgaagagcct | gaaaaaaagg | cataactatt | gttactcttt | agacaaaata | 600 |
| acctatgttc | tcacatcaag | ctatgtaatg | tcataacaac | agcgacgaaa | tacattggaa | 660 |
| taaattgagt | atgtccttaa | tctgtcgttt | tatctcttct | tttaataaac | acagtttatc | 720 |
| tcatagtaag | cagaagaagc | tttacacggg | ttgtaggaac | gtattaaacg | gtttgtttca | 780 |
| atttcactct | ctttggtttt | gaaattctag | tataaaccaa | agtagttggt | gcttcaagtt | 840 |
| gtgttactta | ttcaacaaaa | aaatatatta | tttttaattt | ttaattttcg | taggtaagat | 900 |
| tacatagtaa | caaaatgtta | aatttaacaa | tgtaagatta | ctatgtaaat | gcatgggcac | 960 |
| cagtaatcac | gtatcttgat | gatatatatc | cctaatccaa | gcgagtcggc | atttattggt | 1020 |
| gaagaatctc | aagactcata | gtcatcgcta | gttaacaatc | tttttcggac | aaaagcgtct | 1080 |
| tcgttaaaat | tcggcattat | taacctttt | gcccttttaa | aatcagaaaa | tttctgtttt | 1140 |
| actggtattt | ttctttgacg | attcaatttt | ttagttgtat | tatatatatg | aaagaagctt | 1200 |
| aactctctct | cacagcttga | tatgtcagta | tctaaaacaa | gcaatacata | atttaattaa | 1260 |
| tttatcataa | aatatttatg | attaaaaagt | aaagaagata | aatattaaaa | agctaaatgt | 1320 |
| ctcttataat | ttaaaaataa | aaattaaaaa | ggattgaaaa | gtaaagaaga | taaatataaa | 1380 |
| gaaactatta | gtatcttata | aataaataaa | taaactaaaa | attgaaatat | aattattta | 1440 |
| gttttgaatt | aagaaaatat | taaatataaa | aaaaattaaa | cataaagaaa | ctatatatat | 1500 |
| cttgtaatta | aaaaattaaa | aaaaaatgaa | aaatgagaaa | aaaatataa | actcttcatc | 1560 |
| atataattaa | tgaaatttaa | aaacttattg | cttttaattt | tttgtacaat | aattaaggaa | 1620 |
| atttagaaat | taattattaa | ttttagaaga | aaaatgttaa | aatagtttaa | tagttttgat | 1680 |
| tcactaaata | catgtgtaca | tatatgatgg | tatgaggatc | aagaaagtgc | cgtaaaatgt | 1740 |
| aaaacttcca | atgttcctta | gtgaaaaatg | ttaacttttc | tgttgacaag | acgtgtatat | 1800 |
| aaacatcacc | tataccggag | aagaagaaga | cacaaaacaa | agttaaaaag | aagaaatttt | 1860 |
| tggtgcagtg | aattcgaaga | gcaatatgaa | gaatattggt | tacattatta | tagccacctt | 1920 |
| gcttgttggt | ctcctcctca | tcatggctct | agtggcgagt | ttctattggg | ccaaacgaca | 1980 |
| tgtcaaatgt | tgtggcggag | agggactgtc | gtcaaaggat | gtgttcaatt | tacttataca | 2040 |
| attggttgct | tttattctgc | tttgtggttt | atttgcttat | ttggtatttt | tggtttagat | 2100 | tagtaaccta aagccatagc agatc 2125

<210> SEQ ID NO 99
<211> LENGTH: 1196
<212> TYPE: DNA
<213> ORGANISM: Artificial Sequence
<220> FEATURE:
<223> OTHER INFORMATION: sequence of STAR A15

<400> SEQUENCE: 99

```
gatcagcaat tacagttgga tggaaaaaga gagacgagaa tgtatctgct gctggtgact      60
ttaaggtagg ctgagtacca aattgcattc tgactgttct tacctcgacc acctttctta     120
ctttcccctag ctctaatctt gctattacta gattgaatct ggtggactcg gagcatcagc    180
tcgttatact cgtaaacttt catccaaatc tcatggtcgc attgtgggta gaatcggaag     240
gtatgtttta ttgacaatcc cgagcaacct aatgtatgat gtgcgagagg atagaaatca     300
ttttttaagt tgtcttttaca tgtgtggcgc aatcattgtt ctcattttac tttggaattt    360
ttttttttaac ttattcagca atgctcttga gattgagctc ggtggtggaa ggcaaatttc    420
tgagttcagt acagtaagaa tgatgtatac agtaggactc aaggtaaact actctttaaa    480
actttcggag ccatcttagc cattatgcaa tctgcttatt ccggtactc ttatactttg     540
tttgtagggt atttctgga aagtagagct acaccgtggt agccaaaagc tgattgttcc     600
cgtgagtgtt actttcttcc tttcttttct tgtggtgtca tgtctgctgt cttcggataa    660
gaaccgaaca gattgtgtct taatctgtgg agtagaaat attaaaaaag cataaaccaa      720
tagaaccaaa gaccaatcct aaaagcctag ggatggattc tagagcatta tccttgactc    780
tctgaaacct ttacccaact caattatgga caaagacaaa catccgtatt actctgggga    840
agtctttcac ttttgacacc ttcatgatga ttatctttga aacgtgcaga ttctactctc    900
cgcacattta gctccagtat ttgcaactgg agcattcatt gttccaacat ctctttactt    960
tttgttaaag gtgagtgatt ggaccctcta aatataatct acttttggtc tattgttata   1020
agctgtttac cttattaaac attttcactg ttccacgcag aaatttgtgg tgaagccata   1080
tttgcttaaa agagaaaaac aaaaggcctt ggagaatatg gagaaaactt ggggccaggt   1140
gattgttact tccgagtttg gtagccaagc gagattcctt gtaattgtag atgatc       1196
```

<210> SEQ ID NO 100
<211> LENGTH: 692
<212> TYPE: DNA
<213> ORGANISM: Artificial Sequence
<220> FEATURE:
<223> OTHER INFORMATION: sequence of STAR A16

<400> SEQUENCE: 100

```
gatcgctttc agtctatcat gttttgagcc ttattttggg agcgatgtat taatattttg      60
cctgttcttt atttttttgtg ttgcagacat acaatgaagt gcagcggtgt tttctgactg    120
ttggcttggt ttaccctgag gatttgttta catttcttct taacgtaagg acatcttttg    180
ttttatgatt atggctctag ttattctttg tatatgtaac gcaaacggt ggcaatacct     240
agcactcata ttgagactcaa gaactattcc ttgccacaca tctgtgtgat atttatatgg   300
gcttttttatc ttacatattt gaaatccctg tcttccttgt atactttcac cagaaatgca   360
agttgaaaga agacccttttg acgttttggt ctctttgcat cttgaaacat ctgcttccga   420
ggtgtattct tttatccttc atcagtataa cttatcattg agagttaatt taccatccta   480
```

| acttaatgat gttgcattgt gttcgaaggt tgtttgaagc atggcactca aaacggcctc | 540 |
| tttggtgga tactgcaagt tctttgttag atgagcaaag tttagctgtt cgaaaagccc | 600 |
| tttcagaggt actgagctgg cgtagatttt cttatttact actaaaatat gcatgcttta | 660 |
| gcatagtgct tctactttaa tgacagttga tc | 692 |

<210> SEQ ID NO 101
<211> LENGTH: 1826
<212> TYPE: DNA
<213> ORGANISM: Artificial Sequence
<220> FEATURE:
<223> OTHER INFORMATION: sequence of STAR A17

<400> SEQUENCE: 101

| gatcacgata attttcctta attatctaat tctaagatag tctaaccatg aatattctta | 60 |
| taatatctta actgtatagg agattctatt ttcatcccta aattatattc gtaattttat | 120 |
| tcggatatac ttgcttttat tttcgtcaac agatatatat atatatatat atatatatta | 180 |
| tttatttta attttcatta aaattagtga tttaattctc tattatttgt gtactatata | 240 |
| aaacaaacaa atgaatctta taatgttttgc tttttcgtcc ataaatattt ccgggaaaaa | 300 |
| tcgttagata taaatcgaac ctagtggtga gtgactcaca cacatgtgac aattcccaaa | 360 |
| ataagtcccc cacgtacgct atgtctgttt tagtgtgcat gtagtaacta ttatttactg | 420 |
| atttagaata taactagcat ttggccccta tttagggata acattgtttt agattatatc | 480 |
| tgttacaact tttaactaaa aattttaaaa taaagcagac agtattaata tacaacaaat | 540 |
| ttattatcat tgatcgaaga atatacaaag attaagaaaa agatataaag aaggtacaac | 600 |
| ttttctaccc aatgaatcaa ttgcgatagg caataactaa caaatcaaga gtttagaaat | 660 |
| ataagagagt ataagtacga aaattatgct gggtatatac atgtccgctt atttcatcat | 720 |
| tagctccaac caattgtaat gtgttcttct tctcatcatc agtaattcag tttacaaaca | 780 |
| ttcgttgaca cccaaagctt ggaagtctaa aaaaaaatgt aaaatgtgca caaataagta | 840 |
| actacatgac gcagacgctg cctttgaaac aatatcaaag atattgcaga tataaagaag | 900 |
| taaaataaga gatgacttta aaattgaagt atttgtatta atacaaaaat cttgcgtgaa | 960 |
| aatacaattg cagtttaata caaaaaagaa attgcagata taagaagta aaataagaga | 1020 |
| tgaaagaaga atagtaaaaa gtatgagaat taatttacca tcaaaaaaac acttgagctt | 1080 |
| cgattaagat attaaactca cccttgtttt aaggcaactg ttcagatgag aagccaaaat | 1140 |
| ttgtcgttgt tccttgagtg tttgtgagac gggagaatca taggcattga ttgtattaaa | 1200 |
| gaataatcct atggaaaaat ggagatgtat gagagaaatc gaattcagtc aaataaagca | 1260 |
| gaaacaaagc aaaaaaaaaa aaaaaccata gaaatctaga agaaggatat atgatttcg | 1320 |
| gatctatgga aaatttctat atatataaaa caaaattaca aacagaaata gaagatggta | 1380 |
| aattggttca ttgagatgaa caagtacct gatttctgag taatcgatta atgatgttga | 1440 |
| gaaacccatt tttgagattt tacacagtag tcatggagtt tttggaagag agaaagtgga | 1500 |
| gatgtggaga tcgtggggat gaaagagaaa atcatttgag aaagaaacaa agttaaataa | 1560 |
| aaacgacaca tactatgcgt aaaaatgaaa aaataaaaaa tagtactaag ctgatgtgtc | 1620 |
| aatcactgaa tgcattagtt attggaaaag tgactgctga tttagtatat ttagattaga | 1680 |
| gaaaataaat acttgtaatc attttcttta ttagcaatgt tgaagtgaaa aaaaaaagaa | 1740 |
| gaaaaagtg tatatttatc atactcatag tgggaaattg ataattcaaa attgctgata | 1800 |
| aacgttatga agaaggtgg aggatc | 1826 |

<210> SEQ ID NO 102
<211> LENGTH: 1590
<212> TYPE: DNA
<213> ORGANISM: Artificial Sequence
<220> FEATURE:
<223> OTHER INFORMATION: sequence of STAR A18

<400> SEQUENCE: 102

| | | | | | |
|---|---|---|---|---|---|
| gatctgttga | ttggttaaat | cgacgatctc | aacggcggag | gaagtgacga | tgaaggcgcg | 60 |
| gcagagagga | caattagagt | gagatttcaa | ccaagtatca | atacaaggaa | cgtgaaacgc | 120 |
| gtggttgcat | ttaggtaaca | atctcaagct | ctcgttctct | tgaaactcgc | ttaaacaaac | 180 |
| agagcaatct | gaagattcaa | caaatccatc | catctttctg | tatttgtaaa | cagttatcga | 240 |
| tttaatcaga | gattcatcga | gtccatcgcc | accaccacca | ccaatcgttt | gattcggatt | 300 |
| cgtagctccg | ttgttgttgt | tgttgttggt | tccttgccag | gtgtaatctg | atgagattct | 360 |
| gtttatagct | gcggcggagg | tagaggagga | gttgtggcga | cggcggtggc | agtatttgga | 420 |
| gatgagagtg | tagtagctga | cgaggatgaa | ggcgctagcg | aggattccga | tgagagcgat | 480 |
| gaggagagga | gagaaatcag | aggaggaaga | gtcgtcttcg | tcgtcgagat | agaaggaagg | 540 |
| aggaggaggg | aagatgacgt | aacaccattg | agggcaatag | acactgcata | ctccttgaga | 600 |
| acagtctctg | tatgaatcgt | atgttgtacc | ccatggatta | gggtttcctg | ttgaacccat | 660 |
| tatttgattg | ttggagaaag | atagagagag | agagcaagga | agaagatgga | ggtgtcaagt | 720 |
| gtctctctcc | ttttctttg | ggctctgctt | ttgtctggta | agtgtctatt | ttttatttc | 780 |
| gagttaattg | gtattattag | aggagataat | gaataaatat | atatgttcat | gaaagctttt | 840 |
| gcatgatggt | gttaatacta | attgaatgat | gtttatagtg | aatgttctac | tttatcaaat | 900 |
| ttttatttct | agtatgaata | aaggtgtaga | atttgcttta | ttcatttta | ttctttagct | 960 |
| ttctctttat | gcttccattt | tttttaaga | taaattaata | cattagtaaa | ataaatggag | 1020 |
| ttcatttttt | tttttttga | tttatttg | agaaatgaga | acgtaacata | agaagtgttt | 1080 |
| tagtgttgac | gaaataaaaa | gagagagagg | gtttagtcta | tttcaaggca | taaaaaaatg | 1140 |
| gttggtgaag | tgttgacgaa | ggtggaatac | tataacatgg | gccacgtgga | tgacaaattt | 1200 |
| actcctcgac | gtatctatta | aagttgtggt | cagaaataca | gtacaattta | ccgactacct | 1260 |
| acatggaaga | agaatatttt | catttcattt | caactacagt | agtataacat | tcacgttata | 1320 |
| cgattttca | tttttgtttt | gtaatcaaag | taatgatttt | ccaaaaaaat | cattgctatg | 1380 |
| attcgaatac | atacagtttt | atattagttt | acatatttat | gacaactata | atacaaaatt | 1440 |
| ttaatagttg | ttcaagggac | gattgatgtg | aactcgccaa | ccatatgccc | tacgtacaaa | 1500 |
| ataacatatt | tacatgtaga | agttgaaaat | aataataata | aagtgtgatt | aaaaacaatt | 1560 |
| atacaaatgc | taacaatagg | ctacgagatc | | | | 1590 |

<210> SEQ ID NO 103
<211> LENGTH: 706
<212> TYPE: DNA
<213> ORGANISM: Artificial Sequence
<220> FEATURE:
<223> OTHER INFORMATION: sequence of STAR A19

<400> SEQUENCE: 103

| | | | | | |
|---|---|---|---|---|---|
| gatcttgatg | tgtgttttgt | gttttttgtta | ttgcaggatg | tatgtttcat | agtgagacag | 60 |
| ggcttaagag | ctttgaccat | ccgactaata | tgatgaaggc | aatgccgagg | attgatagtg | 120 |

```
aaggtgttct ttgtggagct agtttcaaag ttgatgcttg ttctaagatc aatagtatcc       180
ctagaagagg aagtgaagct aactgggcgc tggctaattc tcgttgattt tgcttctagt       240
ttcgttaact cttgcttctt tgttgcgttt tcttttatg tactcttgtt tatgtaaata        300
tagccttatg aagacgataa agaaataaaa ttgatttgct tcttcgtgac atagcagtct       360
ttacttagac aactgtgtga taaattcgca atctcactct tgatagata agagggaggg        420 aagaaagcag tggtaaagac aaaactgtgt tgattttgtg aatttagaag tttacaatag       480
caaaaaagaa actttggtcg acttttatca ttcatcgttc cacatgtctg taaattcatc       540
aggctccaat gggtttgaga gttcatgcat cttcttctt gttttgcct ttattttctt         600 agcaaatttc ccagctttat ttcttttctc caaagctcga atctaaaagg caggaaattg       660
gaatatatga gaactctgac agataatcat atatagcaat gtgatc                     706

<210> SEQ ID NO 104
<211> LENGTH: 2064
<212> TYPE: DNA
<213> ORGANISM: Artificial Sequence
<220> FEATURE:
<223> OTHER INFORMATION: sequence of STAR A20

<400> SEQUENCE: 104
atcgtttcaa agcatggtct aatgatgatc ctgatctccg actgatccaa taacggttaa        60
gcaacgctgt ttttgatcct ccattgttgt ttgccatcga tcaacactca gaaataaggt       120
aattaacgca tctcgagact cattgtttta acaatctttg ttttgtttct tccaaattat       180
tctcgtgaat atccgtaatc tctccgtctt ttaatgaaca acacatatca tatgcttttg       240
tttgttttgt tttgtttttt caacatttca ataattttgt ctttttttct tcgatttaat      300
ttgtttattt cctgctataa taaacgaaaa ctataattcc atgtaatgtt cgttgttgtt       360
catagtgatt tatcataacg agcaacaaca taaaaatcaa gagaataaga aattagagtt       420
atgctgctta tttgaattag acaaaaccta cttttacttg ttaaggaaat gaaaagatgt       480
taataaagat gagcacatcg tacgtggcgc acgtggaagc acttctgtac gacggaccca       540
gtccaactcg aaccccacac acatagcaaa ggttgttaag ttggctcgta ggtgaattta       600
atacctgtta tttcctttat agctggctaa ttacctaaat tcgatccata taacacatt       660 cctactatgc caacatttaa ccctagtcaa actaattaaa acgtttctta cttttggcc       720 tattaaaacg tttcattatg ttccgcaaat agtatgaaat atataaagat tttctaacaa      780
aaaattacta agaacagtta gactgattga gattgttttt atttcctttt atttaatttt     840
cttttattat actctgttta tttgtgttta ataattagga ttctatttgt cttgtcttgt      900
ttgctatagt tggagttttg ttcataaaga atggcgttta atacggctat ggcgtctaca       960
tctccagcgg cggcaaatga cgttttaaga gaacatattg gcctccgtag atcgttgtcc      1020
ggtcaagatc tcgtcttaaa aggcggtggt atacggagat cgagttccga caatcacttg      1080
tgttgtcgct ccggtaataa taataatcgc attcttgctg tgtctgttcg tccggggatg      1140
aaaacgagtc gatctgtggg agtgttctcg tttcagatat cgagttctat aatcccaagt     1200
ccgataaaaa cgttgctatt tgaaacggac acgtctcaag acgagcaaga gagcgatgag      1260
attgagattg agacagagcc aaatctagat ggagccaaga aggcaaattg ggtcgagagg      1320
ctgcttgaga taaggagaca gtggaagaga gagcaaaaaa cagagagtgg aaacagtgac      1380
gttgcagagg aaagtgttga cgttacgtgt ggttgtgaag aagaagaagg ttgcattgcg      1440
aattacggat ctgtaaatgg tgattgggga cgagaatcgt tctctagatt gcttgtgaag      1500
```

-continued

```
gtttcttggt ctgaggctaa aaagctttct cagttagctt atttgtgtaa cttggcttac    1560
acgatacctg agatcaaggg tgaggatttg agaagaaact atgggttaaa gtttgtgaca    1620
tcttcattgg aaaagaaagc taaagcagcg atacttagag agaaactaga gcaagatcca    1680
acacatgtcc ctgttattac atccccggat ttagaatccg agaagcagtc tcaacgatca    1740
gcttcatctt ctgcttctgc ttacaagatt gctgcttcag ctgcgtctta cattcactct    1800
tgcaaagagt atgatctttc agaaccaatt tataaatcag ctgctgctgc tcaggctgca    1860
gcgtctacca tgaccgcggt ggttgctgcg ggtgaggagg agaagctaga agcggcaagg    1920
gagttacagt cgctacaatc atctccttgt gagtggtttg tttgtgatga tccaaacaca    1980
tacactaggt gctttgtgat tcaggtaata tgtgttcaaa gttactactt tcaagcaaat    2040
cctctgtttc ctcacatcat gatc                                          2064
```

<210> SEQ ID NO 105
<211> LENGTH: 1834
<212> TYPE: DNA
<213> ORGANISM: Artificial Sequence
<220> FEATURE:
<223> OTHER INFORMATION: sequence of STAR A21

<400> SEQUENCE: 105

```
gatcttcttc tatatatacc ggtataagtc aactggcggc tgaacaaagg tcgtgaggta      60
acaaaatatg agacaaatct acaggtcaga ttgggttctg aattctgata aggtcttaaa     120
aaggagctca ccaacccaca aaaccatgga ttgaacaagt acaggtcatt gccttcattt     180
tattctttac ttttctaagg ctcaagcttc ctttattgcc tttaataaca atatactaat     240
gagtattttg cactcagtaa caaaattcag gagagtaatt ttttgcccta acatgttact     300
tttatgtgtt aagagtttag aattttggat ctatgatttt agttttgtt agggaatcat      360 attcatataa ataaaatatt gccattgact taattgttgt tattcaccta atttctctcc     420
aaatttggtc atttacctca gttgattcta tattatactt gctaagtgtt ctttgtctaa     480
ttctctatca ttgtttgatt taataataac caaaccttaa gacttggaag caaagaagag     540
agaaaatccc aattaatttt taataattca agagagata ttgagtgact tccactaata      600
caaagaaagc ttggtttgtg caatattttg cggttaagct attaattgct gaggcaacac     660
cttttcacac tttgctttcc ttcttccaag ttttcaactt ttctttctta ctctttctat     720
taatcaaact gcaacacaaa atcatttgg ataatacatg tttagaagat gattaagctt      780 tagtttttatt tcaagattat cataattgtt atctgttgtt acctacattc atataatctt    840
atcaaaaacg ataagacaa aaggggata caatataggt ttttattata agaaacagg        900 aaagaaagaa aagggttttc accaaacgaa attagttcaa tcatttaaat tatctttatc     960
cttatgatta gtgtctttat atctgtcata tgctgcttct ccttccaact tcctttggat    1020
tatattctct tctctttatt ttaatttcca tttgtggtag ctgttttatt ttttgtattt    1080
tcacgccgtg tccctttaaa ataatattaa ctacaccact aatgttggaa catgaaaaac    1140
atgaatgagg taattatgat gatgaaccaa atgttaagga caagctcggt gtaactaaga    1200
agataattag tgaaacagaa caagtcaata acttgtaagc atttcagaat tgaaaataaa    1260
gataagggag gatgaatatg aatttagtaa atgggtaatg aaagtgaaag aagaagaggg    1320
aagggttggt tactgtctca agggtttgaa atggagacgg ttgcttgaga atgaggaaaa    1380
agagttagta agttttttaac tctctctttc tctctccctc tctcttttc aacgtcaatt     1440
```

```
cctttaagga atggcctctc tctctctctg aaagtgtgtg tgtatatatt aaacgactcc   1500
atttctcctc tgcttagacc aaaactcatc ttctatactg caacaaagaa ggaggagccg   1560
ttgagactac aaaatgactg cagcagaaaa ccctttgta tctgacacct cttctctgca    1620
aagccagctt aaaggttctt atttttcttt ctgtttattg ttcatcaacc cttatgagta   1680
atttgcttga tgttgaggtt gttctgcttt cttttaattc cactctgcag aaaaagagaa   1740
agagcttttg gctgctaaag ctgaagttga ggctttgaga acaaatgaag agctcaaaga   1800
cagagtcttt aaggaggtaa catgcatgat gatc                               1834
```

<210> SEQ ID NO 106
<211> LENGTH: 751
<212> TYPE: DNA
<213> ORGANISM: Artificial Sequence
<220> FEATURE:
<223> OTHER INFORMATION: sequence of STAR A22

<400> SEQUENCE: 106

```
gatccattaa gaagcagccg caaaatcgga ttgagaacag gaaaagaggc ggttaaggct    60
tatgatgaag tcgttgatgg gatggttgaa aaccattgtg cccttagcta ttgttcaact   120
aaggagcact cggagactcg tggtttgcgt gggagtgaag aaacttggtt cgatttaaga   180
aagagacgaa ggagtaatga agattctatg tgtcaagaag ttgaaatgca gaagacggtt   240
actggagaag agacagtatg tgatgtgttt ggtttgtttg agtttgagga tttgggaagt   300
gattatttgg agacgttatt atcttctttt tgacagaaat acattgaaaa ctaccgttgc   360
taatttgata ggtatacata tatagacatg tatatattgt ataattatat gtcaagatta   420
tttatttatt ttacattttt cacaaaaaaa aacgttaatc tattttttctg tcacaagtgt   480 gttttttattc atactacata ctacaacgcc aatttaacat gccaaatata aaacatacat   540
gggcaaaggc ccaacagcca gtttaaagaa ctttgtctga agagaaagtt gttgtatata   600
tcacaaggga tatgtggtaa ttgggaaaca tgttgggttg acacgtggga aattgaagga   660
gatggagttt ccgtcactgg tagaatcttc taacactaga gagcttcaat tcaggttgaa   720
atcgtcagaa aactaatgca gacggtagat c                                  751
```

<210> SEQ ID NO 107
<211> LENGTH: 653
<212> TYPE: DNA
<213> ORGANISM: Artificial Sequence
<220> FEATURE:
<223> OTHER INFORMATION: sequence of STAR A23

<400> SEQUENCE: 107

```
gatcaaaact tagtcaaatc gttccttcca ttttctttca gtttgattcc actttaatgg    60
cgtcataatc atctcttaaa tcaaacaatg actccactat ctcgtttccg atctcttgtt   120
acataaagtt ttctgtagca ttgagattgt ccttttcgga attgctttta tttgcgcagc   180
ttgatggaaa caacaaacag tgtagtagtt tagtagaaag actgagagat aaaacgaaga   240
gtcaagttcc taagtccatt acttgcatta accgcttaga gatatcgcgt atagcaccat   300
tacacgcaac gatgaatagc ccgaaaggat ttggacctcc tcctaagaaa accaagaagt   360
cgaaaaagcc aaacccgga aaccaaagtg atgaagacga cgacgatgaa gacgaagatg   420
atgatgatga agaagatgaa cgtgagagag gtgtaattcc agagatagtg accaacagaa   480
tgataagcag aatgggattt acagtggggt taccactctt cattggtctt ttgttcttcc   540 cattcttta ctatctcaaa gtgggattga aagttgatgt gcctacatgg gttccgttta   600
```

```
ttgtttcgtt cgtcttcttt ggtacggctt tagctggtgt gagctatggg atc        653

<210> SEQ ID NO 108
<211> LENGTH: 548
<212> TYPE: DNA
<213> ORGANISM: Artificial Sequence
<220> FEATURE:
<223> OTHER INFORMATION: sequence of STAR A24

<400> SEQUENCE: 108
gatcagactg aactcgtgta ctctgagcct tgcttcttgt agctcttttta gctttcacat   60 tttcatcagt attcacatca ttcctgataa ttgtgccaga agtcccacga ctatcttgtt  120
gctcactaat ggttgctgct gcagatgatt ccatgttgtc ctcttgtgaa accccaatgc  180
ttcgtctagc aactgtattt cttgcacttc ctgctttgcg ttttttacat ttggatgatg  240
caactttaac tttaggtagc ttcttttgag taagatcaat ctcatctcta cctaggacct  300
gcaaatcgat gaaatttgag ttcatttcaa cacacttgat gacactatca tagaaaacaa  360
aaagaccttg ctgtaccaga gtgaagaaca gcctttacct tggccttcac aggactaggt  420
agaatctccg gagaacaagg cctctgagtc cattcaaaca tttcgctatc aaacatgtca  480
cctggattgg gcttttgttg ctcgtcttcc tgaaacattc atcggaaaaa agtaagatc   540 aaaggatc                                                          548

<210> SEQ ID NO 109
<211> LENGTH: 1000
<212> TYPE: DNA
<213> ORGANISM: Artificial Sequence
<220> FEATURE:
<223> OTHER INFORMATION: sequence of STAR A25

<400> SEQUENCE: 109
gatccaaact ctgcaatgta tattacgaag tcgtttgata taacacctct cttgataaaa   60
gatgattaga acctaaagta atttttaaaat atggtgaaaa attagactct ggagtatat  120 aaatggctca atctgtattg cccgcaccgc ccaaactccc atggcaaatc cattgacgaa  180
accaaggtaa aaatcacatg ctttgagcgt tttttttaaaa cagaagtgta agcttaaatt  240
ttttagttta atagtagtaa caaattcaac cttgtgaaga gatttattaa taatattaaa  300
atcattcccc taattatttg ccttgagttt cgagccttct actgtaccac tcacacatta  360
aaaatcatca gactattcaa actttcttac atggttgatt agttcatctc atatatgctc  420
agtatcatac tcttgcagat taattttttca ttttaattat caacgaattt tttatttaat  480
tattcatgac caaaatacat ttattttttt taaataaaac aaataataaa tttggaagtc  540
aaaaatacaa tcaatagaaa aaaagtatg acagtgatag ataatatttg cagaatatta  600
tgtgaaagct attttctctg taacaataaa tgagaaaatc tttattattt tacatgaaag  660
aaaaagaaaa caaacagag atattttttcc agctgaaaag aacaaacatc tctcattgat  720
gttcagtgaa cttgcaccaa acttcacttc ttctatactt cttcatagcc acaaactcag  780
ttctttgcaa gaaacacaaa cttaagtatt caaaatatcg tcatcatgtt ctcaagattc  840
catgctctgt ttcttctcct tgttctttca gtaagaacat ataaatgtgt atcttcatct  900
tcttcttctt cttcttcttt ctcattctct tcattttctt cttcgtcttc ttctcaaact  960
cttgtcttgc ctctaaagac ccgaataacc ccaacggatc                       1000

<210> SEQ ID NO 110
```

<211> LENGTH: 1926
<212> TYPE: DNA
<213> ORGANISM: Artificial Sequence
<220> FEATURE:
<223> OTHER INFORMATION: sequence of STAR A26

<400> SEQUENCE: 110

```
gatcctcgat tcttatctgg atacagaaga aaacaccttt ttgtctttta agtactcgga      60
gaaatctgag ggtatctttt tcttgagcag atggaggtga agtcctgagt tggggaggag     120
ggggctctgg aagacttggc cacggtcacc agtccagtct tttggcatc ttaagaagta     180
acaggtttgt tttacttaat ttcaatatcg ttttgtctct ttctcatgca ttttttgctc     240
acaagaattt tcccatttcc tcctttactt tatcatgatt ccttcataat tttcttgtat     300
tgcactgtaa agtatccccc tgattgcagt gagtttactc caaggcttat caaggaactt     360
gaggggatca aggtaatcta gtggtgaaga atatccacct tggatgaaga gtttctagtt     420
acctagtggt ggttttaatc tttagacttt catgcttatg tttttccatt ctttctgtcg     480
agcactaggt cacaaatgtt gctgctggtc tgctgcattc agcatgcact gatggtattg     540
atttactttc ttaaaagtat gaatgttgtg ccatttaccg aactttatga ggtttgtttg     600
caaatgcaga gaatggctct gctttcatgt tcggagagaa atctataaac aagatggtaa     660
gaaaatgtct ttttctttga tttctgtggt catatatgtg aagctatctg atgggaaaat     720
acagggcttt ggaggagtaa gaaatgccac aacaccatcg attatcagtg aagtaccata     780
tgcagaagaa gttgcatgtg gtggctacca cacatgtgta gttacaagta atactctctt     840
attatatcgt tctttctttg atattgagtt tgcttgtata ctgcaaatgc ctgtcctgct     900
caaatttctt tttgttattc tttatagagg cccaaaactg ctctttagtt tctgctaaat     960
ttatgaacat attgtgtttg taagatggtc gataacaact catcgtttga tgtttccttc    1020
gttttttggaa ggaggtgggg agctttacac ctggggctca aacgaaaatg ggtgccttgg    1080
aacagagtaa gttacatacc ccgaaaaaat agaatgtttc cccataagat gaaaacaagg    1140
ttcttgaact gtacctatac tcttatttca aaaaattcag ttcaacgtat gtctcacact    1200
cccctgtgag agttgaaggt cctttcttgg agtctactgt atctcaggta tcttgtgggt    1260
ggaagcacac tgcagctatt tcaggtagca tctcttttga gtaaaacata tttgtttcct    1320
ctctcattgt ataagttaat tcaactcaat ttctgaaact tgtttgcaga taacaatgtc    1380
ttcacctggg gctggggagg atctcacggc acattctctg ttgatggaca ttcctctggt    1440
ggacaattgg tttgtttcat catcttatct tattgatcaa atctctgaaa caacattttc    1500
aagtgtcgaa gagaataaat atggtatgct taatatgtag ggccatggta gtgatgtaga    1560
ctatgcaaga ccagcaatgg tggacttggg aaagaatgta agagcagtgc atatatcttg    1620
tggcttcaat catacagcag cagttcttga acattttga agactcggtc tcaagttaat    1680
atcatataca gatgtttagt ttattcttgc ttaaacatct atagactaaa aaataataa    1740
gaaatttaca ctattgaata gcgatcaatt acaccattgg ttctaacttg aacaatttag    1800
taaataggtg gaatattctt gtcgtgtaaa ttattgattt tatttattta ttttttgaaaa    1860
ctacaacaaa cgatagaaga gttgaggaaa tctctttgta atcataatta tgagaaaatt    1920
aagatc                                                               1926
```

<210> SEQ ID NO 111
<211> LENGTH: 1109
<212> TYPE: DNA
<213> ORGANISM: Artificial Sequence
<220> FEATURE:
<223> OTHER INFORMATION: sequence of STAR A27

<400> SEQUENCE: 111

| | | | | | |
|---|---|---|---|---|---|
| gatcggaatc | attttgggag | tttgaaggaa | ctaaacataa | tatgcatgtc | gaagtcaact | 60 |
| tattgcaaat | aattttgaaa | tgattctgaa | ttggaaattc | atgaagctta | attattttat | 120 |
| ctaaataagt | ttaatatagg | tttgagtgag | atatcgagat | taaatgataa | gagtcttttct | 180 |
| tcgaggagac | attagaattc | tacacaaaaa | tcgaaattaa | tctagtcctt | gacaatcagt | 240 |
| tttcaattaa | tcaaaaacct | ataaaattca | actcaaaacc | aatcgtatga | aacttcatta | 300 |
| taccatataa | tctggttact | tagcttaaat | ctctacccgg | cgatgtttca | tgcttgagag | 360 |
| actaggtaca | taggcacta | ggagtactgc | atatatggtt | acctcatgag | ttctcatcgt | 420 |
| aaaatcatcc | aataaaaaat | ggtttcctgc | ttaggtatac | ggtataccat | cttgtatcgt | 480 |
| taaaatttat | agctcagttc | gttgctaaca | gtcaaatacg | tctttccagg | gtaaaaaatg | 540 |
| tggaaatttg | ttccactgta | aaacctaat | aattttttgac | attaataatt | aaagggatt | 600 |
| ataatgtaat | atatacaaag | ataggggaga | cagagacgaa | ggcccacaca | tctttaacaa | 660 |
| aagaacaaca | agcccgtgac | cccaaaataa | aactagcttt | cagatttatt | attttttcatc | 720 |
| tgacataatt | gcaaccgtta | gatttcattt | ctcaggtccc | attctgactc | agatccaacc | 780 |
| gtccatattc | ctctagtgtc | ttcaatagtt | gggccccttt | tctttttcct | ctcgccgtac | 840 |
| actctccttc | cagcgccaac | gccaccgccc | gagccacttc | ttccgccggc | gccaccgcga | 900 |
| tttcctcgcc | ggaatcccct | ccttcgccgc | ctttcccgta | gaccacgaa | aggatgctta | 960 |
| tggcgtattc | tctccctcta | ccagccaatc | tcgccatcac | cgctaccatc | gccggcaccg | 1020 |
| tcatcgcgtg | agcgcgaacc | tccgccgctc | cttctgccgt | tgtacacatt | agctcaagag | 1080 |
| cagctaaggc | tcgctccacc | gctgagatc | | | | 1109 |

<210> SEQ ID NO 112
<211> LENGTH: 1659
<212> TYPE: DNA
<213> ORGANISM: Artificial Sequence
<220> FEATURE:
<223> OTHER INFORMATION: sequence of STAR A28

<400> SEQUENCE: 112

| | | | | | |
|---|---|---|---|---|---|
| gatcgaactt | tggtaacatg | cttgcttact | gctttctatt | gtctgcaaaa | cctctgttct | 60 |
| gggtgacctt | ctggccctc | tctctcgaag | cttcagaact | atggaggaga | gattggataa | 120 |
| aggagacaaa | aggtgtggtg | tggcgaaatg | ttagggtacc | ggcaattgtg | tatgtatgag | 180 |
| ttgattttgt | tcttttctca | taaagaggat | ttaacaaagg | atgagaaaac | aaatccaact | 240 |
| tgagtactac | gaggagataa | aagctttat | tgggtattga | gtattgacac | gttgttgaaa | 300 |
| gtctgataca | ttttagactt | ttactgcata | tgtccaaata | tttagattttt | ttttcgttt | 360 |
| ctcaaaaaag | taacttgttt | aacaaaaaaa | aatcgttatt | gggcttttcg | tttcttttat | 420 |
| attgggcctt | gagccttttt | agcttttgta | ttttagtcc | ttttcgggtt | tatttatta | 480 |
| ttaataagat | accaaaaaca | taacaaaaat | gtagttttgt | atttttaacc | tagtctttta | 540 |
| aatatttaaa | cttaattaga | aaattctat | ttaaaatatt | ataaaaaaaa | catgattttg | 600 |
| tgattttccc | atattttgtg | taactatttt | tgacaagctt | tgaaacaac | aaagacaaaa | 660 |
| tccatgtgat | aaggtcggtc | aaaaatcttg | cgtagtagag | gagttaaaga | ttttttggatg | 720 |
| gttacaatgg | tatactctta | tttgatatcc | catcaatggt | atatagcttt | gaatggtagg | 780 |

```
acaagtgaga gtaaaatttt ctcatcattg ctaagtttta ttttaggttc tacattgttt      840
cacccttctt aagtatccta ctctcaacta gaaaaaaaaa ttgtgagggc ggttttatcg      900
gctggaatgc agctcatgta gctcccacga cggagttttc tggctaagaa actcggacac      960
aacgttggcc tccaatatct tcaaggcttc ttcattcgtc accgacctcg gtgtcttata     1020
ctgactcaca gaagagcctc tagacagaaa gaagttcatg agcttgtcga aagcgccagg     1080
cttaacaacc ttaatctcaa gtggtccaat gttcttatca ttctttcgtc cttttctgta     1140
aaccgcgtcc agagactcct caatggtgaa gcagcattcc tccaaaacat tctggtcaag     1200
ctcaagcttg gcgtccttga cttttctccc gagttcccag tagagcacgt agtgacctgg     1260
atacgaggag gaatccacac ggctagtgaa atccatgagc attaggtcat gtggctcaag     1320
caggagactc gcgttagtca ctgccttgag gaggtcttcg tcgtaggtct tgtccatgtc     1380
gatgctcaga caactttct gtcttcccac gaaatgaaac tgtggcgcat tgttgtagaa      1440
accagtcact cttaaaacgt cccctaaacg gtacctatac aaacctgtat aaagaatttt     1500
gatacacatt aagaaaatta ttaacatgtc atttagtttt gaaattgaga gagtaaacaa     1560
gaaaaaacac ttaccagcaa acgttgtgac aacaggttca taatcatgac cgattttaac    1620
atcgacaaga tcgactacaa caggattctc tgcgggatc                            1659
```

<210> SEQ ID NO 113
<211> LENGTH: 874
<212> TYPE: DNA
<213> ORGANISM: Artificial Sequence
<220> FEATURE:
<223> OTHER INFORMATION: sequence of STAR A29

<400> SEQUENCE: 113

```
gatcagagtc acaaccatag gagtcggaga cggccatgca tgtgtcttga tagaagaatt       60
aaccggttct aaatctgaaa acgaatccgg tcgtctcgaa ccgaaatcaa taaccggtcc      120
ggtcaaagaa acggttgcac gagtgaagga aacggttacg aaaacggagc cgttaatatg      180
cgatgacgga gtgacaaagg ggaagctgac gatgtgctac gaggtagacg ttgacgttga      240
cggtgggagg tgtgttaacg gagatttaac ggcagttagc tacggaggag gtttgggtaa      300
ttgtggcggg gattggtggg agaaatggga tggagtggtg aggatgagaa atggtgatga      360
cagttggtac cgttacgtgg atttaacggt gattaatgga aatgtggtaa ggttatggga      420
tgacaacaaa acactagtaa cggcggcatg tgtctaaatt agagaagttt catatttcgg      480
aaagttttta aatcttgaga agctttcttg gtttgaagtg tttttttttt gttggttgat      540
taagttgtaa tttgtaaata attttcacac aagagaccaa gaaggaacgc ttaaatcaat      600
atcaattggt gttgattccc agcttttttct agtcgaactt aggtaacacg tccattgcga     660
tgatgaattc gtgacaaggg gtcaactatt tgaacacaac aaacaagtgc gttttcttgt      720
taaggcccat ctaaaattga ctacacacat ttacttttag gcccatttta aacttgactg      780
tagcctgtag gcatgtattt gttcgtgtta ctcccagcct caaacccgca aaatccacga      840
attcttctta cttagtctag actctggtct gatc                                  874
```

<210> SEQ ID NO 114
<211> LENGTH: 2138
<212> TYPE: DNA
<213> ORGANISM: Artificial Sequence
<220> FEATURE:
<223> OTHER INFORMATION: sequence of STAR A30

<400> SEQUENCE: 114

```
gatctggcta atccgtttag cacacaacca gatgtaacat tggttgcaaa gattattgaa      60
gagtctcgat ctaatgtaac acacctctgc gcattcagga gtgcttacgt caacacattc     120
cgggaacgaa aaactgttag cgtatgtgta ttttaaagta ttaccatatt tctttatatc     180
ttctagcacc tcctcacaaa tgtcacgtgc gtcctccgat tccaaagcat aatggttgct     240
tccgaagagc cgaaggtaga caccacccat gtgagcatta ccagcacata tgtaaagaat     300
tgcgcatgca agggttgcag cggcgttcct tggggcgatt cgctctaagt gtaggatagc     360
tccctggatg tcagactcat gtgtaacgag acgcagtcct tcatggtaaa tagccgtggg     420
gttaccagct tgtaagcacc gtttgaagaa gggtctatag cgaccttcgg agttgatgtc     480
atttggatcg tggcctgccg cgtagaagtc atcgggatcg tcgcacatgc tgaaaatgtt     540
tgcatttttg aggacatccg gacagtagac aatgtctctt ccacgaggac cggatttcaa     600
cataggtccg aggtaccacc aacatttgtc agccattttc ttggctatct tcgcaagcaa     660
atcgtcagga atatttgggt ttgtcatatt taggagtaag gtgtttcgag aaaatgaaat     720
ttgaacactt aaataagcat cattgaagat atggttgggt aagttatggt tgtatttatt     780
gcaaaggtat taagtgatga tgtgtattca tattgtcaaa tcaaagtaat agtattccat     840
atataatttg ttatcgttgt tatgagcaac ctctttttat taacagctta aaactagacg     900
tgtacgtttt actgacggtc ttagtgtacg tccacattta catttctaca tttactcaac     960
aaacagtgta cgttgtagtg tatgttttag tgaacgtcca catttacatt tctacatttg    1020
cccaacaaac agtgtacgtt gtagtgtacg tccacattta catttctaca tttgcccaac    1080
aaacagtgta cgttgtagtg tacgtttaag tgtacgtcca catttacatt tctacatttg    1140
cccaacaaac agtgtacgtt gtagtgtacg ttttagtgta cgtccatatt tacatttcta    1200
catttactca acagacagtg tacgctgtag tgtactatta gtgtacgtcc attcataaat    1260
atcaccattt atgagacaaa ccaaagacct catacgtttg catgtgttat tttttagtgt    1320
acgttagagt tgatatctca tgctagtgaa cgtccatatc tagttttccg agacaaagaa    1380
aaaacctcta agtattattt ggtagatgca cgtgtacgga gttgtggacg cttagatttt    1440
aatatccaaa tttacattta ctgcagtgtc taaatatcat atgtgaattt ggctgaaaaa    1500
tattcaactt gagaaacata acacaccttg caaatttctt aagcaataat ataatttcaa    1560
cataaacata aacaacatag tagaaggctt atcataattt gaaacatgac atagcggata    1620
acataaacaa acatataaag tagaatggaa taactatagc atttgactaa cacgcctggc    1680
acacgaccag aggtaacagc ggttgcaaac gttttggaaa gctcctgata ccatgtaaca    1740
atataaggcg caaggaggca tactaattcc atggctggta ggataagaga acgtaggacc    1800
atatgtattg ctgtatggag ggtcaaactt ctttatttcc tcgatgaact catcacccaa    1860
aactcgagtg gcaaccgagt ccaatggata atggttgcgg gtgaagagct gtagaaacaa    1920
gccgcccata taatcatacc cagcacatat gaatacaatg gcgcatgcaa gtgttgcatt    1980
tgctcgtact ggagcatgac gctgtaagag cctgatggct ccattgatgt ttcgttcatg    2040
cgttagaaca cgaataccct cgtaatacac ggccgtggga ttattagctg caaaacacct    2100
taagaaaaat gttcgatgtc ggccttcatc agcggatc                            2138
```

<210> SEQ ID NO 115
<211> LENGTH: 2092
<212> TYPE: DNA
<213> ORGANISM: Artificial Sequence
<220> FEATURE:

<223> OTHER INFORMATION: sequence of STAR A31

<400> SEQUENCE: 115

```
gatcaaaaga atcgtacttg aaatatttag tggaacgcat atgtcagagt tacagatatg      60
gtttaactct ttttatctcc ttttttaat ggtgtttctc tttttatctc ctataatctt     120
ttgggaattt tttattatta aatattaatt aaaaagataa attcttagag aaaatcccaa     180
ctgacttgtt aactagtgag acatatctta tttattctct gcttatctaa aaagaaaatg     240
aaaaagaaaa aaaagtata tattagaaga ttaatataag tttagggga aaatgattat      300
tattactatt tataaaatta gtatatttca aaattgtaca attaattact aagccttaaa     360
ataaaaatgt aaagaagat tatcatcaag aatagtatac catctttgtt tcaaaagaaa     420
agtttactaa agaaaaaac ttttgtttaa tttctactaa agctgaaagg aaaatgattg     480
tcaatttgtt attattatta tttatatgat agatttctta agaacgtat agagttagtt      540
acaaattcta aattaaaaat tgtatgataa gattatctta agaaagttat acaatatatt     600
cctaattcta aagaaaatg gttatttttt tggaatagat atacacaaca aaacaaattt     660
agtataagaa gatatgttag attaactaaa taaacatctc aggcatgaaa ctggattagg     720
ttaaccagag gtccagagac ctatatatct ctaggcatta gggtttaact acggagcaaa     780
gcctcataat caagtttata tcttgcgcat ctttagcaac caatcaatta tctaagaagc     840
catgactaat actaatgttg ctgctacaaa gcctctttct actatggtcg atgaatctcc     900
tagccttctc cgtgattggt ggtgagactc tagatcaatg attttttcta ctttttttccc     960
attactatgt tatgttacgt aacataagat ggattaaact gaatctgatc ctcttaaatt    1020
atattggttg cagtatgaac aagaacctac aatacaactt tgcgatgaac ttcgtcatga    1080
taatcatcaa cattgaagca atcttgtcta tcagaaacca cgaaaatcac gtaaggaaag    1140
attattcaac gatttgata atttccggta tgttcttgcc tttcgcctat taagttgcgt    1200
ttgttgggtt ggcgcaatca gggatgtgac attatgtgaa ctcgcctaca tcttcggacg    1260
catcagtcac aacataggct ttattttctt cctagaactc ctctattgta tttctcccta    1320
cttggctcta ctcgttggtc tacatgtagg ccaatggtat ctaacttcca tgattggact    1380
gtctctatgg gaaggaatgc aagcattacg aactgatatt taacctcgtt taatagtaaa    1440
atctaaactt atttagctgc atattttggt ttaaggcaat cgagaatgtc ttagcatcta    1500
aagcttactt cgtgggacgc atctgtcaca cgttcggctt ttgtattttc gtccacctcc    1560
tctattcggt ttctcctcac ttggctctat acttcggtct cccttgtttg ctaggtttcg    1620
tagccgtcat gattgcacca agttgtccgt atcaatggaa aggcctatgc aacaaagtgc    1680
aagagttacg agactggtgg aagcatgtga atcgaccaca atcctcggtt gttattgttc    1740
aaggatctcc atttctaaga tgtgaatttt aggactcttt tatcccttt gccttttaaa    1800
ttggaatacc aacgtttatt atgtgggtta gttatgtgtg tatatgatat acaaatcaaa    1860
caacatatat aaggagaaga gatattgaat gttgattctt aatttacagg aacatgaagc    1920
tcgggtcttt ccgcaatgc catcaatatc cgaggcggtg cagttcttc gtcagacgag     1980
aaaccagaga gtctagtatc ctaattttga acaaatagag cataaggaa caagttatat    2040
agcttcacat aaccgaaac atgttttaag tttcaatatc aaagacaaga tc             2092
```

<210> SEQ ID NO 116
<211> LENGTH: 1290
<212> TYPE: DNA
<213> ORGANISM: Artificial Sequence
<220> FEATURE:
<223> OTHER INFORMATION: sequence of STAR A32

<400> SEQUENCE: 116

```
gatctagaca tatgtgtgag acgtttcatt gtaggtatct gaatgtaaag ctcaaagctt      60
taacctttga accgataaac ctctaaagct ctctctttc cttggatgag tctcacaagt     120
taagaacttc agtgaaataa tctgacttta ttgaacccaa acttgggtat cactgtttat    180
cttagcatta cagagttttg tttttgttat gtacattgga tttgaagtct acaatgtttt    240
tccaggttta taaaccggaa gaatatagcc gggttctagc tatctgtggt cctgggaaca    300
atggtggtga tggtttggtg gcggcgaggc atttgcacca ctttggatat aaaccgttta    360
tttgttatcc caaacgtaca gccaagccac tttatactgg actggtcact caggtttgtg    420
taaccagtgc ttaatttatg ggggatcttt gttagctttc tccgtttctt tactgcctgc    480
tgaatttgcc tgttttgta gttggattca ctctcagtcc cttttgtttc cgttgaggat     540
ctgccggatg acttgtcaaa ggactttgat gttattgtag atgcaatgtt tgggttttca    600
ttccatggta actattttg tgcatgaatc gttagaattc ttcaaagcat gaaacaatta     660
taagaagtaa attcatcaaa cttttgaaca gcaagttttg gaatcaaagt ctcagagatg    720
caccttattc atttgcatca tgtttcagtt ggcctttgaa aatccatttt ttgcacatgt    780
aggagctccc aggcctcctt tgatgacct catccggcga ttagtatcgt tacagaacta     840
tgagcagact cttcaaaaac acccagtcat tgtctctgtg gatattccct ctggttggca    900
cgttgaagaa ggagaccatg aagatggagg aattaagcct gatatgttgg taagtcttag    960
ccgaaatgct tgtgtttctc tttttctctt gtactcattt gttactatct gatataatga   1020
aaactacttt ataaattgaa catatttact cttttaggt atctttgact gccccaaaat     1080
tatgtgcaaa gagattccgt ggccctcatc acttttagg tgggagattt gtaccacctt     1140
ctgttgcaga aaagtataag ctggagctcc ctagttaccc agggacatct atgtgtgtta   1200
gaattggtaa acctcccaaa gttgacatat ctgctatgag agtgaactat gtctctccag   1260
aattgcttga ggagcaggtt gaaactgatc                                    1290
```

<210> SEQ ID NO 117
<211> LENGTH: 869
<212> TYPE: DNA
<213> ORGANISM: Artificial Sequence
<220> FEATURE:
<223> OTHER INFORMATION: sequence of STAR A33

<400> SEQUENCE: 117

```
gatcccgttc atgtatttt gccagttcga gttggggttg gttctgttta cttttttctag     60
tccatgtatt ttgcagacct attaaaacca ttctgttttt tttttggacc aacaaaaccc   120
atccgttttt agatacgaaa ataaaattt attaaaacca ttatttttct tggaccatca     180
aaacccatcc gtttaaagat acgaaatgaa attcgattga taaatacaaa ataaagttca    240
ccaaacttaa ataaaaaggc atagatggga ccaatgagaa agaaatttct tttctcctca   300
atttccccaa aaatatataa accttaagtt tacttttttg ttgcaaggaa aaacattaat    360
cttttttcaac tttctaaaaa caatcatttc aaacgttaaa ggaacctcct cctttcttta   420
cgcgtttgca atataaccca agaagaccgc ttgtttgtac aactttccaa aaaccaaaca   480
gtagtgtaat aaacctctga cttcttttt cttctctatt tttgtgggtg ataatcaatt    540
cactcggttt gaaatttcgt ccacttttca aagatgagtg aatgaaaag ccacgaaact     600
```

```
ttccatttct tcctctgtgt ataactctca ctgagtacga cttgccattt tctcatccaa    660
aaaaaatgtt tatccaaata catatttgtg aactttgctt ttaaaccact caagattctt    720
ccccatggct tcttcgtctt cttcttctcg gtctcgcacc tggagatacc gcgtcttcac    780
gaacttccat ggacctgacg tccgtaaaac attcctcagc catttacgta aacagtttag    840
ctacaacggg atttcgatgt ttaatgatc                                      869
```

<210> SEQ ID NO 118
<211> LENGTH: 921
<212> TYPE: DNA
<213> ORGANISM: Artificial Sequence
<220> FEATURE:
<223> OTHER INFORMATION: sequence of STAR A34

<400> SEQUENCE: 118

```
gatccatgct tttgagttta agtgatttat ttaagatcct ctaaactttt ttttcttcac     60
ttagtggtgg ttccagtcaa tttagcaagt aagatgttgt atgtgtcaat gctataactg    120
tgaattttca gctattgtag tttgattttt gtctttgtta gcttcaggtg tcttgaatct    180
gaatctgtgg ctatatttgg tgctcggtgg tgagcaggaa gggaggggga tattgtcagg    240
gttttaatgt acgtcagatg aatagagcaa ctaatgttac tggcagtaga aggaggggt     300 ttattctcag cgtccgcgtc tgggtatagt aagggattga cccttctttt ctctggtgat    360
aaagacgtag ataggcccat gagagttgtc ccgtggaatc actaccaggt ggttgaccaa    420
gagcctgagg ctgaccctgt tcttcagctg gattctatta agaaccgagt ttcccgcggt    480
tgcgctgctt ccttcagttg ttttggtggc gcttccgcgg gacttgagac cccttctcct    540
cttaaagttg aacctgtgca gcagcagcat cgtgaaatat catcaccaga gtctgttgtt    600
gttgtttctg aaaagggtaa agaccaaata agtgaagctg ataatggcag cagcaaagaa    660
gctttcaaac tctcgttgag gagtagcttg aagaggccct ctgttgcgga atcacgctct    720
ctagaagata taaaagaata cgagacgttg agtgtggatg gtagcgatct cactggtgac    780
atggcaaggc ggaaagttca gtggcctgat gcttgtggta gtgaactcac tcaagttaga    840
gaatttgagc cgaggtacgt gtgatatgtt ttcctcttat tgagttgctt aaatcccaat    900
acgagttaat ttaagtagat c                                              921
```

<210> SEQ ID NO 119
<211> LENGTH: 1140
<212> TYPE: DNA
<213> ORGANISM: Artificial Sequence
<220> FEATURE:
<223> OTHER INFORMATION: sequence of STAR A35

<400> SEQUENCE: 119

```
gatccatttc atatacatat taccaatttt ggcttttata ggtttgtatc cagaaggcct     60
tttcgtggct acgattaagg aaaatacgaa acaaaagtg aatttactact cttttgtagc    120 atggtttatt ctactttata tacctaagaa atatgagcaa caattacttc tgtaatgact    180
ttttactact tcgtagttgg tacaaactac aaaagattgt gttgttttta catgatactt    240
tataatatct atattaatat atttagtcgt gtttaatcaa aaaagcacca gtggtctagt    300
ggtagaatag taccctgcca cggtacagac ccgggtcga ttcccggctg gtgcattgag     360
ctatgatgat ataggcttca gcattggttg ggtccattgc attcttctga actatcagtt    420
gatgtatgcc acacctctga gctcttcttt ttttttcctc gtcaattaat ttttaaagt     480 tttgtctgcc taaaaacttt cttcttttg attaatcata ttaagcatct cggctataaa    540
```

-continued

```
aaccacggtc tactaactta acatgcattg gactagtttt agtggagagt gttcgagtta    600
aaatgagaag ctcacgattg cataacggaa catttgattc gctaggcatc tccatttgta    660
aaagtagcca ctccaataca aaatggtcga tgatggtgag tgggtgagac aaacccacca    720
ccacctcaag aagatatatt tctctggtta agaatttgaa tggttgacaa agaaacggtc    780
actctatata cttagaaaat atagtcatac atagacacca tcggtctagt tataataata    840
accactggat taatgcccag tgaaaataat tgagtagcca aaacatgaat ataacaatat    900
cccaatttac atacaacaac acaaaggagg ttttacacga ttctatagta caaactcata    960
acaacaaaaa atcacacttt tgtttaacag ttgcctttat ggctttacta cagtatcttg   1020
tccagggttt tcacacataa caatcacagt aaatcgtttc cttttctttg catcttccat   1080
tccttttgta cacgtaacat ctccggcttc ccgaccatca gctaagaacc agatgcgatc   1140
```

<210> SEQ ID NO 120
<211> LENGTH: 6
<212> TYPE: DNA
<213> ORGANISM: Artificial Sequence
<220> FEATURE:
<223> OTHER INFORMATION: palindromic DNA sequence
<220> FEATURE:
<221> NAME/KEY: misc_feature
<222> LOCATION: (3)..(4)
<223> OTHER INFORMATION: "N" stands for any nucleotide

<400> SEQUENCE: 120 canntg                                                                  6

<210> SEQ ID NO 121
<211> LENGTH: 6
<212> TYPE: DNA
<213> ORGANISM: Artificial Sequence
<220> FEATURE:
<223> OTHER INFORMATION: oligonucleotide

<400> SEQUENCE: 121 aaaaaa                                                                  6

<210> SEQ ID NO 122
<211> LENGTH: 6
<212> TYPE: DNA
<213> ORGANISM: Artificial Sequence
<220> FEATURE:
<223> OTHER INFORMATION: oligonucleotide

<400> SEQUENCE: 122 tttttt                                                                  6

<210> SEQ ID NO 123
<211> LENGTH: 6
<212> TYPE: DNA
<213> ORGANISM: Artificial Sequence
<220> FEATURE:
<223> OTHER INFORMATION: hexamer

<400> SEQUENCE: 123 acgtga                                                                  6

<210> SEQ ID NO 124
<211> LENGTH: 26
<212> TYPE: DNA
<213> ORGANISM: Artificial Sequence
<220> FEATURE:

-continued

<223> OTHER INFORMATION: oligonucleotide

<400> SEQUENCE: 124
gtacggatat cagatcttta attaag                                    26

<210> SEQ ID NO 125
<211> LENGTH: 26
<212> TYPE: DNA
<213> ORGANISM: Artificial Sequence
<220> FEATURE:
<223> OTHER INFORMATION: oligonucleotide

<400> SEQUENCE: 125
gtaccttaat taaagatctg atatcc                                    26

<210> SEQ ID NO 126
<211> LENGTH: 51
<212> TYPE: DNA
<213> ORGANISM: Artificial Sequence
<220> FEATURE:
<223> OTHER INFORMATION: primer

<400> SEQUENCE: 126
atcagatctg gcgcgccatt taaatcgtct cgcgcgtttc ggtgatgacg g         51

<210> SEQ ID NO 127
<211> LENGTH: 41
<212> TYPE: DNA
<213> ORGANISM: Artificial Sequence
<220> FEATURE:
<223> OTHER INFORMATION: primer

<400> SEQUENCE: 127
aggcggatcc gaatgtattt agaaaaataa acaaataggg g                   41

<210> SEQ ID NO 128
<211> LENGTH: 36
<212> TYPE: DNA
<213> ORGANISM: Artificial Sequence
<220> FEATURE:
<223> OTHER INFORMATION: primer

<400> SEQUENCE: 128
gatcggatcc ttcgaaatgg ccaagttgac cagtgc                         36

<210> SEQ ID NO 129
<211> LENGTH: 32
<212> TYPE: DNA
<213> ORGANISM: Artificial Sequence
<220> FEATURE:
<223> OTHER INFORMATION: primer

<400> SEQUENCE: 129
aggcgcggcc gcaattctca gtcctgctcc tc                             32

<210> SEQ ID NO 130
<211> LENGTH: 31
<212> TYPE: DNA
<213> ORGANISM: Artificial Sequence
<220> FEATURE:
<223> OTHER INFORMATION: primer

<400> SEQUENCE: 130
gatcgaattc tcgcgacttc gcccaccatg c                              31

<210> SEQ ID NO 131
<211> LENGTH: 47
<212> TYPE: DNA
<213> ORGANISM: Artificial Sequence
<220> FEATURE:
<223> OTHER INFORMATION: primer

<400> SEQUENCE: 131
aggcgaattc accggtgttt aaactcatgt ctgctcgaag cggccgg 47

<210> SEQ ID NO 132
<211> LENGTH: 31
<212> TYPE: DNA
<213> ORGANISM: Artificial Sequence
<220> FEATURE:
<223> OTHER INFORMATION: primer

<400> SEQUENCE: 132
gatcgaattc atggtgagca agggcgagga g 31

<210> SEQ ID NO 133
<211> LENGTH: 40
<212> TYPE: DNA
<213> ORGANISM: Artificial Sequence
<220> FEATURE:
<223> OTHER INFORMATION: primer

<400> SEQUENCE: 133
aggcacgcgt gttaacctac acattgatcc tagcagaagc 40

<210> SEQ ID NO 134
<211> LENGTH: 48
<212> TYPE: DNA
<213> ORGANISM: Artificial Sequence
<220> FEATURE:
<223> OTHER INFORMATION: oligonucleotide C65

<400> SEQUENCE: 134
aacaagcttg atatcagatc tgctagcttg gtcgagctga tacttccc 48

<210> SEQ ID NO 135
<211> LENGTH: 54
<212> TYPE: DNA
<213> ORGANISM: Artificial Sequence
<220> FEATURE:
<223> OTHER INFORMATION: oligonucleotide C66

<400> SEQUENCE: 135
aaactcgagc ggccgcgaat tcgtcgactt taccactccc tatcagtgat agag 54

<210> SEQ ID NO 136
<211> LENGTH: 39
<212> TYPE: DNA
<213> ORGANISM: Artificial Sequence
<220> FEATURE:
<223> OTHER INFORMATION: oligonucleotide C67

<400> SEQUENCE: 136
aaaccgcggc atggaagacg ccaaaaacat aaagaaagg 39

<210> SEQ ID NO 137
<211> LENGTH: 32
<212> TYPE: DNA
<213> ORGANISM: Artificial Sequence
<220> FEATURE:
<223> OTHER INFORMATION: oligonucleotide C68

-continued

<400> SEQUENCE: 137
tatggatcct agaattacac ggcgatcttt cc                          32

<210> SEQ ID NO 138
<211> LENGTH: 33
<212> TYPE: DNA
<213> ORGANISM: Artificial Sequence
<220> FEATURE:
<223> OTHER INFORMATION: oligonucleotide C81

<400> SEQUENCE: 138
aaaccatggc cgagtacaag cccacggtgc gcc                         33

<210> SEQ ID NO 139
<211> LENGTH: 35
<212> TYPE: DNA
<213> ORGANISM: Artificial Sequence
<220> FEATURE:
<223> OTHER INFORMATION: oligonucleotide C82

<400> SEQUENCE: 139
aaatctagat caggcaccgg gcttgcgggt catgc                       35

<210> SEQ ID NO 140
<211> LENGTH: 22
<212> TYPE: DNA
<213> ORGANISM: Artificial Sequence
<220> FEATURE:
<223> OTHER INFORMATION: oligonucleotide C85

<400> SEQUENCE: 140
catttccccg aaaagtgcca cc                                     22

<210> SEQ ID NO 141
<211> LENGTH: 24
<212> TYPE: DNA
<213> ORGANISM: Artificial Sequence
<220> FEATURE:
<223> OTHER INFORMATION: oligonucleotide D30

<400> SEQUENCE: 141
tcactgctag cgagtggtaa actc                                   24

<210> SEQ ID NO 142
<211> LENGTH: 28
<212> TYPE: DNA
<213> ORGANISM: Artificial Sequence
<220> FEATURE:
<223> OTHER INFORMATION: oligonucleotide D41

<400> SEQUENCE: 142
gaagtcgacg aggcaggcag aagtatgc                              28

<210> SEQ ID NO 143
<211> LENGTH: 29
<212> TYPE: DNA
<213> ORGANISM: Artificial Sequence
<220> FEATURE:
<223> OTHER INFORMATION: oligonucleotide D42

<400> SEQUENCE: 143
gagccgcggt ttagttcctc accttgtcg                             29

<210> SEQ ID NO 144
<211> LENGTH: 23

```
<212> TYPE: DNA
<213> ORGANISM: Artificial Sequence
<220> FEATURE:
<223> OTHER INFORMATION: oligonucleotide D51

<400> SEQUENCE: 144
tctggaagct tgctgaaga aac                                              23

<210> SEQ ID NO 145
<211> LENGTH: 17
<212> TYPE: DNA
<213> ORGANISM: Artificial Sequence
<220> FEATURE:
<223> OTHER INFORMATION: oligonucleotide D58

<400> SEQUENCE: 145
ccaagttgac cagtgcc                                                    17

<210> SEQ ID NO 146
<211> LENGTH: 19
<212> TYPE: DNA
<213> ORGANISM: Artificial Sequence
<220> FEATURE:
<223> OTHER INFORMATION: oligonucleotide D70

<400> SEQUENCE: 146
tacaagccaa ccacggcct                                                  19

<210> SEQ ID NO 147
<211> LENGTH: 20
<212> TYPE: DNA
<213> ORGANISM: Artificial Sequence
<220> FEATURE:
<223> OTHER INFORMATION: oligonucleotide D71

<400> SEQUENCE: 147
cggaagtgct tgacattggg                                                 20

<210> SEQ ID NO 148
<211> LENGTH: 20
<212> TYPE: DNA
<213> ORGANISM: Artificial Sequence
<220> FEATURE:
<223> OTHER INFORMATION: oligonucleotide D80

<400> SEQUENCE: 148
gttcgtggac acgacctccg                                                 20

<210> SEQ ID NO 149
<211> LENGTH: 21
<212> TYPE: DNA
<213> ORGANISM: Artificial Sequence
<220> FEATURE:
<223> OTHER INFORMATION: oligonucleotide D89

<400> SEQUENCE: 149
gggcaagatg tcgtagtcag g                                               21

<210> SEQ ID NO 150
<211> LENGTH: 30
<212> TYPE: DNA
<213> ORGANISM: Artificial Sequence
<220> FEATURE:
<223> OTHER INFORMATION: oligonucleotide D90

<400> SEQUENCE: 150
```

-continued aggcccatgg tcacctccat cgctactgtg                                    30

<210> SEQ ID NO 151
<211> LENGTH: 20
<212> TYPE: DNA
<213> ORGANISM: Artificial Sequence
<220> FEATURE:
<223> OTHER INFORMATION: oligonucleotide D91

<400> SEQUENCE: 151
ctaatcactc actgtgtaat                                               20

<210> SEQ ID NO 152
<211> LENGTH: 15
<212> TYPE: DNA
<213> ORGANISM: Artificial Sequence
<220> FEATURE:
<223> OTHER INFORMATION: oligonucleotide D93

<400> SEQUENCE: 152
aattacaggc gcgcc                                                    15

<210> SEQ ID NO 153
<211> LENGTH: 15
<212> TYPE: DNA
<213> ORGANISM: Artificial Sequence
<220> FEATURE:
<223> OTHER INFORMATION: oligonucleotide D94

<400> SEQUENCE: 153
aattggcgcg cctgt                                                    15

<210> SEQ ID NO 154
<211> LENGTH: 25
<212> TYPE: DNA
<213> ORGANISM: Artificial Sequence
<220> FEATURE:
<223> OTHER INFORMATION: oligonucleotide D95

<400> SEQUENCE: 154
tgctttgcat acttctgcct gcctc                                         25

<210> SEQ ID NO 155
<211> LENGTH: 20
<212> TYPE: DNA
<213> ORGANISM: Artificial Sequence
<220> FEATURE:
<223> OTHER INFORMATION: oligonucleotide E12

<400> SEQUENCE: 155 tagggggat ccaaatgttc                                                20

<210> SEQ ID NO 156
<211> LENGTH: 20
<212> TYPE: DNA
<213> ORGANISM: Artificial Sequence
<220> FEATURE:
<223> OTHER INFORMATION: oligonucleotide E13

<400> SEQUENCE: 156
cctaaaagaa gatctttagc                                               20

<210> SEQ ID NO 157
<211> LENGTH: 20
<212> TYPE: DNA
<213> ORGANISM: Artificial Sequence

```
<220> FEATURE:
<223> OTHER INFORMATION: oligonucleotide E14

<400> SEQUENCE: 157
aagtgttgga tccactttgg                                                   20

<210> SEQ ID NO 158
<211> LENGTH: 20
<212> TYPE: DNA
<213> ORGANISM: Artificial Sequence
<220> FEATURE:
<223> OTHER INFORMATION: oligonucleotide E15

<400> SEQUENCE: 158
tttgaagatc taccaaatgg                                                   20

<210> SEQ ID NO 159
<211> LENGTH: 20
<212> TYPE: DNA
<213> ORGANISM: Artificial Sequence
<220> FEATURE:
<223> OTHER INFORMATION: oligonucleotide E16

<400> SEQUENCE: 159
gttcgggatc cacctggccg                                                   20

<210> SEQ ID NO 160
<211> LENGTH: 20
<212> TYPE: DNA
<213> ORGANISM: Artificial Sequence
<220> FEATURE:
<223> OTHER INFORMATION: oligonucleotide E17

<400> SEQUENCE: 160
taggcaagat cttggccctc                                                   20

<210> SEQ ID NO 161
<211> LENGTH: 20
<212> TYPE: DNA
<213> ORGANISM: Artificial Sequence
<220> FEATURE:
<223> OTHER INFORMATION: oligonucleotide E18

<400> SEQUENCE: 161
cctctctagg gatccgaccc                                                   20

<210> SEQ ID NO 162
<211> LENGTH: 20
<212> TYPE: DNA
<213> ORGANISM: Artificial Sequence
<220> FEATURE:
<223> OTHER INFORMATION: oligonucleotide E19

<400> SEQUENCE: 162
ctagagagat cttccagtat                                                   20

<210> SEQ ID NO 163
<211> LENGTH: 20
<212> TYPE: DNA
<213> ORGANISM: Artificial Sequence
<220> FEATURE:
<223> OTHER INFORMATION: oligonucleotide E20

<400> SEQUENCE: 163
agagttccgg atccgcctgg                                                   20
```

<210> SEQ ID NO 164
<211> LENGTH: 20
<212> TYPE: DNA
<213> ORGANISM: Artificial Sequence
<220> FEATURE:
<223> OTHER INFORMATION: oligonucleotide E21

<400> SEQUENCE: 164
ccaggcagac tcggaactct                                           20

<210> SEQ ID NO 165
<211> LENGTH: 20
<212> TYPE: DNA
<213> ORGANISM: Artificial Sequence
<220> FEATURE:
<223> OTHER INFORMATION: oligonucleotide E22

<400> SEQUENCE: 165
tggtgaaacc ggatccctac                                           20

<210> SEQ ID NO 166
<211> LENGTH: 20
<212> TYPE: DNA
<213> ORGANISM: Artificial Sequence
<220> FEATURE:
<223> OTHER INFORMATION: oligonucleotide E23

<400> SEQUENCE: 166
aggtcaggag atctagacca                                           20

<210> SEQ ID NO 167
<211> LENGTH: 22
<212> TYPE: DNA
<213> ORGANISM: Artificial Sequence
<220> FEATURE:
<223> OTHER INFORMATION: oligonucleotide E25

<400> SEQUENCE: 167
ccattttcgc ttccttagct cc                                        22

<210> SEQ ID NO 168
<211> LENGTH: 22
<212> TYPE: DNA
<213> ORGANISM: Artificial Sequence
<220> FEATURE:
<223> OTHER INFORMATION: oligonucleotide E42

<400> SEQUENCE: 168
cgatgtaacc cactcgtgca cc                                        22

<210> SEQ ID NO 169
<211> LENGTH: 20
<212> TYPE: DNA
<213> ORGANISM: Artificial Sequence
<220> FEATURE:
<223> OTHER INFORMATION: oligonucleotide E57

<400> SEQUENCE: 169
agagatctag gataatttcg                                           20

<210> SEQ ID NO 170
<211> LENGTH: 36
<212> TYPE: DNA
<213> ORGANISM: Artificial Sequence
<220> FEATURE:
<223> OTHER INFORMATION: oligonucleotide E92

-continued

<400> SEQUENCE: 170
aggcgctagc acgcgttcta ctcttttcct actctg    36

<210> SEQ ID NO 171
<211> LENGTH: 35
<212> TYPE: DNA
<213> ORGANISM: Artificial Sequence
<220> FEATURE:
<223> OTHER INFORMATION: oligonucleotide E93

<400> SEQUENCE: 171
gatcaagctt acgcgtctaa aggcatttta tatag    35

<210> SEQ ID NO 172
<211> LENGTH: 35
<212> TYPE: DNA
<213> ORGANISM: Artificial Sequence
<220> FEATURE:
<223> OTHER INFORMATION: oligonucleotide E94

<400> SEQUENCE: 172
aggcgctagc acgcgttcag agttagtgat ccagg    35

<210> SEQ ID NO 173
<211> LENGTH: 35
<212> TYPE: DNA
<213> ORGANISM: Artificial Sequence
<220> FEATURE:
<223> OTHER INFORMATION: oligonucleotide E95

<400> SEQUENCE: 173
gatcaagctt acgcgtcagt aaaggtttcg tatgg    35

<210> SEQ ID NO 174
<211> LENGTH: 36
<212> TYPE: DNA
<213> ORGANISM: Artificial Sequence
<220> FEATURE:
<223> OTHER INFORMATION: oligonucleotide E96

<400> SEQUENCE: 174
aggcgctagc acgcgttcta ctctttcatt actctg    36

<210> SEQ ID NO 175
<211> LENGTH: 26
<212> TYPE: DNA
<213> ORGANISM: Artificial Sequence
<220> FEATURE:
<223> OTHER INFORMATION: oligonucleotide E97

<400> SEQUENCE: 175
cgaggaagct ggagaaggag aagctg    26

<210> SEQ ID NO 176
<211> LENGTH: 25
<212> TYPE: DNA
<213> ORGANISM: Artificial Sequence
<220> FEATURE:
<223> OTHER INFORMATION: oligonucleotide E98

<400> SEQUENCE: 176
caagggccgc agcttacaca tgttc    25

<210> SEQ ID NO 177

```
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 177 ccccac                                                                    6

<210> SEQ ID NO 178
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 178 cagcgg                                                                    6

<210> SEQ ID NO 179
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 179 ggcccc                                                                    6

<210> SEQ ID NO 180
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 180 cagccc                                                                    6

<210> SEQ ID NO 181
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 181 gccccc                                                                    6

<210> SEQ ID NO 182
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 182 cggggc                                                                    6

<210> SEQ ID NO 183
<211> LENGTH: 6
```

```
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 183 ccccgc                                                                    6

<210> SEQ ID NO 184
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 184 cggcag                                                                    6

<210> SEQ ID NO 185
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 185 agcccc                                                                    6

<210> SEQ ID NO 186
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 186 ccaggg                                                                    6

<210> SEQ ID NO 187
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 187 ggaccc                                                                    6

<210> SEQ ID NO 188
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 188 gcggac                                                                    6

<210> SEQ ID NO 189
<211> LENGTH: 6
<212> TYPE: DNA
```

```
<213> ORGANISM: Artificial Sequence
<220> FEATURE:
<223> OTHER INFORMATION: oligonucleotide patterns over-represented in
      STAR elements

<400> SEQUENCE: 189 ccagcg                                                                   6

<210> SEQ ID NO 190
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 190 gcagcc                                                                   6

<210> SEQ ID NO 191
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 191 ccggca                                                                   6

<210> SEQ ID NO 192
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 192 agcggc                                                                   6

<210> SEQ ID NO 193
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 193 cagggg                                                                   6

<210> SEQ ID NO 194
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 194 ccgccc                                                                   6

<210> SEQ ID NO 195
<211> LENGTH: 6
<212> TYPE: DNA
<213> ORGANISM: Artificial Sequence
```

```
<220> FEATURE:
<223> OTHER INFORMATION: oligonucleotide patterns over-represented in
      STAR elements

<400> SEQUENCE: 195 cccccg                                                                    6

<210> SEQ ID NO 196
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 196 gccgcc                                                                    6

<210> SEQ ID NO 197
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 197 gccggc                                                                    6

<210> SEQ ID NO 198
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 198 cggacc                                                                    6

<210> SEQ ID NO 199
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 199 cgcccc                                                                    6

<210> SEQ ID NO 200
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 200 cgccag                                                                    6

<210> SEQ ID NO 201
<211> LENGTH: 6
<212> TYPE: DNA
<213> ORGANISM: Artificial Sequence
<220> FEATURE:
```

-continued

```
<223> OTHER INFORMATION: oligonucleotide patterns over-represented in
      STAR elements

<400> SEQUENCE: 201 cgcagc                                                                    6

<210> SEQ ID NO 202
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 202 cagccg                                                                    6

<210> SEQ ID NO 203
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 203 cccacg                                                                    6

<210> SEQ ID NO 204
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 204 gctgcc                                                                    6

<210> SEQ ID NO 205
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 205 ccctcc                                                                    6

<210> SEQ ID NO 206
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 206 ccctgc                                                                    6

<210> SEQ ID NO 207
<211> LENGTH: 6
<212> TYPE: DNA
<213> ORGANISM: Artificial Sequence
<220> FEATURE:
<223> OTHER INFORMATION: oligonucleotide patterns over-represented in
```

STAR elements

<400> SEQUENCE: 207 caccccc                                                              6

<210> SEQ ID NO 208
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 208 gcgcca                                                               6

<210> SEQ ID NO 209
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 209 aggggc                                                               6

<210> SEQ ID NO 210
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 210 gagggc                                                               6

<210> SEQ ID NO 211
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 211 gcgaac                                                               6

<210> SEQ ID NO 212
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 212 ccggcg                                                               6

<210> SEQ ID NO 213
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

```
<400> SEQUENCE: 213 agccgg                                                                    6

<210> SEQ ID NO 214
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 214 ggagcc                                                                    6

<210> SEQ ID NO 215
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 215 ccccag                                                                    6

<210> SEQ ID NO 216
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 216 ccgctc                                                                    6

<210> SEQ ID NO 217
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 217 cccctc                                                                    6

<210> SEQ ID NO 218
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 218 caccgc                                                                    6

<210> SEQ ID NO 219
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements
```

```
<400> SEQUENCE: 219 ctgccc                                                                    6

<210> SEQ ID NO 220
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 220 gggcca                                                                    6

<210> SEQ ID NO 221
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 221 cgctgc                                                                    6

<210> SEQ ID NO 222
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 222 cagcgc                                                                    6

<210> SEQ ID NO 223
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 223 cggccc                                                                    6

<210> SEQ ID NO 224
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 224 ccgccg                                                                    6

<210> SEQ ID NO 225
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 225
``` ccccgg                                                                 6

<210> SEQ ID NO 226
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 226 agccgc                                                                 6

<210> SEQ ID NO 227
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 227 gcaccc                                                                 6

<210> SEQ ID NO 228
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 228 aggacc                                                                 6

<210> SEQ ID NO 229
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 229 agggcg                                                                 6

<210> SEQ ID NO 230
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 230 cagggc                                                                 6

<210> SEQ ID NO 231
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 231

-continued cccgcc                                                              6

<210> SEQ ID NO 232
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 232 gccagc                                                              6

<210> SEQ ID NO 233
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 233 agcgcc                                                              6

<210> SEQ ID NO 234
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 234 aggccc                                                              6

<210> SEQ ID NO 235
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 235 cccacc                                                              6

<210> SEQ ID NO 236
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 236 cgctca                                                              6

<210> SEQ ID NO 237
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 237 aacgcg                                                              6

-continued

```
<210> SEQ ID NO 238
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 238 gcggca                                                                     6

<210> SEQ ID NO 239
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 239 aggtcc                                                                     6

<210> SEQ ID NO 240
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 240 ccgtca                                                                     6

<210> SEQ ID NO 241
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 241 cagagg                                                                     6

<210> SEQ ID NO 242
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 242 cccgag                                                                     6

<210> SEQ ID NO 243
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 243 ccgagg                                                                     6
```

```
<210> SEQ ID NO 244
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 244 cgcgga                                                                     6

<210> SEQ ID NO 245
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 245 ccaccc                                                                     6

<210> SEQ ID NO 246
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 246 cctcgc                                                                     6

<210> SEQ ID NO 247
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 247 caagcc                                                                     6

<210> SEQ ID NO 248
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 248 tccgca                                                                     6

<210> SEQ ID NO 249
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 249 cgccgc                                                                     6
```

```
<210> SEQ ID NO 250
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 250 gggaac                                                                    6

<210> SEQ ID NO 251
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 251 ccagag                                                                    6

<210> SEQ ID NO 252
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 252 cgttcc                                                                    6

<210> SEQ ID NO 253
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 253 cgagga                                                                    6

<210> SEQ ID NO 254
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 254 gggacc                                                                    6

<210> SEQ ID NO 255
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 255 ccgcga                                                                    6

<210> SEQ ID NO 256
```

```
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 256 cctgcg                                                                     6

<210> SEQ ID NO 257
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 257 ctgcgc                                                                     6

<210> SEQ ID NO 258
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 258 gacccc                                                                     6

<210> SEQ ID NO 259
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 259 gctcca                                                                     6

<210> SEQ ID NO 260
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 260 cgccac                                                                     6

<210> SEQ ID NO 261
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 261 gcggga                                                                     6

<210> SEQ ID NO 262
<211> LENGTH: 6
```

```
<210> SEQ ID NO 262
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 262 ctgcga                                                                  6

<210> SEQ ID NO 263
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 263 ctgctc                                                                  6

<210> SEQ ID NO 264
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 264 cagacg                                                                  6

<210> SEQ ID NO 265
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 265 cgagag                                                                  6

<210> SEQ ID NO 266
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 266 cggtgc                                                                  6

<210> SEQ ID NO 267
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 267 ctcccc                                                                  6

<210> SEQ ID NO 268
<211> LENGTH: 6
<212> TYPE: DNA
```

```
<213> ORGANISM: Artificial Sequence
<220> FEATURE:
<223> OTHER INFORMATION: oligonucleotide patterns over-represented in
      STAR elements

<400> SEQUENCE: 268 gcggcc                                                                      6

<210> SEQ ID NO 269
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 269 cggcgc                                                                      6

<210> SEQ ID NO 270
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 270 aagccc                                                                      6

<210> SEQ ID NO 271
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 271 ccgcag                                                                      6

<210> SEQ ID NO 272
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 272 gcccac                                                                      6

<210> SEQ ID NO 273
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 273 caccca                                                                      6

<210> SEQ ID NO 274
<211> LENGTH: 6
<212> TYPE: DNA
<213> ORGANISM: Artificial Sequence
```

```
<220> FEATURE:
<223> OTHER INFORMATION: oligonucleotide patterns over-represented in
      STAR elements

<400> SEQUENCE: 274 gcgccc                                                                       6

<210> SEQ ID NO 275
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 275 accggc                                                                       6

<210> SEQ ID NO 276
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 276 ctcgca                                                                       6

<210> SEQ ID NO 277
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 277 acgctc                                                                       6

<210> SEQ ID NO 278
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 278 ctggac                                                                       6

<210> SEQ ID NO 279
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 279 gcccca                                                                       6

<210> SEQ ID NO 280
<211> LENGTH: 6
<212> TYPE: DNA
<213> ORGANISM: Artificial Sequence
<220> FEATURE:
```

```
<223> OTHER INFORMATION: oligonucleotide patterns over-represented in
      STAR elements

<400> SEQUENCE: 280 accgtc                                                                  6

<210> SEQ ID NO 281
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 281 ccctcg                                                                  6

<210> SEQ ID NO 282
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 282 agcccg                                                                  6

<210> SEQ ID NO 283
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 283 acccga                                                                  6

<210> SEQ ID NO 284
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 284 agcagc                                                                  6

<210> SEQ ID NO 285
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 285 accgcg                                                                  6

<210> SEQ ID NO 286
<211> LENGTH: 6
<212> TYPE: DNA
<213> ORGANISM: Artificial Sequence
<220> FEATURE:
<223> OTHER INFORMATION: oligonucleotide patterns over-represented in
```

```
    STAR elements

<400> SEQUENCE: 286 cgaggc                                                                    6

<210> SEQ ID NO 287
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 287 agctgc                                                                    6

<210> SEQ ID NO 288
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 288 ggggac                                                                    6

<210> SEQ ID NO 289
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 289 ccgcaa                                                                    6

<210> SEQ ID NO 290
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 290 cgtcgc                                                                    6

<210> SEQ ID NO 291
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 291 cgtgac                                                                    6

<210> SEQ ID NO 292
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements
```

-continued

```
<400> SEQUENCE: 292 cgccca                                                                      6

<210> SEQ ID NO 293
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 293 ctctgc                                                                      6

<210> SEQ ID NO 294
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 294 agcggg                                                                      6

<210> SEQ ID NO 295
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 295 accgct                                                                      6

<210> SEQ ID NO 296
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 296 cccagg                                                                      6

<210> SEQ ID NO 297
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 297 ccctca                                                                      6

<210> SEQ ID NO 298
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements
```

```
<400> SEQUENCE: 298 cccca                                                                    6

<210> SEQ ID NO 299
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 299 ggcgaa                                                                   6

<210> SEQ ID NO 300
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 300 cggctc                                                                   6

<210> SEQ ID NO 301
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 301 ctcgcc                                                                   6

<210> SEQ ID NO 302
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 302 cggaga                                                                   6

<210> SEQ ID NO 303
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 303 tcccca                                                                   6

<210> SEQ ID NO 304
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 304
``` gacacc                                                                6

<210> SEQ ID NO 305
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 305 ctccga                                                                6

<210> SEQ ID NO 306
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 306 ctcgtc                                                                6

<210> SEQ ID NO 307
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 307 cgacca                                                                6

<210> SEQ ID NO 308
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 308 atgacg                                                                6

<210> SEQ ID NO 309
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 309 ccatcg                                                                6

<210> SEQ ID NO 310
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 310 aggggа 6

<210> SEQ ID NO 311
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 311 gctgca 6

<210> SEQ ID NO 312
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 312 acccca 6

<210> SEQ ID NO 313
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 313 cggagc 6

<210> SEQ ID NO 314
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 314 cctccg 6

<210> SEQ ID NO 315
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 315 cgggac 6

<210> SEQ ID NO 316
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 316 cctgga 6

<210> SEQ ID NO 317
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 317 aggcga                                                                   6

<210> SEQ ID NO 318
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 318 acccct                                                                   6

<210> SEQ ID NO 319
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 319 gctccc                                                                   6

<210> SEQ ID NO 320
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 320 cgtcac                                                                   6

<210> SEQ ID NO 321
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 321 agcgca                                                                   6

<210> SEQ ID NO 322
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 322 gaagcc                                                                   6

```
<210> SEQ ID NO 323
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 323 gaggcc                                                                   6

<210> SEQ ID NO 324
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 324 accctc                                                                   6

<210> SEQ ID NO 325
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 325 cccggc                                                                   6

<210> SEQ ID NO 326
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 326 cgagaa                                                                   6

<210> SEQ ID NO 327
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 327 ccaccg                                                                   6

<210> SEQ ID NO 328
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 328 acttcg                                                                   6
```

```
<210> SEQ ID NO 329
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 329 gatgac                                                                   6

<210> SEQ ID NO 330
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 330 acgagg                                                                   6

<210> SEQ ID NO 331
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 331 ccggag                                                                   6

<210> SEQ ID NO 332
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 332 acccac                                                                   6

<210> SEQ ID NO 333
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 333 ctgggc                                                                   6

<210> SEQ ID NO 334
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 334 ccacgg                                                                   6

<210> SEQ ID NO 335
```

```
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 335 cggtcc                                                                  6

<210> SEQ ID NO 336
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 336 agcacc                                                                  6

<210> SEQ ID NO 337
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 337 acaccc                                                                  6

<210> SEQ ID NO 338
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 338 agggcc                                                                  6

<210> SEQ ID NO 339
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 339 cgcgaa                                                                  6

<210> SEQ ID NO 340
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 340 gagccc                                                                  6

<210> SEQ ID NO 341
<211> LENGTH: 6
```

-continued

```
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 341 ctgagc                                                                      6

<210> SEQ ID NO 342
<211> LENGTH: 6
<212> TYPE: DNA
<213> ORGANISM: Artificial Sequence
<220> FEATURE:
<223> OTHER INFORMATION: oligonucleotide patterns over-represented in
      STAR elements

<400> SEQUENCE: 342 aatcgg                                                                      6

<210> SEQ ID NO 343
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 343 cccnncgg                                                                    8

<210> SEQ ID NO 344
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 344
ccgnnnnnnc cc                                                              12

<210> SEQ ID NO 345
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 345 cagcgg                                                                      6

<210> SEQ ID NO 346
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide
```

-continued

<400> SEQUENCE: 346
cgcnnnnnnn nnnnnnnncc c         21

<210> SEQ ID NO 347
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 347
cggnnnnnnn nngcc         15

<210> SEQ ID NO 348
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 348
cccnnnnnnn nncgc         15

<210> SEQ ID NO 349
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 349 cccngcg         7

<210> SEQ ID NO 350
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 350 ccccac         6

<210> SEQ ID NO 351
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 351
agcnnnnnnn nnnnnnnnnc cg         22

```
<210> SEQ ID NO 352
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 352 cccnnnncgc                                                                 10

<210> SEQ ID NO 353
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 353
cgcnnnnnnn nnnnnngga                                                       19

<210> SEQ ID NO 354
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 354
gcgnnnnnnn nnnnnnnnnc cc                                                   22

<210> SEQ ID NO 355
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 355
cgcnnnnngc a                                                               11

<210> SEQ ID NO 356
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 356
```

```
cccnnnnnnn nnnnnnnccc                                                    20
```

<210> SEQ ID NO 357
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 357

```
ctgnnnncgc                                                               10
```

<210> SEQ ID NO 358
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 358

```
ccannnnnnn nnnnngcg                                                      18
```

<210> SEQ ID NO 359
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 359

```
cggnnnnnnn nnnncag                                                       17
```

<210> SEQ ID NO 360
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 360

```
cccnnnnngc c                                                             11
```

<210> SEQ ID NO 361
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 361

```
gccccc                                                                    6
```

```
<210> SEQ ID NO 362
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 362 cgcnnnngac                                                              10

<210> SEQ ID NO 363
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 363 cggcag                                                                   6

<210> SEQ ID NO 364
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 364 cccnnncgc                                                                9

<210> SEQ ID NO 365
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 365 cgcngac                                                                  7

<210> SEQ ID NO 366
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 366 gcgnngcc                                                                 8

<210> SEQ ID NO 367
<211> LENGTH: 10
<212> TYPE: DNA
```

```
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 367 cccnnngcc                                                                      10

<210> SEQ ID NO 368
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 368 cccnccc                                                                         7

<210> SEQ ID NO 369
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 369
ccgnnnnnnn nnnnnncag                                                           19

<210> SEQ ID NO 370
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 370 gccnnnngga                                                                     10

<210> SEQ ID NO 371
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 371 ccgnnngga                                                                       9

<210> SEQ ID NO 372
<211> LENGTH: 8
```

```
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 372 aggnnggg                                                                        8

<210> SEQ ID NO 373
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 373
cacnnnnngc g                                                                   11

<210> SEQ ID NO 374
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 374
cgcnnnnnnn nnnnnnnnnn cca                                                      23

<210> SEQ ID NO 375
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 375
cccnnnnnnn nnggc                                                               15

<210> SEQ ID NO 376
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 376
cctnnnnngc g                                                                   11

<210> SEQ ID NO 377
```

```
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 377 gcggac                                                                      6

<210> SEQ ID NO 378
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 378 gccggc                                                                      6

<210> SEQ ID NO 379
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 379 gcgnnccc                                                                    8

<210> SEQ ID NO 380
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 380
ccgnnnnnnn nnnnccc                                                         17

<210> SEQ ID NO 381
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 381
cccnnnnnnn ntcg                                                            14

<210> SEQ ID NO 382
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
```

-continued

```
<222> LOCATION: (4)..(20)
<223> OTHER INFORMATION: "N" stands for any nucleotide

<400> SEQUENCE: 382
ccgnnnnnnn nnnnnnnnnn gcc                                          23

<210> SEQ ID NO 383
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 383
gggnnnnngg a                                                       11

<210> SEQ ID NO 384
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 384
ggcnnnnnng ga                                                      12

<210> SEQ ID NO 385
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 385 ccannnnccc                                                         10

<210> SEQ ID NO 386
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 386
cctnnnnnnn nnnnnnnccg                                              20

<210> SEQ ID NO 387
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
```

```
<221> NAME/KEY: misc_feature
<222> LOCATION: (4)..(15)
<223> OTHER INFORMATION: "N" stands for any nucleotide

<400> SEQUENCE: 387
gacnnnnnnn nnnnnggc                                                            18

<210> SEQ ID NO 388
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 388
cgcnnnnnnn nnnnnnccc                                                           19

<210> SEQ ID NO 389
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 389
cagnnnnnnn nnnnnnnnnc cc                                                       22

<210> SEQ ID NO 390
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 390
agcnnnnnnn nnnggg                                                              16

<210> SEQ ID NO 391
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 391
cggnnnnnnn nnnnnnggc                                                           19

<210> SEQ ID NO 392
<211> LENGTH: 7
<212> TYPE: DNA
<213> ORGANISM: Artificial Sequence
<220> FEATURE:
<223> OTHER INFORMATION: Dyad patterns over-represented in STAR elements
```

```
<220> FEATURE:
<221> NAME/KEY: misc_feature
<222> LOCATION: (4)..(4)
<223> OTHER INFORMATION: "N" stands for any nucleotide

<400> SEQUENCE: 392 cggngcc                                                                    7

<210> SEQ ID NO 393
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 393 agcggc                                                                     6

<210> SEQ ID NO 394
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 394
cccnnnnnnn nnnnnnnnng gc                                                  22

<210> SEQ ID NO 395
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 395
gctnnnnnnn nnnnnnnnnn nnccc                                               25

<210> SEQ ID NO 396
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 396
cccnnnnnnn nnnnnnnnng gg                                                  22

<210> SEQ ID NO 397
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
```

-continued

<223> OTHER INFORMATION: "N" stands for any nucleotide

<400> SEQUENCE: 397
cccnnnnnnn nncgg                                                    15

<210> SEQ ID NO 398
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 398
cccnnnnnnn nnncgg                                                   16

<210> SEQ ID NO 399
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 399 ccagcg                                                               6

<210> SEQ ID NO 400
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 400
gccnnnnnnn nnnnnnnnn cgc                                            23

<210> SEQ ID NO 401
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 401
cctnnnnnnc gc                                                       12

<210> SEQ ID NO 402
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 402 ggancccc                                                          7

<210> SEQ ID NO 403
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 403
cgcnnnnnnn nnnnnnnnnn ncac                                        24

<210> SEQ ID NO 404
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 404
cgcnnnnnnn nnnnnnnnnn nnnccg                                      26

<210> SEQ ID NO 405
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 405 ccggca                                                            6

<210> SEQ ID NO 406
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 406
cgcnnnnnnn nnnnnnnnnn nnnccc                                      26

<210> SEQ ID NO 407
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 407
agcnnnnnnn nnnnnnncc c                                            21

```
<210> SEQ ID NO 408
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 408
cctnnnnnnn ggc                                                      13

<210> SEQ ID NO 409
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 409
gccnnnnncg c                                                        11

<210> SEQ ID NO 410
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 410
gccnnnnnnn nnnnnnncgc                                               20

<210> SEQ ID NO 411
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 411
cagnnnnnnn nnnnccc                                                  17

<210> SEQ ID NO 412
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 412
gggnnnnnnn nnnnnnnnng ac                                            22
```

```
<210> SEQ ID NO 413
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 413
cccnnnnnnn nnnnnnnngc g                                          21

<210> SEQ ID NO 414
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 414 ccccgc                                                            6

<210> SEQ ID NO 415
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 415
cccnnnnnnn nnnnnnnnna gc                                         22

<210> SEQ ID NO 416
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 416
aggnnnnnnn nnggg                                                 15

<210> SEQ ID NO 417
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 417
cgcnnnnnnn nnnnnctc                                              18

<210> SEQ ID NO 418
```

```
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 418
cacnnnnnnn ncgc                                                          14

<210> SEQ ID NO 419
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 419
ccannnnnnn ccg                                                           13

<210> SEQ ID NO 420
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 420 cggngca                                                                   7

<210> SEQ ID NO 421
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 421
cgcnnnnnnn nnnnnnnccc                                                    20

<210> SEQ ID NO 422
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 422 agcccc                                                                    6

<210> SEQ ID NO 423
<211> LENGTH: 19
<212> TYPE: DNA
<213> ORGANISM: Artificial Sequence
```

```
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 423
cgcnnnnnnn nnnnnngtc                                                19

<210> SEQ ID NO 424
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 424 gcgnnngca                                                            9

<210> SEQ ID NO 425
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 425 cggggc                                                               6

<210> SEQ ID NO 426
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 426
gccnnnnnnn nnnnnnnccc                                               20

<210> SEQ ID NO 427
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 427
accnnnnnnn cgc                                                      13

<210> SEQ ID NO 428
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
```

<221> NAME/KEY: misc_feature
<222> LOCATION: (4)..(10)
<223> OTHER INFORMATION: "N" stands for any nucleotide

<400> SEQUENCE: 428
aggnnnnnnn cgg                                                          13

<210> SEQ ID NO 429
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 429
cccnnnnnnn nnnnnnnnnc ga                                                22

<210> SEQ ID NO 430
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 430
cgcnnnnnnc ag                                                           12

<210> SEQ ID NO 431
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 431
cagnnnnnnn nnnngcg                                                      17

<210> SEQ ID NO 432
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 432
ccgnnnnnnn nnnnnccg                                                     18

<210> SEQ ID NO 433
<211> LENGTH: 24
<212> TYPE: DNA
<213> ORGANISM: Artificial Sequence
<220> FEATURE:
<223> OTHER INFORMATION: Dyad patterns over-represented in STAR elements

```
<220> FEATURE:
<221> NAME/KEY: misc_feature
<222> LOCATION: (4)..(21)
<223> OTHER INFORMATION: "N" stands for any nucleotide

<400> SEQUENCE: 433
cgcnnnnnnn nnnnnnnnnn ncag                                              24

<210> SEQ ID NO 434
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 434 cagnggg                                                                  7

<210> SEQ ID NO 435
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 435 cgcccc                                                                   6

<210> SEQ ID NO 436
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 436
gcgnnnnnnn nnnnnnnnnn ngcc                                              24

<210> SEQ ID NO 437
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 437
cggnnnnnnn nnnnnnnggg c                                                 21

<210> SEQ ID NO 438
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
```

<223> OTHER INFORMATION: "N" stands for any nucleotide

<400> SEQUENCE: 438
cccnnnnnnn nnnnnnnnag g    21

<210> SEQ ID NO 439
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 439
aggnnnnnnn nnnnnnnnnn nnngcg    26

<210> SEQ ID NO 440
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 440
cggnnnnnct c    11

<210> SEQ ID NO 441
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 441
tccnnnnnnn nnnnnnnnnn cga    23

<210> SEQ ID NO 442
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 442 gcgnnnnccc    10

<210> SEQ ID NO 443
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature -continued

```
<222> LOCATION: (4)..(5)
<223> OTHER INFORMATION: "N" stands for any nucleotide

<400> SEQUENCE: 443 cccnncgc                                                                 8

<210> SEQ ID NO 444
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 444 cgtnnncag                                                                9

<210> SEQ ID NO 445
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 445
ccgnnnnnnn nnnnnngag                                                    19

<210> SEQ ID NO 446
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 446
ctcnnnnnnc gc                                                           12

<210> SEQ ID NO 447
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 447 cgcnnnngag                                                              10

<210> SEQ ID NO 448
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
```

-continued

```
<221> NAME/KEY: misc_feature
<222> LOCATION: (4)..(8)
<223> OTHER INFORMATION: "N" stands for any nucleotide

<400> SEQUENCE: 448
gcgnnnnngg a                                                              11

<210> SEQ ID NO 449
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 449 ccgncag                                                                    7

<210> SEQ ID NO 450
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 450
cgcnnnnnnn nnnnccg                                                        17

<210> SEQ ID NO 451
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 451
gcgnnnnnnn nnnnnnnnnn nnccc                                               25

<210> SEQ ID NO 452
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 452
cgcnnnnnnn nnnnnnnnnn ngaa                                                24

<210> SEQ ID NO 453
<211> LENGTH: 25
<212> TYPE: DNA
<213> ORGANISM: Artificial Sequence
<220> FEATURE:
<223> OTHER INFORMATION: Dyad patterns over-represented in STAR elements
```

```
<220> FEATURE:
<221> NAME/KEY: misc_feature
<222> LOCATION: (4)..(22)
<223> OTHER INFORMATION: "N" stands for any nucleotide

<400> SEQUENCE: 453
gggnnnnnnn nnnnnnnnnn nngga                                              25

<210> SEQ ID NO 454
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 454 ccancgg                                                                   7

<210> SEQ ID NO 455
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 455
cccnnnnnnn gcg                                                           13

<210> SEQ ID NO 456
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 456
aggnnnnnnn nnnccc                                                        16

<210> SEQ ID NO 457
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 457 ccaggg                                                                    6

<210> SEQ ID NO 458
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
```

<223> OTHER INFORMATION: "N" stands for any nucleotide

<400> SEQUENCE: 458
cagnnnnnnn nnnccc                                                                              16

<210> SEQ ID NO 459
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 459
ccgnnnnnnn nnnnnnnnnn nccg                                                                     24

<210> SEQ ID NO 460
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 460
ccgnnnnnnn nnnnnnnnnn nggc                                                                     24

<210> SEQ ID NO 461
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 461 cccnngcg                                                                                        8

<210> SEQ ID NO 462
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 462 cgcnggc                                                                                         7

<210> SEQ ID NO 463
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 463
ccgnnnnnga c                                                          11

<210> SEQ ID NO 464
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 464 ggaccc                                                                 6

<210> SEQ ID NO 465
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 465 cccnccg                                                                7

<210> SEQ ID NO 466
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 466
cccnnnnnnn nnnnnnnnac g                                               21

<210> SEQ ID NO 467
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 467
agcnnnnnnn nccc                                                       14

<210> SEQ ID NO 468
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide -continued

<400> SEQUENCE: 468 cccnnnggc                                                                9

<210> SEQ ID NO 469
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 469
aggnnnnnnn nncgg                                                        15

<210> SEQ ID NO 470
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 470
cccnnnnnnn nnnnnnncgc                                                   20

<210> SEQ ID NO 471
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 471 ccgccg                                                                   6

<210> SEQ ID NO 472
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 472
cgcnnnnnnn nagc                                                         14

<210> SEQ ID NO 473
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 473
cgcnnnnnnn nnnnnnnnnn nnacc                                             25

<210> SEQ ID NO 474
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 474
gcgnnnnnnn nnnnnnnnnn gac                                         23

<210> SEQ ID NO 475
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 475 agcngcg                                                            7

<210> SEQ ID NO 476
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 476
ccgnnnnnnn nnnnggc                                                17

<210> SEQ ID NO 477
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 477 cggnnnnaga                                                        10

<210> SEQ ID NO 478
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 478

```
cgcnnnnnnn nnnnnnnccg                                          20
```

<210> SEQ ID NO 479
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 479

```
cctnnnnnnn nnnnnnnnnn nnngcg                                   26
```

<210> SEQ ID NO 480
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 480

```
ccannnnnnn nnncgc                                              16
```

<210> SEQ ID NO 481
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 481

```
cccnnnnnnn nnnnnnnnnn nnncac                                   26
```

<210> SEQ ID NO 482
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 482

```
ccgnnnnnnn nnnngcc                                             17
```

<210> SEQ ID NO 483
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 483
cgcnnnnnnn nnnnnnnnnn nccc                                                    24

<210> SEQ ID NO 484
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 484
cggnnnnnnn nnnnnnnncg c                                                       21

<210> SEQ ID NO 485
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 485
cgcnnnnnnn nnnnnnnnng cc                                                      22

<210> SEQ ID NO 486
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 486
cgcnnnnnnn nnnnnnnnnn nnnggc                                                  26

<210> SEQ ID NO 487
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 487
cgcnnnnnnn nnnnnnnnnn nnccg                                                   25

<210> SEQ ID NO 488
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide -continued

<400> SEQUENCE: 488
cggnnnnnnn nnncca                                                    16

<210> SEQ ID NO 489
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 489
cgcnnnnnnn nnnnnnnnnn ccc                                            23

<210> SEQ ID NO 490
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 490
cgcnnnnnnn nnnnaca                                                   17

<210> SEQ ID NO 491
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 491 cggacc                                                                6

<210> SEQ ID NO 492
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 492
gcgnnnnnnn nnngcc                                                    16

<210> SEQ ID NO 493
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 493
gcgnnnnnnn ngac                                                      14

<210> SEQ ID NO 494
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 494
cccnnnnnnn nnnnnnnngg g                                              21

<210> SEQ ID NO 495
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (1)..(19)
<223> OTHER INFORMATION: "N" stands for any nucleotide

<400> SEQUENCE: 495
cggnnnnnnn nnnnnnnnng gc                                             22

<210> SEQ ID NO 496
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 496
cgcnnnnnnn nnnnnnnnnc ca                                             22

<210> SEQ ID NO 497
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 497 gccnnnccc                                                             9

<210> SEQ ID NO 498
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 498

-continued cagnnnnggg                                                          10

<210> SEQ ID NO 499
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 499
cccnnnnnng cg                                                       12

<210> SEQ ID NO 500
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 500
ccgnnnnnnn nnnnnnnnnc gc                                            22

<210> SEQ ID NO 501
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 501
cccnnnnnnn nnnnnnnnnn gca                                           23

<210> SEQ ID NO 502
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 502
cgcnnnnnnn nnnnntcc                                                 19

<210> SEQ ID NO 503
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 503 gccncgc                                                              7

<210> SEQ ID NO 504
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 504
ccgnnnnnnn nnnnnnnnnn nngag                                          25

<210> SEQ ID NO 505
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 505
gggnnnnnnn nnngga                                                    16

<210> SEQ ID NO 506
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 506
cagnnnnncc g                                                         11

<210> SEQ ID NO 507
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 507 cgcnnnaga                                                             9

<210> SEQ ID NO 508
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 508 gccgcc                                                                6

<210> SEQ ID NO 509
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 509
cccnnnnnnn nggc                                                    14

<210> SEQ ID NO 510
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 510
cctnnnnnng cg                                                      12

<210> SEQ ID NO 511
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 511
gacnnnnnnc cc                                                      12

<210> SEQ ID NO 512
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 512 cggnccc                                                             7

<210> SEQ ID NO 513
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 513
cccnnnnnnn nnnnnnnncc g                                            21

-continued

<210> SEQ ID NO 514
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 514
cagnnnnnnn nnccc                                                         15

<210> SEQ ID NO 515
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 515
cggnnnnnnn nnnggc                                                        16

<210> SEQ ID NO 516
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 516
cgannnnnnn nnnacg                                                        16

<210> SEQ ID NO 517
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 517 gcgnnntcc                                                                 9

<210> SEQ ID NO 518
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 518

```
cccnnngcc                                                              9

<210> SEQ ID NO 519
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 519 gcgnacc                                                                7

<210> SEQ ID NO 520
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 520
ccgnnnnnnn nnagg                                                      15

<210> SEQ ID NO 521
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 521
cgcnnnnnnn nnnnnnnnnc ag                                              22

<210> SEQ ID NO 522
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 522 ggcccc                                                                 6

<210> SEQ ID NO 523
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 523
aggnnnnnnn nnnnnccg                                                   18
```

```
<210> SEQ ID NO 524
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 524 ccggcg                                                                    6

<210> SEQ ID NO 525
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 525 ccgnngcc                                                                  8

<210> SEQ ID NO 526
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 526
ccgnnnnnnn nnnngtc                                                       17

<210> SEQ ID NO 527
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 527 cagccc                                                                    6

<210> SEQ ID NO 528
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 528
cccnnnnncc g                                                             11

<210> SEQ ID NO 529
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
```

```
<221> NAME/KEY: misc_feature
<222> LOCATION: (4)..(23)
<223> OTHER INFORMATION: "N" stands for any nucleotide

<400> SEQUENCE: 529
gccnnnnnnn nnnnnnnnnn nnnccc                                          26

<210> SEQ ID NO 530
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 530 gacnncgc                                                               8

<210> SEQ ID NO 531
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 531
cgcnnnnnnc ac                                                         12

<210> SEQ ID NO 532
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 532
aggnnnnnnn nnnnnnngcg                                                 20

<210> SEQ ID NO 533
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 533
gacnnnnncg c                                                          11

<210> SEQ ID NO 534
<211> LENGTH: 25
<212> TYPE: DNA
<213> ORGANISM: Artificial Sequence
<220> FEATURE:
<223> OTHER INFORMATION: Dyad patterns over-represented in STAR elements
```

```
<220> FEATURE:
<221> NAME/KEY: misc_feature
<222> LOCATION: (4)..(22)
<223> OTHER INFORMATION: "N" stands for any nucleotide

<400> SEQUENCE: 534
cctnnnnnnn nnnnnnnnnn nnccg                                          25

<210> SEQ ID NO 535
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 535
ccgnnnnnnn nnnnngga                                                  18

<210> SEQ ID NO 536
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 536
ggcnnnnnnn nngac                                                     15

<210> SEQ ID NO 537
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 537
aggnnnnnnn nnnggg                                                    16

<210> SEQ ID NO 538
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 538
ccgnnnnnnn nnngag                                                    16

<210> SEQ ID NO 539
<211> LENGTH: 12
<212> TYPE: DNA
<213> ORGANISM: Artificial Sequence
<220> FEATURE:
```

```
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 539
cgcnnnnnng ga                                                              12

<210> SEQ ID NO 540
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 540
cgcnnnnnnn agc                                                             13

<210> SEQ ID NO 541
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 541
ccannnnnnn nnnnnncgg                                                       19

<210> SEQ ID NO 542
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 542
cggnnnnnng ga                                                              12

<210> SEQ ID NO 543
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 543
cgcnnnnnnn nnnnnnnnnn nngcc                                                25

<210> SEQ ID NO 544
<211> LENGTH: 18
<212> TYPE: DNA
<213> ORGANISM: Artificial Sequence
```

```
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 544
ccannnnnnn nnnnncgc                                                    18

<210> SEQ ID NO 545
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 545 cggnggc                                                                 7

<210> SEQ ID NO 546
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 546 gcgnnncca                                                               9

<210> SEQ ID NO 547
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 547 aggncgc                                                                 7

<210> SEQ ID NO 548
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 548
ctcnnnnncg c                                                           11

<210> SEQ ID NO 549
<211> LENGTH: 6
<212> TYPE: DNA
```

-continued

<213> ORGANISM: Artificial Sequence
<220> FEATURE:
<223> OTHER INFORMATION: Dyad patterns over-represented in STAR elements

<400> SEQUENCE: 549 cccacg                                                                  6

<210> SEQ ID NO 550
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 550
cagnnnnnnn nnnnnnnnnn ccg                                              23

<210> SEQ ID NO 551
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 551 ggcnnnnccc                                                             10

<210> SEQ ID NO 552
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 552
aggnnnnnnn ngcg                                                        14

<210> SEQ ID NO 553
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 553 ctgnccc                                                                 7

<210> SEQ ID NO 554
<211> LENGTH: 22
<212> TYPE: DNA
<213> ORGANISM: Artificial Sequence
<220> FEATURE:
<223> OTHER INFORMATION: Dyad patterns over-represented in STAR elements

```
<220> FEATURE:
<221> NAME/KEY: misc_feature
<222> LOCATION: (4)..(19)
<223> OTHER INFORMATION: "N" stands for any nucleotide

<400> SEQUENCE: 554
cccnnnnnnn nnnnnnnnnc ag                                              22

<210> SEQ ID NO 555
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 555
cgcnnnnnnn nngac                                                      15

<210> SEQ ID NO 556
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 556
cagnnnnnnc cg                                                         12

<210> SEQ ID NO 557
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 557
cgtnnnnnnn nnnnncgc                                                   18

<210> SEQ ID NO 558
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 558
ctcnnnnnnn gcc                                                        13

<210> SEQ ID NO 559
<211> LENGTH: 25
<212> TYPE: DNA
<213> ORGANISM: Artificial Sequence
<220> FEATURE:
```

```
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 559
cgcnnnnnnn nnnnnnnnnn nntcc                                         25

<210> SEQ ID NO 560
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 560
cccnnnnnnn gcc                                                      13

<210> SEQ ID NO 561
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 561
cagnnnnnnn nnnnnncgg                                                19

<210> SEQ ID NO 562
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 562 cgcngcc                                                              7

<210> SEQ ID NO 563
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 563
cgcnnnnnnn nnnnnnnnnn ccg                                           23

<210> SEQ ID NO 564
<211> LENGTH: 10
<212> TYPE: DNA
<213> ORGANISM: Artificial Sequence
```

```
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 564 aggnnnnccc                                                              10

<210> SEQ ID NO 565
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 565
agcnnnnnnn nnncgc                                                       16

<210> SEQ ID NO 566
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 566
cccnnnnnnn nnnncgg                                                      17

<210> SEQ ID NO 567
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 567
cccnnnnnnn ngcc                                                         14

<210> SEQ ID NO 568
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 568 ccgncgg                                                                  7

<210> SEQ ID NO 569
<211> LENGTH: 7
<212> TYPE: DNA
```

```
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 569 cccnacc                                                                    7

<210> SEQ ID NO 570
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 570 cgccag                                                                     6

<210> SEQ ID NO 571
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 571
ccgnnnnnnn nnnnnnnnnn nntgc                                               25

<210> SEQ ID NO 572
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 572 gcgnnnncga                                                                10

<210> SEQ ID NO 573
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 573
ccgnnnnnnn nnnnnnnnnn nngcc                                               25

<210> SEQ ID NO 574
<211> LENGTH: 16
<212> TYPE: DNA
<213> ORGANISM: Artificial Sequence
<220> FEATURE:
<223> OTHER INFORMATION: Dyad patterns over-represented in STAR elements
```

```
<220> FEATURE:
<221> NAME/KEY: misc_feature
<222> LOCATION: (4)..(13)
<223> OTHER INFORMATION: "N" stands for any nucleotide

<400> SEQUENCE: 574
ccannnnnnn nnnccc                                                         16

<210> SEQ ID NO 575
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 575
cagnnnnnnn nnnnnnggg                                                      19

<210> SEQ ID NO 576
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 576
agcnnnnnnn nnnnnnnnnn ncgg                                                24

<210> SEQ ID NO 577
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 577
cgannnnnnn ncgc                                                           14

<210> SEQ ID NO 578
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 578 agcnnnnccc                                                                10

<210> SEQ ID NO 579
<211> LENGTH: 12
<212> TYPE: DNA
<213> ORGANISM: Artificial Sequence
<220> FEATURE:
```

<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 579
ggannnnnnc cc                                                         12

<210> SEQ ID NO 580
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 580
cggnnnnnnn nnnnnnaag                                                  19

<210> SEQ ID NO 581
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 581
accnnnnnnn nnnncgc                                                    17

<210> SEQ ID NO 582
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 582
ccgnnnnnnn nnnnncag                                                   18

<210> SEQ ID NO 583
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 583
cccnnnnnnn nnnnnggg                                                   18

<210> SEQ ID NO 584
<211> LENGTH: 23
<212> TYPE: DNA
<213> ORGANISM: Artificial Sequence

```
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 584
cacnnnnnnn nnnnnnnnnn acg                                              23

<210> SEQ ID NO 585
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 585
cagnnnnnnn nnnnnnnnnn nccc                                             24

<210> SEQ ID NO 586
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 586
cgtnnnnnnn nnngtc                                                      16

<210> SEQ ID NO 587
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 587
cccnnnnnnn nnnnnngcg                                                   19

<210> SEQ ID NO 588
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 588 gcancgc                                                                 7

<210> SEQ ID NO 589
<211> LENGTH: 10
<212> TYPE: DNA
```

```
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 589 agannnnccg                                                               10

<210> SEQ ID NO 590
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 590
gcgnnnnnnn nnnagc                                                        16

<210> SEQ ID NO 591
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 591 cgcgga                                                                    6

<210> SEQ ID NO 592
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 592 cggnnnngac                                                               10

<210> SEQ ID NO 593
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 593
cccnnnnnnn nnnnncgc                                                      18

<210> SEQ ID NO 594
<211> LENGTH: 21
<212> TYPE: DNA
<213> ORGANISM: Artificial Sequence
<220> FEATURE:
<223> OTHER INFORMATION: Dyad patterns over-represented in STAR elements
```

```
<220> FEATURE:
<221> NAME/KEY: misc_feature
<222> LOCATION: (4)..(18)
<223> OTHER INFORMATION: "N" stands for any nucleotide

<400> SEQUENCE: 594
gccnnnnnnn nnnnnnnncc c                                              21

<210> SEQ ID NO 595
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 595
gcgnnnnnnt cc                                                        12

<210> SEQ ID NO 596
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 596 cggnnncag                                                             9

<210> SEQ ID NO 597
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 597 cccnnncca                                                             9

<210> SEQ ID NO 598
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 598 agcnnnccc                                                             9

<210> SEQ ID NO 599
<211> LENGTH: 22
<212> TYPE: DNA
<213> ORGANISM: Artificial Sequence
<220> FEATURE:
```

```
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 599
gggnnnnnnn nnnnnnnnng ca                                              22

<210> SEQ ID NO 600
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 600
aggnnnnnnn nccg                                                       14

<210> SEQ ID NO 601
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 601 cccccg                                                                 6

<210> SEQ ID NO 602
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 602
gcgnnnnnga c                                                          11

<210> SEQ ID NO 603
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 603
cccnnnnnnn nnacc                                                      15

<210> SEQ ID NO 604
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
```

```
<222> LOCATION: (4)..(8)
<223> OTHER INFORMATION: "N" stands for any nucleotide

<400> SEQUENCE: 604 ctgnnnncg c                                                           11

<210> SEQ ID NO 605
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 605
cgcnnnnnnn nnnnnnnctc                                                 20

<210> SEQ ID NO 606
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 606
cggnnnnnnn nnnnnnngca                                                 20

<210> SEQ ID NO 607
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 607
ccgnnnnnnn ngcc                                                       14

<210> SEQ ID NO 608
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 608
ccgnnnnnnn cac                                                        13

<210> SEQ ID NO 609
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
```

```
<221> NAME/KEY: misc_feature
<222> LOCATION: (4)..(11)
<223> OTHER INFORMATION: "N" stands for any nucleotide

<400> SEQUENCE: 609
agcnnnnnnn ngcg                                                              14

<210> SEQ ID NO 610
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 610
cggnnnnnnn nnnnnnnnng ga                                                     22

<210> SEQ ID NO 611
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 611
ccannnnnnn nnnnnccg                                                          18

<210> SEQ ID NO 612
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 612 cggnnccc                                                                      8

<210> SEQ ID NO 613
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 613
ccannnnnnn nnnnnnggg                                                         19

<210> SEQ ID NO 614
<211> LENGTH: 21
<212> TYPE: DNA
<213> ORGANISM: Artificial Sequence
<220> FEATURE:
<223> OTHER INFORMATION: Dyad patterns over-represented in STAR elements
```

```
<220> FEATURE:
<221> NAME/KEY: misc_feature
<222> LOCATION: (4)..(18)
<223> OTHER INFORMATION: "N" stands for any nucleotide

<400> SEQUENCE: 614
cggnnnnnnn nnnnnnnngc a                                              21

<210> SEQ ID NO 615
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 615
cgcnnnnnnn nngca                                                     15

<210> SEQ ID NO 616
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 616
cggnnnnnnn nnnnnnnnnn nncca                                          25

<210> SEQ ID NO 617
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 617
gggnnnnnnn nnnnnnnncg a                                              21

<210> SEQ ID NO 618
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 618
cccnnnnnnn nnncgc                                                    16

<210> SEQ ID NO 619
<211> LENGTH: 20
<212> TYPE: DNA
<213> ORGANISM: Artificial Sequence
<220> FEATURE:
```

```
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 619
ctcnnnnnnn nnnnnncgc                                              20

<210> SEQ ID NO 620
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 620
cacnnnnnnn nnnngcg                                                17

<210> SEQ ID NO 621
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 621 ccgnnggc                                                           8

<210> SEQ ID NO 622
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 622
ctgnnnnnnn nnnnnnnnnn nccc                                        24

<210> SEQ ID NO 623
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 623
gggnnnnnnn nnnnnncac                                              19

<210> SEQ ID NO 624
<211> LENGTH: 21
<212> TYPE: DNA
<213> ORGANISM: Artificial Sequence
```

```
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 624
cctnnnnnnn nnnnnnnggc                                              21

<210> SEQ ID NO 625
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 625
cccnnnnnnn nnnnnnnnnn nnncga                                       26

<210> SEQ ID NO 626
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 626
cccnnnnnnn ncga                                                    14

<210> SEQ ID NO 627
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 627
gagnnnnnnn ccc                                                     13

<210> SEQ ID NO 628
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 628 cgcnnccg                                                            8

<210> SEQ ID NO 629
<211> LENGTH: 6
<212> TYPE: DNA
```

```
<213> ORGANISM: Artificial Sequence
<220> FEATURE:
<223> OTHER INFORMATION: Dyad patterns over-represented in STAR elements

<400> SEQUENCE: 629 ccctcc                                                                      6

<210> SEQ ID NO 630
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 630 agcgcc                                                                      6

<210> SEQ ID NO 631
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 631 cccnntcc                                                                    8

<210> SEQ ID NO 632
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 632
ccgnnnnncc c                                                               11

<210> SEQ ID NO 633
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 633
cgcnnnnnnn nnnnnncgc                                                       19

<210> SEQ ID NO 634
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide
```

```
<400> SEQUENCE: 634 cccncgc                                                                 7

<210> SEQ ID NO 635
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 635
gccnnnnnnn nnnnnnnnng ca                                               22

<210> SEQ ID NO 636
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 636
cccnnnnnnn nnnnnnnnnc ca                                               22

<210> SEQ ID NO 637
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 637
ccgnnnnnnn nnnnnncgc                                                   19

<210> SEQ ID NO 638
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 638
ccgnnnnnnn nnnnnnnnnn cag                                              23

<210> SEQ ID NO 639
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
```

<223> OTHER INFORMATION: "N" stands for any nucleotide

<400> SEQUENCE: 639
cggnnnnnnn nnnnnnnnnn nggc                                              24

<210> SEQ ID NO 640
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 640
ccgnnnnnnn nnnnnnnagg                                                   20

<210> SEQ ID NO 641
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 641
cccnnnnncg g                                                            11

<210> SEQ ID NO 642
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 642
cccnnnnnng ga                                                           12

<210> SEQ ID NO 643
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 643 acgnnccc                                                                 8

<210> SEQ ID NO 644
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 644
ccannnnnnn nnccg                                                        15

<210> SEQ ID NO 645
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 645
cccnnnnnnn nnnnnnnnnn nncca                                             25

<210> SEQ ID NO 646
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 646 cagggg                                                                   6

<210> SEQ ID NO 647
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 647 agcnccc                                                                  7

<210> SEQ ID NO 648
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 648
gcgnnnnnnn tcc                                                          13

<210> SEQ ID NO 649
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

```
<400> SEQUENCE: 649
acgnnnnnnn nnnnnnnnnn ncca                                              24

<210> SEQ ID NO 650
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 650
gctnnnnnnn nnnnnnnccc                                                   20

<210> SEQ ID NO 651
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 651
gcgnnnnnnn nnnnnnnccc                                                   20

<210> SEQ ID NO 652
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 652
gcgnnnnnnn nnnnnnnnnn nnagc                                             25

<210> SEQ ID NO 653
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 653
ccgnnnnnnn ncag                                                         14

<210> SEQ ID NO 654
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide
```

```
<400> SEQUENCE: 654
gcgnnnnnng cc                                                            12

<210> SEQ ID NO 655
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 655
gcgnnnnnnn nnngca                                                        16

<210> SEQ ID NO 656
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 656
cctnnnnnnn gcc                                                           13

<210> SEQ ID NO 657
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 657
gccnnnnnnn nnnnnngcc                                                     19

<210> SEQ ID NO 658
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 658
cccnnnnnnn nnnnnnngcc                                                    20

<210> SEQ ID NO 659
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
```

<223> OTHER INFORMATION: "N" stands for any nucleotide

<400> SEQUENCE: 659
cccnnnnnnn nnnnnnncg g    21

<210> SEQ ID NO 660
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 660
ccannnnnnn nnnnncgc    19

<210> SEQ ID NO 661
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 661
agcnnnnnnn nnnnggg    17

<210> SEQ ID NO 662
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 662 ggagcc    6

<210> SEQ ID NO 663
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 663 gccnnntcc    9

<210> SEQ ID NO 664
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 664

```
cctnnnnngc c                                                            11

<210> SEQ ID NO 665
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 665
cggnnnnnnn nnnnnnnnnn nccc                                              24

<210> SEQ ID NO 666
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 666 cctnnnggc                                                                9

<210> SEQ ID NO 667
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 667 ccgctc                                                                   6

<210> SEQ ID NO 668
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (1)..(20)
<223> OTHER INFORMATION: "N" stands for any nucleotide

<400> SEQUENCE: 668
agcnnnnnnn nnnnnnnnnn gcg                                               23

<210> SEQ ID NO 669
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 669
acgnnnnnnn nnnnnnnggg                                                   20
```

```
<210> SEQ ID NO 670
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 670
cgannnnnnn nnnnnggc                                                18

<210> SEQ ID NO 671
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 671
cccnnnnnnn nnnnnnnnnn nnncgc                                       26

<210> SEQ ID NO 672
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 672
acgnnnnnnn nnnnnctg                                                18

<210> SEQ ID NO 673
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 673 ccgccc                                                              6

<210> SEQ ID NO 674
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 674
ccgnnnnnnn nnngga                                                  16

<210> SEQ ID NO 675
<211> LENGTH: 9
```

```
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 675 cccnnngcg                                                                      9

<210> SEQ ID NO 676
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 676
gcgnnnnnnn nnnnnnncgc                                                         20

<210> SEQ ID NO 677
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 677
ccgnnnnnnn ncgc                                                               14

<210> SEQ ID NO 678
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 678
cgcnnnnnnn nnnaca                                                             16

<210> SEQ ID NO 679
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 679
cccnnnnnnn nnnnnnnnnn nnccg                                                   25

<210> SEQ ID NO 680
```

```
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 680
cacnnnnnnn nnnnnnncgc                                                   20

<210> SEQ ID NO 681
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 681 gacnnnggc                                                                9

<210> SEQ ID NO 682
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 682
gaannnnnnn cgc                                                          13

<210> SEQ ID NO 683
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 683
cgcnnnnnnn nnnnnnnnng gc                                                22

<210> SEQ ID NO 684
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 684
ggcnnnnnnn nnccc                                                        15
```

```
<210> SEQ ID NO 685
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 685
cccnnnnnnn nngcc                                                          15

<210> SEQ ID NO 686
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 686 cgctgc                                                                     6

<210> SEQ ID NO 687
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 687
cctnnnnnnn nggc                                                           14

<210> SEQ ID NO 688
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 688
ccannnnnnn nccc                                                           14

<210> SEQ ID NO 689
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 689 gacnnccc                                                                   8

<210> SEQ ID NO 690
<211> LENGTH: 7
<212> TYPE: DNA
```

```
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 690 ggcnccc                                                                     7

<210> SEQ ID NO 691
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 691 cgcagc                                                                      6

<210> SEQ ID NO 692
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 692 aggnnnngcg                                                                 10

<210> SEQ ID NO 693
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 693
cggnnnnnnt cc                                                              12

<210> SEQ ID NO 694
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 694
acgnnnnnnn nnnnnnnnnn nnggc                                                25

<210> SEQ ID NO 695
<211> LENGTH: 14
<212> TYPE: DNA
<213> ORGANISM: Artificial Sequence
<220> FEATURE:
<223> OTHER INFORMATION: Dyad patterns over-represented in STAR elements
```

```
<220> FEATURE:
<221> NAME/KEY: misc_feature
<222> LOCATION: (4)..(11)
<223> OTHER INFORMATION: "N" stands for any nucleotide

<400> SEQUENCE: 695
cccnnnnnnn nacg                                                           14

<210> SEQ ID NO 696
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 696
cccnnnnnnn nnnnnnnnnn ngcc                                                24

<210> SEQ ID NO 697
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 697 gccnncga                                                                   8

<210> SEQ ID NO 698
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 698
cccnnnnnnn ngcg                                                           14

<210> SEQ ID NO 699
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 699 ccctc                                                                      6

<210> SEQ ID NO 700
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
```

```
<223> OTHER INFORMATION: "N" stands for any nucleotide

<400> SEQUENCE: 700
gccnnnnnnn nnnncgc                                                         17

<210> SEQ ID NO 701
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 701
agcnnnnnnn nnccc                                                           15

<210> SEQ ID NO 702
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 702 gctgcc                                                                      6

<210> SEQ ID NO 703
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 703 cgcnnnccc                                                                   9

<210> SEQ ID NO 704
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 704 cccnnccc                                                                    8

<210> SEQ ID NO 705
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 705
```
gccnnnnnnn nncgc					15

<210> SEQ ID NO 706
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 706
gcannnnnnn nnnnnnnnnn nncgc					25

<210> SEQ ID NO 707
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 707 cagnnnncgg					10

<210> SEQ ID NO 708
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 708 cagnnggg					8

<210> SEQ ID NO 709
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 709
gccnnnnnnn nnnnnnnnnc cc					22

<210> SEQ ID NO 710
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide -continued

<400> SEQUENCE: 710
gagnnnnncc c                                                                                      11

<210> SEQ ID NO 711
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 711
cctnnnnnnn nnnnnnnnnt cg                                                                          22

<210> SEQ ID NO 712
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 712 cccnnnggc                                                                                          9

<210> SEQ ID NO 713
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 713
gcgnnnnnnn nnnnnngga                                                                              19

<210> SEQ ID NO 714
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 714
gccnnnnnnn nnnnnnnnnn ggc                                                                         23

<210> SEQ ID NO 715
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

```
<400> SEQUENCE: 715
cccnnnnnnn nnnnnnnggc                                                 20

<210> SEQ ID NO 716
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 716 aggnnnccg                                                              9

<210> SEQ ID NO 717
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 717 caccgc                                                                 6

<210> SEQ ID NO 718
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 718
cggnnnnnnn nnnnnnnnnn ncag                                            24

<210> SEQ ID NO 719
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 719 agcngcc                                                                7

<210> SEQ ID NO 720
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 720
```

-continued

```
cgcnnnnnnn nnnnnnnnnn nggc                                           24
```

<210> SEQ ID NO 721
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 721

```
cccnnnnnag g                                                         11
```

<210> SEQ ID NO 722
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 722

```
aacgcg                                                                6
```

<210> SEQ ID NO 723
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 723

```
cccnnnnnnn nnncca                                                    16
```

<210> SEQ ID NO 724
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 724

```
cgcnnnnnnn nnnnnngag                                                 19
```

<210> SEQ ID NO 725
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 725

```
cgcnnnnnnn gcc                                                       13
```

<210> SEQ ID NO 726
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 726
cccnnnnnnn nnccg                                                    15

<210> SEQ ID NO 727
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 727
cgcnnnnnnn nnnnnnnnnc cc                                            22

<210> SEQ ID NO 728
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 728
gaannnnnnn nnnnnncgc                                                19

<210> SEQ ID NO 729
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 729 ggcnnnccc                                                            9

<210> SEQ ID NO 730
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 730
tccnnnnnnn nnnncca                                                  17

-continued

<210> SEQ ID NO 731
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 731 cacccc                                                                6

<210> SEQ ID NO 732
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 732
cgcnnnnnnn nnnnnnnnnc cg                                              22

<210> SEQ ID NO 733
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 733
cggnnnnnnn nnnnnnnag c                                                21

<210> SEQ ID NO 734
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 734
cccnnnnnnn nnnngcg                                                    18

<210> SEQ ID NO 735
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 735
cccnnnnnnn nngag                                                      15

<210> SEQ ID NO 736
<211> LENGTH: 26

```
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 736
ccgnnnnnnn nnnnnnnnnn nnntcc                                          26

<210> SEQ ID NO 737
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 737 cgccgc                                                                 6

<210> SEQ ID NO 738
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 738
atgnnnnnnn cgg                                                        13

<210> SEQ ID NO 739
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 739
gggnnnnnnn nnnnnnnnnn nnngca                                          26

<210> SEQ ID NO 740
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 740 cggnnnnggc                                                            10

<210> SEQ ID NO 741
<211> LENGTH: 22
<212> TYPE: DNA
<213> ORGANISM: Artificial Sequence
<220> FEATURE:
```

<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 741
cggnnnnnnn nnnnnnnnna gc					22

<210> SEQ ID NO 742
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 742
cggnnnnngg c					11

<210> SEQ ID NO 743
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 743 gcggga					6

<210> SEQ ID NO 744
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 744
ggcnnnnnnn nnnnnnnnnn nnncac					26

<210> SEQ ID NO 745
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 745
cccnnnnnnn nnccc					15

<210> SEQ ID NO 746
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature

```
<222> LOCATION: (4)..(20)
<223> OTHER INFORMATION: "N" stands for any nucleotide

<400> SEQUENCE: 746
accnnnnnnn nnnnnnnnnn ggc                                              23

<210> SEQ ID NO 747
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 747
cccnnnnnnc ga                                                          12

<210> SEQ ID NO 748
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 748
aagnnnnnnn nnncgg                                                      16

<210> SEQ ID NO 749
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 749
cgcnnnnnnn nnnnnnnnnn cac                                              23

<210> SEQ ID NO 750
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 750
cccnnnnnnn nnnnnnnnc gg                                                22

<210> SEQ ID NO 751
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
```

```
<221> NAME/KEY: misc_feature
<222> LOCATION: (4)..(21)
<223> OTHER INFORMATION: "N" stands for any nucleotide

<400> SEQUENCE: 751
gacnnnnnnn nnnnnnnnnn nggc                                              24

<210> SEQ ID NO 752
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 752
gggnnnnnnn nnnnnnnga c                                                  21

<210> SEQ ID NO 753
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 753 gccnnnntcc                                                              10

<210> SEQ ID NO 754
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 754
ggcnnnnnnn nnnnnnncc c                                                  21

<210> SEQ ID NO 755
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 755
cagnnnnnnn nnnncgc                                                      18

<210> SEQ ID NO 756
<211> LENGTH: 9
<212> TYPE: DNA
<213> ORGANISM: Artificial Sequence
<220> FEATURE:
<223> OTHER INFORMATION: Dyad patterns over-represented in STAR elements
```

```
<220> FEATURE:
<221> NAME/KEY: misc_feature
<222> LOCATION: (4)..(6)
<223> OTHER INFORMATION: "N" stands for any nucleotide

<400> SEQUENCE: 756 ccanngcg                                                                    9

<210> SEQ ID NO 757
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 757
ccgnnnnnnn nnnnnnnnng ag                                                   22

<210> SEQ ID NO 758
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 758 agcnncgc                                                                    8

<210> SEQ ID NO 759
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 759 gagnnnnccc                                                                 10

<210> SEQ ID NO 760
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 760 aggnnncgc                                                                   9

<210> SEQ ID NO 761
<211> LENGTH: 19
<212> TYPE: DNA
<213> ORGANISM: Artificial Sequence
<220> FEATURE:
```

```
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 761
cacnnnnnnn nnnnnnagg                                                    19

<210> SEQ ID NO 762
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 762 cccnnnncag                                                              10

<210> SEQ ID NO 763
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 763 cccnngaa                                                                 8

<210> SEQ ID NO 764
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 764
cgcnnnnnnn nnnnnnnnnn nngag                                             25

<210> SEQ ID NO 765
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 765
acgnnnnnnn nnnnnnnnn nggg                                               24

<210> SEQ ID NO 766
<211> LENGTH: 10
<212> TYPE: DNA
<213> ORGANISM: Artificial Sequence
```

```
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 766 cccnnnggc                                                                     10

<210> SEQ ID NO 767
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 767
cggnnnnnnn nngag                                                              15

<210> SEQ ID NO 768
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 768 cccnnnggg                                                                      9

<210> SEQ ID NO 769
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 769 gagnnnnggc                                                                    10

<210> SEQ ID NO 770
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 770
cgcnnnnnga g                                                                  11

<210> SEQ ID NO 771
<211> LENGTH: 26
<212> TYPE: DNA
```

<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 771
ccgnnnnnnn nnnnnnnnnn nnnagg                                      26

<210> SEQ ID NO 772
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 772
cccnnnnnnn nnnnnnncc c                                            21

<210> SEQ ID NO 773
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 773
aggnnnnnnn nnnnnnnnnn ccg                                         23

<210> SEQ ID NO 774
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 774
aggnnnnnng gg                                                     12

<210> SEQ ID NO 775
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 775
ggcnnnnnnn nnnnnnnnnn nnnccc                                      26

<210> SEQ ID NO 776
<211> LENGTH: 23

```
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 776
gcannnnnnn nnnnnnnnnn cgc                                                  23

<210> SEQ ID NO 777
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 777
cgannnnnnn nnnnacg                                                         17

<210> SEQ ID NO 778
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 778 cgcnngga                                                                    8

<210> SEQ ID NO 779
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 779
ctgnnnnncc c                                                               11

<210> SEQ ID NO 780
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 780
tccnnnnnnn nnnnnnnnnn nnncca                                               26

<210> SEQ ID NO 781
```

```
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 781 ccannggg                                                                   8

<210> SEQ ID NO 782
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 782
ccgnnnnnnn nnnnnnnngc g                                                   21

<210> SEQ ID NO 783
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 783
ccannnnngg g                                                              11

<210> SEQ ID NO 784
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 784 cggntgc                                                                    7

<210> SEQ ID NO 785
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 785
cccnnnnnnn nnnnnnngcg                                                     20
```

<210> SEQ ID NO 786
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 786 cagccg                                                                  6

<210> SEQ ID NO 787
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 787
gccnnnnnnn nntcc                                                        15

<210> SEQ ID NO 788
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 788
aggnnnnnnn nnnnnnnnnn nnncgc                                            26

<210> SEQ ID NO 789
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 789
cccnnnnnng ac                                                           12

<210> SEQ ID NO 790
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 790
cggnnnnnnn nnnncca                                                      17

<210> SEQ ID NO 791
<211> LENGTH: 20
<212> TYPE: DNA

```
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 791
gggnnnnnnn nnnnnncac                                                    20

<210> SEQ ID NO 792
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 792
gcannnnnnn nnnnnnncg c                                                  21

<210> SEQ ID NO 793
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 793 cgcnnaca                                                                 8

<210> SEQ ID NO 794
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 794
accnnnnnnn nnccc                                                        15

<210> SEQ ID NO 795
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 795
gcgnnnnnnn nncgc                                                        15

<210> SEQ ID NO 796
<211> LENGTH: 21
```

```
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 796
cagnnnnnnn nnnnnnnngc g                                           21

<210> SEQ ID NO 797
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 797
cccnnnnnnn nnnnnnnnnn ngtc                                        24

<210> SEQ ID NO 798
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 798 gcgnnnccc                                                          9

<210> SEQ ID NO 799
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 799
cggnnnnnnn nnnngcc                                                17

<210> SEQ ID NO 800
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 800 cccncgg                                                            7

<210> SEQ ID NO 801
```

```
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 801 gccnnnncca                                                              10

<210> SEQ ID NO 802
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 802 cccnnnnccg                                                              10

<210> SEQ ID NO 803
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 803 cgtnngca                                                                 8

<210> SEQ ID NO 804
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 804
agcnnnnnnn tcg                                                          13

<210> SEQ ID NO 805
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 805
ccgnnnnnnn nnnnnnnga a                                                  21
```

```
<210> SEQ ID NO 806
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 806
accnnnnncc c                                                                11

<210> SEQ ID NO 807
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 807
cgcnnnnnnn nnnnnnngag                                                       20

<210> SEQ ID NO 808
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 808
cccnnnnnnn cgc                                                              13

<210> SEQ ID NO 809
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 809
gagnnnnnnn nnnncgc                                                          18

<210> SEQ ID NO 810
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 810
ggcnnnnnnn nnnnnnnnnn ccc                                                   23
```

```
<210> SEQ ID NO 811
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 811
acgnnnnnnn nnnnctc                                                      17

<210> SEQ ID NO 812
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 812
acannnnnnn nncgg                                                        15

<210> SEQ ID NO 813
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 813
ctgnnnnnnn ccc                                                          13

<210> SEQ ID NO 814
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 814 cccngcc                                                                  8

<210> SEQ ID NO 815
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 815 cggnngca                                                                 8
```

```
<210> SEQ ID NO 816
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 816 ccctgc                                                                      6

<210> SEQ ID NO 817
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 817
cgcnnnnnnn acc                                                             13

<210> SEQ ID NO 818
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 818 gcanngcc                                                                    8

<210> SEQ ID NO 819
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 819
gcgnnnnnnn ncca                                                            14

<210> SEQ ID NO 820
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 820 agccgc                                                                      6

<210> SEQ ID NO 821
<211> LENGTH: 8
<212> TYPE: DNA
<213> ORGANISM: Artificial Sequence
<220> FEATURE:
```

```
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 821 gcgnngca                                                                  8

<210> SEQ ID NO 822
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 822 ccgnngtc                                                                  8

<210> SEQ ID NO 823
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 823 ccgnnnaca                                                                 9

<210> SEQ ID NO 824
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 824
acgnnnnnnn nnnnnntgg                                                     19

<210> SEQ ID NO 825
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 825
ccannnnnnn ncgc                                                          14

<210> SEQ ID NO 826
<211> LENGTH: 15
<212> TYPE: DNA
<213> ORGANISM: Artificial Sequence
```

```
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 826
ccgnnnnnnn nnggc                                                          15

<210> SEQ ID NO 827
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 827
ccannnnncc g                                                              11

<210> SEQ ID NO 828
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 828 aggnnnggg                                                                  9

<210> SEQ ID NO 829
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 829 cagnnggc                                                                   8

<210> SEQ ID NO 830
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 830
cccnnnnnnn ncag                                                           14

<210> SEQ ID NO 831
<211> LENGTH: 11
<212> TYPE: DNA
```

```
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 831
agcnnnnnca g                                                          11

<210> SEQ ID NO 832
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 832
cggnnnnnnn nnnnnnnnng cc                                              22

<210> SEQ ID NO 833
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 833
gcgnnnnnnn nnnnnnncc c                                                21

<210> SEQ ID NO 834
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 834
cccnnnnnnn nnnngcc                                                    17

<210> SEQ ID NO 835
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 835 cgannacg                                                               8

<210> SEQ ID NO 836
<211> LENGTH: 10
```

```
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 836 cggnnngcc                                                                  10

<210> SEQ ID NO 837
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 837
cacnnnnnnc gc                                                              12

<210> SEQ ID NO 838
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 838
cggnnnnnac g                                                               11

<210> SEQ ID NO 839
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 839 ctgnnnngcc                                                                 10

<210> SEQ ID NO 840
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 840
gggnnnnnnn nnnnnnnnnn ncga                                                 24

<210> SEQ ID NO 841
```

```
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 841
cctnnnnnnn ncgc                                                      14

<210> SEQ ID NO 842
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 842 gccnnnnccc                                                           10

<210> SEQ ID NO 843
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 843
cggnnnnnnn nnngcc                                                    16

<210> SEQ ID NO 844
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 844
gccnnnnngg a                                                         11

<210> SEQ ID NO 845
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 845
accnnnnnnn gcg                                                       13
```

<210> SEQ ID NO 846
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 846 cccnnnnnnnn ncgc                                                     14

<210> SEQ ID NO 847
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 847
cagnnnnncc c                                                         11

<210> SEQ ID NO 848
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 848
cacnnnnnnn nnnnnnnnga                                                20

<210> SEQ ID NO 849
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 849 cccngcc                                                              7

<210> SEQ ID NO 850
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 850
cccnnnnnag c                                                         11

```
<210> SEQ ID NO 851
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 851
ggcnnnnngg a                                                              11

<210> SEQ ID NO 852
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 852
cgannnnnnn nnnnnnnnnn gag                                                 23

<210> SEQ ID NO 853
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 853
cgcnnnnnnn aca                                                            13

<210> SEQ ID NO 854
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 854
ccannnnnnn nnnnnnccc                                                      19

<210> SEQ ID NO 855
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 855
cggnnnnnnn nnnnnnnnnn nnnggc                                              26
```

<210> SEQ ID NO 856
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 856
cccnnnnnnn nnnnnnnnnn gcc                                              23

<210> SEQ ID NO 857
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 857
cctnnnnnnn nnnccg                                                      16

<210> SEQ ID NO 858
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 858
cccnnnnnnn nccg                                                        14

<210> SEQ ID NO 859
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 859 cgcnnngag                                                               9

<210> SEQ ID NO 860
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 860

```
cgcnnnnnnn aag                                                        13
```

<210> SEQ ID NO 861
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 861

```
cggnnnnnnn nnnngga                                                    17
```

<210> SEQ ID NO 862
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 862

```
ccgnnnnnnn nnnnnnnncc g                                               21
```

<210> SEQ ID NO 863
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 863

```
cccnnngca                                                              9
```

<210> SEQ ID NO 864
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 864

```
cggnncag                                                               8
```

<210> SEQ ID NO 865
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 865

-continued aggnnccg     8

<210> SEQ ID NO 866
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 866 cccnnnncac     10

<210> SEQ ID NO 867
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 867
ggannnnnnn nnnnnnnnnn nnccc     25

<210> SEQ ID NO 868
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 868
cccnnnnnnn ncac     14

<210> SEQ ID NO 869
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 869
accnnnnnnc cg     12

<210> SEQ ID NO 870
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

```
<400> SEQUENCE: 870
cccnnnnnng gc                                                              12

<210> SEQ ID NO 871
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 871
cccnnnnnnc cg                                                              12

<210> SEQ ID NO 872
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 872
cgcnnnnnnn nnnnnnngcc                                                      20

<210> SEQ ID NO 873
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 873
ccgnnnnntc c                                                               11

<210> SEQ ID NO 874
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 874
gccnnnnnng cc                                                              12

<210> SEQ ID NO 875
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide
```

```
<400> SEQUENCE: 875
cggnnnnnnn gga                                                           13

<210> SEQ ID NO 876
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 876
gggnnnnnng ga                                                            12

<210> SEQ ID NO 877
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 877
gccnnnnnnn nnnntcc                                                       18

<210> SEQ ID NO 878
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 878
agtnnnnnnn nnnnnnnnnc cg                                                 22

<210> SEQ ID NO 879
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 879
ggcnnnnnnn nnnnnnnnnn nngcc                                              25

<210> SEQ ID NO 880
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
```

-continued

```
<223> OTHER INFORMATION: "N" stands for any nucleotide

<400> SEQUENCE: 880 ccgnnnccg                                                                  9

<210> SEQ ID NO 881
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 881
cccnnnnnnn nacc                                                           14

<210> SEQ ID NO 882
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 882
cagnnnnnnn nnnnnnnngc c                                                   21

<210> SEQ ID NO 883
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 883
cccnnnnnnn nnnnnnnnnn cgg                                                 23

<210> SEQ ID NO 884
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 884 gcgncca                                                                    7

<210> SEQ ID NO 885
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
```

```
<222> LOCATION: (4)..(17)
<223> OTHER INFORMATION: "N" stands for any nucleotide

<400> SEQUENCE: 885
cccnnnnnnn nnnnnnncag                                            20

<210> SEQ ID NO 886
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 886
cccnnnnnnn nccc                                                  14

<210> SEQ ID NO 887
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 887
acannnnnnn nnnnngcg                                              18

<210> SEQ ID NO 888
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 888 aggnnnnccg                                                       10

<210> SEQ ID NO 889
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 889
cgcnnnnnnn nnnnnngcc                                             19

<210> SEQ ID NO 890
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
```

```
<221> NAME/KEY: misc_feature
<222> LOCATION: (4)..(5)
<223> OTHER INFORMATION: "N" stands for any nucleotide

<400> SEQUENCE: 890 gagnncgc                                                                    8

<210> SEQ ID NO 891
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 891
cccnnnnnnn nngcg                                                           15

<210> SEQ ID NO 892
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 892
cgcnnnnnnn nnnnnnnnnn aca                                                  23

<210> SEQ ID NO 893
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 893
gcgnnnnnnn nnnnnnnnnn cca                                                  23

<210> SEQ ID NO 894
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 894
aagnnnnnnn nnnnnnnnnn nccg                                                 24

<210> SEQ ID NO 895
<211> LENGTH: 7
<212> TYPE: DNA
<213> ORGANISM: Artificial Sequence
<220> FEATURE:
<223> OTHER INFORMATION: Dyad patterns over-represented in STAR elements
```

```
<220> FEATURE:
<221> NAME/KEY: misc_feature
<222> LOCATION: (4)..(4)
<223> OTHER INFORMATION: "N" stands for any nucleotide

<400> SEQUENCE: 895 cgcngga                                                                    7

<210> SEQ ID NO 896
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 896 ccanccc                                                                    7

<210> SEQ ID NO 897
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 897
cgtnnnnnnn nnnnnnnnnn ntgc                                                24

<210> SEQ ID NO 898
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 898
tccnnnnnnn nnnnnncga                                                      20

<210> SEQ ID NO 899
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 899
cacnnnnngg g                                                              11

<210> SEQ ID NO 900
<211> LENGTH: 18
<212> TYPE: DNA
<213> ORGANISM: Artificial Sequence
<220> FEATURE:
```

-continued

<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 900
ccgnnnnnnn nnnnngca                                                 18

<210> SEQ ID NO 901
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 901
ctgnnnnnnc cc                                                       12

<210> SEQ ID NO 902
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 902
cggnnnnnnn nggc                                                     14

<210> SEQ ID NO 903
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 903
ccannnnnnn nnnnggg                                                  17

<210> SEQ ID NO 904
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 904
acgnnnnnnn nnnnnnnnnn nncaa                                         25

<210> SEQ ID NO 905
<211> LENGTH: 26
<212> TYPE: DNA
<213> ORGANISM: Artificial Sequence

```
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 905
gggnnnnnnn nnnnnnnnnn nnnccc                                       26

<210> SEQ ID NO 906
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 906 cgcnnnncag                                                         10

<210> SEQ ID NO 907
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 907
agcnnnnnnn nnnnnnnnnn ggg                                          23

<210> SEQ ID NO 908
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 908
cacnnnnnnn nnnnnnnnnn nnnccg                                       26

<210> SEQ ID NO 909
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 909
acgnnnnnnn nnnnnnnnnn cag                                          23

<210> SEQ ID NO 910
<211> LENGTH: 7
<212> TYPE: DNA
```

```
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 910 aggnccc                                                                      7

<210> SEQ ID NO 911
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 911
cgtnnnnnnn nnnnncac                                                         18

<210> SEQ ID NO 912
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 912
cggnnnnnnn nnggc                                                            15

<210> SEQ ID NO 913
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 913
cgcnnnnnnn nnngcg                                                           16

<210> SEQ ID NO 914
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 914
cccnnnnnnc tc                                                               12

<210> SEQ ID NO 915
<211> LENGTH: 16
```

```
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 915
ccgnnnnnnn nnnagg                                                  16

<210> SEQ ID NO 916
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 916
cccnnnnnnn nnnnnnnnnn ncag                                         24

<210> SEQ ID NO 917
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 917
agcnnnnnnn nnnnnnnnn ccg                                           23

<210> SEQ ID NO 918
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 918
agcnnnnnnn nngcg                                                   15

<210> SEQ ID NO 919
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 919 ccannnggc                                                           9

<210> SEQ ID NO 920
```

```
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 920
cccnnnnnnn nnnnggc                                                  17

<210> SEQ ID NO 921
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 921
acgnnnnngc a                                                        11

<210> SEQ ID NO 922
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 922
cccnnnnnnn nnnnnnncgg                                               20

<210> SEQ ID NO 923
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 923
cccnnnnncc a                                                        11

<210> SEQ ID NO 924
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 924 ccgnagg                                                              7
```

```
<210> SEQ ID NO 925
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 925
gggnnnnnnn nnngac                                                        16

<210> SEQ ID NO 926
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 926
cgcnnnnnnn nnnnnnnncc a                                                  21

<210> SEQ ID NO 927
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 927
cctnnnnnnn nnnnnnnnnn nncgc                                              25

<210> SEQ ID NO 928
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 928 cgtnnncgc                                                                 9

<210> SEQ ID NO 929
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 929
agcnnnnnnn nnnnnnnccg                                                    20
```

<210> SEQ ID NO 930
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 930 ggcnncga                                                                8

<210> SEQ ID NO 931
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 931
cagnnnnnnn nccc                                                        14

<210> SEQ ID NO 932
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 932 ccgnngac                                                                8

<210> SEQ ID NO 933
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 933
agcnnnnnnn nnnnnnnnnn nnagg                                            25

<210> SEQ ID NO 934
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 934 cctnnnnggc                                                             10

<210> SEQ ID NO 935
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 935
ccgnnnnnnn nnnnagc                                                  17

<210> SEQ ID NO 936
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 936 cacnnnncgc                                                          10

<210> SEQ ID NO 937
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 937 ccgnccc                                                              7

<210> SEQ ID NO 938
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 938
ctgnnnnnnn nnnnnggc                                                 19

<210> SEQ ID NO 939
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 939

```
cgcnnnnnnn nnnnnnnnna cc                                              22
```

<210> SEQ ID NO 940
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 940

```
cacnnnnnnn nnnnnnnnnn ncag                                            24
```

<210> SEQ ID NO 941
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 941

```
ggcnnnnnnn ngcc                                                       14
```

<210> SEQ ID NO 942
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 942

```
gggnnnnnnn nnnnnnnngg a                                               21
```

<210> SEQ ID NO 943
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 943

```
ccgnnnnnnn nnnnnnnng cc                                               22
```

<210> SEQ ID NO 944
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 944
ccgnnnnnnn nnnnnnnnn nnnacc                                              26

<210> SEQ ID NO 945
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 945
cgannnnnnn ccc                                                           13

<210> SEQ ID NO 946
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 946
ccgnnnnnnc tc                                                            12

<210> SEQ ID NO 947
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 947
cggnnnnnnn nnnctc                                                        16

<210> SEQ ID NO 948
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 948
cagnnnnnnn nnnnnnnnnc gc                                                 22

<210> SEQ ID NO 949
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

```
<400> SEQUENCE: 949 ccannnagg                                                                 9

<210> SEQ ID NO 950
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 950
gccnnnnnnn nnnnnnnnnn ngcc                                               24

<210> SEQ ID NO 951
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 951
cgcnnnnnnn nnnnnnnnnn ngga                                               24

<210> SEQ ID NO 952
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 952
ccgnnnnnnn nnnnnnnnnn nnnggc                                             26

<210> SEQ ID NO 953
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 953
acannnnnnn nnngcg                                                        16

<210> SEQ ID NO 954
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide
```

```
<400> SEQUENCE: 954
cggnnnnncc c                                                            11

<210> SEQ ID NO 955
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 955
cccnnnnnnn tcc                                                          13

<210> SEQ ID NO 956
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 956
acgnnnnnnn nnncgc                                                       16

<210> SEQ ID NO 957
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 957 cccnnntcc                                                                9

<210> SEQ ID NO 958
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 958
ccgnnnnnnn ncgg                                                         14

<210> SEQ ID NO 959
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
```

<223> OTHER INFORMATION: "N" stands for any nucleotide

<400> SEQUENCE: 959
ccannnnnnn nnnnnnnncg g                                    21

<210> SEQ ID NO 960
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 960
ccgnnnnnnc cg                                              12

<210> SEQ ID NO 961
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 961 cagnnngcg                                                  9

<210> SEQ ID NO 962
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 962 gagnccc                                                    7

<210> SEQ ID NO 963
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 963
ccgnnnnnnn nnnnnnnnnn ntgc                                 24

<210> SEQ ID NO 964
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature

```
<222> LOCATION: (4)..(10)
<223> OTHER INFORMATION: "N" stands for any nucleotide

<400> SEQUENCE: 964
cccnnnnnnn cca                                                          13

<210> SEQ ID NO 965
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 965 cggnnncca                                                                9

<210> SEQ ID NO 966
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 966 acgnccc                                                                  7

<210> SEQ ID NO 967
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 967
cggnnnnnnn nnnnnntga                                                    19

<210> SEQ ID NO 968
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 968
ctcnnnnnng gc                                                           12

<210> SEQ ID NO 969
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
```

-continued

```
<221> NAME/KEY: misc_feature
<222> LOCATION: (4)..(5)
<223> OTHER INFORMATION: "N" stands for any nucleotide

<400> SEQUENCE: 969 gcgnngac                                                                    8

<210> SEQ ID NO 970
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 970
gggnnnnnnn nnnnacc                                                         17

<210> SEQ ID NO 971
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 971 cgcnnnngga                                                                 10

<210> SEQ ID NO 972
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 972
cccnnnnnnn nnnnccg                                                         17

<210> SEQ ID NO 973
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 973
ccgnnnnnnn nnnnnnnnn nngca                                                 25

<210> SEQ ID NO 974
<211> LENGTH: 6
<212> TYPE: DNA
<213> ORGANISM: Artificial Sequence
<220> FEATURE:
<223> OTHER INFORMATION: Dyad patterns over-represented in STAR elements
```

```
<400> SEQUENCE: 974 gcggca                                                               6

<210> SEQ ID NO 975
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 975
agannnnnnn ccc                                                      13

<210> SEQ ID NO 976
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 976 cggnncca                                                             8

<210> SEQ ID NO 977
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 977
cccnnnnnnc cc                                                       12

<210> SEQ ID NO 978
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 978 accnnnngcg                                                          10

<210> SEQ ID NO 979
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
```

<223> OTHER INFORMATION: "N" stands for any nucleotide

<400> SEQUENCE: 979
cctnnnnnnn nnnnnnnncg c                                              21

<210> SEQ ID NO 980
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 980
agcnnnnnnn nngtc                                                     15

<210> SEQ ID NO 981
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 981
cccnnnnnnn nnnnnnnnnn nctc                                           24

<210> SEQ ID NO 982
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 982
cgcnnnnnnn nnnnnnnnnn ncga                                           24

<210> SEQ ID NO 983
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 983
cccnnnnnnn nnnnnnngc c                                               21

<210> SEQ ID NO 984
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 984
accnnnnnnn nnnnggc                                                17

<210> SEQ ID NO 985
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 985
aggnnnnnnn nnnnnnnncg c                                           21

<210> SEQ ID NO 986
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 986 gcgcca                                                             6

<210> SEQ ID NO 987
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 987
gcgnnnnnnn nnagc                                                  15

<210> SEQ ID NO 988
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 988
gggnnnnnnn nnnnnnnnnn ngca                                        24

<210> SEQ ID NO 989
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide -continued

<400> SEQUENCE: 989
cccnnnnnnn nnnnnnnnnn cag                                              23

<210> SEQ ID NO 990
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 990
ccannnnnnn ncgg                                                        14

<210> SEQ ID NO 991
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 991
ccgnnnnnnn nnnggc                                                      16

<210> SEQ ID NO 992
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 992 gcagcc                                                                  6

<210> SEQ ID NO 993
<211> LENGTH: 8
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(5)
<223> OTHER INFORMATION: "N" stands for any nucleotide

<400> SEQUENCE: 993 cagnncgc                                                                8

<210> SEQ ID NO 994
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 994
cgcnnnnnnn nggc                                                        14

<210> SEQ ID NO 995
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 995
ctgnnnnnnn nnnnnnnnnn ggc                                             23

<210> SEQ ID NO 996
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 996
gggnnnnnnn nnnnnnnacc                                                 20

<210> SEQ ID NO 997
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 997 ccgntgc                                                                7

<210> SEQ ID NO 998
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 998
cagnnnnnnn ncgc                                                       14

<210> SEQ ID NO 999
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 999
aagnnnnnnn nnnncgc                                               17

<210> SEQ ID NO 1000
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 1000
ccgnnnnnnt cc                                                    12

<210> SEQ ID NO 1001
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 1001
ccannnnnnn nnnnnnnnnn nccc                                       24

<210> SEQ ID NO 1002
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 1002 ccaccc                                                            6

<210> SEQ ID NO 1003
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 1003
gagnnnnnnc cc                                                    12

<210> SEQ ID NO 1004
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 1004
agcnnnnnnn nnnnnnnnnn nnnggc                                     26

<210> SEQ ID NO 1005
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 1005 cagcgc                                                                    6

<210> SEQ ID NO 1006
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 1006
ccgnnnnnnn nnnnnctc                                                       18

<210> SEQ ID NO 1007
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 1007
cgcnnnnnnn nnnnnnnac g                                                    21

<210> SEQ ID NO 1008
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 1008
ggcnnnnnnn nnnnnnnnn cga                                                  23

<210> SEQ ID NO 1009
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 1009
ccgnnnnnnn nnnnnnnna ag                                                   22

<210> SEQ ID NO 1010
<211> LENGTH: 20
<212> TYPE: DNA

```
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 1010
cgcnnnnnnn nnnnnntcc                                                    20

<210> SEQ ID NO 1011
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 1011
aggnnnnnnn cgc                                                          13

<210> SEQ ID NO 1012
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 1012
cggnnnnnnn ccc                                                          13

<210> SEQ ID NO 1013
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 1013 cgcnnnngcc                                                              10

<210> SEQ ID NO 1014
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 1014
cgannnnnnc cc                                                           12

<210> SEQ ID NO 1015
<211> LENGTH: 25
```

```
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 1015
cccnnnnnnn nnnnnnnnnn nngga                                        25

<210> SEQ ID NO 1016
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 1016
cccnnnnnnn nnnnnnnnng cg                                           22

<210> SEQ ID NO 1017
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 1017
ccannnnnnn cgc                                                     13

<210> SEQ ID NO 1018
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 1018
cccnnnnnng cc                                                      12

<210> SEQ ID NO 1019
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 1019
gccnnnnnnn nnnnnnntcc                                              20

<210> SEQ ID NO 1020
```

```
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 1020
aggnnnnnnn nnnnnnngcc                                              20

<210> SEQ ID NO 1021
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 1021
cgcnnnnnnn nnnngcc                                                 17

<210> SEQ ID NO 1022
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 1022 tccgca                                                              6

<210> SEQ ID NO 1023
<211> LENGTH: 14
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 1023
gcgnnnnnnn nccc                                                    14

<210> SEQ ID NO 1024
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 1024
ccannnnnnn nnnngcg                                                 17

<210> SEQ ID NO 1025
<211> LENGTH: 10
<212> TYPE: DNA
<213> ORGANISM: Artificial Sequence
```

```
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 1025 cacnnnnggg                                                              10

<210> SEQ ID NO 1026
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 1026
cggnnnnnnn tcc                                                          13

<210> SEQ ID NO 1027
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 1027
gcgnnnnngc c                                                            11

<210> SEQ ID NO 1028
<211> LENGTH: 18
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(15)
<223> OTHER INFORMATION: "N" stands for any nucleotide

<400> SEQUENCE: 1028
acgnnnnnnn nnnnncag                                                     18

<210> SEQ ID NO 1029
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 1029
ccgnnnnnnn nnnnnnnnnn nncgc                                             25

<210> SEQ ID NO 1030
<211> LENGTH: 14
<212> TYPE: DNA
```

<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(11)
<223> OTHER INFORMATION: "N" stands for any nucleotide

<400> SEQUENCE: 1030
cggnnnnnnn ntgc                                                         14

<210> SEQ ID NO 1031
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 1031 cccngag                                                                  7

<210> SEQ ID NO 1032
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 1032
gcgnnnnnnn nnnnnnnnnn nntga                                             25

<210> SEQ ID NO 1033
<211> LENGTH: 21
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(18)
<223> OTHER INFORMATION: "N" stands for any nucleotide

<400> SEQUENCE: 1033
ggcnnnnnnn nnnnnnngc c                                                  21

<210> SEQ ID NO 1034
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 1034
ccgnnnnnnn ccc                                                          13

<210> SEQ ID NO 1035
<211> LENGTH: 25

```
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 1035
acannnnnnn nnnnnnnnnn nnccc                                      25

<210> SEQ ID NO 1036
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 1036
accnnnnnnn nnnnnnnnng gg                                         22

<210> SEQ ID NO 1037
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 1037 aganggc                                                           7

<210> SEQ ID NO 1038
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 1038
gggnnnnnnn nnnnnnnnnn tga                                        23

<210> SEQ ID NO 1039
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 1039
cagnnnnngg g                                                     11

<210> SEQ ID NO 1040
```

```
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 1040
gccnnnnnnn nnnnnncgc                                                      19

<210> SEQ ID NO 1041
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 1041
gcgnnnnnnn gga                                                            13

<210> SEQ ID NO 1042
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 1042
cagnnnnnnn nnnnnnncca                                                     20

<210> SEQ ID NO 1043
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 1043 ccgnnnngtc                                                                10

<210> SEQ ID NO 1044
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 1044
cccnnnnnnn nnnnnncgc                                                      19
```

```
<210> SEQ ID NO 1045
<211> LENGTH: 20
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(17)
<223> OTHER INFORMATION: "N" stands for any nucleotide

<400> SEQUENCE: 1045
gcgnnnnnnn nnnnnnnacc                                          20

<210> SEQ ID NO 1046
<211> LENGTH: 26
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(23)
<223> OTHER INFORMATION: "N" stands for any nucleotide

<400> SEQUENCE: 1046
cagnnnnnnn nnnnnnnnnn nnnggg                                   26

<210> SEQ ID NO 1047
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 1047 ccgnnnnccc                                                     10

<210> SEQ ID NO 1048
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 1048
cgcnnnnngg c                                                   11

<210> SEQ ID NO 1049
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 1049
cctnnnnnng gc                                                  12
```

```
<210> SEQ ID NO 1050
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 1050 aggnnnggc                                                                    9

<210> SEQ ID NO 1051
<211> LENGTH: 17
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(14)
<223> OTHER INFORMATION: "N" stands for any nucleotide

<400> SEQUENCE: 1051
cggnnnnnnn nnnncgc                                                          17

<210> SEQ ID NO 1052
<211> LENGTH: 24
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(21)
<223> OTHER INFORMATION: "N" stands for any nucleotide

<400> SEQUENCE: 1052
ctgnnnnnnn nnnnnnnnnn ngga                                                  24

<210> SEQ ID NO 1053
<211> LENGTH: 23
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(20)
<223> OTHER INFORMATION: "N" stands for any nucleotide

<400> SEQUENCE: 1053
cacnnnnnnn nnnnnnnnnn cca                                                   23

<210> SEQ ID NO 1054
<211> LENGTH: 9
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(6)
<223> OTHER INFORMATION: "N" stands for any nucleotide

<400> SEQUENCE: 1054 cggnnngag                                                                    9
```

```
<210> SEQ ID NO 1055
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 1055
cccnnnnnnn nncca                                                      15

<210> SEQ ID NO 1056
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 1056 cccnacg                                                                7

<210> SEQ ID NO 1057
<211> LENGTH: 7
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(4)
<223> OTHER INFORMATION: "N" stands for any nucleotide

<400> SEQUENCE: 1057 cagngcc                                                                7

<210> SEQ ID NO 1058
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 1058
aggnnnnnnc cg                                                         12

<210> SEQ ID NO 1059
<211> LENGTH: 15
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(12)
<223> OTHER INFORMATION: "N" stands for any nucleotide

<400> SEQUENCE: 1059
```

-continued

```
agcnnnnnnn nnggg                                               15

<210> SEQ ID NO 1060
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 1060
cccnnnnnnn ggc                                                 13

<210> SEQ ID NO 1061
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 1061
cctnnnnnnn nnnnnnccc                                           19

<210> SEQ ID NO 1062
<211> LENGTH: 25
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(22)
<223> OTHER INFORMATION: "N" stands for any nucleotide

<400> SEQUENCE: 1062
ccgnnnnnnn nnnnnnnnnn nnttc                                    25

<210> SEQ ID NO 1063
<211> LENGTH: 13
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(10)
<223> OTHER INFORMATION: "N" stands for any nucleotide

<400> SEQUENCE: 1063
cccnnnnnnn ccg                                                 13

<210> SEQ ID NO 1064
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 1064
```

```
cgannnnnng gc                                                             12

<210> SEQ ID NO 1065
<211> LENGTH: 10
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(7)
<223> OTHER INFORMATION: "N" stands for any nucleotide

<400> SEQUENCE: 1065 cggnnnnctc                                                                10

<210> SEQ ID NO 1066
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 1066 cggcgc                                                                    6

<210> SEQ ID NO 1067
<211> LENGTH: 19
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(16)
<223> OTHER INFORMATION: "N" stands for any nucleotide

<400> SEQUENCE: 1067
cctnnnnnnn nnnnnnacg                                                      19

<210> SEQ ID NO 1068
<211> LENGTH: 12
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(9)
<223> OTHER INFORMATION: "N" stands for any nucleotide

<400> SEQUENCE: 1068
gggnnnnnnc ac                                                             12

<210> SEQ ID NO 1069
<211> LENGTH: 22
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(19)
<223> OTHER INFORMATION: "N" stands for any nucleotide

<400> SEQUENCE: 1069
cccnnnnnnn nnnnnnnnnc gc                                                  22
```

```
<210> SEQ ID NO 1070
<211> LENGTH: 16
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(13)
<223> OTHER INFORMATION: "N" stands for any nucleotide

<400> SEQUENCE: 1070
cccnnnnnnn nnnctc                                                         16

<210> SEQ ID NO 1071
<211> LENGTH: 6
<212> TYPE: DNA
<213> ORGANISM: Artificial Sequence
<220> FEATURE:
<223> OTHER INFORMATION: Dyad patterns over-represented in STAR elements

<400> SEQUENCE: 1071 ccccag                                                                     6

<210> SEQ ID NO 1072
<211> LENGTH: 11
<212> TYPE: DNA
<213> ORGANISM: Artificial Sequence
<220> FEATURE:
<223> OTHER INFORMATION: Dyad patterns over-represented in STAR elements
<220> FEATURE:
<221> NAME/KEY: misc_feature
<222> LOCATION: (4)..(8)
<223> OTHER INFORMATION: "N" stands for any nucleotide

<400> SEQUENCE: 1072
gccnnnnncc c                                                              11
```